(12) United States Patent
Kamenecka et al.

(10) Patent No.: US 9,018,205 B2
(45) Date of Patent: Apr. 28, 2015

(54) SUBSTITUTED PYRIMIDINYL-AMINES AS PROTEIN KINASE INHIBITORS

(71) Applicants: Theodore Mark Kamenecka, Palm Beach Gardens, FL (US); Rong Jiang, Fuquay Varina, NC (US); Xinyi Song, Jupiter, FL (US); Philip LoGrasso, Jupiter, FL (US); Michael Darin Cameron, Port Saint Lucie, FL (US); Derek R. Duckett, Jupiter, FL (US)

(72) Inventors: Theodore Mark Kamenecka, Palm Beach Gardens, FL (US); Rong Jiang, Fuquay Varina, NC (US); Xinyi Song, Jupiter, FL (US); Philip LoGrasso, Jupiter, FL (US); Michael Darin Cameron, Port Saint Lucie, FL (US); Derek R. Duckett, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 102 days.

(21) Appl. No.: 13/766,075

(22) Filed: Feb. 13, 2013

(65) Prior Publication Data
US 2013/0231336 A1 Sep. 5, 2013

Related U.S. Application Data

(62) Division of application No. 12/676,411, filed as application No. PCT/US2008/075151 on Sep. 3, 2008, now Pat. No. 8,530,480.

(60) Provisional application No. 60/969,849, filed on Sep. 4, 2007.

(51) Int. Cl.
| | | |
|---|---|---|
| *A61K 31/505* | (2006.01) | |
| *A61K 31/506* | (2006.01) | |
| *A61K 31/4196* | (2006.01) | |
| *A61K 31/454* | (2006.01) | |
| *A61K 31/4545* | (2006.01) | |
| *A61K 31/496* | (2006.01) | |
| *A61K 31/4965* | (2006.01) | |
| *A61K 31/5377* | (2006.01) | |
| *C07D 239/42* | (2006.01) | |
| *C07D 401/12* | (2006.01) | |
| *C07D 401/14* | (2006.01) | |
| *C07D 403/12* | (2006.01) | |
| *C07D 403/14* | (2006.01) | |
| *C07D 405/14* | (2006.01) | |
| *C07D 413/12* | (2006.01) | |
| *C07D 491/10* | (2006.01) | |

(52) U.S. Cl.
CPC .......... *C07D 239/42* (2013.01); *C07D 401/12* (2013.01); *C07D 401/14* (2013.01); *C07D 403/12* (2013.01); *C07D 403/14* (2013.01); *C07D 405/14* (2013.01); *C07D 413/12* (2013.01); *C07D 491/10* (2013.01)

(58) Field of Classification Search
CPC .............. A61K 31/505; A61K 31/506; A61K 31/4196; A61K 31/454; A61K 31/4545; A61K 31/496; A61K 31/4965; A61K 31/497; A61K 31/5377; C07D 239/42; C07D 403/12; C07D 401/14
USPC .......... 514/232.2, 236.2, 252.18, 252.19, 275
See application file for complete search history.

(56) References Cited

U.S. PATENT DOCUMENTS

| | | |
|---|---|---|
| 4,788,195 A | 11/1988 | Torley et al. |
| 4,876,252 A | 10/1989 | Torley et al. |
| 5,521,184 A | 5/1996 | Zimmermann |
| 5,705,502 A | 1/1998 | Zimmermann |
| 6,093,716 A | 7/2000 | Davis |
| 6,579,983 B1 | 6/2003 | Batchelor et al. |
| 6,838,464 B2 | 1/2005 | Pease et al. |
| 6,949,544 B2 | 9/2005 | Bethiel et al. |
| 7,067,522 B2 | 6/2006 | Pease et al. |
| 7,129,242 B2 | 10/2006 | Satoh et al. |
| 7,169,791 B2 | 1/2007 | Breitenstein et al. |
| 7,259,161 B2 | 8/2007 | Bethiel et al. |
| 7,312,227 B2 | 12/2007 | Ledeboer et al. |
| 7,348,335 B2 | 3/2008 | Bethiel et al. |
| 7,569,566 B2 | 8/2009 | Breitenstein et al. |
| 7,956,053 B2 | 6/2011 | Breitenstein et al. |
| 8,486,941 B2 | 7/2013 | Burns et al. |
| 8,530,480 B2 | 9/2013 | Kamenecka et al. |
| 2003/0176443 A1 | 9/2003 | Stein-Gerlach et al. |
| 2005/0171134 A1* | 8/2005 | Davis et al. ................... 514/275 |
| 2007/0021419 A1 | 1/2007 | Wang et al. |
| 2007/0043048 A1 | 2/2007 | Bollbuck et al. |
| 2009/0298830 A1 | 12/2009 | Mann et al. |
| 2010/0048597 A1 | 2/2010 | Beckwith et al. |
| 2010/0298312 A1 | 11/2010 | Kamenecka et al. |

FOREIGN PATENT DOCUMENTS

| | | |
|---|---|---|
| CA | 2093203 A1 | 10/1993 |
| JP | 62-223177 A | 10/1987 |
| JP | 06-087834 A | 3/1994 |

(Continued)

OTHER PUBLICATIONS

Beenken et al., Nature Review Drug Discovery, (2009), vol. 8, p. 235-253.*

(Continued)

*Primary Examiner* — Yong Chu
(74) *Attorney, Agent, or Firm* — Schwegman Lundberg & Woessner, P.A.

(57) ABSTRACT

The present invention provides novel substituted pyrimidinyl-amines that are useful as inhibitors of protein kinases, especially c-Jun N-terminal kinases (JNK) and pharmaceutical compositions thereof and methods of using the same for treating conditions responsive to the inhibition of the JNK pathway.

10 Claims, No Drawings

(56) References Cited

FOREIGN PATENT DOCUMENTS

| | | | |
|---|---|---|---|
| JP | 08-503970 A | 4/1996 |
| JP | 2001-500153 A | 1/2001 |
| JP | 2003-502406 A | 1/2003 |
| JP | 2003-525279 A | 8/2003 |
| JP | 2004-529140 A | 9/2004 |
| JP | 2004-534728 A | 11/2004 |
| JP | 2005-533827 A | 11/2005 |
| JP | 2006-508107 A | 3/2006 |
| JP | 2006-512314 A | 4/2006 |
| JP | 2006-514006 A | 4/2006 |
| JP | 2006-522768 A | 10/2006 |
| JP | 2007-500179 A | 1/2007 |
| JP | 2010-514689 A | 5/2010 |
| JP | 2010-520892 A | 6/2010 |
| WO | WO-95/09851 A1 | 4/1995 |
| WO | WO-97/19065 A1 | 5/1997 |
| WO | WO-01/64656 A1 | 9/2001 |
| WO | WO-2006/021458 A2 | 3/2006 |
| WO | WO-2006/044457 A1 | 4/2006 |
| WO | WO-2007/081690 A2 | 7/2007 |
| WO | WO-2007/089768 A2 | 8/2007 |
| WO | WO-2008/075151 A2 | 6/2008 |
| WO | WO-2008/090181 A1 | 7/2008 |
| WO | WO-2008/124085 A2 | 10/2008 |
| WO | WO-2009/017838 A2 | 2/2009 |
| WO | WO-2009/032861 A1 | 3/2009 |
| WO | WO 2009/103032 A1 | 8/2009 |
| WO | WO-2009/103652 A1 | 8/2009 |

OTHER PUBLICATIONS

"Canadian Application Serial No. 2,698,511, Office Action mailed Jul. 21, 2014", 3 pgs.
"Japanese Application Serial No. 2010-524122, Response filed Nov. 15, 2013 to Notice of Reason for Refusal mailed Jul. 23, 2013", (w/ English Translation of Claims), 49 pgs.
"U.S. Appl. No. 12/676,411, Notice of Allowance mailed Apr. 26, 2013", 8 pgs.
"European Application Serial No. 08829943.3, Examination Notification Art. 94(3) mailed Aug. 8, 2013", 3 pgs.
"International Application Serial No. PCT/US2008/075151, International Preliminary Report on Patentability dated Mar. 9, 2010", 6 pgs.
"International Application Serial No. PCT/US2008/075151, International Search Report mailed Nov. 26, 2008", 1 pg.
"International Application Serial No. PCT/US2008/075151, Written Opinion mailed Nov. 26, 2008", 5 pgs.
"Japanese Application Serial No. 2010-524122, Notice of Reason for Refusal mailed Jul. 23, 2013", (w/ English Translation), 17 pgs.
Hughes, T. V., et al., "4-Aryl-5-cyano-2-aminopyrimidines as VEGF-R2 inhibitors: *Synthesis and biological evaluation*", Bioorganic and Medicinal Chemistry Letters, 17(12), (Jun. 15, 2007), 3266-3270.
"Canadian Application Serial No. 2,698,511, Voluntary Amendment filed Sep. 9, 2013", 17 pgs.
"European Application Serial No. 8829943.3, Response filed Oct. 9, 2013 to Office Action mailed Aug. 8, 2013", 62 pgs.
"U.S. Appl. No. 12/676,411, Response filed Aug. 24, 2012 to Final Office Action mailed Jun. 6, 2012", 54 pgs.
"U.S. Appl. No. 12/676,411, Response filed Apr. 11, 2012 to Non Final Office Action mailed Jan. 11, 2012", 61 pgs.
"U.S. Appl. No. 12/676,411, Response filed Jul. 9, 2012 to Final Office Action mailed Jun. 6, 2012", 57 pgs.
"U.S. Appl. No. 12/676,411, Advisory Action mailed Jul. 17, 2012", 3 pgs.
"U.S. Appl. No. 12/676,411, Final Office Action mailed Jun. 6, 2012", 8 pgs.
"U.S. Appl. No. 12/676,411, Non Final Office Action mailed Jan. 11, 2012", 12 pgs.
"U.S. Appl. No. 12/676,411, Notice of Allowance mailed Oct. 2, 2012", 11 pgs.
"U.S. Appl. No. 12/676,411, Restriction Requirement mailed Nov. 4, 2011", 8 pgs.
"European Application Serial No. 08829943.3, Extended Search Report mailed Nov. 29, 2011", 8 pgs.
"European Application Serial No. 08829943.3, Office Action mailed Sep. 10, 2012", 4 pgs.
"European Application Serial No. 08829943.3, Response filed Jun. 25, 2012 to Extended Search Report mailed Nov. 29, 2011", 19 pgs.
"European Application Serial No. 8829943.3, Response filed Jan. 16, 2013 to Office Action mailed Sep. 10, 2012", 51 pgs.
Chu, Yong, "STN Preliminary 12676411", (Oct. 31, 2011), 4 pgs.
Rolf, Paul, et al., "Preparation of Substituted N-phenyl-4-aryl-2-pyrimidinamines as Mediator Inhibitors", Journal of Medicinal Chemistry 36, (Jan. 1, 1993), 2716-2725.
Zimmermann, J, et al., "Potent and selective inhibitors of the Abl-kinase: phenylamino-pyrimidine (PAP) derivatives", Bioorganic and Medicinal Chemistry Letters 7 (2), (1997), 187-192.
"U.S. Appl. No. 12/676,411, Response filed Dec. 1, 2011 to Restriction Requirement mailed Nov. 4, 2011", 15 pgs.
"Japanese Application Serial No. 2010-524122, Office Action mailed Mar. 18, 2014", (w/ English Translation), 7 pgs.
Van Der Walt, Joelle M., et al., "Fibroblast Growth Factor 20 Polymorphisms and Haplotypes Strongly Influence Risk of Parkinson Disease", American Journal Human Genetics, vol. 74, Issue 6, 1121-1127, (2004).
US 8,389,528, 03/2013, Kamenecka et al. (withdrawn)

* cited by examiner

US 9,018,205 B2

SUBSTITUTED PYRIMIDINYL-AMINES AS PROTEIN KINASE INHIBITORS

CLAIM OF PRIORITY

This application is a divisional of and claims the benefit of priority under 35 U.S.C. §120 to U.S. patent application Ser. No. 12/676,411, filed on Aug. 6, 2010, which claims the benefit of priority to national stage application under 35 U.S.C. §371 of PCT/US2008/075151, filed Sep. 3, 2008, and published as WO 2009/032861 A1 on Mar. 12, 2009, which claims priority to U.S. Provisional Application No. 60/969,849, filed Sep. 4, 2007, which applications and publication are incorporated by reference as if reproduced herein and made a part hereof in their entirety, and the benefit of priority of each of which is claimed herein.

FIELD OF THE INVENTION

The present invention relates to substituted pyrimidinyl-amines that are inhibitors of protein kinases (e.g., c-Jun N-terminal kinases (JNK)). The present invention also relates to pharmaceutical compositions comprising the inhibitors and methods of using the inhibitors.

BACKGROUND OF THE INVENTION

The c-jun-N-terminal Kinases (JNKs) are members of the mitogen activated protein (MAP) kinase family, a group of serine/threonine kinases that are intimately involved with many cell signaling pathways. As a member of the mitogen-activated protein kinase (MAPK) family, the c-Jun N-terminal kinases (JNKs) regulate, for example, the serine/threonine phosphorylation of several transcription factors when they are activated via upstream kinase signaling cascade in response to environmental stress. There are three genes (Jnk1[1], Jnk2[2,3], and Jnk3[4]) that encode for human JNK, and from these, ten splice variants have been described[5]. [See 1.) Derijard, B.; Hibi, M.; Wu, I. H.; Barrett, T.; Su, B.; Deng, T.; Karin, M.; Davis, R. J., JNK1: a protein kinase stimulated by UV light and Ha-Ras that binds and phosphorylates the c-Jun activation domain. *Cell* 1994, 76, (6), 1025-37; 2) Kallunki, T.; Su, B.; Tsigelny, I.; Sluss, H. K.; Derijard, B.; Moore, G.; Davis, R.; Karin, M., JNK2 contains a specificity-determining region responsible for efficient c-Jun binding and phosphorylation. *Genes Dev* 1994, 8, (24), 2996-3007; 3) Sluss, H. K.; Barrett, T.; Derijard, B.; Davis, R. J., Signal transduction by tumor necrosis factor mediated by JNK protein kinases. *Mol Cell Biol* 1994, 14, (12), 8376-84; 4) Mohit, A. A.; Martin, J. H.; Miller, C. A., p493; F12 kinase: a novel MAP kinase expressed in a subset of neurons in the human nervous system. *Neuron* 1995, 14, (1), 67-78; and 5) Gupta, S.; Barrett, T.; Whitmarsh, A. J.; Cavanagh, J.; Sluss, H. K.; Derijard, B.; Davis, R. J., Selective interaction of JNK protein kinase isoforms with transcription factors. *Embo J* 1996, 15, (11), 2760-70.]

It has been reported that there are four JNK1 splice variants, four JNK2 splice variants, and two JNK3 splice variants. JNK1 and JNK2 are ubiquitously expressed in mammalian tissue, whereas JNK3 has much more limited tissue expression being confined primarily to the nervous system with only low level expression in the heart and testis[4]. (See Mohit, A. A.; Martin, J. H.; Miller, C. A., p493; F12 kinase: a novel MAP kinase expressed in a subset of neurons in the human nervous system. *Neuron* 1995, 14, (1), 67-78).

JNKs are also typically referred to as stress-activated kinases due to their role in cell signaling and cell death pathways associated with stress activation. JNKs may be activated by a number of stress stimuli including cytokines (See Kimberly, W. T.; Zheng, J. B.; Town, T.; Flavell, R. A.; Selkoe, D. J., Physiological regulation of the beta-amyloid precursor protein signaling domain by c-Jun N-terminal kinase JNK3 during neuronal differentiation. *J Neurosci* 2005, 25, (23), 5533-43; and Larsen, C. M.; Dossing, M. G.; Papa, S.; Franzoso, G.; Billestrup, N.; Mandrup-Poulsen, T., Growth arrest- and DNA-damage-inducible 45beta gene inhibits c-Jun N-terminal kinase and extracellular signal-regulated kinase and decreases IL-1beta-induced apoptosis in insulin-producing INS-1E cells. *Diabetologia* 2006, 49, (5), 980-9), UV light (See Derijard, B.; Hibi, M.; Wu, I. H.; Barrett, T.; Su, B.; Deng, T.; Karin, M.; Davis, R. J., JNK1: a protein kinase stimulated by UV light and Ha-Ras that binds and phosphorylates the c-Jun activation domain. *Cell* 1994, 76, (6), 1025-37), hypoxia (See Yang, D. D.; Kuan, C. Y.; Whitmarsh, A. J.; Rincon, M.; Zheng, T. S.; Davis, R. J.; Rakic, P.; Flavell, R. A., Absence of excitotoxicity-induced apoptosis in the hippocampus of mice lacking the Jnk3 gene. *Nature* 1997, 389, (6653), 865-70; and Pirianov, G.; Brywe, K. G.; Mallard, C.; Edwards, A. D.; Flavell, R. A.; Hagberg, H.; Mehmet, H., Deletion of the c-Jun N-terminal kinase 3 gene protects neonatal mice against cerebral hypoxic-ischaemic injury. *J Cereb Blood Flow Metab* 2007, 27, (5), 1022-32), endoplasmic reticulum (ER) stress (including protein misfolding) (See Kerkela, R.; Grazette, L.; Yacobi, R.; Iliescu, C.; Patten, R.; Beahm, C.; Walters, B.; Shevtsov, S.; Pesant, S.; Clubb, F. J.; Rosenzweig, A.; Salomon, R. N.; Van Etten, R. A.; Alroy, J.; Durand, J. B.; Force, T., Cardiotoxicity of the cancer therapeutic agent imatinib mesylate. *Nat Med* 2006, 12, (8), 908-16; Nishitoh, H.; Matsuzawa, A.; Tobiume, K.; Saegusa, K.; Takeda, K.; Inoue, K.; Hori, S.; Kakizuka, A.; Ichijo, H., ASK1 is essential for endoplasmic reticulum stress-induced neuronal cell death triggered by expanded polyglutamine repeats. *Genes Dev* 2002, 16, (11), 1345-55; and Urano, F.; Wang, X.; Bertolotti, A.; Zhang, Y.; Chung, P.; Harding, H. P.; Ron, D., Coupling of stress in the ER to activation of JNK protein kinases by transmembrane protein kinase IRE1. *Science* 2000, 287, (5453), 664-6), growth factors, FAS ligand, and reactive oxygen species (See Luo, Y.; Umegaki, H.; Wang, X.; Abe, R.; Roth, G. S., Dopamine induces apoptosis through an oxidation-involved SAPK/JNK activation pathway. *J Biol Chem* 1998, 273, (6), 3756-64).

Once activated, the JNKs may phosphorylate many substrates including the transcription factors, c-jun (See Derijard, B.; Hibi, M.; Wu, I. H.; Barrett, T.; Su, B.; Deng, T.; Karin, M.; Davis, R. J., JNK1: a protein kinase stimulated by UV light and Ha-Ras that binds and phosphorylates the c-Jun activation domain. *Cell* 1994, 76, (6), 1025-37; Yang, D. D.; Kuan, C. Y.; Whitmarsh, A. J.; Rincon, M.; Zheng, T. S.; Davis, R. J.; Rakic, P.; Flavell, R. A., Absence of excitotoxicity-induced apoptosis in the hippocampus of mice lacking the Jnk3 gene. *Nature* 1997, 389, (6653), 865-70; Hibi, M.; Lin, A.; Smeal, T.; Minden, A.; Karin, M., Identification of an oncoprotein- and UV-responsive protein kinase that binds and potentiates the c-Jun activation domain. *Genes Dev* 1993, 7, (11), 2135-48; and Wilhelm, D.; van Dam, H.; Herr, I.; Baumann, B.; Herrlich, P.; Angel, P., Both ATF-2 and c-Jun are phosphorylated by stress-activated protein kinases in response to UV irradiation. *Immunobiology* 1995, 193, (2-4), 143-8, ATF2 (See Wilhelm, D.; van Dam, H.; Herr, I.; Baumann, B.; Herrlich, P.; Angel, P., Both ATF-2 and c-Jun are phosphorylated by stress-activated protein kinases in response to UV irradiation. *Immunobiology* 1995, 193, (2-4), 143-8; Hu, M. C.; Qiu, W. R.; Wang, Y. P., JNK1, JNK2 and JNK3 are p53 N-terminal serine 34 kinases. *Oncogene* 1997, 15, (19), 2277-87; and Livingstone, C.; Patel, G.; Jones, N., ATF-2 contains a phosphorylation-dependent transcriptional activation domain. *Embo J* 1995, 14, (8), 1785-97, Elk1, nuclear factor of activated T cells (NFAT, See Chow, C. W.; Rincon, M.; Cavanagh, J.; Dickens, M.; Davis, R. J., Nuclear accumulation of NFAT4 opposed by the JNK signal transduction pathway. *Science* 1997, 278, (5343), 1638-41), tumor suppressor p53 (See Hibi, M.; Lin, A.; Smeal, T.; Minden, A.; Karin, M., Identification of an oncoprotein- and UV-responsive protein kinase that binds and potentiates the c-Jun activation domain. *Genes Dev* 1993, 7, (11), 2135-48), mitogen-activated kinase activating domain (MADD, See Zhang, Y.; Thou, L.; Miller, C. A., A splicing variant of a death domain protein that is regulated by a mitogen-activated kinase is a substrate for c-Jun N-terminal kinase in the human central nervous system. *Proc Natl Acad Sci USA* 1998, 95, (5), 2586-91), Tau (See Ferrer, I., Stress kinases involved in tau phosphorylation in Alzheimer's disease, tauopathies and APP transgenic mice. *Neurotox Res* 2004, 6, (6), 469-75; and Puig, B.; Gomez-Isla, T.; Ribe, E.; Cuadrado, M.; Torrejon-Escribano, B.; Dalfo, E.; Ferrer, I., Expression of stress-activated kinases c-Jun N-terminal kinase (SAPK/JNK-P) and p38 kinase (p38-P), and tau hyperphosphorylation in neurites surrounding betaA plaques in APP Tg2576 mice. *Neuropathol Appl Neurobiol* 2004, 30, (5), 491-502), and amyloid β-precursor protein (APP, See Kimberly, W. T.; Zheng, J. B.; Town, T.; Flavell, R. A.; Selkoe, D. J., Physiological regulation of the beta-amyloid precursor protein signaling domain by c-Jun N-terminal kinase JNK3 during neuronal differentiation. *J Neurosci* 2005, 25, (23), 5533-43; and Hunot, S.; Vila, M.; Teismann, P.; Davis, R. J.; Hirsch, E. C.; Przedborski, S.; Rakic, P.; Flavell, R. A., JNK-mediated induction of cyclooxygenase 2 is required for neurodegeneration in a mouse model of Parkinson's disease. *Proc Natl Acad Sci USA* 2004, 101, (2), 665-70). It is more generally believed that phosphorylation of these substrates that contributes to many cell death pathways and is what has associated JNK with many diseases and provides the rationale for targeting JNK inhibition for the treatment of disease.

U.S. Pat. No. 6,949,544 describes inhibitors of c-Jun N-terminal kinases and other protein kinases, which are described by formulas A and B:

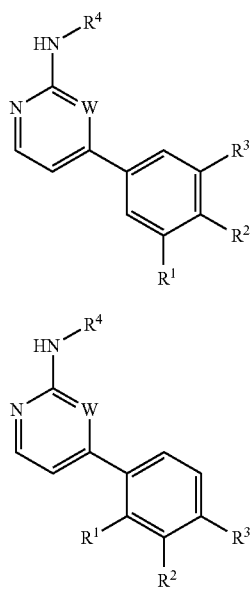

wherein W is N or CH, each of $R^1$-$R^3$ is a substituent (i.e., present and other than H), and $R^4$ is an aromatic ring attached directly or through a linker. Thus, US '544 describes substituted-(tri-substituted phenyl)-pyridyl/pyrimidyl-amines.

U.S. Pat. No. 7,129,242 describes inhibitors of the JNK pathway, which are described by formula C:

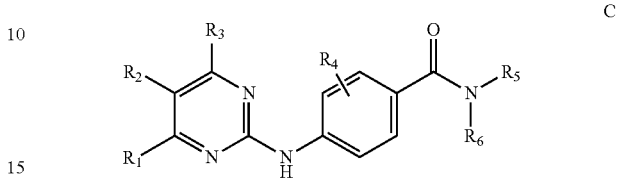

wherein $R_1$ is aryl or heteroaryl; $R_2$ is H; $R_3$ is H or lower alkyl; $R_4$ is H, halogen, hydroxyl, lower alkyl, and lower alkoxy; and, $R_5$ and $R_6$ are a variety of substituents.

In view of the above, it is highly desirable to find effective and highly selective inhibitors of protein kinases, particularly inhibitors of c-Jun N-terminal kinases. The present invention is directed to these and other important ends.

SUMMARY OF THE INVENTION

Accordingly, in an aspect, the present invention provides novel substituted pyrimidinyl-amines or pharmaceutically acceptable salts thereof that are inhibitors of protein kinases (e.g., c-Jun N-terminal kinases).

In another aspect, the present invention provides novel pharmaceutical compositions, comprising: a pharmaceutically acceptable carrier and a therapeutically effective amount of at least one of the compounds of the present invention or a pharmaceutically acceptable salt form thereof.

In another aspect, the present invention provides novel methods for treating a condition responsive to the inhibition of the JNK pathway, comprising: administering to a patient in need thereof a therapeutically effective amount of at least one of the compounds of the present invention or a pharmaceutically acceptable salt form thereof.

In another aspect, the present invention provides processes for preparing the novel compounds of the present invention.

In another aspect, the present invention provides novel compounds or pharmaceutically acceptable salts for use in therapy.

In another aspect, the present invention provides the use of novel compounds for the manufacture of a medicament for the treatment of a condition responsive to the inhibition of the JNK pathway.

These and other objects, which will become apparent during the following detailed description, have been achieved by the inventors' discovery that the presently claimed compounds or stereoisomers or pharmaceutically acceptable salt forms thereof are expected to be effective inhibitors of at least one JNK enzyme.

DETAILED DESCRIPTION OF THE INVENTION

All references cited herein are incorporated in their entireties herein by reference.

The present invention is generally directed to novel substituted pyrimidinyl-amines that are inhibitors of protein kinases, for example c-Jun N-terminal kinases (JNK) which is a member of the mitogen-activated protein (MAP) kinase family. Other protein kinases that compounds of the present have been shown to inhibit include GSKa and b, CLK1, JAK3, MAP3K9, IKK, Aurora, FMS, and Kit. The present invention is also generally directed to pharmaceutical compositions containing the substituted pyrimidinyl-amines and methods of their pharmaceutical use.

[1] In an embodiment, the present invention provides novel compounds of formula I or a stereoisomer or pharmaceutically acceptable salt thereof:

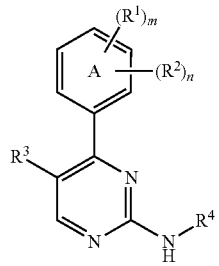

I wherein:

ring A is selected from phenyl (as shown), pyridyl, and pyrimidyl;

$R^1$ is independently selected from H, Cl, F, Br, I, $CF_3$, $OCF_3$, $C_{1-6}$ alkyl substituted with 0-2 $R^5$, $C_{2-6}$ alkenyl substituted with 0-2 $R^5$, $C_{2-6}$ alkynyl substituted with 0-2 $R^5$, $(CH_2)_pNO_2$, $(CH_2)_pCN$, $(CH_2)_pOR$, $(CH_2)_pNR_2$, $(CH_2)_pCOR$, $(CH_2)_pOCOR$, $(CH_2)_pCO_2R$, $(CH_2)_pCONR_2$, $(CH_2)_pOCONR_2$, $(CH_2)_pNRCOR$, $(CH_2)_pNRCO_2R$, $(CH_2)_pNRCONR_2$, $(CH_2)_pC(=NH)NH_2$, $(CH_2)_pSO_2R$, $(CH_2)_pSO_2NR_2$, $(CH_2)_pNRSO_2R$, $(CH_2)_pNRSO_2NR_2$, $(CH_2)_p$-3-10 membered carbocycle substituted with 0-2 $R^5$, and a $(CH_2)_p$-4-10 membered heterocycle substituted with 0-2 $R^5$ and consisting of: carbon atoms and 1-4 heteroatoms selected from O, $S(O)_q$, and N;

alternatively, when two $R^1$'s are present on adjacent carbon atoms, they combine to form a group selected from —OCH$_2$O— and —OCH$_2$CH$_2$O—;

$R^2$ is independently selected from H, Cl, F, Br, I, $CF_3$, $OCF_3$, $C_{1-4}$ alkyl, $C_{2-4}$ alkenyl, $C_{2-4}$ alkynyl, $NO_2$, —CN, $OR^a$, $NR^a_2$, $COR^a$, $CO_2R^a$, and $CONR^a_2$;

$R^3$ is selected from H, $CH_3$, $CH_2CH_3$, Cl, F, Br, and I;

$R^4$ is selected from a 3-10 membered carbocycle substituted with 0-2 $R^{4a}$ and a 5-10 membered heterocycle substituted with 0-2 $R^{4a}$ and consisting of: carbon atoms and 1-4 heteroatoms selected from O, $S(O)_q$, and N;

$R^{4a}$ is selected from H, =O, Cl, F, Br, I, $CF_3$, $OCF_3$, $C_{1-6}$ alkyl substituted with 0-3 $R^5$, $C_{2-6}$ alkenyl substituted with 0-3 $R^5$, $C_{2-6}$ alkynyl substituted with 0-3 $R^5$, (CH$_4$NO$_2$, $(CH_2)_pCN$, $(CH_2)_pOR$, $(CH_2)_pNR_2$, $(CH_2)_pCOR$, $(CH_2)_pO$-COR, $(CH_2)_pCO_2R$, $(CH_2)_pCONR_2$, $(CH_2)_pOCONR_2$, $(CH_2)_pNRCOR$, $(CH_2)_pNRCO_2R$, $(CH_2)_pNRCONR_2$, $(CH_2)_pC(=NH)NH_2$, $(CH_2)_pSO_2R$, (CH$_4$SO$_2$NR$_2$, $(CH_2)_pNRSO_2R$, $(CH_2)_pNRSO_2NR_2$, $CH(CF_3)NH_2$, and $(CH_2)_p$-5-6 membered heterocycle substituted with 0-3 $R^{5a}$ and consisting of: carbon atoms and 1-4 heteroatoms selected from O, $S(O)_q$, and N;

R is independently selected from H, $C_{1-6}$ alkyl substituted with 0-2 $R^5$, $C_{2-6}$ alkenyl substituted with 0-2 $R^5$, $C_{2-6}$ alkynyl substituted with 0-2 $R^5$, 3-10 membered carbocycle substituted with 0-2 $R^5$, and a 5-10 membered heterocycle substituted with 0-2 $R^5$ and consisting of: carbon atoms and 1-4 heteroatoms selected from O, $S(O)_q$, and N;

optionally, $NR_2$ forms a 5-8 membered cyclic amine substituted with 0-2 $R^5$;

$R^5$ is selected from =O, Cl, F, Br, I, $CF_3$, $OCF_3$, $C_{1-4}$ alkyl, $C_{2-4}$ alkenyl, $C_{2-4}$ alkynyl, $NO_2$, —CN, $OR^a$, $NR^a_2$, $COR^a$, $CO_2R^a$, $CONR^a_2$, $NR^aCOR^a$, $NR^aCO_2R^a$, $NR^aCONR^a_2$, $C(=NH)NH_2$, $SO_2R^a$, $SO_2NR^a_2$, $NR^aSO_2R^a$, $NR^aSO_2NR^a_2$, $(CH_2)_p$-3-10 membered carbocycle substituted with 0-2 $R^b$, and a $(CH_2)_p$-5-10 membered heterocycle substituted with 0-2 $R^b$ and consisting of: carbon atoms and 1-4 heteroatoms selected from O, $S(O)_q$, and N;

$R^{5a}$ is selected from =O, Cl, F, Br, I, $CF_3$, $OCF_3$, $C_{1-4}$ alkyl, $C_{2-4}$ alkenyl, $C_{2-4}$ alkynyl, $NO_2$, —CN, $(CH_2)_pOR^a$, $NR^a_2$, $COR^a$, $CO_2R^a$, $CONR^a_2$, $NR^aCOR^a$, $NR^aCO_2R^a$, $NR^aCONR^a_2$, $C(=NH)NH_2$, $SO_2R^a$, $SO_2NR^a_2$, $NR^aSO_2R^a$, $NR^aSO_2NR^a_2$, $(CH_2)_p$-3-10 membered carbocycle substituted with 0-2 $R^b$, and a $(CH_2)_p$-5-10 membered heterocycle substituted with 0-2 $R^b$ and consisting of: carbon atoms and 1-4 heteroatoms selected from O, $S(O)_q$, and N;

$R^a$ is independently selected from H, $C_{1-4}$ alkyl, $C_{3-6}$ cycloalkyl, $CH_2$—$C_{3-6}$ cycloalkyl, phenyl, and benzyl;

optionally, $NR^a_2$ forms a 5-6 membered cyclic amine;

$R^b$ is independently selected from H, Cl, F, Br, I, $CF_3$, $OCF_3$, $C_{1-4}$ alkyl, $C_{2-4}$ alkenyl, $C_{2-4}$ alkynyl, $NO_2$, —CN, $OR^a$, $NR^a_2$, $COR^a$, $CO_2R^a$, and $CONR^a_2$;

p is selected from 0, 1, 2, 3, and 4;

m+n is selected from 0, 1, and 2;

provided that:

a. when $R^4$ is phenyl and $R^{4a}$ is a para-substituted C(O)$NR_2$, then a second $R^{4a}$ is present and is other than halo, alkyl, OH, and O-alkyl; and b. when $R^4$ is phenyl, $R^{4a}$ is C(O)R, and R is a heterocycle attached via a N, then a second $R^{4a}$ is present and is other than halo, alkyl, OH, and O-alkyl.

[2] In another embodiment, the present invention provides novel compounds of formula Ia or a stereoisomer or pharmaceutically acceptable salt thereof:

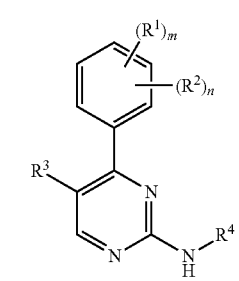

Ia wherein:

$R^1$ is independently selected from H, Cl, F, Br, I, $CF_3$, $OCF_3$, $C_{1-6}$ alkyl substituted with 0-2 $R^5$, $(CH_2)_pCN$, $(CH_2)_pOR$, $(CH_2)_pNR_2$, $(CH_2)_pOCOR$, $(CH_2)_pCO_2R$, $(CH_2)_pCONR_2$, $(CH_2)_pOCONR_2$, $(CH_2)_pNRCOR$, $(CH_2)_pNRCO_2R$, $(CH_2)_pSO_2R$, $(CH_2)_pSO_2NR_2$, $(CH_2)_pNRSO_2R$, and a $(CH_2)_p$-5-6 membered heterocycle substituted with 0-2 $R^5$ and consisting of: carbon atoms and 1-4 heteroatoms selected from O, $S(O)_q$, and N;

$R^2$ is independently selected from H, Cl, F, Br, I, $CF_3$, $OCF_3$, $C_{1-4}$ alkyl, —CN, $OR^a$, $NR^a_2$, $COR^a$, $CO_2R^a$, and $CONR^a_2$;

$R^3$ is selected from H and F;

$R^4$ is selected from a phenyl substituted with 0-2 $R^{4a}$ and a 5-6 membered heteroaryl substituted with 0-2 $R^{4a}$ and consisting of: carbon atoms and 1-4 heteroatoms selected from O, $S(O)_q$, and N;

$R^{4a}$ is selected from H, =O, Cl, F, Br, I, CF$_3$, OCF$_3$, C$_{1-6}$ alkyl substituted with 0-3 R$^5$, (CH$_2$)$_p$CN, (CH$_2$)$_p$OR, (CH$_2$)$_p$NR$_2$, (CH$_2$)$_p$CONR$_2$, CH$_2$)$_p$NRCOR, (CH$_2$)$_p$SO$_2$R, (CH$_2$)$_p$SO$_2$NR$_2$, (CH$_2$)$_p$NRSO$_2$R, CH(CF$_3$)NH$_2$, and (CH$_2$)$_p$-5-6 membered heterocycle substituted with 0-3 R$^{5a}$ and consisting of: carbon atoms and 1-4 heteroatoms selected from O, S(O)$_q$, and N;

R is independently selected from H, C$_{1-6}$ alkyl substituted with 0-2 R$^5$, 3-6 membered carbocycle substituted with 0-2 R$^5$, and a 5-6 membered heterocycle substituted with 0-2 R$^5$ and consisting of: carbon atoms and 1-4 heteroatoms selected from O, S(O)$_q$, and N;

optionally, NR$_2$ forms a 5-6 membered cyclic amine substituted with 0-2 R$^5$;

R$^5$ is selected from =O, Cl, F, Br, I, CF$_3$, OCF$_3$, C$_{1-4}$ alkyl, —CN, OR$^a$, NR$^a{}_2$, CONR$^a{}_2$, NR$^a$COR$^a$, SO$_2$R$^a$, SO$_2$NR$^a{}_2$, NR$^a$SO$_2$R$^a$, (CH$_2$)$_p$-3-6 membered carbocycle substituted with 0-2 R$^b$, and a (CH$_2$)$_p$-5-6 membered heterocycle substituted with 0-2 R$^b$ and consisting of: carbon atoms and 1-4 heteroatoms selected from O, S(O)$_q$, and N;

R$^{5a}$ is selected from =O, Cl, F, Br, I, CF$_3$, OCF$_3$, C$_{1-4}$ alkyl, —CN, (CH$_2$)$_p$OR$^a$, NR$^a{}_2$, COR$^a$, CO$_2$R$^a$, CONR$^a{}_2$, NR$^a$COR$^a$, SO$_2$R$^a$, SO$_2$NR$^a{}_2$, NR$^a$SO$_2$R$^a$, NR$^a$SO$_2$NR$^a{}_2$, (CH$_2$)$_p$-3-6 membered carbocycle substituted with 0-2 R$^b$, and a (CH$_2$)$_p$-5-6 membered heterocycle substituted with 0-2 R$^b$ and consisting of: carbon atoms and 1-4 heteroatoms selected from O, S(O)$_q$, and N;

R$^a$ is independently selected from H, C$_{1-4}$ alkyl, C$_{3-6}$ cycloalkyl, CH$_2$—C$_{3-6}$ cycloalkyl, phenyl, and benzyl;

optionally, NR$^a{}_2$ forms a 5-6 membered cyclic amine;

R$^b$ is independently selected from H, Cl, F, Br, I, CF$_3$, OCF$_3$, C$_{1-4}$ alkyl, —CN, OR$^a$, NR$^a{}_2$, COR$^a$, CO$_2$R$^a$, and CONR$^a{}_2$;

p is selected from 0, 1, and 2;

m+n is selected from 0, 1, and 2;

provided that:

c. when R$^4$ is phenyl and R$^{4a}$ is a para-substituted C(O)NR$_2$, then a second R$^{4a}$ is present and is other than halo, alkyl, OH, and O-alkyl; and d. when R$^4$ is phenyl, R$^{4a}$ is C(O)R, and R is a heterocycle attached via a N, then a second R$^{4a}$ is present and is other than halo, alkyl, OH, and O-alkyl.

[3] In another embodiment, the present invention provides novel compounds of formula Ia or a stereoisomer or pharmaceutically acceptable salt thereof:

wherein:

R$^3$ is H; and,

R$^4$ is phenyl substituted with 0-2 R$^{4a}$.

In other embodiments, the present invention is directed to compounds or pharmaceutically acceptable salts thereof of formula Ib:

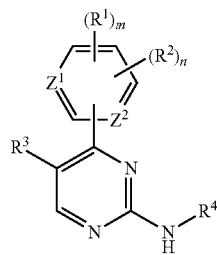

Ib wherein:

Z$^1$ and Z$^2$ are each independently CH or N;

each R$^1$ is independently Cl, F, Br, I, CF$_3$, OCF$_3$, C$_{1-6}$ alkyl substituted with 0-2 R$^5$, C$_{2-6}$alkenyl substituted with 0-2 R$^5$, C$_{2-6}$alkynyl substituted with 0-2 R$^5$, (CH$_2$)$_p$NO$_2$, (CH$_2$)$_p$CN, (CH$_2$)$_p$OR, (CH$_2$)$_p$N(R)$_2$, (CH$_2$)$_p$COR, (CH$_2$)$_p$OCOR, (CH$_2$)$_p$CO$_2$R, (CH$_2$)$_p$CON(R)$_2$, (CH$_2$)$_p$OCON(R)$_2$, (CH$_2$)$_p$NRCOR, (CH$_2$)$_p$NRCO$_2$R, (CH$_2$)$_p$NRCON(R)$_2$, (CH$_2$)$_p$C(=NH)NH$_2$, (CH$_2$)$_p$SOR, (CH$_2$)$_p$SO$_2$R, (CH$_2$)$_p$SO$_2$N(R)$_2$, (CH$_2$)$_p$NRSO$_2$R, (CH$_2$)$_p$NRSO$_2$N(R)$_2$, (CH$_2$)$_p$-(3- to 10-membered carbocyclic ring substituted with 0-2 R$^5$), or (CH$_2$)$_p$-(4- to 10-membered heterocyclic ring having 1 to 4 heteroatom ring members selected from O, S(O)$_q$, and N), wherein the heterocyclic ring is substituted with 0-2 R$^5$, or two of R$^1$ that are attached to adjacent ring carbon atoms are taken together with the ring atoms through which they are connected to form a 5- to 6-membered heterocycloalkyl having 1 or 2 oxygen ring heteroatoms;

each R$^2$ is independently Cl, F, Br, I, CF$_3$, OCF$_3$, C$_{1-4}$alkyl, C$_{2-4}$alkenyl, C$_{2-4}$alkynyl, NO$_2$, —CN, OR$^a$, N(R$^a$)$_2$, COR$^a$, CO$_2$R$^a$, or CON(R$^a$)$_2$; or R$^1$ and R$^2$ that are attached to adjacent ring carbon atoms are taken together with the ring atoms through which they are connected to form a 5- to 6-membered heterocycloalkyl having 1 or 2 oxygen ring members;

R$^3$ is H, CH$_3$, CH$_2$CH$_3$, cyano, Cl, F, Br, or I;

R$^4$ is 3- to 10-membered carbocyclic ring substituted with 0-2 R$^{4a}$ or 5- to 10-membered heterocyclic ring having 1 to 4 heteroatom ring members selected from O, S(O)$_q$, and N, wherein the heterocyclic ring is substituted with 0-2 R$^{4a}$;

each R$^{4a}$ is independently =O, Cl, F, Br, I, CF$_3$, OCF$_3$, C$_{1-6}$alkyl substituted with 0-3 R$^5$, C$_{2-6}$alkenyl substituted with 0-3 R$^5$, C$_{2-6}$alkynyl substituted with 0-3 R$^5$, (CH$_2$)$_p$NO$_2$, (CH$_2$)$_p$CN, (CH$_2$)$_p$OR, (CH$_2$)$_p$N(R)$_2$, (CH$_2$)$_p$COR, (CH$_2$)$_p$OCOR, (CH$_2$)$_p$CO$_2$R, (CH$_2$)$_p$CON(R)$_2$, (CH$_2$)$_p$OCON(R)$_2$, (CH$_2$)$_p$NRCOR, (CH$_2$)$_p$NRCO$_2$R, (CH$_2$)$_p$NRCON(R)$_2$, (CH$_2$)$_p$C(=NH)NH$_2$, (CH$_2$)$_p$SO$_2$R, (CH$_2$)$_p$SO$_2$N(R)$_2$, (CH$_2$)$_p$NRSO$_2$R, (CH$_2$)$_p$NRSO$_2$N(R)$_2$, CH(CF$_3$)NH$_2$, or (CH$_2$)$_p$-(5- to 6-membered heterocyclic ring) having 1 to 4 heteroatom ring members selected from O, S(O)$_q$, and N), wherein the heterocyclic ring is substituted with 0-3 R$^{5a}$;

each R is independently H, C$_{1-6}$alkyl substituted with 0-2 R$^5$, C$_{2-6}$alkenyl substituted with 0-2 R$^5$, C$_{2-6}$alkynyl substituted with 0-2 R$^5$, 3- to 10-membered carbocyclic ring substituted with 0-2 R$^5$, or 5- to 10-membered heterocyclic ring having 1 to 4 heteroatom ring members selected from O, S(O)$_q$, and N, wherein the heterocyclic ring is substituted with 0-2 R$^5$; or two R attached to the same N atom are taken together with the nitrogen atom to which they are attached to form a 5- to 8-membered heterocyloalkyl substituted with 0-2 R$^5$ each R$^5$ is independently =O, Cl, F, Br, I, CF$_3$, OCF$_3$, C$_{1-4}$alkyl, C$_{2-4}$alkenyl, C$_{2-4}$alkynyl, NO$_2$, —CN, OR$^a$, N(R$^a$)$_2$, COR$^a$, CO$_2$R$^a$, CON(R$^a$)$_2$, NR$^a$COR$^a$, NR$^a$CO$_2$R$^a$, NR$^a$CON(R$^a$)$_2$, C(=NH)NH$_2$, SO$_2$R$^a$, SO$_2$N(R$^a$)$_2$, NR$^a$SO$_2$R$^a$, NR$^a$SO$_2$N(R$^a$)$_2$, (CH$_2$)$_p$— (3- to 10-membered carbocyclic ring substituted with 0-2 R$^b$), or (CH$_2$)$_p$-(5- to 10-membered heterocyclic ring having 1 to 4 heteroatom ring members selected from O, S(O)$_q$, and N), wherein the heterocyclic ring is substituted with substituted with 0-2 R$^b$; or two R$^5$ taken together with a carbon atom to which they are both connected form a 1,3-dioxolane ring wherein the two oxygen ring atoms are attached to the connecting carbon atom;

R$^{5a}$ is selected from =O, Cl, F, Br, I, CF$_3$, OCF$_3$, C$_{1-4}$alkyl, C$_{2-4}$alkenyl, C$_{2-4}$alkynyl, NO$_2$, —CN, (CH$_2$)$_p$OR$^a$, N(R$^a$)$_2$, COR$^a$, CO$_2$R$^a$, CON(R$^a$)$_2$, NR$^a$COR$^a$, $NR^aCO_2R^a$, $NR^aCON(R^a)_2$, $C(=NH)NH_2$, $SO_2R^a$, $SO_2N(R^a)_2$, $NR^aSO_2R^a$, $NR^aSO_2N(R^a)_2$, $(CH_2)_p$-(3- to 10-membered carbocyclic ring substituted with 0-2 $R^b$, or $(CH_2)_p$-(5- to 10-membered heterocyclic ring having 1 to 4 heteroatom ring members selected from O, $S(O)_q$, and N), wherein the heterocyclic ring is substituted with 0-2 $R^b$;

each $R^a$ is independently H, $C_{1-4}$alkyl, $C_{3-6}$ cycloalkyl, $CH_2$—$C_{3-6}$ cycloalkyl, phenyl, or benzyl; or two $R^a$ attached to the same N atom are taken together with the nitrogen atom to which they are attached to form a 5- to 8-membered heterocycloalkyl;

$R^b$ is H, Cl, F, Br, I, $CF_3$, $OCF_3$, $C_{1-4}$alkyl optionally substituted with $OR^a$, $C_{2-4}$alkenyl, $C_{2-4}$alkynyl, $NO_2$, —CN, $OR^a$, $N(R^a)_2$, $COR^a$, $CO_2R^a$, or $CON(R^a)_2$;

p is 0, 1, 2, 3, or 4; and m and n are each independently the integer 0, 1, or 2, provided that the sum of m+n is 0, 1, or 2.

In certain preferred embodiments, the invention is directed to compounds or pharmaceutically acceptable salts thereof of formula Ib:

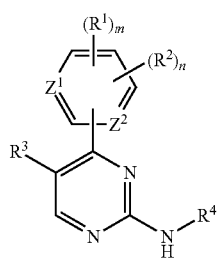

Ib wherein:

$Z^1$ and $Z^2$ are each independently CH or N;

each $R^1$ is independently Cl, F, Br, I, $CF_3$, $OCF_3$, $C_{1-6}$alkyl substituted with 0-2 $R^5$, $C_{2-6}$alkenyl substituted with 0-2 $R^5$, $C_{2-6}$alkynyl substituted with 0-2 $R^5$, $(CH_2)_pNO_2$, $(CH_2)_pCN$, $(CH_2)_pOR$, $(CH_2)_pN(R)_2$, $(CH_2)_pCOR$, $(CH_2)_pOCOR$, $(CH_2)_pCO_2R$, $(CH_2)_pCON(R)_2$, $(CH_2)_pOCON(R)_2$, $(CH_2)_pNRCOR$, $(CH_2)_pNRCO_2R$, $(CH_2)_pNRCON(R)_2$, $(CH_2)_pC(=NH)NH_2$, $(CH_2)_pSOR$, $(CH_2)_pSO_2R$, $(CH_2)_pSO_2N(R)_2$, $(CH_2)_pNRSO_2R$, $(CH_2)_pNRSO_2N(R)_2$, $(CH_2)_p$-(3- to 10-membered carbocyclic ring substituted with 0-2 $R^5$), or $(CH_2)_p$-(4- to 10-membered heterocyclic ring having 1 to 4 heteroatom ring members selected from O, $S(O)_q$, and N), wherein the heterocyclic ring is substituted with 0-2 $R^5$, or two of $R^1$ that are attached to adjacent ring carbon atoms are taken together with the ring atoms through which they are connected to form a 5- to 6-membered heterocycloalkyl having 1 or 2 oxygen ring heteroatoms;

each $R^2$ is independently Cl, F, Br, I, $CF_3$, $OCF_3$, $C_{1-4}$alkyl, $C_{2-4}$alkenyl, $C_{2-4}$alkynyl, $NO_2$, —CN, $OR^a$, $N(R^a)_2$, $COR^a$, $CO_2R^a$, or $CON(R^a)_2$; or $R^1$ and $R^2$ that are attached to adjacent ring carbon atoms are taken together with the ring atoms through which they are connected to form a 5- to 6-membered heterocycloalkyl having 1 or 2 oxygen ring members;

$R^3$ is H, $CH_3$, $CH_2CH_3$, cyano, Cl, F, Br, or I;

$R^4$ is 3- to 10-membered carbocyclic ring substituted with 0-2 $R^{4a}$ or 5- to 10-membered heterocyclic ring having 1 to 4 heteroatom ring members selected from O, $S(O)_q$, and N, wherein the heterocyclic ring is substituted with 0-2 $R^{4a}$;

each $R^{4a}$ is independently =O, Cl, F, Br, I, $CF_3$, $OCF_3$, $C_{1-6}$alkyl substituted with 0-3 $R^5$, $C_{2-6}$alkenyl substituted with 0-3 $R^5$, $C_{2-6}$alkynyl substituted with 0-3 $R^5$, $(CH_2)_pNO_2$, $(CH_2)_pCN$, $(CH_2)_pOR$, $(CH_2)_pN(R)_2$, $(CH_2)_pCOR$, $(CH_2)_pOCOR$, $(CH_2)_pCO_2R$, $(CH_2)_pCON(R)_2$, $(CH_2)_pOCON(R)_2$, $(CH_2)_pNRCOR$, $(CH_2)_pNRCO_2R$, $(CH_2)_pNRCON(R)_2$, $(CH_2)_pC(=NH)NH_2$, $(CH_2)_pSO_2R$, $(CH_2)_pSO_2N(R)_2$, $(CH_2)_pNRSO_2R$, $(CH_2)_pNRSO_2N(R)_2$, $CH(CF_3)NH_2$, or $(CH_2)_p$-(5- to 6-membered heterocyclic ring) having 1 to 4 heteroatom ring members selected from O, $S(O)_q$, and N), wherein the heterocyclic ring is substituted with 0-3 $R^{5a}$;

each R is independently H, $C_{1-6}$alkyl substituted with 0-2 $R^5$, $C_{2-6}$alkenyl substituted with 0-2 $R^5$, $C_{2-6}$alkynyl substituted with 0-2 $R^5$, 3- to 10-membered carbocyclic ring substituted with 0-2 $R^5$, or 5- to 10-membered heterocyclic ring having 1 to 4 heteroatom ring members selected from O, $S(O)_q$, and N, wherein the heterocyclic ring is substituted with 0-2 $R^5$; or two R attached to the same N atom are taken together with the nitrogen atom to which they are attached to form a 5- to 8-membered heterocyloalkyl substituted with 0-2 $R^5$ each $R^5$ is independently =O, Cl, F, Br, I, $CF_3$, $OCF_3$, $C_{1-4}$alkyl, $C_{2-4}$alkenyl, $C_{2-4}$alkynyl, $NO_2$, —CN, $OR^a$, $N(R^a)_2$, $COR^a$, $CO_2R^a$, $CON(R^a)_2$, $NR^aCOR^a$, $NR^aCO_2R^a$, $NR^aCON(R^a)_2$, $C(=NH)NH_2$, $SO_2R^a$, $SO_2N(R^a)_2$, $NR^aSO_2R^a$, $NR^aSO_2N(R^a)_2$, $(CH_2)_p$— (3- to 10-membered carbocyclic ring substituted with 0-2 $R^b$), or $(CH_2)_p$-(5- to 10-membered heterocyclic ring having 1 to 4 heteroatom ring members selected from O, $S(O)_q$, and N), wherein the heterocyclic ring is substituted with substituted with 0-2 $R^b$; or two $R^5$ taken together with a carbon atom to which they are both connected form a 1,3-dioxolane ring wherein the two oxygen ring atoms are attached to the connecting carbon atom;

$R^{5a}$ is selected from =O, Cl, F, Br, I, $CF_3$, $OCF_3$, $C_{1-4}$alkyl, $C_{2-4}$alkenyl, $C_{2-4}$alkynyl, $NO_2$, —CN, $(CH_2)_pOR^a$, $N(R^a)_2$, $COR^a$, $CO_2R^a$, $CON(R^a)_2$, $NR^aCOR^a$, $NR^aCO_2R^a$, $NR^aCON(R^a)_2$, $C(=NH)NH_2$, $SO_2R^a$, $SO_2N(R^a)_2$, $NR^aSO_2R^a$, $NR^aSO_2N(R^a)_2$, $(CH_2)_p$-(3- to 10-membered carbocyclic ring substituted with 0-2 $R^b$, or $(CH_2)$— (5- to 10-membered heterocyclic ring having 1 to 4 heteroatom ring members selected from O, $S(O)_q$, and N), wherein the heterocyclic ring is substituted with 0-2 $R^b$;

each $R^a$ is independently H, cycloalkyl, $CH_2$—$C_{3-5}$cycloalkyl, phenyl, or benzyl; or two $R^a$ attached to the same N atom are taken together with the nitrogen atom to which they are attached to form a 5- to 8-membered heterocycloalkyl;

$R^b$ is H, Cl, F, Br, I, $CF_3$, $OCF_3$, $C_{1-4}$alkyl optionally substituted with $OR^a$, $C_{2-4}$alkenyl, $C_{2-4}$alkynyl, $NO_2$, —CN, $OR^a$, $N(R^a)_2$, $COR^a$, $CO_2R^a$, or $CON(R^a)_2$;

p is 0, 1, 2, 3, or 4; and m and n are each independently the integer 0, 1, or 2, provided that the sum of m+n is 0, 1, or 2;

with the provisos that:

(1) when $R^4$ is:

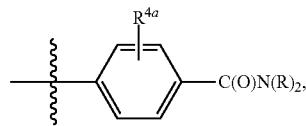

then $R^{4a}$ is other than =O, halo, $C_{1-6}$alkyl, OH, or O—$C_{1-6}$alkyl;

(2) when $R^4$ is:

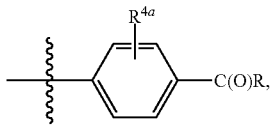

wherein R is a heterocyclic ring attached through a nitrogen ring atom; then $R^{4a}$ is other than halo, alkyl, OH, or O-alkyl.

(3) when $R^4$ is phenyl and at least one of $R^{4a}$ is $(CH_2)_p$-(5- to 6-membered heterocyclic ring wherein p is 0, 1, or 2, then the heterocyclic ring has 3 or 4 heteroatom ring members;

(4) when $R^4$ is phenyl and at least one of $R^{4a}$ is $(CH_2)_p$-(5- to 6-membered heterocyclic ring having one or two heteroatom ring members, then p is 3 or 4, (5) when $R^4$ is phenyl and is substituted with only one $R^{4a}$, then $R^{4a}$ is =O, Br, I, $CF_3$, $OCF_3$, $C_{1-6}$alkyl substituted with 0-3 $R^5$, $C_{2-6}$alkenyl substituted with 0-3 $R^5$, $C_{2-6}$alkynyl substituted with 0-3 $R^5$, $(CH_2)_pNO_2$, $(CH_2)_pOCOR$, $(CH_2)_pOCON(R)_2$, $(CH_2)_pNRCON(R)_2$, $(CH_2)_pC(=NH)NH_2$, $(CH_2)_pNRSO_2N(R)_2$, $CH(CF_3)NH_2$, or $(CH_2)_p$-(5- to 6-membered heterocyclic ring; and (6) the compound of formula I or pharmaceutically acceptable salt thereof is other than:
N-[3-({4-[4-(acetylamino)phenyl]pyrimidin-2-yl}amino) cyclohexyl]-2,6-dichlorobenzamide;
N-[4-(2-{[4-(1,4-dioxa-8-azaspiro[4.5]dec-8-yl)phenyl] amino}pyrimidin-4-yl)phenyl]acetamide;
N-{4-[2-(1H-indazol-6-ylamino)-5-methylpyrimidin-4-yl] phenyl}acetamide;
N-{4-[2-(1H-indol-5-ylamino)-5-methylpyrimidin-4-yl] phenyl}acetamide;
N-{4-[2-(1H-indazol-5-ylamino)-5-methylpyrimidin-4-yl] phenyl}acetamide;
'N-[6-({4-[4-(acetylamino)phenyl]pyrimidin-2-yl}amino) pyridin-2-yl]-2,6-dichlorobenzamide
'N-[6-({4-[4-(acetylamino)phenyl]pyrimidin-2-yl}amino) pyrimidin-4-yl]-2,6-dichlorobenzamide;
N-(4-{2-[(6-aminopyridin-2-yl)amino]pyrimidin-4-yl}phenyl)acetamide;
N-(4-{2-[(6-aminopyrimidin-4-yl)amino]pyrimidin-4-yl}phenyl)acetamide;
(R)—N-(4-(2-(1,2,3,4-tetrahydroquinolin-6-ylamino)pyrimidin-4-yl)phenyl) pyrrolidine-2-carboxamide;
(R)—N-(4-(2-(6-morpholinopyridin-3-ylamino)pyrimidin-4-yl)phenyl)pyrrolidine-2-carboxamide;
N-{4-[2-(1H-benzimidazol-6-ylamino)-5-methylpyrimidin-4-yl]phenyl}acetamide;
ethyl 4-({4-[(acetylamino)phenyl]pyrimidin-2-yl}aminopiperidine-1-carboxylate;
1,1-dimethylethyl 4-({4-[4-(acetylamino)phenyl]pyrimidin-2-yl}amino)piperidine-1-carboxylate;
N-{4-[2-(piperidin-4-ylamino)pyrimidin-4-yl] phenyl}acetamide; or
N-{4-[2-({1-[(2,6-dichlorophenyl)carbonyl]piperidin-4-yl}amino)pyrimidin-4-yl]phenyl}acetamide.

In other preferred embodiments of the present invention, the compounds of formula Ib are selected from the group consisting of Examples 1, 4-25, 27-43, 45-47, 49-55, 57, 59, 72-77, 79-85, 89-94, 96, 98-101, 103, 105-119, 121, 122, 125-174, and 176-337.

In still other preferred embodiments of the present invention, the compounds are selected from the group consisting of Examples 2, 3, 26, 44, 48, 56, 58, 60, 61, 78, 86, 87, 88, 95, 97, 102, 104, 120, 123, 124, and 175.

In certain preferred embodiments, at least one of $Z^1$ and $Z^2$ is CH. More preferably, $Z^1$ and $Z^2$ are each CH.

To the extent that there is any overlap or repetition within the various substituents enumerated in the $R^1$ or any other group, any substituent is intended to be covered only once.

In certain embodiments of the present invention, each $R^1$ is independently Cl, F, Br, I, $CF_3$, $OCF_3$, $C_{1-6}$alkyl substituted with 0-2 $R^5$, $C_{2-6}$alkenyl substituted with 0-2 $R^5$, $C_{2-6}$alkynyl substituted with 0-2 $R^5$, $(CH_2)_pNO_2$, $(CH_2)_pCN$, $(CH_2)_pOR$, $(CH_2)_pN(R)_2$, $(CH_2)_pCOR$, $(CH_2)_pOCOR$, $(CH_2)_pCO_2R$, $(CH_2)_pCON(R)_2$, $(CH_2)_pOCON(R)_2$, $(CH_2)_pNRCOR$, $(CH_2)_pNRCO_2R$, $(CH_2)_pNRCON(R)_2$, $(CH_2)_pC(=NH)NH_2$, $(CH_2)_pSOR$, $(CH_2)_pSO_2R$, $(CH_2)_pSO_2N(R)_2$, $(CH_2)_pNRSO_2R$, $(CH_2)_pNRSO_2N(R)_2$, $(CH_2)_p$-(3- to 10-membered carbocyclic ring substituted with 0-2 $R^5$), or $(CH_2)_p$-(4- to 10-membered heterocyclic ring having 1 to 4 heteroatom ring members selected from O, $S(O)_q$, and N), wherein the heterocyclic ring is substituted with 0-2 $R^5$, or two of $R^1$ that are attached to adjacent ring carbon atoms are taken together with the ring atoms through which they are connected to form a 5- to 6-membered heterocycloalkyl having 1 or 2 oxygen ring heteroatoms.

In other embodiments, each $R^1$ is independently Cl, F, Br, I, $CF_3$, $OCF_3$, $C_{2-6}$alkenyl substituted with 0-2 $R^5$, $C_{2-6}$alkynyl substituted with 0-2 $R^5$, $(CH_2)_pNO_2$, $(CH_2)_pCN$, $(CH_2)_pOR$, $(CH_2)_pN(R)_2$, $(CH_2)_pCOR$, $(CH_2)_pOCOR$, $(CH_2)_pCO_2R$, $(CH_2)_pCON(R)_2$, $(CH_2)_pOCON(R)_2$, $(CH_2)_pNRCOR$, $(CH_2)_pNRCO_2R$, $(CH_2)_pNRCON(R)_2$, $(CH_2)_pC(=NH)NH_2$, $(CH_2)_pSOR$, $(CH_2)_pSO_2R$, $(CH_2)_pSO_2N(R)_2$, $(CH_2)_pNRSO_2R$, $(CH_2)_pNRSO_2N(R)_2$, $(CH_2)_p$-(3- to 10-membered carbocyclic ring substituted with 0-2 $R^5$), or $(CH_2)_p$-(4- to 10-membered heterocyclic ring having 1 to 4 heteroatom ring members selected from O, $S(O)_q$, and N), wherein the heterocyclic ring is substituted with 0-2 $R^5$, or two of $R^1$ that are attached to adjacent ring carbon atoms are taken together with the ring atoms through which they are connected to form a 5- to 6-membered heterocycloalkyl having 1 or 2 oxygen ring heteroatoms.

In still other embodiments, each $R^1$ is independently Cl, F, Br, I, $CF_3$, $OCF_3$, $C_{1-6}$alkyl substituted with 0-2 $R^5$, $C_{2-6}$alkenyl substituted with 0-2 $R^5$, or $C_{2-6}$alkynyl substituted with 0-2 $R^5$.

In still other embodiments, $R^1$ is $C_{1-6}$ alkyl substituted with 0-2 $R^5$, $C_{2-6}$alkenyl substituted with 0-2 $R^5$ and $C_{2-6}$alkynyl substituted with 0-2 $R^5$, wherein when $C_{1-6}$alkyl is a terminally substituted straight chain alkyl, it is preferably $(CH_2)_pNO_2$, $(CH_2)_pCN$, $(CH_2)_pOR$, $(CH_2)_pN(R)_2$, $(CH_2)_pCOR$, $(CH_2)_pOCOR$, $(CH_2)_pCO_2R$, $(CH_2)_pCON(R)_2$, $(CH_2)_pOCON(R)_2$, $(CH_2)_pNRCOR$, $(CH_2)_pNRCO_2R$, $(CH_2)_pNRCON(R)_2$, $(CH_2)_pC(=NH)NH_2$, $(CH_2)_pSOR$, $(CH_2)_pSO_2R$, $(CH_2)_pSO_2N(R)_2$, $(CH_2)_pNRSO_2R$, $(CH_2)_pNRSO_2N(R)_2$, $(CH_2)_p$-(3- to 10-membered carbocyclic ring substituted with 0-2 $R^5$), or $(CH_2)_p$-(4- to 10-membered heterocyclic ring having 1 to 4 heteroatom ring members selected from O, $S(O)_q$, and N), wherein the heterocyclic ring is substituted with 0-2 $R^5$, or two of $R^1$ that are attached to adjacent ring carbon atoms are taken together with the ring atoms through which they are connected to form a 5- to 6-membered heterocycloalkyl having 1 or 2 oxygen ring heteroatoms; and wherein p is an integer from about 1 to about 4.

In certain other preferred embodiments, $R^1$ is Cl, F, Br, $CF_3$, $(CH_2)_pCN$, $(CH_2)_pOR$, $(CH_2)_pN(R)_2$, $(CH_2)_pCOR$, $(CH_2)_pOCOR$, $(CH_2)_pCO_2R$, $(CH_2)_pCON(R)_2$, $(CH_2)_pO- $CON(R)_2$, $(CH_2)_pSOR$, $(CH_2)_pSO_2R$, $(CH_2)_pNRSO_2R$, $(CH_2)_p$-(3- to 10-membered carbocyclic ring substituted with 0-2 $R^5$), or $(CH_2)_p$-(4- to 10-membered heterocyclic ring having 1 to 4 heteroatom ring members selected from O, $S(O)_q$, and N), wherein the heterocyclic ring is substituted with 0-2 $R^5$, or two of $R^1$ that are attached to adjacent ring carbon atoms are taken together with the ring atoms through which they are connected to form a 5- to 6-membered heterocycloalkyl having 1 or 2 oxygen ring heteroatoms.

In still other preferred embodiments of the present invention, $R^2$ is Cl, F, Br, $CF_3$, $NO_2$, —CN, $OR^a$, $N(R^a)_2$, or $CON(R^a)_2$; or $R^1$ and $R^2$ that are attached to adjacent ring carbon atoms are taken together with the ring atoms through which they are connected to form a 5- to 6-membered heterocycloalkyl having 1 or 2 oxygen ring members.

In some preferred embodiments of the present invention, $R^3$ is H, $CH_3$, cyano, or F; more preferably H, cyano, or F; still more preferably H or F, with H being even more preferred.

In certain preferred embodiments of the present invention, $R^4$ is 3- to 10-membered carbocyclic ring substituted with 0-2 $R^{4a}$. When $R^4$ is a carbocyclic ring it is preferably an aromatic carbocyclic ring, more preferably, phenyl substituted with 0-2 $R^{4a}$.

In certain other preferred embodiments of the present invention, $R^4$ is a 5- to 10-membered heterocyclic ring having 1 to 4 heteroatom ring members selected from O, $S(O)_q$, and N, wherein the heterocyclic ring is substituted with 0-2 $R^{4a}$.

In certain preferred embodiments, when $R^4$ is a heterocyclic ring it is preferably a heteroaromatic ring, more preferably a 5- or 6-membered heteroaromatic ring, still more preferably with 1 to 3 heteroatoms selected independently from O and N heteroatoms.

In other preferred embodiments of the present invention, when $R^4$ is a heterocyclic ring, the heterocyclic ring is indazolyl, pyrazolyl, or piperidinyl, each optionally substituted.

In some other preferred embodiments of the present invention, at least one of $R^{4a}$ is —$(CH_2)_p$-(5- to 6-membered heterocyclic ring). more preferably a -(5- to 6-membered heteroaromatic ring), with a -(5-membered heteroaromatic ring) being even more preferred. In some even more preferred embodiments, the 5-membered heteroaromatic ring is triazolyl, tetrazolyl, or oxadiazolyl, each substituted with 0-3 $R^{5a}$; with triazolyl substituted with 0-3 $R^{5a}$ being still more preferred.

When $R^{4a}$ is a heteroaromatic ring, preferably the heteroaromatic ring has 2, 3, or 4 heteroatom ring members are selected from N, O, and S heteroatoms, more preferably selected from N and O heteroatoms. Even more preferred, $R^{4a}$ is a heteroaromatic ring wherein the heteroaromatic ring of $R^{4a}$ has 3 or 4 heteroatom ring members selected from N, O, and S heteroatoms, more preferably selected from N and O heteroatoms still more preferably from N heteroatoms.

In other preferred embodiments of the present invention, $R^{4a}$ is Cl, F, $C_{1-6}$alkyl substituted with 0-3 $R^5$, $(CH_2)_pOR$, $(CH_2)_pCON(R)_2$, $(CH_2)_pNRCO_2R$, or $CH(CF_3)NH_2$.

In certain preferred embodiments of the present invention, $R^{5a}$ is Cl, F, Br, $CF_3$, $C_{1-4}$alkyl substituted with 0-3 $R^5$, $C_{2-4}$alkenyl, $(CH_2)_pOR^a$, $N(R^a)_2$, $(CH_2)_p$-(3- to 10-membered carbocyclic ring substituted with 0-2 $R^b$, or $(CH_2)_p$-(5- to 10-membered heterocyclic ring having 1 to 4 heteroatom ring members selected from O, $S(O)_q$, and N, wherein the heterocyclic ring is substituted with 0-2 $R^b$.

In other preferred embodiments of the present invention, wherein $R^{5a}$ is $(CH_2)_p$-(3- to 10-membered carbocyclic ring substituted with 0-2 $R^b$, preferably the $(CH_2)_p$-(3- to 10-membered carbocyclic ring is phenyl or benzyl.

In yet other preferred embodiments of the present invention, wherein $R^{5a}$ is $(CH_2)_p$-(5- to 10-membered heterocyclic ring) having 1 to 4 heteroatom ring members selected from O, $S(O)_q$, and N, wherein the heterocyclic ring is substituted with 0-2 $R^b$, preferably the $(CH_2)_p$-(5- to 10-membered heterocyclic ring is optionally substituted with Cl, F, $CF_3$, $C_{1-4}$alkyl optionally substituted with $OR^a$, —CN, or $OR^a$. Alternatively, when $R^{5a}$ is $(CH_2)_p$-(5- to 10-membered heterocyclic ring), the heterocyclic ring is pyridinyl, morpholinyl, piperidinyl, or piperazinyl, each optionally substituted.

In some preferred embodiments of the present invention, $R^{5a}$ is Cl, F, $CF_3$, $C_{1-4}$alkyl optionally substituted with $OR^a$, —CN, or $OR^a$.

In certain preferred embodiments, p is an integer from about 1 to about 4, more preferably from about 1 to about 3, still more preferably 1 or 2.

The compounds of the present invention are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosure of which is hereby incorporated herein by reference, in its entirety.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides novel pharmaceutical compositions, comprising: a pharmaceutically acceptable carrier, a therapeutically effective amount of a compound of the present invention or a pharmaceutically acceptable salt form thereof, and a therapeutically effective amount of an additional therapeutic agent selected from anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, and an agent for treating immunodeficiency disorders.

Validation for JNK as a compelling target for a variety of diseases including neurodegeneration, metabolic disorders, inflammation, cardiovascular disease, and cancer come in the form of data from knock out (KO) mouse studies, peptide inhibitors of JNK, and small molecule inhibitors of JNK. Numerous gene deletion studies in mice provide evidence that the inhibition of JNK may be very valuable as a therapeutic approach for a variety of diseases. In 1997, Yang et al., *Nature* 1997, 389, (6653), 865-70, showed that mice lacking the Jnk3 gene were resistant to kainic acid induced seizures. Not only were seizure scores for the mice dramatically reduced for the Jnk3 treatment group compared to wild-type controls, but there was also a significant decrease in excitotoxicity-induced hippocampal apoptosis as measured by TUNEL assay in the Jnk3 KO group as compared to wild type. Jnk1 and Jnk2 KO mice were not resistant to the kainic acid-induced seizure effects suggesting a unique role for Jnk3 as a potential therapy for seizure. Similarly, deletion of Jnk3 protects neonatal mice against cerebral hypoxic-ischemic injury suggesting that JNK3 inhibitors may be effective in the treatment of stroke (See Pirianov, G.; Brywe, K. G.; Mallard, C.; Edwards, A. D.; Flavell, R. A.; Hagberg, H.; Mehmet, H., Deletion of the c-Jun N-terminal kinase 3 gene protects neonatal mice against cerebral hypoxic-ischaemic injury. *J Cereb Blood Flow Metab* 2007, 27, (5), 1022-32). Indeed, in this study significant attenuation of injury was observed in the cerebral cortex, hippocampus, striatum, and thalamus in Jnk3

KO mice compared to control mice Id. A third compelling knockout mouse study linking JNK3 and JNK2 to neurodegenerative disease was reported in 2004 by Flavell and colleagues. In this study the authors showed that Jnk3 KOs, Jnk2 KOs, and compound Jnk3/Jnk2 KOs were resistant to 1-methyl-4-phenyl-1,2,3,6-tetrahydropyridine (MPTP)-induced neurodegeneration and motor deficits in this mouse model of Parkinson's disease (See Hunot, S.; Vila, M.; Teismann, P.; Davis, R. J.; Hirsch, E. C.; Przedborski, S.; Rakic, P.; Flavell, R. A., JNK-mediated induction of cyclooxygenase 2 is required for neurodegeneration in a mouse model of Parkinson's disease. *Proc Natl Acad Sci USA* 2004, 101, (2), 665-70). Measurements of striatal dopamine, survival of tyrosine hydroxylase(TH)-immunoreactive dopaminergic neurons in the substantia nigra pars compacta (SNpc), and motor function on a rotarod all showed statistically significant improvement compared to wild-type MPTP-lesioned mice Id. This dramatic result further validated the potential for JNK inhibitors in the treatment of neurodegenerative disease. Similarly, KO studies have helped define the role of JNK in peripheral diseases such as type II diabetes mellitus, and obesity. In 2002, Hirosumi et al. showed that Jnk1−/− mice had decreased adiposity, significantly improved insulin sensitivity, and enhanced insulin receptor signaling capacity in both a diet-induced obesity (DIO) model and a genetic obesity model (using ob/ob mice). In addition, the DIO Jnk1−/− mice had decreased body weights compared to DIO wild type mice and also showed decreased blood glucose levels (See Hirosumi, J.; Tuncman, G.; Chang, L.; Gorgun, C. Z.; Uysal, K. T.; Maeda, K.; Karin, M.; Hotamisligil, G. S., A central role for JNK in obesity and insulin resistance. *Nature* 2002, 420, (6913), 333-6). These data are strong evidence that a JNK1 inhibitor may be efficacious in the treatment of type II diabetes mellitus as well as in obesity.

The above sets of experiments are just some of the validation examples for treatment of disease for which JNK inhibitors may be used. Other examples where JNK inhibition may provide therapeutic benefit include: Parkinson's disease, Lewy body dementia, Alzheimer's disease, amyotrophic lateral sclerosis, multiple sclerosis, spinal cord injury, head trauma, seizure, stroke, epilepsy, diabetes, (such as type II diabetes, type I diabetes, diabetes mellitus, insulin-dependent diabetes, non-insulin dependent diabetes, adult-onset diabetes, juvenile diabetes, ketosis prone diabetes, ketosis-resistant diabetes and diabetes insipidus), diabetic neuropathy, peripheral neuropathy, obesity, diet-induced obesity, medication-induced obesity, hormone-related obesity, myocardial infarction, congestive heart failure, cardiac hypertrophy, abdominal aortic aneurysm, inflammation, atherosclerosis, restenosis, ischemia, ischemia-reperfusion injury, rheumatoid arthritis, osteoarthritis, Crohn's disease, irritable bowel syndrome, ulcerative colitis, pancreatitis, esophagitis, nephropathy, scleroderma, systemic lupus erythematosus, sepsis, psoriasis, eczema, glaucoma, glaucomateous retinopathy, chemotherapy-induced neuropathy, cancer (such as colon, lung, breast, prostate, head and neck, esophageal, pancreatic, bone, stomach, kidney, ovarian, testicular, cervical, uterine, blood, lymph, skin, brain, central nervous system, eye, liver), hepatitis, alcohol-induced liver disease, xenobiotic-induced liver disease, and Huntington's disease.

Accordingly, in another embodiment, the present invention provides a novel method for treating a disease or condition responsive to inhibition of the JNK pathway, comprising administering to a patient in need thereof an effective amount of a compound of the present invention.

Examples of such diseases and/or conditions where JNK inhibition may provide therapeutic benefit include: Parkinson's disease, Lewy body dementia, Alzheimer's disease, amyotrophic lateral sclerosis, multiple sclerosis, spinal cord injury, head trauma, seizure, stroke, epilepsy, diabetes, (such as type II diabetes, type I diabetes, diabetes mellitus, insulin-dependent diabetes, non-insulin dependent diabetes, adult-onset diabetes, juvenile diabetes, ketosis prone diabetes, ketosis-resistant diabetes and diabetes insipidus), diabetic neuropathy, peripheral neuropathy, obesity, diet-induced obesity, medication-induced obesity, hormone-related obesity, myocardial infarction, congestive heart failure, cardiac hypertrophy, abdominal aortic aneurysm, inflammation, atherosclerosis, restenosis, ischemia, ischemia-reperfusion injury, rheumatoid arthritis, osteoarthritis, Crohn's disease, irritable bowel syndrome, ulcerative colitis, pancreatitis, esophagitis, nephropathy, scleroderma, systemic lupus erythematosus, sepsis, psoriasis, eczema, glaucoma, glaucomateous retinopathy, chemotherapy-induced neuropathy, cancer (such as colon, lung, breast, prostate, head and neck, esophageal, pancreatic, bone, stomach, kidney, ovarian, testicular, cervical, uterine, blood, lymph, skin, brain, central nervous system, eye, liver), hepatitis, alcohol-induced liver disease, xenobiotic-induced liver disease, and Huntington's disease.

In another embodiment, the present invention provides a novel method for treating a disease or condition, comprising: administering to a patient in need thereof a therapeutically effective amount of a compound of the present invention or a pharmaceutically acceptable salt form thereof, wherein the disease or condition is selected from an inflammatory disease, an autoimmune disease, a cardiovascular disease, a metabolic disease, an ischemic disease, an infectious disease (e.g., viral diseases), and a proliferative disease (e.g., cancer). Alternatively preferred, the disease or condition is selected from the group consisting of all types or forms of: Parkinson's disease, stroke, diabetes, cancer, myocardial infarction, multiple sclerosis, pulmonary fibrosis, and Alzheimers or pre-Alzheimers disease.

In another embodiment, the present invention provides a compound of the present invention for use in therapy.

In another embodiment, the present invention provides the use of compounds of the present invention for the manufacture of a medicament for the treatment of an indication listed herein.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

The examples provided in the definitions present in this application are non-inclusive unless otherwise stated. The definitions include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

Examples of molecular weights for compounds of the present invention include weights less than about 500, 550, 600, 650, 700, 750, or 800 grams per mole.

"Substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

As used herein, the term "$R^1$ and $R^2$ that are attached to adjacent ring carbon atoms are taken together with the ring atoms through which they are connected to form a 5- to 6-membered heterocycloalkyl having 1 or 2 oxygen ring members" may be explained by the following non-limiting example. In compounds of formula Ic or Id, $R^1$ and $R^2$ may each be attached to the same core 6-membered ring, said ring being either a benzene, pyridine or pyrimidine ring, depending on the value of $Z^1$ and/or $Z^2$. In any case, when $R^1$ and $R^2$ are adjacent to one another on the 6 membered ring (as shown in one possible combination below wherein the ring is benzene, i.e., $Z^1$ and $Z^2$ are each CH);

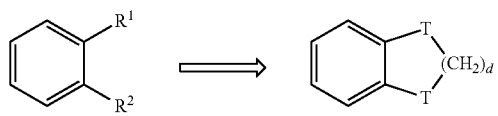

then taken together they may form a 5- or 6-membered ring wherein d is 1 or 2, and one or two of T are oxygen atoms.

As used herein, the term "two $R^5$ taken together with a carbon atom to which they are both connected form a 1,3-dioxolane ring wherein the two oxygen ring atoms are attached to the connecting carbon atom" may be explained by the following pictorial non-limiting example. When two of $R^5$ are geminally disposed at the ring carbon atom of cyclopentane, then a spiro juncture is formed as shown below:

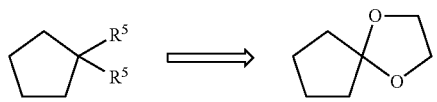

The present invention is intended to include all isotopes of atoms occurring in the present compounds. Isotopes include those atoms having the same atomic number but different mass numbers. Isotopes of hydrogen include tritium and deuterium. Isotopes of carbon include C-13 and C-14.

When any variable occurs more than one time in any constituent or formula for a compound, its definition at each occurrence is independent of its definition at every other occurrence. Thus, for example, if a group is shown to be substituted with 0-2 $R^5$, then said group may optionally be substituted with up to two $R^5$ groups and $R^5$ at each occurrence is selected independently from the definition of $R^5$. Also, combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

"Alkyl" includes both branched and straight-chain saturated aliphatic hydrocarbon groups having the specified number of carbon atoms. $C_{1-6}$alkyl, for example, includes $C_1$, $C_2$, $C_3$, $C_4$, $C_5$, and $C_6$alkyl groups; preferably $C_{1-4}$alkyl, more preferably $C_{1-3}$alkyl, with $C_1$alkyl being even more preferred. Examples of alkyl include methyl, ethyl, n-propyl, i-propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$alkenyl includes $C_2$, $C_3$, $C_4$, $C_5$, and $C_6$ alkenyl groups, more preferably $C_{2-4}$alkenyl.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cyclic amine" is a hydrocarbon ring wherein one carbon atom of the ring has been replaced by a nitrogen atom. The cyclic amine can be unsaturated, partially saturated, or fully saturated. The cyclic amine can also be bicyclic, tricyclic, and polycyclic. Examples of cyclic amine include pyrrolidine and piperidine.

Halo" or "halogen" refers to fluoro, chloro, bromo, and iodo.

"Carbocycle" and "carbocyclic ring" each refer to any stable 3, 4, 5, 6, or 7-membered monocyclic or bicyclic or 7, 8, 9, 10, 11, 12, or 13-membered bicyclic or tricyclic ring, preferably 3- to 10-membered mono or bicyclic, more preferably 3- to 7-membered monocyclic, still more preferably 3- to 6-membered monocyclic ring, any of which rings may be saturated, partially unsaturated, or unsaturated (aromatic).

Examples of such carbocycles include cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2] bicyclooctane). A bridged ring occurs when one or more carbon atoms link two non-adjacent carbon atoms (e.g., one or two carbon atom bridges). A bridge always converts a monocyclic ring into a tricyclic ring. When a ring is bridged, the substituents recited for the ring may also be present on the bridge.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$cycloalkyl includes $C_3$, $C_4$, $C_5$, $CO$, $C_7$, and $C_8$ cycloalkyl groups; preferably $C_{3-6}$cycloalkyl.

"Aryl" refers to any stable 6, 7, 8, 9, 10, 11, 12, or 13 membered monocyclic, bicyclic, or tricyclic ring, wherein at least one ring, if more than one is present, is aromatic. Preferably aryl is $C_{6-10}$aryl, more preferably $C_6$aryl. Examples of aryl include fluorenyl, phenyl, naphthyl, indanyl, adamantyl, and tetrahydronaphthyl.

"Heterocycle" and "heterocyclic ring" each refer to any stable 5, 6, or 7-membered monocyclic or bicyclic or 7, 8, 9, or 10-membered bicyclic heterocyclic ring that is saturated, partially unsaturated, or unsaturated (aromatic), and consisting of: carbon atoms and 1, 2, 3, or 4 ring heteroatoms independently selected from the group consisting of N, O and S and including any bicyclic group in which any of the above-defined heterocyclic rings is fused to a benzene ring. The N group may be N, NH, or N-substituent, depending on the chosen ring and if substituents are recited. The nitrogen and sulfur heteroatoms may optionally be oxidized (e.g., S, S(O), $S(O)_2$, and N—O). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. Typically, the total number of S and O atoms in the heterocycle is not more than 1. Bridged rings are also included in the definition of heterocycle. A bridged ring occurs when one or more atoms (i.e., C, O, N, or S) link two non-adjacent carbon or nitrogen atoms. Examples of bridges include one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge. In certain preferred embodiments, the heterocycle is 5- to 10-membered, more preferably 5- to 6-membered, with 5-membered being even more preferred.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), $S(O)_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heterocycles include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "patient" refers to animals, including mammals, preferably humans. "Mammal" covers warm blooded mammals, preferably those that are typically under medical care (e.g., humans and domesticated animals). Examples include feline, canine, equine, bovine, and human, as well as just human.

"Treating" or "treatment" covers the treatment of a disease-state in a patient, preferably mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat an indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

The compounds of the invention may be administered in an effective amount by any of the conventional techniques well-established in the medical field. The compounds employed in the methods of the present invention including, for example, the compounds of Formula I or II, may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound (and all combinations and subcombinations of ranges of active compound and specific amounts of active compound therein).

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the invention may vary depending upon various factors such as, for example, the pharmacodynamic characteristics of the particular agent and its mode and route of administration, the age, health and weight of the recipient, the nature and extent of the symptoms, the kind of concurrent treatment, the frequency of treatment, and the effect desired. Generally, small dosages may be used initially and, if necessary, increased by small increments until the desired effect under the circumstances is reached. Generally speaking, oral administration may require higher dosages.

Although the proper dosage of the compounds of this invention will be readily ascertainable by one skilled in the art, once armed with the present disclosure, typically a dosage of the compound of the invention, preferably a compound of Formula I and/or pharmaceutically acceptable salts thereof, may range from about 0.001 to about 1000 milligrams, and all combinations and subcombinations of ranges therein and specific dosage amounts therein. Preferably, the dosage may be about 0.01 to about 100 milligrams of the compound or pharmaceutically acceptable salt of the invention, with from about 0.01 to about 10 milligrams being more preferred.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

Pharmaceutical kits useful in, for example, the treatment of hypertension, pulmonary hypertension, atherosclerosis, stroke, angina, heart failure, myocardial protection, arterial obstruction, peripheral arterial disease, peripheral circulation disorder, vasospasm, erectile dysfunction, acute pain, chronic pain, dementia, Alzheimer's disease, Parkinson's disease, neuronal degeneration, asthma, amyotrophic lateral sclerosis, spinal cord injury, rheumatoid arthritis, osteoarthritis, osteoporosis, psoriasis, multiple sclerosis, diabetes, urinary organ diseases such as overactive bladder, benign prostatic hypertrophy, metastasis, cancer, glaucoma, ocular hypertension, retinopathy, autoimmune disease, viral infection, osteoarthritis, rheumatoid arthritis and/or osteoporosis, which comprise a therapeutically effective amount of a benzo[d]oxazole and/or benzo[d]thiazole compound of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

A possible example of a tablet of the present invention is as follows.

| Ingredient | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Tablet |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

A possible example of an injection solution of the present invention is as follows.

| Ingredient | mg/Tablet |
|---|---|
| Active substance | 1.0 mg |
| 1N HCl | 20.0 µl |
| acetic acid | 0.5 mg |
| NaCl | 8.0 mg |
| Phenol | 10.0 mg |
| 1N NaOH | q.s. ad pH 5 |
| $H_2O$ | q.s. ad 1 mL |

Synthesis

The compounds of the present invention can be prepared in a number of ways known to one skilled in the art of organic synthesis (e.g., see U.S. Pat. No. 6,476,060 B2, *J Med Chem* 2004, 47, 627). The compounds of the present invention can be synthesized using the methods described below, together with synthetic methods known in the art of synthetic organic chemistry, or by variations thereon as appreciated by those skilled in the art. Preferred methods include, but are not limited to, those described below. All processes disclosed in association with the present invention are contemplated to be practiced on any scale, including milligram, gram, multigram, kilogram, multikilogram or commercial industrial scale. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. As will be readily understood, functional groups present may contain protecting groups during the course of synthesis. Protecting groups are known per se as chemical functional groups that can be selectively appended to and removed from functionalities, such as hydroxyl groups and carboxy groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl groups. Preferred hydroxyl protecting groups include the benzyl and the tertiary-butyldimethylsilyl groups. Other preferred protecting groups that may be employed in accordance with the present invention may be described in Greene, T. W. and Wuts, P. G. M., *Protective Groups in Organic Synthesis* 3$^{rd}$. Ed., Wiley & Sons, 1991, or Kocienski, P. J., *Protecting Groups*, 3$^{rd}$ Ed., Georg Thieme Verlag, Stuttgart, 2005.

Compounds of the present invention can be prepared according to the following methods. The substituents are the same as in Formula (I) except where defined otherwise, or apparent to one in the art. Other representative methods are found in the Experimental Examples Section below.

In the below-described Scheme, $R_1$, $R_2$, $R_3$, X and Z are as defined above. Other variables are understood by one in the art by the context in which they are used.

Scheme 1

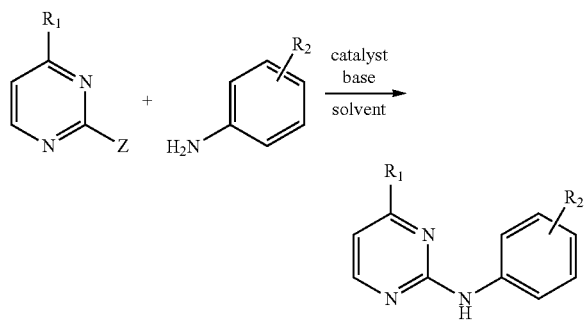

Thus, in Scheme 1, a suitably substituted pyrimidine containing a halogen atom Z (Cl, Br, or I) may be coupled with an appropriately functionalized 3- or 4-substituted aniline in the presence of a stoichiometric or catalytic amount of a palladium catalyst such as Pd(Ph$_3$P)$_4$, PdCl$_2$(Ph$_3$P)$_2$, Pd$_2$dba$_3$, Pd(OAc)$_2$, PdCl$_2$dppf and the like. Typically a base (e.g. K$_2$CO$_3$, Cs$_2$CO$_3$, K$_3$PO$_4$, Et$_3$N, NaOtBu, KOtBu, etc. . . . ) will also be present and the reaction carried out in a suitable solvent (DCM, THF, DME, DMF, DMAC, CH$_3$CN, dioxane, toluene, benzene, etc. . . . ). Additionally, ligands such as BINAP, di-tert-butyl phosphinobiphenyl, di-cyclohexylphosphino biphenyl, tri tert-butylphosphine, XANTPHOS, triphenylarsine and the like may be added. The reaction is conducted under an inert atmosphere (N2 or argon) at a temperature between 50-120° C. The reaction mixture is then maintained at a suitable temperature for a time in the range of about 2 up to 48 h with 12 h typically being sufficient (see for example Yang, B. H.; Buchwald, S. L. *J. Organomet. Chem.* 1999, 576, 125-46 and Wolfe, J. P.; Tomori, H.; Sadighi, J. P.; Yin, J.; Buchwald, S. L. *J. Org. Chem.* 2000, 65, 1158-1174). Alternatively, the reaction may be carried out under microwave irradiation in a sealed tube. These reactions are typically conducted at a temperature between 110-180° C. for a time range of 5 min to 2 h with 20 min typically being sufficient. The product from the reaction can be isolated and purified employing standard techniques, such as solvent extraction, chromatography, crystallization, distillation and the like.

Scheme 2

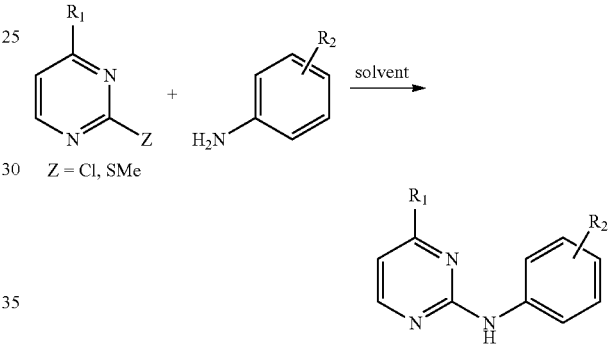

Z = Cl, SMe

Another embodiment of the present invention is illustrated in Scheme 2. A 4-substituted pyrimidine containing a leaving group (Z=Cl or SMe) at C-2 may be coupled with an appropriately functionalized 3- or 4-substituted aniline under thermal conditions either neat or in a suitable solvent (DCM, THF, DME, DMF, DMAC, CH$_3$CN, DMSO, dioxane, toluene, benzene, etc. . . . ). The reaction is conducted under an inert atmosphere (N$_2$ or argon) at a temperature between 70-190° C. The reaction mixture is then maintained at a suitable temperature for a time in the range of about 1 up to 48 h with 12 h typically being sufficient. Alternatively, the reaction may be carried out under microwave irradiation in a sealed tube. These reactions are typically conducted at a temperature between 110-180° C. for a time range of 5 min to 8 h with 2 h typically being sufficient. The product from the reaction can be isolated and purified employing standard techniques, such as solvent extraction, chromatography, crystallization, distillation and the like.

Scheme 3

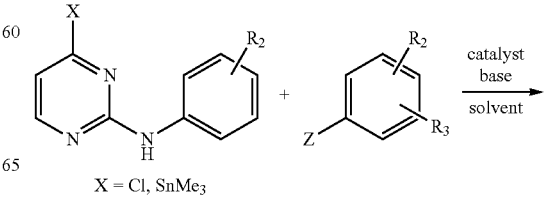

X = Cl, SnMe$_3$

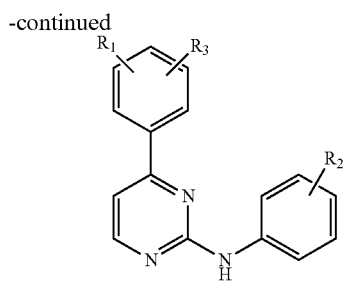

Another embodiment of the present invention is illustrated in Scheme 3. This 4-substituted pyrimidine (X=Cl, SnMe$_3$) may then be coupled with an appropriately substituted aryl group under metal-catalyzed cross-coupling conditions where Z is a metallic or metalloid species (for X=Cl) such as B(OR)$_2$, Li, MgHal, SnR$_3$, ZnHal, SiR$_3$ and the like or Z may be a halogen such as Cl, Br, I (for X=SnMe$_3$). The coupling may be promoted by a homogeneous catalyst such as Pd(PPh$_3$)$_4$, or by a heterogeneous catalyst such as Pd on carbon in a suitable solvent (e.g. THF, DME, toluene, MeCN, DMF, H$_2$O etc.). Typically a base, such as K$_2$CO$_3$, NEt$_3$, and the like, will also be present in the reaction mixture. Other promoters may also be used such as CsF. The reaction mixture is maintained at rt, or heated to a temperature between 30° C. to 150° C. The reaction mixture is then maintained at a suitable temperature for a time in the range of about 4 up to 48 h, with about 18 h typically being sufficient (see for example 1. Miyaura, N.; Suzuki, A. Chem. Rev. 1995, 95, 2457-2483; 2. Farina, V.; Krishnamurthy, V.; Scott, W. J. The Stille reaction. Organic Reactions 1997, 50, 1-652). Alternatively, the reaction may be carried out under microwave irradiation in a sealed tube. These reactions are typically conducted at a temperature between 110-180° C. for a time range of 5 min to 2 h with 20 min typically being sufficient. The product from the reaction can be isolated and purified employing standard techniques, such as solvent extraction, chromatography, crystallization, distillation and the like.

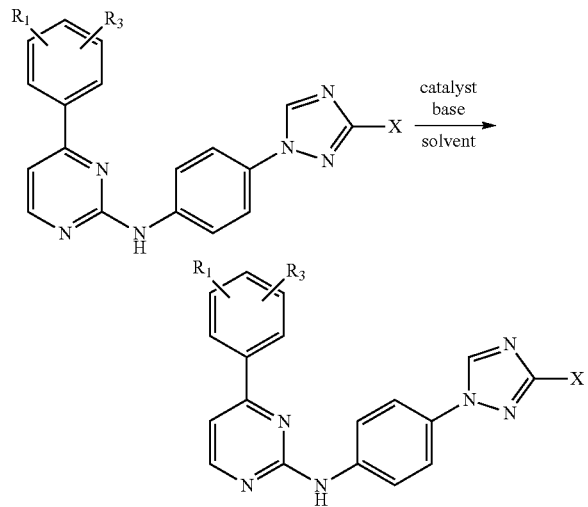

Scheme 4

Another embodiment of the present invention is illustrated in Scheme 4. A suitably substituted halotriazole (X=Cl, Br, or I) may be coupled with an amine or aryl ring in the presence of a stoichiometric or catalytic amount of a palladium catalyst such as Pd(Ph$_3$P)$_4$, PdCl$_2$(Ph$_3$P)$_2$, Pd$_2$ dba$_3$, Pd(OAc)$_2$, PdCl$_2$dppf and the like. Typically a base (e.g. K$_2$CO$_3$, Cs$_2$CO$_3$, K$_3$PO$_4$, Et$_3$N, NaOtBu, KOtBu, etc....) will also be present and the reaction carried out in a suitable solvent (DCM, THF, DME, DMF, DMAC, CH$_3$CN, dioxane, toluene, benzene, etc....). Additionally, ligands such as BINAP, di-tert-butyl phosphinobiphenyl, di-cyclohexylphosphino biphenyl, tri tert-butylphosphine, XANTPHOS, triphenylarsine and the like may be added. The reaction is conducted under an inert atmosphere (N$_2$ or argon) at a temperature between 50-120° C. The reaction mixture is then maintained at a suitable temperature for a time in the range of about 2 up to 48 h with 12 h typically being sufficient. The reaction may also be carried out under microwave irradiation in a sealed tube. These reactions are typically conducted at a temperature between 110-180° C. for a time range of 5 min to 2 h with 20 min typically being sufficient. The product from the reaction can be isolated and purified employing standard techniques, such as solvent extraction, chromatography, crystallization, distillation and the like.

Alternatively, the halogen (X=Cl, Br, I) may be substituted for by an amine in a thermal addition/elimination reaction. These reactions may be carried out with the amine nucleophile as solvent, or with a stoichiometric amount of nucleophile in the presence of an additional base (e.g. K$_2$CO$_3$, Cs$_2$CO$_3$, K$_3$PO$_4$, Et$_3$N, NaOtBu, KOtBu, etc....). The reaction carried out in a suitable solvent (DCM, THF, DME, DMF, DMAC, CH$_3$CN, dioxane, toluene, benzene, etc....) under an inert atmosphere (N$_2$ or argon) at a temperature between 100-190° C. The reaction mixture is then maintained at a suitable temperature for a time in the range of about 1 up to 48 h with 12 h typically being sufficient. The reaction may also be carried out under microwave irradiation in a sealed tube. These reactions are typically conducted at a temperature between 110-180° C. for 1-2 h with 1 h typically being sufficient. The product from the reaction can be isolated and purified employing standard techniques, such as solvent extraction, chromatography, crystallization, distillation and the like.

One stereoisomer of a compound of the present invention may be a more potent cannabinoid receptor antagonist than its counterpart(s). Thus, stereoisomers are included in the present invention. When required, separation of the racemic material can be achieved by HPLC using a chiral column or by a resolution using a resolving agent such as described in Wilen, S. H. Tables of Resolving Agents and Optical Resolutions 1972, 308 or using enantiomerically pure acids and bases. A chiral compound of the present invention may also be directly synthesized using a chiral catalyst or a chiral ligand, e.g., Jacobsen, E. Acc. Chem. Res. 2000, 33, 421-431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

Unless specifically stated otherwise, the experimental procedures were performed under the following conditions. All operations were carried out at room or ambient temperature—that is, at a temperature in the range of 18-25° C. Evaporation of solvent was carried out using a rotary evaporator under reduced pressure (600-4000 pascals: 4.5-30 mm. Hg) with a bath temperature of up to 60° C. The course of reactions was followed by thin layer chromatography (TLC) and reaction times are given for illustration only. The structure and purity of all final products were assured by at least one of the following techniques: TLC, mass spectrometry, nuclear magnetic resonance (NMR) spectrometry or HPLC analysis. When given, yields are for illustration only. When given, NMR data is in the form of delta (δ) values for major diagnostic protons, given in parts per million (ppm) relative to tetramethylsilane (TMS) as internal standard, determined at 400 MHz using the indicated solvent. Conventional abbreviations used for signal shape are: s. singlet; d. doublet; t. triplet; m. multiplet; br. broad; etc. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Example 1

2-Fluoro-4-(2-(4-(3-methyl-1H-1,2,4-triazol-1-yl)phenylamino)pyrimidin-4-yl)benzonitrile

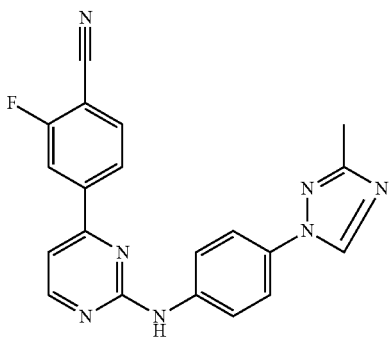 [SMILES: Cc1ncn(-c2ccc(Nc3nccc(-c4ccc(C#N)c(F)c4)n3)cc2)n1]

Part I

2-Fluoro-4-(4,4,5,5-tetramethyl-1,3,2-dioxaborolan-2-yl)benzonitrile

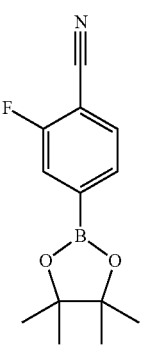

General Procedure A

Preparation of Arylboronate Ester from Aryl Halide

A mixture of 4-bromo-2-fluorobenzonitrile (4.00 g, 20 mmol), bis(pinacolato)diboron (6.60 g, 26 mmol), Pd(dppf)Cl$_2$(CH$_2$Cl$_2$) (0.82 g, 1.0 mmol), KOAc (5.89 g, 60 mmol) and DMSO (20 mL) was heated in a sealed tube at 100° C. overnight. The reaction mixture was cooled down to room temperature, diluted with water and extracted with ethyl acetate (2×). The combined organic solution was dried over anhydrous MgSO$_4$ and concentrated in vacuo to give an oil. Purification of this material by column chromatography on silica gel (5% EtOAc/hexane) provided the desired product as a yellow solid. $^1$H NMR (CDCl$_3$, 400 MHz) δ 7.68 (d, 1H), 7.64 (d, 1H), 7.62 (d, 1H), 1.37 (s, 12H).

Part II 4-(2-Chloropyrimidin-4-yl)-2-fluorobenzonitrile

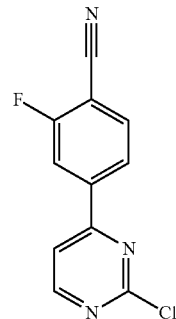

General Procedure B

Suzuki Coupling of 2,4-dicholoripyrimidine with arylboronate ester or arylboronic acid A mixture of 2-fluoro-4-(4,4,5,5-tetramethyl-1,3,2-dioxaborolan-2-yl)benzonitrile (2.47 g, 10 mmol), 2,4-dichloropyrimidine (1.64 g, 11 mmol), Pd(PPh$_3$)$_4$ (0.58 g, 0.50 mmol), K$_2$CO$_3$ (15 mL of 2 M aq. solution) and DME (30 mL) was purged with Ar for 10 min, then heated in a sealed tube at 90° C. overnight. The reaction mixture was cooled down to room temperature, extracted with EtOAc (2×). The combined organic solution was dried over anhydrous MgSO$_4$ and concentrated in vacuo to give an oil. Purification of this material by column chromatography on silica gel (25% EtOAc/hexane) provided the desired product as an off-white solid. $^1$H NMR (CDCl$_3$, 400 MHz) δ 8.85 (d, 1H), 8.09 (d, 1H), 8.06 (d, 1H), 7.87 (dd, 1H), 7.75 (d, 1H).

Part III

3-Methyl-1-(4-nitrophenyl)-1H-1,2,4-triazole

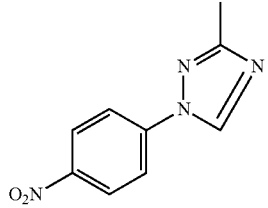

5-Methyl-1-(4-nitrophenyl)-1H-1,2,4-triazole

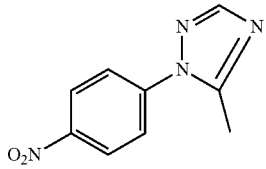

General Procedure C

Preparation of 3- or 5-substituted-1-(4-nitrophenyl)-1H-1,2,4-triazole

A mixture of 4-fluoro-1-nitrobenzene (0.28 g, 2.0 mmol), 3-methyl-1H-1,2,4-triazole (0.18 g, 2.2 mmol), $K_2CO_3$ (0.55 g, 4.0 mmol) and DMF (2 mL) was heated at 70° C. overnight. The reaction mixture was cooled down to room temperature, diluted with water, extracted with EtOAc (3×). The organic solution was dried over anhydrous $MgSO_4$ and concentrated in vacuo to provide a solid. Purification of this material by column chromatography on silica gel (40% EtOAc/hexane) provided 3-methyl-1-(4 nitrophenyl)-1H-1,2,4-triazole as the major product. $^1$H NMR (CDCl$_3$, 400 MHz) δ 8.59 (s, 1H), 8.39 (d, 2H), 7.88 (d, 2H), 2.53 (s, 3H). Further elution with 65% EtOAc/hexane provided 5-methyl-1-(4-nitrophenyl)-1H-1,2,4-triazole as the minor product. $^1$H NMR (CDCl$_3$, 400 MHz) δ 8.34 (d, 2H), 7.93 (s, 1H), 7.66 (d, 2H), 2.59 (s, 3H).

Part IV 4-(3-Methyl-1H-1,2,4-triazol-1-yl)aniline

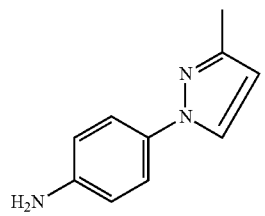

General Procedure D

Preparation of 4-(3-substituted-1H-1,2,4-triazol-1-yl)aniline via hydrogenation

A mixture of 3-methyl-1-(4-nitrophenyl)-1H-1,2,4-triazole (0.24 g, 1.2 mmol), 5% Pt/C and MeOH (12 mL) was stirred at room temperature under $H_2$ balloon overnight. The reaction mixture was filtered through Celite and concentrated in vacuo to provide the desired product as a beige solid which was used without further purification. $^1$H NMR (CDCl$_3$, 400 MHz) δ 8.31 (s, 1H), 7.40 (d, 2H), 6.77 (d, 2H), 2.51 (s, 3H).

Part V

General Procedure E

Substitution of 4-substituted-2-chloropyrimidine with 4-substituted anilines

A mixture of 4-(2-chloropyrimidin-4-yl)-2-fluorobenzonitrile (0.23 g, 1.0 mmol) and 4-(3-methyl-1H-1,2,4-triazol-1-yl)aniline (0.17 g, 1.0 mmol) in 2-ethoxyethanol (1.6 mL) was heated in a sealed tube at 190° C. for 1 h (or at 120° C. overnight if aqueous 2-ethoxyethanol was used). The reaction mixture was cooled down to room temperature and diluted with water. The precipitate was filtered, washed with water and dried under air to provide the desired product as a yellow solid. $^1$H NMR (MeOH-d$_4$, 400 MHz) δ 9.33 (brs, 1H), 8.53 (d, 1H), 8.10 (d, 1H), 8.05 (d, 1H), 7.90 (d, 2H), 7.83 (dd, 1H), 7.68 (d, 2H), 7.37 (d, 1H), 2.45 (s, 3H). MS (ESI) 372.23 (M+H).

Example 2

3-(4-Phenylpyrimidin-2-ylamino)benzamide

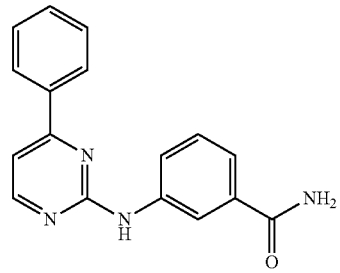 [SMILES: NC(=O)c1cccc(Nc2nccc(-c3ccccc3)n2)c1]

3-(4-Phenylpyrimidin-2-ylamino)benzamide was obtained by following procedure E using 3-aminobenzamide and 2-chloro-4-phenylpyrimidine which was prepared from 2,4-dichloropyrimidine and phenylboronic acid according to procedure B. MS (ESI) 291.1 (M+H).

Example 3

3-(4-(3-(Phenylamino)phenyl)pyrimidin-2-ylamino) benzamide

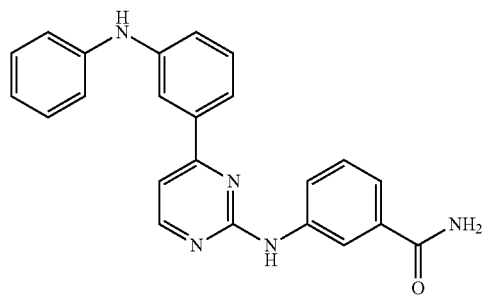 [SMILES: NC(=O)c1cccc(Nc2nccc(-c3cccc(Nc4ccccc4)c3)n2)c1]

3-(4-(3-(Phenylamino)phenyl)pyrimidin-2-ylamino)benzamide was obtained by following procedure E using 3-aminobenzamide and 3-(2-chloropyrimidin-4-yl)-N-phenylaniline which was prepared by following procedure B from N-phenyl-3-(4,4,5,5-tetramethyl-1,3,2-dioxaborolan-2-yl)aniline and 2,4-dichloropyrimidine. $^1$H NMR (DMSO-$d_6$, 400 MHz) δ 9.78 (s, 1H), 8.55 (d, 1H), 8.44 (t, 1H), 8.34 (s, 1H), 7.95-7.93 (m, 2H), 7.61 (d, 1H), 7.46 (d, 1H), 7.41-7.23 (m, 7H), 7.18-7.16 (dd, 1H), 6.90-6.86 (m, 1H). MS (ESI) 382 (M+H).

Example 4

N-(3-(4H-1,2,4-triazol-3-yl)phenyl)-4-(3-(phenylamino)phenyl)pyrimidin-2-amine

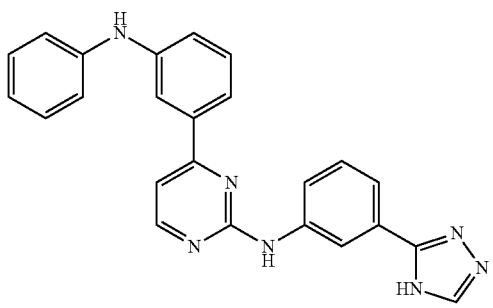 [SMILES: c1ccc(Nc2cccc(-c3ccnc(Nc4cccc(-c5nnc[nH]5)c4)n3)c2)cc1]

N-(3-(4H-1,2,4-triazol-3-yl)phenyl)-4-(3-(phenylamino)phenyl)pyrimidin-2-amine was obtained by following procedure E using 3-(4H-1,2,4-triazol-3-yl)aniline and 3-(2-chloropyrimidin-4-yl)-N-phenylaniline which was prepared from N-phenyl-3-(4,4,5,5-tetramethyl-1,3,2-dioxaborolan-2-yl)aniline and 2,4-dichloropyrimidine according to procedure B. $^1$H NMR (DMSO-$d_6$, 400 MHz) δ 8.59 (s, 1H), 8.57 (d, 1H), 8.32 (s, 1H), 7.91 (s, 1H), 7.89 (s, 1H), 7.69 (d, 1H), 7.61 (d, 1H), 7.41 (t, 1H), 7.37-7.32 (m, 1H), 7.26-7.21 (m, 3H), 7.14 (d, 2H), 6.86 (t, 1H). MS (ESI) 406 (M+H).

Example 5

1-Methyl-3-(4-phenylpyrimidin-2-ylamino)-1H-pyrazole-5-carboxamide

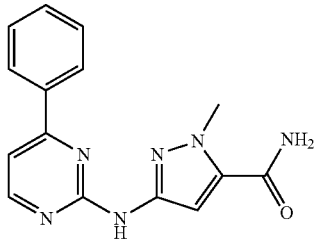 [SMILES: Cn1nc(Nc2nccc(-c3ccccc3)n2)cc1C(N)=O]

1-Methyl-3-(4 phenylpyrimidin-2-ylamino)-1H-pyrazole-5-carboxamide was obtained by following procedure E using 3-amino-1-methyl-1H-pyrazole-5-carboxamide and 2-chloro-4-phenylpyrimidine. MS (ESI) 295.1 (M+H).

Example 6

N-(4-(4H-1,2,4-triazol-3-yl)phenyl)-4-(3-(phenylamino)phenyl)pyrimidin-2-amine

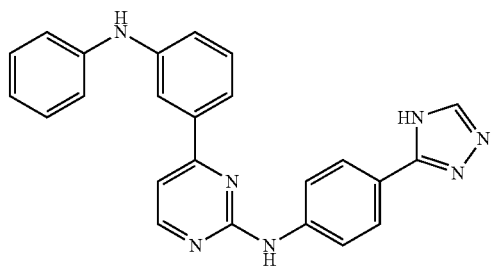 [SMILES: c1ccc(Nc2cccc(-c3ccnc(Nc4ccc(-c5nnc[nH]5)cc4)n3)c2)cc1]

N-(4-(4H-1,2,4-triazol-3-yl)phenyl)-4-(3-(phenylamino)phenyl)pyrimidin-2-amine was obtained by following procedure E using 4-(4H-1,2,4-triazol-3-yl)aniline and 3-(2-chloropyrimidin-4-yl)-N-phenylaniline which was prepared by following procedure B from N-phenyl-3-(4,4,5,5-tetramethyl-1,3,2-dioxaborolan-2-yl)aniline and 2,4-dichloropyrimidine. MS (ESI) 406 (M+H).

Example 7

N-(4-phenylpyrimidin-2-yl)-1H-indazol-6-amine

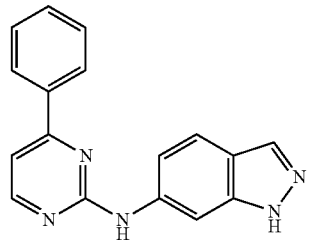 [SMILES: c1ccc(-c2ccnc(Nc3ccc4cn[nH]c4c3)n2)cc1]

N-(4-phenylpyrimidin-2-yl)-1H-indazol-6-amine was obtained by following procedure E using 1H-indazol-6-amine and 2-chloro-4-phenylpyrimidine. MS (ESI) 288.3 (M+H).

Example 8

4-(2-(4-(3-Methyl-1H-1,2,4-triazol-1-yl)phenylamino)pyrimidin-4-yl)-2-morpholinobenzonitrile

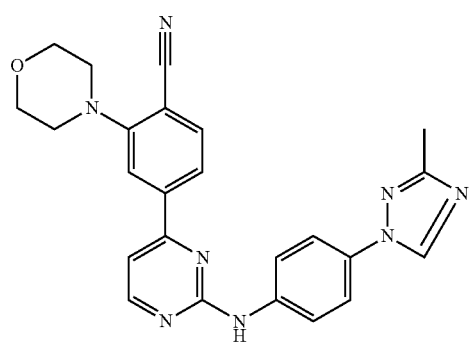 [SMILES: Cc1ncn(-c2ccc(Nc3nccc(-c4ccc(C#N)c(N5CCOCC5)c4)n3)cc2)n1]

General Procedure F

Substitution of Aryl Fluoride with Primary or Secondary Amines

A mixture of 2-fluoro-4-(2-(4-(3-methyl-1H-1,2,4-triazol-1-yl)phenylamino)pyrimidin-4-yl)benzonitrile (0.037 g, 0.10 mmol), morpholine (0.035 g, 0.40 mmol) and $K_2CO_3$ (0.028 g, 0.20 mmol) in DMSO (0.2 mL) was heated in a sealed tube at 190° C. until the starting fluoride was consumed (1~24 h). The reaction mixture was cooled down to room temperature and diluted with water. The precipitate was filtered, washed with water and dried under air to provide the desired product as a yellow solid. $^1$H NMR (DMSO-$d_6$, 400 MHz) δ 10.04 (s, 1H), 9.07 (s, 1H), 8.70 (d, 1H), 7.99 (d, 2H), 7.94 (s, 1H), 7.91 (s, 1H), 7.89 (d, 1H), 7.77 (d, 2H), 7.61 (d, 1H), 3.85 (m, 4H), 3.31 (m, 4H), 2.39 (s, 3H). MS (ESI) 439.26 (M+H).

Example 9

4-(2-(4-(3-Methyl-1H-1,2,4-triazol-1-yl)phenylamino)pyrimidin-4-yl)-2-(4-methylpiperazin-1-yl)benzonitrile

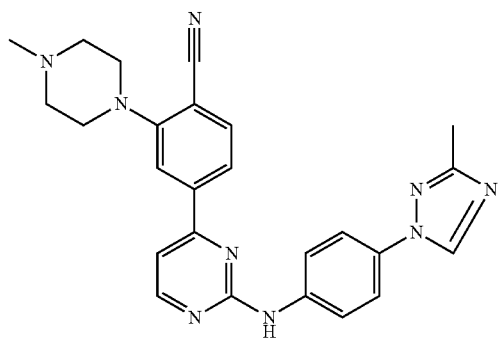 [SMILES: Cc1ncn(-c2ccc(Nc3nccc(-c4ccc(C#N)c(N5CCN(C)CC5)c4)n3)cc2)n1]

4-(2-(4-(3-Methyl-1H-1,2,4-triazol-1-yl)phenylamino)pyrimidin-4-yl)-2-(4-methylpiperazin-1-yl)benzonitrile was obtained by following procedure F using 2-fluoro-4-(2-(4-(3-methyl-1H-1,2,4-triazol-1-yl)phenylamino)pyrimidin-4-yl)benzonitrile and 1-methylpiperazine. $^1$H NMR (DMSO-$d_6$, 400 MHz) δ 9.95 (s, 1H), 9.00 (s, 1H), 8.62 (d, 1H), 7.92 (d, 2H), 7.86 (d, 1H), 7.83 (s, 1H), 7.80 (s, 1H), 7.70 (d, 2H), 7.52 (d, 1H), 2.63 (m, 4H), 2.32 (s, 3H), 2.28 (m, 4H), 2.23 (s, 3H). MS (ESI) 452.31 (M+H).

Example 10

2-(4-Hydroxypiperidin-1-yl)-4-(2-(4-(3-methyl-1H-1,2,4-triazol-1-yl)phenylamino)pyrimidin-4-yl)benzonitrile

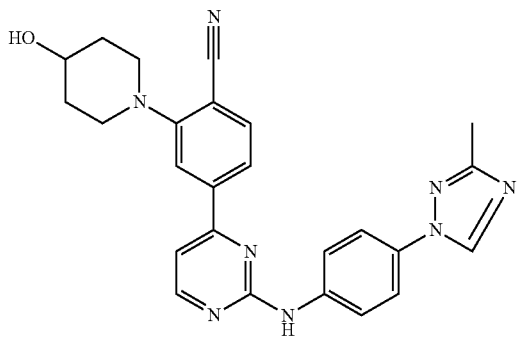 [SMILES: Cc1ncn(-c2ccc(Nc3nccc(-c4ccc(C#N)c(N5CCC(O)CC5)c4)n3)cc2)n1]

2-(4-Hydroxypiperidin-1-yl)-4-(2-(4-(3-methyl-1H-1,2,4-triazol-1-yl)phenylamino)pyrimidin-4-yl)benzonitrile was obtained by following procedure F using 2-fluoro-4-(2-(4-(3-methyl-1H-1,2,4-triazol-1-yl)phenylamino)pyrimidin-4-yl)benzonitrile and piperidin-4-ol. $^1$H NMR (DMSO-$d_6$, 400 MHz) δ 10.00 (s, 1H), 9.03 (s, 1H), 8.66 (d, 1H), 7.97 (d, 2H), 7.94 (s, 1H), 7.87 (d, 1H), 7.81 (d, 1H), 7.74 (d, 2H), 7.56 (d, 1H), 4.77 (d, 1H), 3.70 (m, 1H), 3.52 (m, 2H), 3.06 (m, 2H), 2.37 (s, 3H), 1.94 (m, 2H), 1.63 (m, 2H). MS (ESI) 453.18 (M+H).

Example 11

4-(2-(4-(3-Methyl-1H-1,2,4-triazol-1-yl)phenylamino)pyrimidin-4-yl)-2-(piperidin-1-yl)benzonitrile

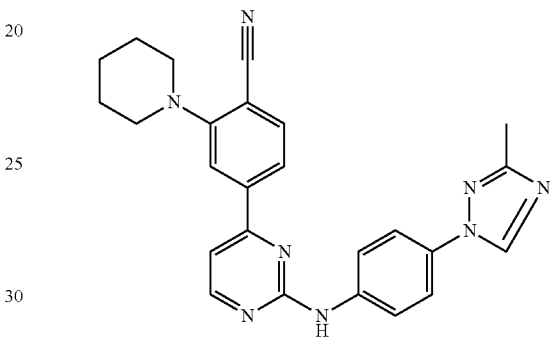

4-(2-(4-(3-Methyl-1H-1,2,4-triazol-1-yl)phenylamino)pyrimidin-4-yl)-2-(piperidin-1-yl)benzonitrile was obtained by following procedure F using 2-fluoro-4-(2-(4-(3-methyl-1H-1,2,4-triazol-1-yl)phenylamino)pyrimidin-4-yl)benzonitrile and piperidine. $^1$H NMR (DMSO-$d_6$, 400 MHz) δ 9.93 (s, 1H), 9.04 (s, 1H), 8.66 (d, 1H), 7.97 (d, 2H), 7.91 (s, 1H), 7.86 (d, 1H), 7.82 (d, 1H), 7.74 (d, 2H), 7.56 (d, 1H), 3.25 (m, 4H), 2.37 (s, 3H), 1.74 (m, 4H), 1.60 (m, 2H). MS (ESI) 437.27 (M+H).

Example 12

4-(2-(4-(3-Methyl-1H-1,2,4-triazol-1-yl)phenylamino)pyrimidin-4-yl)-2-(pyrrolidin-1-yl)benzonitrile

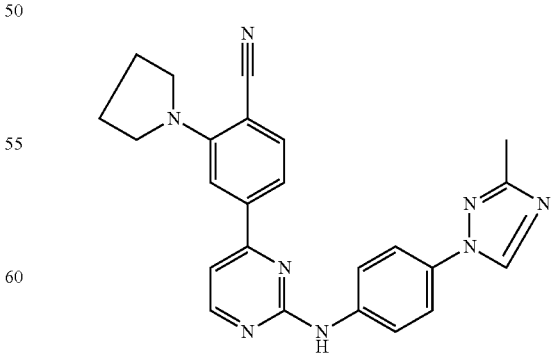

4-(2-(4-(3-Methyl-1H-1,2,4-triazol-1-yl)phenylamino)pyrimidin-4-yl)-2-(pyrrolidin-1-yl)benzonitrile was obtained by following procedure F using 2-fluoro-4-(2-(4-(3- methyl-1H-1,2,4-triazol-1-yl)phenylamino)pyrimidin-4-yl)benzonitrile and pyrrolidine. $^1$H NMR (DMSO-d$_6$, 400 MHz) δ 9.99 (s, 1H), 9.04 (s, 1H), 8.64 (d, 1H), 7.98 (d, 2H), 7.74 (d, 2H), 7.67 (d, 1H), 7.57 (s, 1H), 7.51 (d, 1H), 7.44 (d, 1H), 3.65 (m, 4H), 2.37 (s, 3H), 2.01 (m, 4H). MS (ESI) 423.29 (M+H).

Example 13

2-(Benzylamino)-4-(2-(4-(3-methyl-1H-1,2,4-triazol-1-yl)phenylamino)pyrimidin-4-yl)benzonitrile

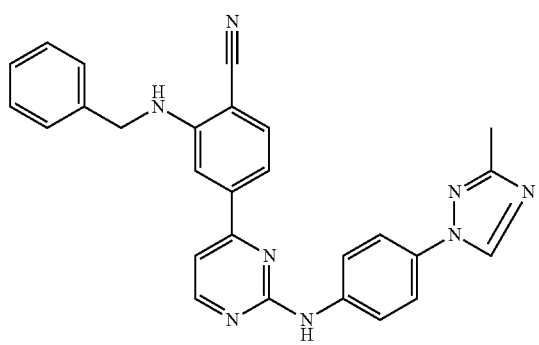 [SMILES: Cc1ncn(-c2ccc(Nc3nccc(-c4ccc(C#N)c(NCc5ccccc5)c4)n3)cc2)n1]

2-(Benzylamino)-4-(2-(4-(3-methyl-1H-1,2,4-triazol-1-yl)phenylamino)pyrimidin-4-yl)benzonitrile was obtained by following procedure F using 2-fluoro-4-(2-(4-(3-methyl-1H-1,2,4-triazol-1-yl)phenylamino)pyrimidin-4-yl)benzonitrile and benzylamine. $^1$H NMR (DMSO-d$_6$, 400 MHz) δ 9.94 (s, 1H), 9.03 (s, 1H), 8.60 (d, 2H), 7.92 (d, 2H), 7.71 (d, 2H), 7.68 (d, 1H), 7.39 (m, 3H), 7.31 (m, 4H), 7.20 (m, 1H), 7.10 (m, 1H), 4.59 (d, 1H), 2.34 (s, 3H). MS (ESI) 459.19 (M+H).

Example 14

2-(Diethylamino)-4-(2-(4-(3-methyl-1H-1,2,4-triazol-1-yl)phenylamino)pyrimidin-4-yl)benzonitrile

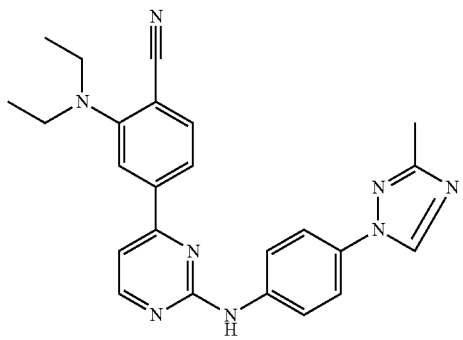 [SMILES: CCN(CC)c1cc(-c2ccnc(Nc3ccc(-n4cnc(C)n4)cc3)n2)ccc1C#N]

2-(Diethylamino)-4-(2-(4-(3-methyl-1H-1,2,4-triazol-1-yl)phenylamino)pyrimidin-4-yl)benzonitrile was obtained by following procedure F using 2-fluoro-4-(2-(4-(3-methyl-1H-1,2,4-triazol-1-yl)phenylamino)pyrimidin-4-yl)benzonitrile and diethylamine $^1$H NMR (CDCl$_3$, 400 MHz) δ 8.57 (d, 1H), 8.40 (s, 1H), 7.86 (d, 2H), 7.72 (s, 1H), 7.66 (d, 1H), 7.62 (d, 2H), 7.41 (d, 1H), 7.34 (s, 1H), 7.21 (d, 1H), 3.55 (q, 4H), 2.53 (s, 3H), 1.29 (t, 6H). MS (ESI) 425.28 (M+H).

Example 15

2-(Dimethylamino)-4-(2-(4-(3-methyl-1H-1,2,4-triazol-1-yl) phenylamino)pyrimidin-4-yl)benzonitrile

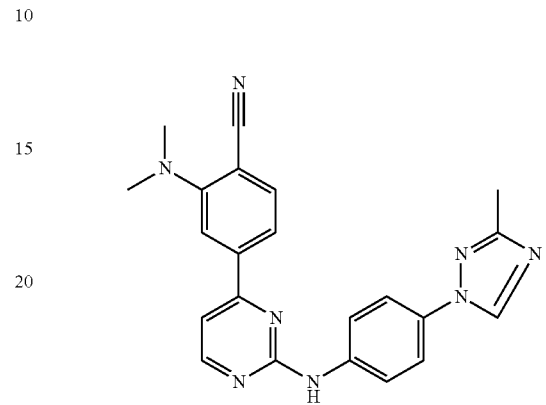

2-(Dimethylamino)-4-(2-(4-(3-methyl-1H-1,2,4-triazol-1-yl)phenylamino)pyrimidin-4-yl)benzonitrile was obtained by following procedure F using 2-fluoro-4-(2-(4-(3-methyl-1H-1,2,4-triazol-1-yl)phenylamino)pyrimidin-4-yl)benzonitrile and dimethylamine (THF solution). $^1$H NMR (CDCl$_3$, 400 MHz) δ 8.58 (d, 1H), 8.41 (s, 1H), 7.87 (d, 2H), 7.70 (d, 1H), 7.66 (d, 2H), 7.45 (d, 1H), 7.29 (s, 1H), 7.22 (d, 1H), 3.20 (s, 6H), 2.53 (s, 3H). MS (ESI) 397.30 (M+H).

Example 16

2-(Isopropylamino)-4-(2-(4-(3-methyl-1H-1,2,4-triazol-1-yl)phenylamino)pyrimidin-4-yl)benzonitrile

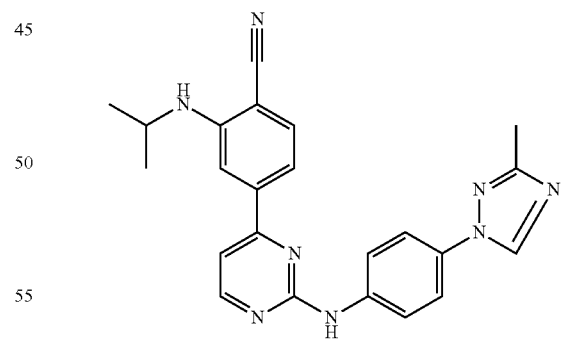

2-(Isopropylamino)-4-(2-(4-(3-methyl-1H-1,2,4-triazol-1-yl)phenylamino)pyrimidin-4-yl)benzonitrile was obtained by following procedure F using 2-fluoro-4-(2-(4-(3-methyl-1H-1,2,4-triazol-1-yl)phenylamino)pyrimidin-4-yl)benzonitrile and isopropylamine. $^1$H NMR (CDCl$_3$, 400 MHz) δ 8.54 (d, 1H), 8.37 (s, 1H), 7.84 (d, 2H), 7.60 (d, 2H), 7.51 (d, 1H), 7.47 (s, 1H), 7.44 (s, 1H), 7.24 (dd, 1H), 7.17 (d, 1H), 4.53 (d, 1H), 3.87 (m, 1H), 2.50 (s, 3H), 1.33 (d, 6H). MS (ESI) 411.23 (M+H).

Example 17

2-(3-Hydroxypiperidin-1-yl)-4-(2-(4-(3-methyl-1H-1,2,4-triazol-1-yl)phenylamino)pyrimidin-4-yl)benzonitrile

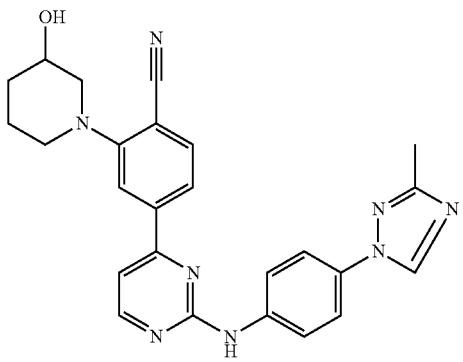 [SMILES: Cc1ncn(-c2ccc(Nc3nccc(-c4ccc(C#N)c(N5CCCC(O)C5)c4)n3)cc2)n1]

2-(3-Hydroxypiperidin 1-yl)-4-(2-(4-(3-methyl-1H-1,2,4-triazol-1-yl)phenylamino)pyrimidin-4-yl)benzonitrile was obtained by following procedure F using 2-fluoro-4-(2-(4-(3-methyl-1H-1,2,4-triazol-1-yl)phenylamino)pyrimidin-4-yl)benzonitrile and piperidin-3-ol. $^1$H NMR (DMSO-d$_6$, 400 MHz) δ 10.03 (s, 1H), 9.02 (s, 1H), 8.66 (d, 1H), 7.99 (d, 2H), 7.96 (d, 1H), 7.87 (d, 1H), 7.82 (d, 1H), 7.75 (d, 2H), 7.57 (d, 1H), 5.03 (d, 1H), 3.72 (m, 1H), 3.62 (m, 1H), 3.50 (m, 1H), 2.85 (m 1H), 2.72 (m, 1H), 2.37 (s, 3H), 1.97 (m, 1H), 1.85 (m, 1H), 1.65 (m, 1H), 1.30 (m, 1H). MS (ESI) 453.13 (M+H).

Example 18

2-Fluoro-5-(2-(4-(3-methyl-1H-1,2,4-triazol-1-yl)phenylamino)pyrimidin-4-yl)benzonitrile

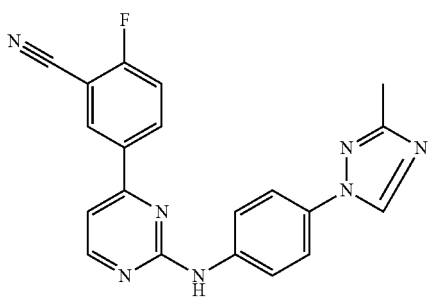 [SMILES: Cc1ncn(-c2ccc(Nc3nccc(-c4ccc(F)c(C#N)c4)n3)cc2)n1]

Part I

2-Fluoro-5-(4,4,5,5-tetramethyl-1,3,2-dioxaborolan-2-yl)benzonitrile

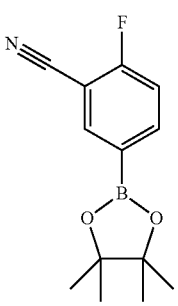 [SMILES: CC1(C)OB(c2ccc(F)c(C#N)c2)OC1(C)C]

2-Fluoro-5-(4,4,5,5-tetramethyl-1,3,2-dioxaborolan-2-yl)benzonitrile was obtained by following procedure A using 5-bromo-2-fluorobenzonitrile and bis(pinacolato)diboron. $^1$H NMR (CDCl$_3$, 400 MHz) δ 8.10 (d, 1H), 8.05 (m, 1H), 7.23 (t, 1H), 1.37 (s, 12H).

Part II 5-(2-Chloropyrimidin-4-yl)-2-fluorobenzonitrile

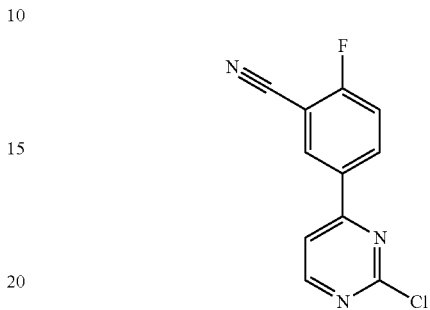

5-(2-Chloropyrimidin-4-yl)-2-fluorobenzonitrile was obtained by following procedure B using 2-fluoro-5-(4,4,5,5-tetramethyl-1,3,2-dioxaborolan-2-yl)benzonitrile and 2,4-dicholorrpyrimidine. $^1$H NMR (CDCl$_3$, 400 MHz) δ 8.53 (d, 1H), 8.21 (m, 1H), 8.15 (m, 1H), 7.43 (d, 1H), 7.19 (t, 1H).

Part III

2-Fluoro-5-(2-(4-(3-methyl-1H-1,2,4-triazol-1-yl)phenylamino)pyrimidin-4-yl)benzonitrile was obtained by following procedure E using 5-(2-chloropyrimidin-4-yl)-2-fluorobenzonitrile and 4-(3-methyl-1H-1,2,4-triazol-1-yl)aniline. $^1$H NMR (DMSO-d$_6$, 400 MHz) δ 10.02 (s, 1H), 9.05 (s, 1H), 8.72 (d, 1H), 8.67 (d, 1H), 8.50 (m, 1H), 7.96 (d, 2H), 7.76 (m, 3H), 7.58 (d, 1H). MS (ESI) 372.20 (M+H).

Example 19

5-(2-(4-(3-Methyl-1H-1,2,4-triazol-1-yl)phenylamino)pyrimidin-4-yl)-2-morpholinobenzonitrile

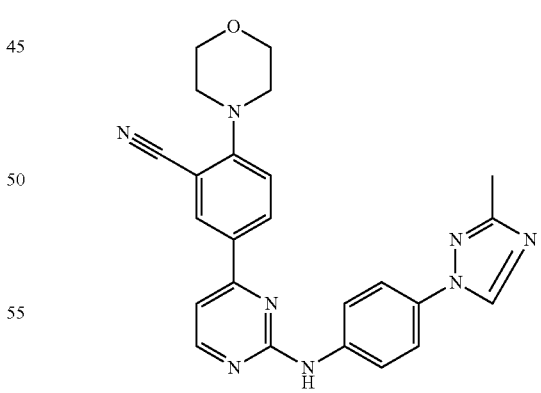

5-(2-(4-(3-Methyl-1H-1,2,4-triazol-1-yl)phenylamino)pyrimidin-4-yl)-2-morpholinobenzonitrile was obtained by following procedure F using 2-fluoro-5-(2-(4-(3-methyl-1H-1,2,4-triazol-1-yl)phenylamino)pyrimidin-4-yl)benzonitrile and morpholine. $^1$H NMR (DMSO-d$_6$, 400 MHz) δ 9.98 (s, 1H), 9.10 (s, 1H), 8.64 (d, 1H), 8.58 (dd, 1H), 8.47 (d, 1H), 8.02 (d, 2H), 7.80 (d, 2H), 7.57 (d, 1H), 7.39 (d, 1H), 3.86 (m, 4H), 3.37 (m, 4H), 2.42 (s, 3H). MS (ESI) 439.31 (M+H).

Example 20

5-(2-(4-(3-Methyl-1H-1,2,4-triazol-1-yl)phenylamino)pyrimidin-4-yl)-2-(4-methylpiperazin-1-yl)benzonitrile

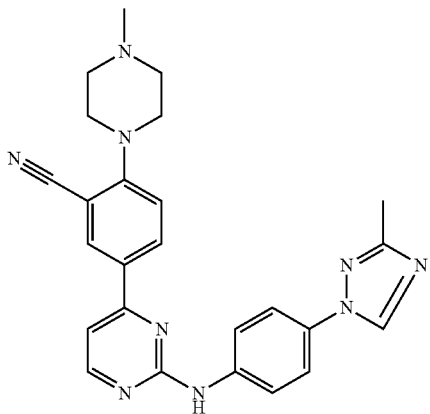 [SMILES: Cc1ncn(-c2ccc(Nc3nccc(-c4ccc(N5CCN(C)CC5)c(C#N)c4)n3)cc2)n1]

5-(2-(4-(3-Methyl-1H-1,2,4-triazol-1-yl)phenylamino)pyrimidin-4-yl)-2-(4-methylpiperazin-1-yl)benzonitrile was obtained by following procedure F using 2-fluoro-5-(2-(4-(3-methyl-1H-1,2,4-triazol-1-yl)phenylamino)pyrimidin-4-yl)benzonitrile and 1-methylpiperazine. $^1$H NMR (DMSO-d$_6$, 400 MHz) δ 9.91 (s, 1H), 9.04 (s, 1H), 8.58 (d, 1H), 8.50 (d, 1H), 8.38 (dd, 1H), 7.96 (d, 2H), 7.74 (d, 2H), 7.49 (d, 1H), 7.30 (d, 1H), 3.32 (m, 4H), 2.52 (m, 4H), 2.37 (s, 3H), 2.26 (s, 3H). MS (ESI) 452.28 (M+H).

Example 21

2-(4-Hydroxypiperidin-1-yl)-5-(2-(4-(3-methyl-1H-1,2,4-triazol-1-yl)phenylamino)pyrimidin-4-yl)benzonitrile

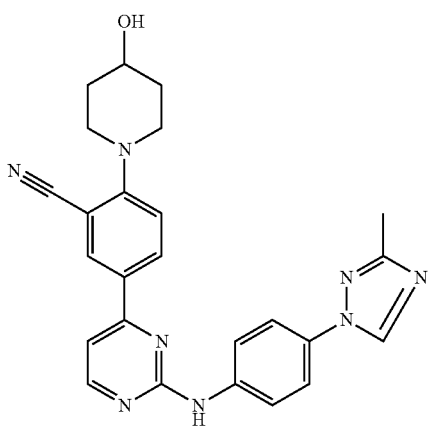 [SMILES: Cc1ncn(-c2ccc(Nc3nccc(-c4ccc(N5CCC(O)CC5)c(C#N)c4)n3)cc2)n1]

2-(4-Hydroxypiperidin 1-yl)-5-(2-(4-(3-methyl-1H-1,2,4-triazol-1-yl)phenylamino)pyrimidin-4-yl)benzonitrile was obtained by following procedure F using 2-fluoro-5-(2-(4-(3-methyl-1H-1,2,4-triazol-1-yl)phenylamino)pyrimidin-4-yl)benzonitrile and piperidin-4-ol. $^1$H NMR (DMSO-d$_6$, 400 MHz) δ 9.90 (s, 1H), 9.04 (s, 1H), 8.57 (d, 1H), 8.48 (d, 1H), 8.35 (d, 1H), 7.96 (d, 2H), 7.74 (d, 2H), 7.48 (d, 1H), 7.30 (d, 1H), 4.80 (brs, 1H), 3.72 (m, 1H), 3.55 (m, 2H), 3.10 (m, 2H), 2.37 (s, 3H), 1.90 (m, 2H), 1.57 (m, 2H). MS (ESI) 453.25 (M+H).

Example 22

5-(2-(4-(3-Methyl-1H-1,2,4-triazol-1-yl)phenylamino)pyrimidin-4-yl)-2-(piperidin-1-yl)benzonitrile

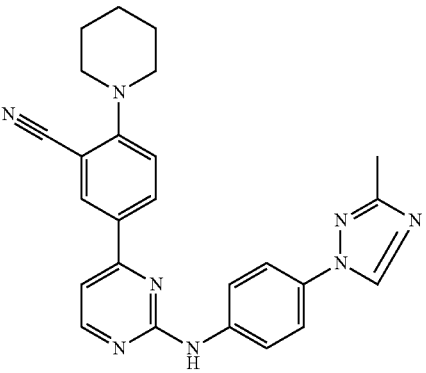 [SMILES: Cc1ncn(-c2ccc(Nc3nccc(-c4ccc(N5CCCCC5)c(C#N)c4)n3)cc2)n1]

5-(2-(4-(3-Methyl-1H-1,2,4-triazol-1-yl)phenylamino)pyrimidin-4-yl)-2-(piperidin-1-yl)benzonitrile was obtained by following procedure F using 2-fluoro-5-(2-(4-(3-methyl-1H-1,2,4-triazol-1-yl)phenylamino)pyrimidin-4-yl)benzonitrile and piperidine. $^1$H NMR (DMSO-d$_6$, 400 MHz) δ 9.71 (s, 1H), 8.85 (s, 1H), 8.37 (d, 1H), 8.28 (d, 1H), 8.18 (dd, 1H), 7.77 (d, 2H), 7.54 (d, 2H), 7.29 (d, 1H), 7.09 (d, 1H), 3.11 (m, 4H), 2.17 (s, 3H), 1.51 (m, 4H), 1.40 (m, 2H). MS (ESI) 437.28 (M+H).

Example 23

2-(Diethylamino)-5-(2-(4-(3-methyl-1H-1,2,4-triazol-1-yl)phenylamino)pyrimidin-4-yl)benzonitrile

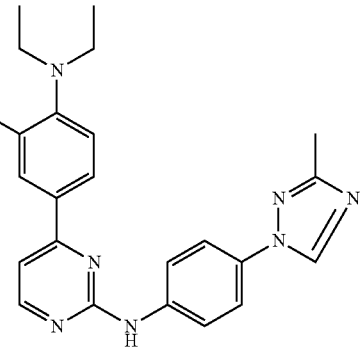

2-(Diethylamino)-5-(2-(4-(3-methyl-1H-1,2,4-triazol-1-yl)phenylamino)pyrimidin-4-yl)benzonitrile was obtained by following procedure F using 2-fluoro-5-(2-(4-(3-methyl-1H-1,2,4-triazol-1-yl)phenylamino)pyrimidin-4-yl)benzonitrile and diethylamine. $^1$H NMR (CDCl$_3$, 400 MHz) δ 8.47 (d, 1H), 8.42 (s, 1H), 8.26 (d, 1H), 8.12 (dd, 1H), 7.85 (d, 2H), 7.65 (d, 2H), 7.26 (d, 1H), 7.11 (d, 1H), 6.95 (d, 1H), 3.63 (q, 4H), 2.53 (s, 3H), 1.32 (t, 6H). MS (ESI) 425.39 (M+H).

Example 24

2-(Tert-butylamino)-5-(2-(4-(3-methyl-1H-1,2,4-triazol-1-yl)phenylamino)pyrimidin-4-yl)benzonitrile

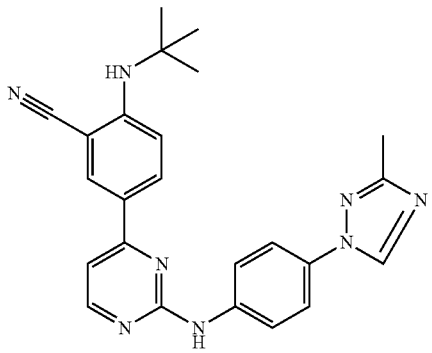 [SMILES: Cc1ncn(-c2ccc(Nc3nccc(-c4ccc(NC(C)(C)C)c(C#N)c4)n3)cc2)n1]

2-(Tert-butylamino)-5-(2-(4-(3-methyl-1H-1,2,4-triazol-1-yl)phenylamino)pyrimidin-4-yl)benzonitrile was obtained by following procedure F using 2-fluoro-5-(2-(4-(3-methyl-1H-1,2,4-triazol-1-yl)phenylamino)pyrimidin-4-yl)benzonitrile and t-butylamine. $^1$H NMR (CDCl$_3$, 400 MHz) δ 10.60 (brs, 1H), 8.80 (brs, 1H), 8.15 (brs, 1H), 8.10 (s, 1H), 8.08 (s, 1H), 7.82 (d, 2H), 7.64 (d, 2H), 3.42 (s, 3H), 1.45 (s, 9H). MS (ESI) 425.15 (M+H).

Example 25

2-(3-Hydroxypiperidin-1-yl)-5-(2-(4-(3-methyl-1H-1,2,4-triazol-1-yl)phenylamino)pyrimidin-4-yl)benzonitrile

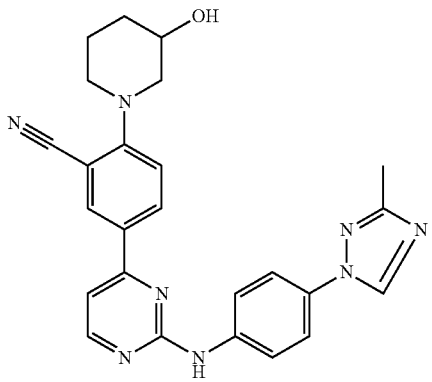 [SMILES: Cc1ncn(-c2ccc(Nc3nccc(-c4ccc(N5CCCC(O)C5)c(C#N)c4)n3)cc2)n1]

2-(3-Hydroxypiperidin 1-yl)-5-(2-(4-(3-methyl-1H-1,2,4-triazol-1-yl)phenylamino)pyrimidin-4-yl)benzonitrile was obtained by following procedure F using 2-fluoro-5-(2-(4-(3-methyl-1H-1,2,4-triazol-1-yl)phenylamino)pyrimidin-4-yl)benzonitrile and piperidin-3-ol. $^1$H NMR (DMSO-d$_6$, 400 MHz) δ 9.78 (s, 1H), 8.92 (s, 1H), 8.44 (d, 1H), 8.35 (d, 1H), 8.24 (dd, 1H), 7.84 (d, 2H), 7.62 (d, 2H), 7.36 (d, 1H), 7.17 (d, 1H), 4.84 (d, 1H), 3.55 (m, 2H), 3.43 (m, 1H), 2.85 (m, 1H), 2.67 (m 1H), 2.24 (s, 3H), 1.85 (m, 1H), 1.70 (m, 1H), 1.50 (m, 1H), 1.20 (m, 1H). MS (ESI) 453.16 (M+H).

Example 26

2-(3-(Hydroxymethyl)piperidin-1-yl)-5-(2-(4-(3-methyl-1H-1,2,4-triazol-1-yl)phenylamino)pyrimidin-4-yl)benzonitrile

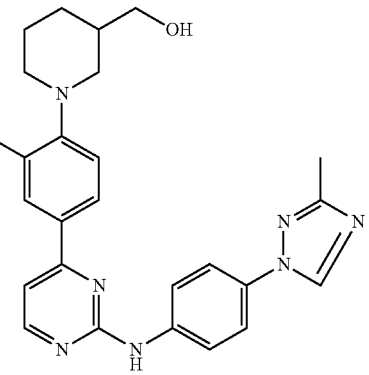

2-(3-(Hydroxymethyl)piperidin-1-yl)-5-(2-(4-(3-methyl-1H-1,2,4-triazol-1-yl)phenylamino)pyrimidin-4-yl)benzonitrile was obtained by following procedure F using 2-fluoro-5-(2-(4-(3-methyl-1H-1,2,4-triazol-1-yl)phenylamino)pyrimidin-4-yl)benzonitrile and piperidin-3-ylmethanol. $^1$H NMR (DMSO-d$_6$, 400 MHz) δ 9.91 (s, 1H), 9.04 (s, 1H), 8.57 (d, 1H), 8.48 (d, 1H), 8.38 (dd, 1H), 7.97 (d, 2H), 7.74 (d, 2H), 7.49 (d, 1H), 7.28 (d, 1H), 4.58 (m, 1H), 3.68 (m, 2H), 3.40 (m, 2H), 2.95 (m, 1H), 2.72 (m 1H), 2.55 (s, 2H), 2.37 (s, 3H), 1.65 (m, 1H), 1.18 (m, 1H). MS (ESI) 467.27 (M+H).

Example 27

2-(4-Benzyl-4-hydroxypiperidin-1-yl)-5-(2-(4-(3-methyl-1H-1,2,4-triazol-1-yl)phenylamino)pyrimidin-4-yl)benzonitrile

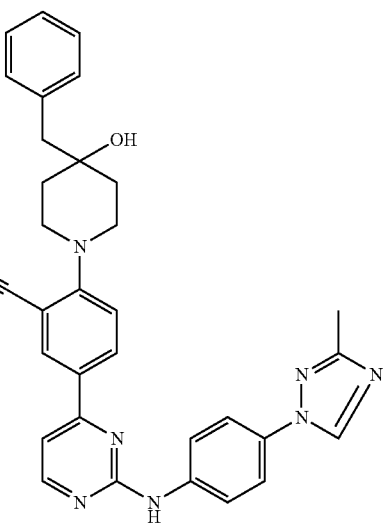

2-(4-Benzyl-4-hydroxypiperidin-1-yl)-5-(2-(4-(3-methyl-1H-1,2,4-triazol-1-yl)phenylamino)pyrimidin-4-yl)benzonitrile was obtained by following procedure F using 2-fluoro-5-(2-(4-(3-methyl-1H-1,2,4-triazol-1-yl)phenylamino)pyrimidin-4-yl)benzonitrile and 4-benzylpiperidin-4-ol. $^1$H NMR (CDCl$_3$, 400 MHz) δ 8.40 (d, 1H), 8.32 (s, 1H), 8.19 (s, 1H), 8.08 (d, 1H), 7.74 (d, 2H), 7.54 (d, 2H), 7.38 (s, 1H), 7.28 (m, 2H), 7.23 (d, 1H), 7.19 (m, 3H), 7.03 (d, 1H), 7.01 (d, 1H), 3.49 (m, 2H), 3.18 (m, m, 2H), 2.78 (s, 2H), 2.43 (s, 3H), 1.90 (m, 1H), 1.63 (m, 2H). MS (ESI) 543.12 (M+H).

Example 28

5-(2-(4-(3-Methyl-1H-1,2,4-triazol-1-yl)phenylamino)pyrimidin-4-yl)-2-(4-phenylpiperidin-1-yl)benzonitrile

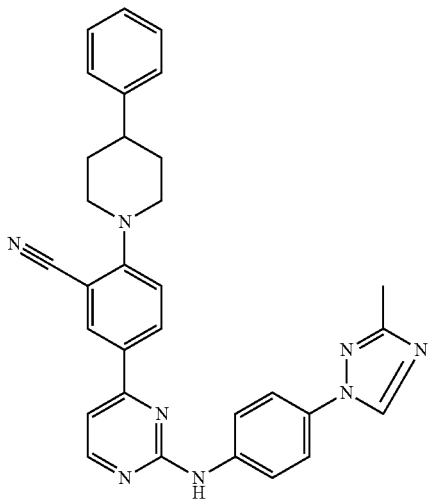 [SMILES: Cc1ncn(-c2ccc(Nc3nccc(-c4ccc(N5CCC(c6ccccc6)CC5)c(C#N)c4)n3)cc2)n1]

5-(2-(4-(3-Methyl-1H-1,2,4-triazol-1-yl)phenylamino)pyrimidin-4-yl)-2-(4-phenylpiperidin-1-yl)benzonitrile was obtained by following procedure F using 2-fluoro-5-(2-(4-(3-methyl-1H-1,2,4-triazol-1-yl)phenylamino)pyrimidin-4-yl)benzonitrile and 4-phenylpiperidine. $^1$H NMR (DMSO-d$_6$, 400 MHz) δ 9.92 (s, 1H), 9.05 (s, 1H), 8.58 (d, 1H), 8.52 (d, 1H), 8.40 (dd, 1H), 7.98 (d, 2H), 7.75 (d, 2H), 7.51 (d, 1H), 7.35 (m, 5H), 7.22 (m, 1H), 3.86 (m, 2H), 3.10 (m, 2H), 2.80 (m, 1H), 2.37 (s, 3H), 1.95 (m, 2H), 1.85 (m, 2H). MS (ESI) 513.32 (M+H).

Example 29

5-(2-(4-(3-Methyl-1H-1,2,4-triazol-1-yl)phenylamino)pyrimidin-4-yl)-2-(1,4-dioxa-8-azaspiro[4.5]decan-8-yl)benzonitrile

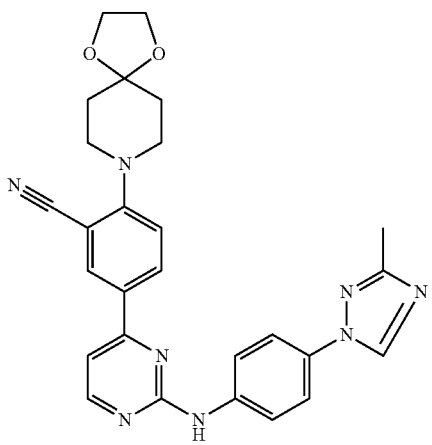 [SMILES: Cc1ncn(-c2ccc(Nc3nccc(-c4ccc(N5CCC6(CC5)OCCO6)c(C#N)c4)n3)cc2)n1]

5-(2-(4-(3-Methyl-1H-1,2,4-triazol-1-yl)phenylamino)pyrimidin-4-yl)-2-(1,4-dioxa-8-azaspiro[4.5]decan-8-yl)benzonitrile was obtained by following procedure F using 2-fluoro-5-(2-(4-(3-methyl-1H-1,2,4-triazol-1-yl)phenylamino)pyrimidin-4-yl)benzonitrile and 1,4-dioxa-8-azaspiro[4.5]decane. $^1$H NMR (DMSO-d$_6$, 400 MHz) δ 9.91 (s, 1H), 9.05 (s, 1H), 8.58 (d, 1H), 8.50 (d, 1H), 8.38 (dd, 1H), 7.96 (d, 2H), 7.74 (d, 2H), 7.50 (d, 1H), 7.35 (d, 1H), 3.95 (s, 4H), 3.41 (m, 4H), 2.37 (s, 3H), 1.83 (m, 4H). MS (ESI) 495.15 (M+H).

Example 30

5-(2-(4-(3-Methyl-1H-1,2,4-triazol-1-yl)phenylamino)pyrimidin-4-yl)-2-phenoxybenzonitrile

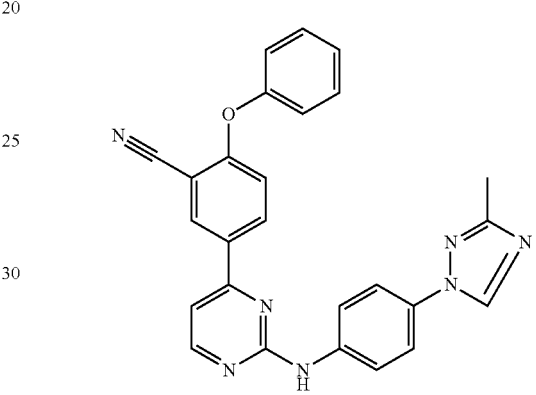

5-(2-(4-(3-Methyl-1H-1,2,4-triazol-1-yl)phenylamino)pyrimidin-4-yl)-2-phenoxybenzonitrile was obtained by following procedure F using 2-fluoro-5-(2-(4-(3-methyl-1H-1,2,4-triazol-1-yl)phenylamino)pyrimidin-4-yl)benzonitrile and phenol with microwave irradiation. $^1$H NMR (CDCl$_3$, 400 MHz) δ 8.46 (d, 1H), 8.32 (s, 1H), 8.31 (d, 1H), 8.10 (d, 1H), 7.74 (d, 2H), 7.55 (d, 2H), 7.40 (m, 2H), 7.29 (s, 1H), 7.25 (d, 1H), 7.08 (m, 3H), 6.88 (d, 1H), 2.43 (s, 3H). MS (ESI) 446.26 (M+H).

Example 31

2-Methoxy-5-(2-(4-(3-methyl-1H-1,2,4-triazol-1-yl)phenylamino)pyrimidin-4-ylbenzonitrile

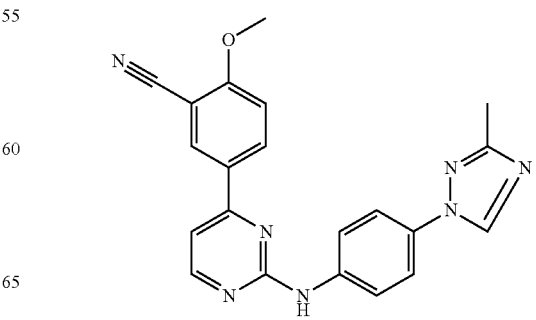

2-Methoxy-5-(2-(4-(3-methyl-1H-1,2,4-triazol-1-yl)phenylamino)pyrimidin-4-yl)benzonitrile was obtained by following procedure F using 2-fluoro-5-(2-(4-(3-methyl-1H-1,2,4-triazol-1-yl)phenylamino)pyrimidin-4-yl)benzonitrile and MeONa in the absence of $K_2CO_3$. $^1$H NMR (CDCl$_3$, 400 MHz) δ 8.55 (s, 1H), 8.34 (d, 1H), 8.11 (s, 1H), 7.99 (d, 1H), 7.64 (d, 2H), 7.47 (d, 2H), 6.95 (m, 2H), 3.61 (s, 3H), 2.46 (s, 3H). MS (ESI) 384.23 (M+H).

Example 32

2-(2-(4-(3-Methyl-1H-1,2,4-triazol-1-yl)phenylamino)pyrimidin-4-yl)-4-morpholinobenzonitrile

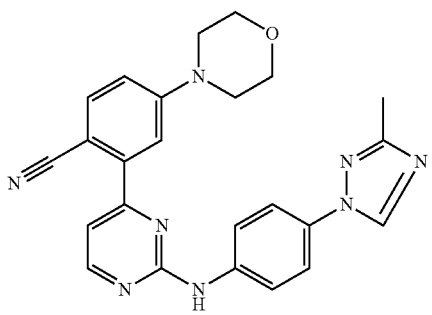 [SMILES: Cc1ncn(-c2ccc(Nc3nccc(-c4cc(N5CCOCC5)ccc4C#N)n3)cc2)n1]

Part I 4-methoxy-N-(4-(3-methyl-1H-1,2,4-triazol-1-yl)phenyl)pyrimidin-2-amine

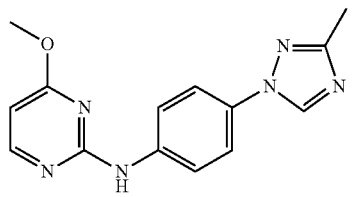 [SMILES: COc1ccnc(Nc2ccc(-n3cnc(C)n3)cc2)n1]

To a solution 2-chloro-4-methoxypyrimidine (2 g, 13.8 mmol) in ethoxyethanol (50 mL) was added 4-(3-methyl-1H-1,2,4-triazol-1-yl)aniline (1.7 g, 10.6 mmol). The reaction was warmed to 75° C. for 16 h, cooled, and diluted with water and EtOAc. The layers were separated, and the aqueous layer was extracted with EtOAc (4×). The combined organics were dried (MgSO$_4$), and concentrated to give a near colorless solid which was homogeneous by analytical HPLC analysis and was used without further purification.

Part II 4-chloro-N-(4-(3-methyl-1H-1,2,4-triazol-1-yl)phenyl)pyrimidin-2-amine

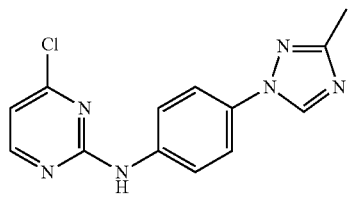 [SMILES: Cc1ncn(-c2ccc(Nc3nccc(Cl)n3)cc2)n1]

A solution 4-methoxy-N-(4-(3-methyl-1H-1,2,4-triazol-1-yl)phenyl)pyrimidin-2-amine (4 g, 14.2 mmol) in conc. HCl (50 mL) was aged at 90° C. until starting material was consumed as judged by analytical HPLC analysis (~12 h). The reaction was concentrated in vacuo to give a near colorless solid which was triturated with Et$_2$O, dried in vacuo, and used without further purification.

The crude solid residue was added to POCl$_3$ (50 mL) and warmed to 90° C. until starting material was consumed as judged by analytical HPLC analysis. The resulting solution was concentrated in vacuo to give a yellow residue which was dissolved in EtOAc and carefully neutralized with saturated aqueous NaHCO$_3$ solution. The layers were separated, and the aqueous layer was extracted with EtOAc (2×). The combined organics were dried (MgSO$_4$) and concentrated to give the title compound as a pale yellow solid (~3 g) which was used without further purification.

Part III

N-(4-(3-methyl-1H-1,2,4-triazol-1-yl)phenyl)-4-(trimethylstannyl)pyrimidin-2-amine

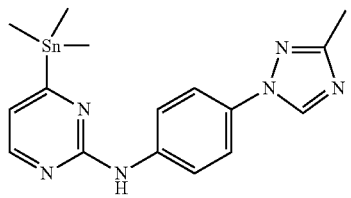 [SMILES: Cc1ncn(-c2ccc(Nc3ncc[c]([Sn]([CH3])([CH3])[CH3])n3)cc2)n1]

A mixture of 4-chloro-N-(4-(3-methyl-1H-1,2,4-triazol-1-yl)phenyl)pyrimidin-2-amine (3.0 g, 10.5 mmol), hexamethyldistannane (3.3 mL, 15.5 mmol), Pd(PPh$_3$)$_4$ (1.21 g, 1.1 mmol) and THF (100 mL) was degassed and heated to 80° C. for 12 h under argon. The reaction mixture was diluted with EtOAc and washed with brine. The organic layer was separated, dried (MgSO$_4$), and concentrated to afford N-(4-(3-methyl-1H-1,2,4-triazol-1-yl)phenyl)-4-(trimethylstannyl)pyrimidin-2-amine which was used without further purification. MS (ESI) 417.0 (M+H).

Part IV

2-Bromo-4-morpholinobenzonitrile

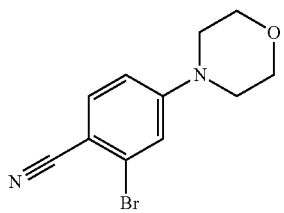 [SMILES: N#Cc1ccc(N2CCOCC2)cc1Br]

2-Bromo-4-morpholinobenzonitrile was obtained by following procedure F using 2-bromo-4-fluorobenzonitrile and morpholine. $^1$H NMR (CDCl$_3$, 400 MHz) δ 7.47 (d, 1H), 7.06 (d, 1H), 6.78 (dd, 1H), 3.84 (m, 4H), 3.29 (m, 4H). MS (ESI) 267.14 & 269.17 (M+H).

Part V

General Procedure G

Stille Coupling of Substituted Phenyl Bromide with Alkyl Trimethylstannane

A mixture of 2-bromo-4-morpholinobenzonitrile (0.080 g, 0.30 mmol), N-(4-(3-methyl-1H-1,2,4-triazol-1-yl)phenyl)-4-(trimethylstannyl)pyrimidin-2-amine (0.13 g, 0.30 mmol) and Pd(PPh$_3$)$_4$ (0.035 g, 0.03 mmol) in THF (2 mL) was heated in a sealed tube at 90° C. overnight. The reaction mixture was cooled down to room temperature and filtered. The filtrate was concentrated to a yellow solid. Purification of this material by column chromatography on silica gel (85% EtOAc/hexane) provided the desired product as a yellow solid. $^1$H NMR (CDCl$_3$, 400 MHz) δ 8.50 (d, 1H), 8.31 (s, 1H), 7.74 (d, 2H), 7.71 (d, 1H), 7.58 (d, 1H), 7.49 (d, 2H), 7.21 (d, 1H), 7.17 (d, 1H), 6.87 (dd, 1H), 3.79 (m, 4H), 3.27 (m, 4H), 2.42 (s, 3H). MS (ESI) 439.30 (M+H).

Example 33

2-(2-(4-(3-Methyl-1H-1,2,4-triazol-1-yl)phenylamino)pyrimidin-4-yl)-5-morpholinobenzonitrile

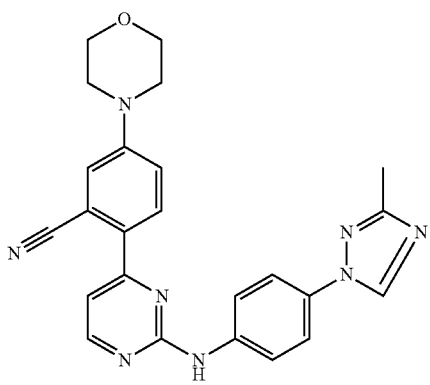 [SMILES: Cc1ncn(-c2ccc(Nc3nccc(-c4ccc(N5CCOCC5)cc4C#N)n3)cc2)n1]

2-Bromo-5-morpholinobenzonitrile

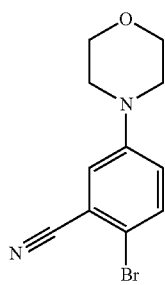 [SMILES: N#Cc1cc(N2CCOCC2)ccc1Br]

2-Bromo-5-morpholinobenzonitrile was made by following procedure F using 2-bromo-5-fluorobenzonitrile and morpholine. $^1$H NMR (CDCl$_3$, 400 MHz) δ 7.53 (d, 1H), 7.12 (d, 1H), 6.99 (dd, 1H), 3.88 (m, 4H), 3.18 (m, 4H). MS (ESI) 267.07 & 269.07 (M+H).

2-(2-(4-(3-Methyl-1H-1,2,4-triazol-1-yl)phenylamino)pyrimidin-4-yl)-5-morpholinobenzonitrile was obtained by following procedure G using N-(4-(3-methyl-1H-1,2,4-triazol-1-yl)phenyl)-4-(trimethylstannyl)pyrimidin-2-amine and 2-bromo-5-morpholinobenzonitrile. $^1$H NMR (CDCl$_3$, 400 MHz) δ 8.45 (d, 1H), 8.31 (s, 1H), 7.76 (m, 3H), 7.51 (d, 2H), 7.49 (s, 1H), 7.17 (s, 1H), 7.15 (d, 1H), 7.08 (dd, 1H), 3.81 (m, 4H), 3.22 (m, 4H), 2.42 (s, 3H). MS (ESI) 439.31 (M+H).

Example 34

2-(2-(4-(3-Methyl-1H-1,2,4-triazol-1-yl)phenylamino)pyrimidin-4-yl)-6-morpholinobenzonitrile

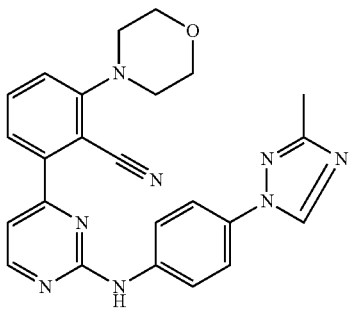 [SMILES: Cc1ncn(-c2ccc(Nc3nccc(-c4cccc(N5CCOCC5)c4C#N)n3)cc2)n1]

2-Bromo-6-morpholinobenzonitrile

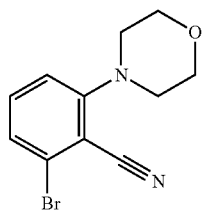 [SMILES: N#Cc1c(Br)cccc1N1CCOCC1]

2-Bromo-6-morpholinobenzonitrile was made by following procedure F using 2-bromo-6-fluorobenzonitrile and morpholine. $^1$H NMR (CDCl$_3$, 400 MHz) δ 7.36 (t, 1H), 7.31 (d, 1H), 6.98 (d, 1H), 3.92 (m, 4H), 3.24 (m, 4H). MS (ESI) 267.02 & 268.97 (M+H).

2-(2-(4-(3-Methyl-1H-1,2,4-triazol-1-yl)phenylamino)pyrimidin-4-yl)-6-morpholinobenzonitrile was obtained by following procedure G using N-(4-(3-methyl-1H-1,2,4-triazol-1-yl)phenyl)-4-(trimethylstannyl)pyrimidin-2-amine and 2-bromo-6-morpholinobenzonitrile. $^1$H NMR (CDCl$_3$, 400 MHz) δ 8.51 (d, 1H), 8.31 (s, 1H), 7.75 (d, 2H), 7.56 (m, 2H), 7.53 (d, 2H), 7.50 (d, 1H), 7.10 (m, 2H), 3.87 (m, 4H), 3.19 (m, 4H), 2.43 (s, 3H). MS (ESI) 439.27 (M+H).

Example 35

4-(Dimethylamino)-3-(2-(4-(3-methyl-1H-1,2,4-triazol-1-yl)phenylamino)pyrimidin-4-yl)benzonitrile

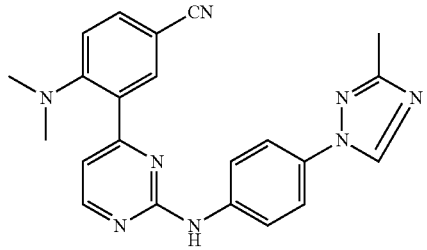 [SMILES: Cc1ncn(-c2ccc(Nc3nccc(-c4cc(C#N)ccc4N(C)C)n3)cc2)n1]

3-Bromo-4-(dimethylamino)benzonitrile

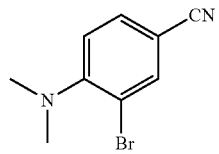

3-Bromo-4-(dimethylamino)benzonitrile was made by following procedure F using 3-bromo-4-fluorobenzonitrile and dimethylamine (THF solution). $^1$H NMR (CDCl$_3$, 400 MHz) δ 7.82 (d, 1H), 7.54 (dd, 1H), 7.03 (d, 1H), 2.94 (s, 6H). MS (ESI) 225.13 & 227.10 (M+H).

4-(Dimethylamino) 3-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-4-(dimethylamino)benzonitrile. $^1$H NMR (CDCl$_3$, 400 MHz) δ 8.65 (s, 1H), 8.22 (d, 1H), 7.88 (d, 1H), 7.86 (d, 2H), 7.62 (d, 2H), 7.59 (d, 1H), 7.23 (d, 1H), 7.05 (d, 1H), 2.82 (s, 6H), 2.48 (s, 3H). MS (ESI) 397.24 (M+H).

Example 36

4-(2-(4-(3-Tert-butyl-1H-1,2,4-triazol-1-yl)phenylamino)pyrimidin-4-yl)-2-fluorobenzonitrile

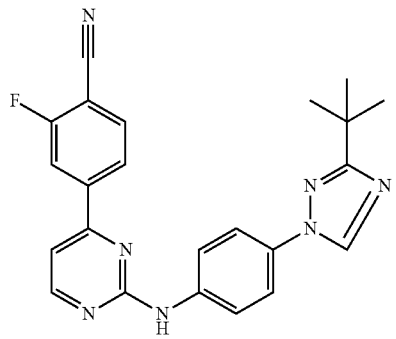 [SMILES: CC(C)(C)c1ncn(-c2ccc(Nc3nccc(-c4ccc(C#N)c(F)c4)n3)cc2)n1]

Part I

3-Tert-butyl-1H-1,2,4-triazole

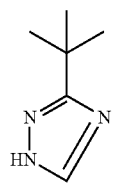

General Procedure H

Substituted Triazole Synthesis 3-tert-butyl-1H-1,2,4-triazole was obtained by following the general synthetic protocol described in Jones, R. G.; Ainsworth, C. *J. Am. Chem. Soc.*, 1955, 77, 1538 using thiosemicarbazide, pivaloyl chloride and nitric acid. $^1$H NMR (CDCl$_3$, 400 MHz) δ 8.01 (br s, 1H), 1.45 (s, 9H).

Part II

3-Tert-butyl-1-(4-nitrophenyl)-1H-1,2,4-triazole

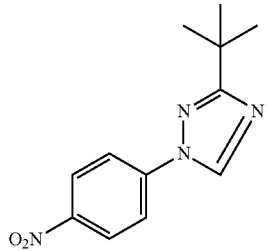 [SMILES: CC(C)(C)c1ncn(-c2ccc([N+](=O)[O-])cc2)n1]

3-Tert-butyl-1-(4-nitrophenyl)-1H-1,2,4-triazole was obtained as a single product by following procedure C using 3-tert-butyl-1H-1,2,4-triazole and 4-fluoro-1-nitrobenzene and no purification was necessary. $^1$H NMR (CDCl$_3$, 400 MHz) δ 8.60 (s, 1H), 8.39 (d, 2H), 7.92 (d, 2H), 1.47 (s, 9H).

Part III 4-(3-Tert-butyl-1H-1,2,4-triazol-1-yl)aniline

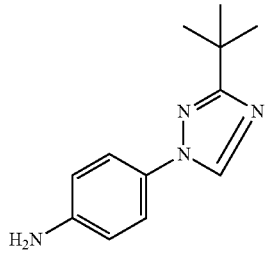

4-(3-Tert-butyl-1H-1,2,4-triazol-1-yl)aniline was obtained by following procedure D from 3-tert-butyl-1-(4-nitrophenyl)-1H-1,2,4-triazole. $^1$H NMR (CDCl$_3$, 400 MHz) δ 8.20 (s, 1H), 7.32 (d, 2H), 6.67 (d, 2H), 1.36 (s, 9H).

Part IV 4-(2-(4-(3-Tert-butyl-1H-1,2,4-triazol-1-yl)phenylamino)pyrimidin-4-yl)-2-fluorobenzonitrile was obtained by following procedure E using 4-(2-chloropyrimidin-4-yl)-2-fluorobenzonitrile and 4-(3-tert-butyl-1H-1,2,4-triazol-1-yl)aniline. $^1$H NMR (DMSO-d$_6$, 400 MHz) δ 10.07 (s, 1H), 9.03 (s, 1H), 8.72 (d, 1H), 8.29 (d, 1H), 8.24 (dd, 1H), 8.15 (dd, 1H), 7.95 (d, 2H), 7.77 (d, 2H), 7.62 (d, 1H), 1.37 (s, 9H). MS (ESI) 414.30 (M+H).

Example 37

2-(4-(4-phenylpyrimidin-2-ylamino)phenyl)acetamide

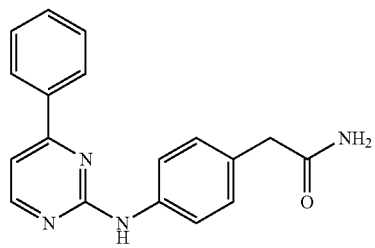 [SMILES: NC(=O)Cc1ccc(Nc2nccc(-c3ccccc3)n2)cc1]

Part I 2-(4-(4-phenylpyrimidin-2-ylamino)phenyl)acetic acid

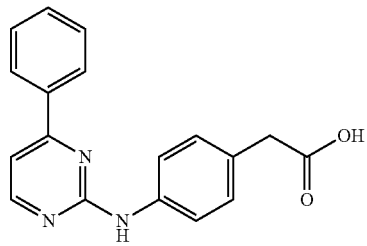 [SMILES: O=C(O)Cc1ccc(Nc2nccc(-c3ccccc3)n2)cc1]

General Procedure I

Microwave Assisted Halogen Displacement with Amino Group

A mixture of 2-chloro-4-phenylpyrimidine (0.19 g, 1.0 mmol), 2-(4-aminophenyl)acetic acid (0.38 g, 2.5 mmol), diisopropylethylamine (0.38 mL, 2.0 mmol), THF (3.0 mL) and water (1.0 mL) was placed in a seal tube and heated up to 160° C. in a microwave (Biotage, Model: Initiator) for 10 h. The reaction mixture was diluted with ether and washed with brine. The organic layer was separated, dried (MgSO$_4$), and concentrated to afford 2-(4-(4-phenylpyrimidin-2-ylamino) phenyl)acetic acid in 77% yield. MS (ESI) 306 (M+H).

Part II

SOCl$_2$ (0.08 mL, 1.2 mmol) was added dropwise to a mixture of 2-(4-(4-phenylpyrimidin-2-ylamino)phenyl)acetic acid (90 mg, 0.3 mmol) in dichloroethane (10 mL). The mixture was refluxed for 1 hr at 85° C., cooled to room temperature, and quenched with 0.5 M ammonia in dioxane (5 mL). The mixture was stirred at room temperature for 1 h and diluted with water. The reaction mixture was extracted with EtOAc (3×). The combined organics were dried (MgSO$_4$) and concentrated to afford a crude product which was purified by chromatography on silica gel (ethyl acetate/hexanes) to give 2-(4-(4-phenylpyrimidin-2-ylamino)phenyl)acetamide. $^1$H NMR (DMSO-d$_6$, 400 MHz) δ 9.61 (s, 1H), 8.54 (d, 1H), 8.26-8.15 (m, 2H), 7.74 (d, 2H), 7.59-7.54 (m, 3H), 7.40 (d, 2H), 7.20 (d, 2H), 6.84 (br s, 1H), 3.32 (s, 2H). MS (ESI) 305 (M+H).

Example 38

5-(2-(4-(3-Tert-butyl-1H-1,2,4-triazol-1-yl)phenylamino)pyrimidin-4-yl)-2-(4-hydroxypiperidin-1-yl)benzonitrile

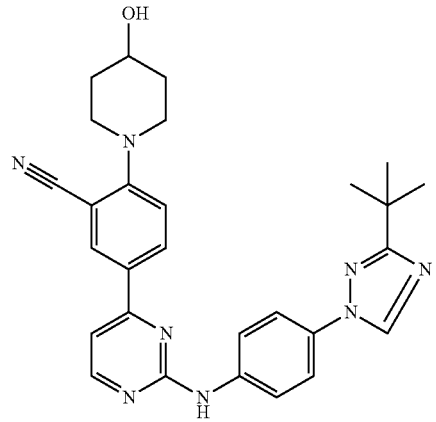 [SMILES: CC(C)(C)c1ncn(-c2ccc(Nc3nccc(-c4ccc(N5CCC(O)CC5)c(C#N)c4)n3)cc2)n1]

Part I

5-Bromo-2-(4-hydroxypiperidin-1-yl)benzonitrile

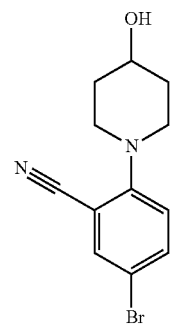 [SMILES: N#Cc1cc(Br)ccc1N1CCC(O)CC1]

5-Bromo-2-(4-hydroxypiperidin-1-yl)benzonitrile was obtained by following procedure F using 5-bromo-2-fluorobenzonitrile and piperidin-4-ol. $^1$H NMR (CDCl$_3$, 400 MHz) δ 7.67 (d, 1H), 7.56 (dd, 1H), 6.92 (d, 1H), 3.95 (m, 1H), 3.47 (m, 2H), 3.04 (m, 2H), 2.09 (m, 2H), 1.81 (m, 2H), 1.44 (d, 1H). MS (ESI) 281.06 & 283.04 (M+H).

Part II 2-(4-Hydroxypiperidin-1-yl)-5-(4,4,5,5-tetramethyl-1,3,2-dioxaborolan-2-yl)benzonitrile

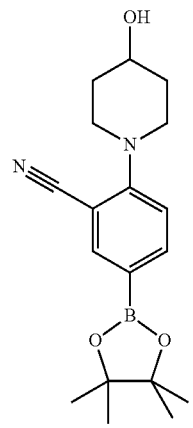 [SMILES: CC1(C)OB(c2ccc(N3CCC(O)CC3)c(C#N)c2)OC1(C)C]

2-(4-Hydroxypiperidin-1-yl)-5-(4,4,5,5-tetramethyl-1,3,2-dioxaborolan-2-yl)benzonitrile was obtained by following procedure A using 5-bromo-2-(4-hydroxypiperidin-1-yl)benzonitrile and bis(pinacolato)diboron. ¹H NMR (CDCl₃, 400 MHz) δ 7.98 (d, 1H), 7.83 (dd, 1H), 6.95 (d, 1H), 3.90 (m, 1H), 3.56 (m, 2H), 3.07 (m, 2H), 2.40 (brs, 1H), 2.05 (m, 2H), 1.78 (m, 2H), 1.31 (s, 12H). MS (ESI) 329.20 (M+H).

Part III 5-(2-Chloropyrimidin-4-yl)-2-(4-hydroxypiperidin-1-yl)benzonitrile

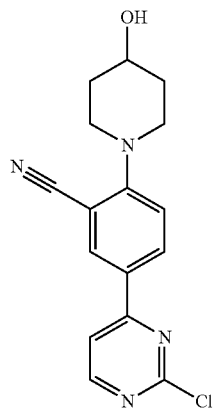 [SMILES: N#Cc1cc(-c2ccnc(Cl)n2)ccc1N1CCC(O)CC1]

5-(2-Chloropyrimidin-4-yl)-2-(4 hydroxypiperidin-1-yl)benzonitrile was obtained by following procedure B using 2-(4-hydroxypiperidin-1-yl)-5-(4,4,5,5-tetramethyl-1,3,2-dioxaborolan-2-yl)benzonitrile and 2,4-dicholorrpyrimidine. ¹H NMR (CDCl₃, 400 MHz) δ 8.64 (d, 1H), 8.33 (d, 1H), 8.22 (dd, 1H), 7.56 (d, 1H), 7.10 (d, 1H), 4.02 (m, 1H), 3.70 (m, 2H), 3.26 (m, 2H), 2.13 (m, 2H), 1.85 (m, 2H), 1.49 (d, 1H). MS (ESI) 315.10 & 317.11 (M+H).

Part IV 5-(2-(4-(3-Tert-butyl-1H-1,2,4-triazol-1-yl)phenylamino)pyrimidin-4-yl)-2-(4-hydroxypiperidin-1-yl)benzonitrile was obtained by following procedure E using 5-(2-chloropyrimidin-4-yl)-2-(4 hydroxypiperidin-1-yl)benzonitrile and 4-(3-tert-butyl-1H-1,2,4-triazol-1-yl)aniline. ¹H NMR (DMSO-d₆, 400 MHz) δ 9.90 (s, 1H), 9.02 (s, 1H), 8.57 (d, 1H), 8.48 (d, 1H), 8.38 (dd, 1H), 7.97 (d, 2H), 7.75 (d, 2H), 7.49 (d, 1H), 7.31 (d, 1H), 3.73 (m, 1H), 3.58 (m, 2H), 3.12 (m, 2H), 1.90 (m, 2H), 1.59 (m, 2H), 1.37 (s, 9H). MS (ESI) 495.38 (M+H).

Example 39

5-(2-(4-(3-Bromo-1H-1,2,4-triazol-1-yl)phenylamino)pyrimidin-4-yl)-2-(4-hydroxypiperidin-1-yl)benzonitrile

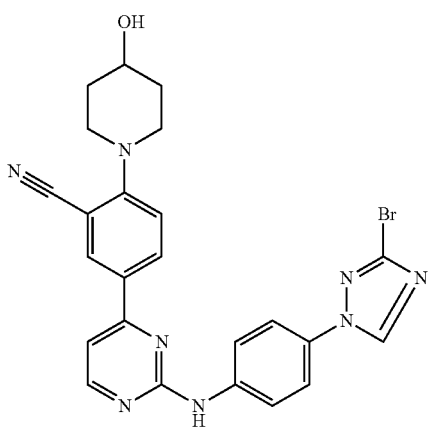 [SMILES: N#Cc1cc(-c2ccnc(Nc3ccc(-n4cnc(Br)n4)cc3)n2)ccc1N1CCC(O)CC1]

Part I

3-Bromo-1-(4-nitrophenyl)-1H-1,2,4-triazole

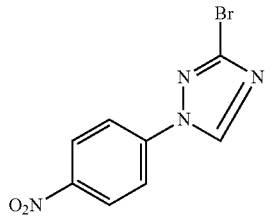

3-Bromo-1-(4-nitrophenyl)-1H-1,2,4-triazole was obtained as a single product by following procedure C using 3-bromo-1H-1,2,4-triazole and 4-fluoro-1-nitrobenzene and no purification was necessary. ¹H NMR (CDCl₃, 400 MHz) δ 8.60 (s, 1H), 8.44 (d, 2H), 7.91 (d, 2H).

Part II 4-(3-Bromo-1H-1,2,4-triazol-1-yl)aniline

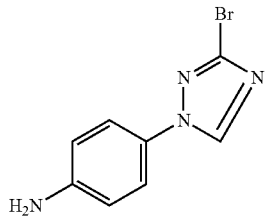 [SMILES: O=[N+]([O-])c1ccc(-n2cnc(Br)n2)cc1]

General Procedure J

Preparation of 4-(3-bromo-1H-1,2,4-triazol-1-yl)aniline via reduction

A mixture of 3-bromo-1-(4-nitrophenyl)-1H-1,2,4-triazole (0.51 g, 1.9 mmol), SnCl₂·2H₂O (2.14 g, 9.5 mmol) and EtOH (4 mL) was heated at reflux for 4 h. The reaction mixture was cooled to room temperature and basified with NaOH (2M aq.) until pH 7~9. The resulting precipitate was filtered through Celite and washed with EtOH. The EtOH filtrate was concentrated in vacuo and the crude residue was dissolved in water and extracted with EtOAc (3×). The combined organics were dried (MgSO₄) and concentrated in vacuo to provide the desired product as a white solid. ¹H NMR (CDCl₃, 400 MHz) δ 8.28 (s, 1H), 7.40 (d, 2H), 6.79 (d, 2H), 3.90 (br s, 2H).

Part III 5-(2-(4-(3-Bromo-1H-1,2,4-triazol-1-yl)phenylamino)pyrimidin-4-yl)-2-(4-hydroxypiperidin-1-yl)benzonitrile was obtained following procedure E using 5-(2-chloropyrimidin-4-yl)-2-(4 hydroxypiperidin-1-yl)benzonitrile and 4-(3-bromo-1H-1,2,4-triazol-1-yl)aniline. ¹H NMR (DMSO-d₆, 400 MHz) δ 9.98 (s, 1H), 9.22 (s, 1H), 8.58 (d, 1H), 8.49 (d, 1H), 8.37 (d, 1H), 8.00 (d, 2H), 7.76 (d, 2H), 7.51 (d, 1H), 7.30 (d, 1H), 4.75 (brs, 1H), 3.62 (m, 1H), 3.55 (m, 2H), 3.11 (m, 2H), 2.34 (m, 2H), 1.60 (m, 2H). MS (ESI) 517.21 & 519.21 (M+H).

Example 40

2-(4-Hydroxypiperidin-1-yl)-5-(2-(4-(3-(pyridin-4-yl)-1H-1,2,4-triazol-1-yl)phenylamino)pyrimidin-4-yl)benzonitrile

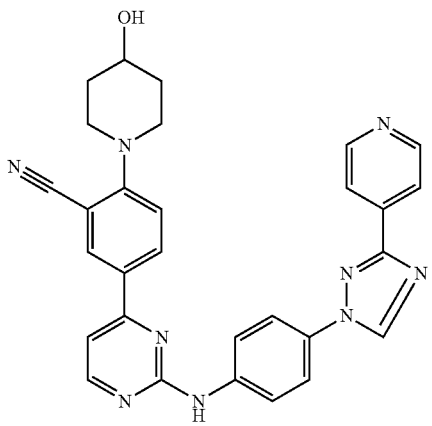 [SMILES: N#Cc1cc(-c2ccnc(Nc3ccc(-n4cnc(-c5ccncc5)n4)cc3)n2)ccc1N1CCC(O)CC1]

General Procedure K

Suzuki reaction of 3-bromo-1-substituted-1,2,4-triazole with arylboronic acid or arylborate A mixture of 5-(2-(4-(3-bromo-1H-1,2,4-triazol-1-yl)phenylamino)pyrimidin-4-yl)-2-(4-hydroxypiperidin-1-yl)benzonitrile (0.052 g, 0.10 mmol), pyridin-4-ylboronic acid (0.037 g, 0.30 mmol), $K_2CO_3$ (0.083 g, 0.60 mmol), Pd(PPh$_3$)$_4$ (0.012 g, 0.01 mmol), toluene (0.60 mL) and MeOH (0.15 mL) was heated in a sealed tube at 140° C. with microwave irradiation for 2 h. The reaction mixture was cooled down to room temperature and filtered. The filtrate was concentrated to a yellow solid. Purification of this material by column chromatography on silica gel (20% MeOH/$CH_2Cl_2$) provided the desired product as a pale yellow solid. $^1$H NMR (CDCl$_3$, 400 MHz) δ 8.67 (d, 2H), 8.53 (d, 1H), 8.43 (d, 1H), 8.23 (d, 1H), 8.01 (d, 2H), 7.82 (d, 2H), 7.67 (d, 2H), 7.51 (s, 1H), 7.38 (d, 1H), 7.07 (d, 1H), 7.04 (d, 1H), 3.92 (m, 1H), 3.57 (m, 2H), 3.13 (m, 2H), 3.03 (m, 1H), 2.05 (m, 2H), 1.75 (m, 2H). MS (ESI) 516.34 (M+H).

Example 41

4-(4-(Methylsulfonyl)phenyl)-N-(4-(5-morpholino-1H-1,2,3-triazol-1-yl)phenyl)pyrimidin-2-amine

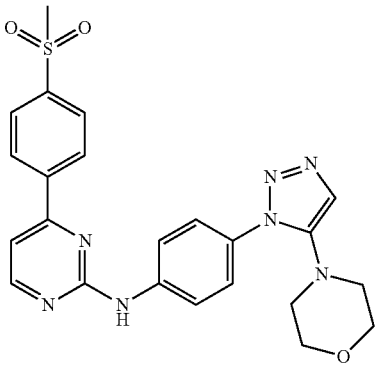 [SMILES: CS(=O)(=O)c1ccc(-c2ccnc(Nc3ccc(-n4nncc4N4CCOCC4)cc3)n2)cc1]

Part I 4-(5-Morpholino-4-(trimethylsilyl)-1H-1,2,3-triazol-1-yl)aniline

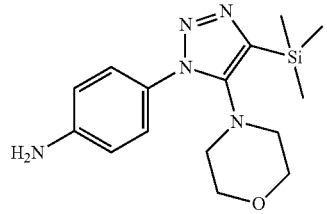 [SMILES: C[Si](C)(C)c1nnn(-c2ccc(N)cc2)c1N1CCOCC1]

General Procedure L

Synthesis of 4-(1H-1,2,3-triazol-1-yl)aniline derivatives from 1-azido-4-nitrobenzene A mixture of 1-azido-4-nitrobenzene (0.5 g, 3.0 mmol), 4-((trimethylsilyl)ethynyl)morpholine (1.0 g, 9.0 mmol) and toluene (10 mL) was heated in a sealed tube to 60° C. for 24 h. The reaction mixture was concentrated in vacuo to give 4-(1-(4-nitrophenyl)-4-(trimethylsilyl)-1H-1,2,3-triazol-5-yl)morpholine which was further reduced following procedure D to afford 4-(5-morpholino-4-(trimethylsilyl)-1H-1,2,3-triazol-1-yl)aniline.

Part II 4-(4-(Methylsulfonyl)phenyl)-N-(4-(5-morpholino-1H-1,2,3-triazol-1-yl)phenyl)pyrimidin-2-amine was obtained by following procedure I utilizing 4-(5-morpholino-4-(trimethylsilyl)-1H-1,2,3-triazol-1-yl)aniline and 2-chloro-4-(4-(methylsulfonyl)phenyl)pyrimidine. MS (ESI) 478 (M+H).

Example 42

N-(4-(2-(4-(5-(hydroxymethyl)-1H-1,2,3-triazol-1-yl)phenylamino)pyrimidin-4-yl)phenyl)methanesulfonamide

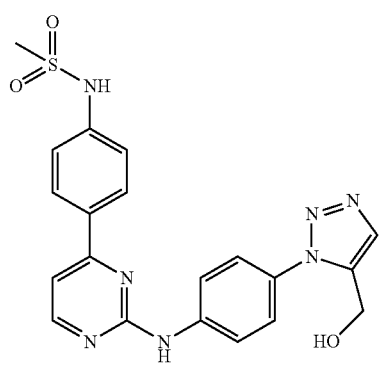 [SMILES: CS(=O)(=O)Nc1ccc(-c2ccnc(Nc3ccc(-n4nncc4CO)cc3)n2)cc1]

N-(4-(2-(4-(5-(hydroxymethyl)-1H-1,2,3-triazol-1-yl)phenylamino)pyrimidin-4-yl)phenyl)methanesulfonamide was obtained by following procedure E using N-(4-(2-chloropyrimidin-4-yl)phenyl)methanesulfonamide and (1-(4-aminophenyl)-4-(trimethylsilyl)-1H-1,2,3-triazol-5-yl)methanol, which was obtained from 1-azido-4-nitrobenzene and 3-(trimethylsilyl)prop-2-yn-1-ol by following general procedure L. MS (ESI) 430 (M+H).

Example 43

N-(4-(1H-1,2,3-triazol-1-yl)phenyl)-4-(4-(methylsulfonylmethyl)phenyl)pyrimidin-2-amine

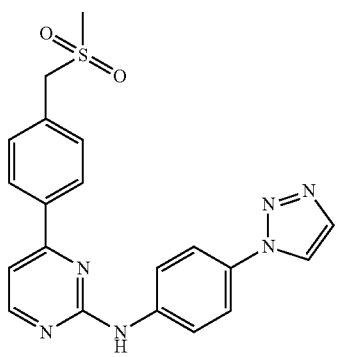 [SMILES: CS(=O)(=O)Cc1ccc(-c2ccnc(Nc3ccc(-n4ccnn4)cc3)n2)cc1]

Part 1

2-Chloro-4-(4-(methylsulfonylmethyl)phenyl)pyrimidine

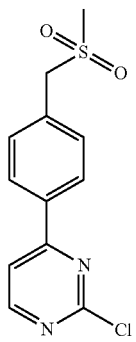

A mixture of 2-(4-(bromomethyl)phenyl)-4,4,5,5-tetramethyl-1,3,2-dioxaborolane (300 mg, 1 mmol), NaSMe (78 mg, 1.1 mmol) and anhydrous ethanol (5 mL) was refluxed for 5 h. The reaction mixture was cooled to room temperature and concentrated in vacuo. The residue was diluted with ethyl acetate and washed with water. The organic layer was separated, dried (MgSO₄), and concentrated to give 4,4,5,5-tetramethyl-2-(4-(methylthiomethyl)phenyl)-1,3,2-dioxaborolane in 90% yield.

A mixture of 2-chloro-4-(4-(methylthiomethyl)phenyl)pyrimidine (240 mg, 1.0 mmol) [obtained from 4,4,5,5-tetramethyl-2-(4-(methylthiomethyl)phenyl)-1,3,2-dioxaborolane and 2,4-dichloropyrimidine according to procedure B], in CH₂Cl₂ and meta-chloroperbenzoic acid (500 mg, 3.0 mmol) was stirred at room temperature for 2 h and then quenched with saturated aqueous NaHCO₃. The layers were separated, and the aqueous layer was extracted with CH₂Cl₂ (2×). The combined organics were washed with NaHCO₃, dried (MgSO₄), and concentrated to give 2-chloro-4-(4-(methylsulfonylmethyl)phenyl)pyrimidine in 90% yield.

Part 1I

N-(4-(1H-1,2,3-triazol-1-yl)phenyl)-4-(4-(methylsulfonylmethyl)phenyl)pyrimidin-2-amine was obtained by following procedure E using 4-(1H-1,2,3-triazol-1-yl)aniline and 2-chloro-4-(4-(methylsulfonylmethyl)phenyl)pyrimidine which was prepared according procedure L. MS (ESI) 407 (M+H).

Example 44

N-(4-(1H-pyrazol-1-yl)phenyl)-4-phenylpyrimidin-2-amine

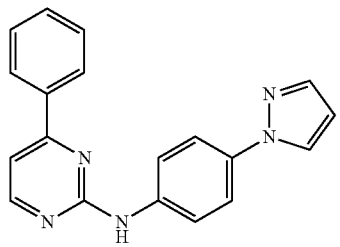 [SMILES: c1ccc(-c2ccnc(Nc3ccc(-n4cccn4)cc3)n2)cc1]

N-(4-(1H-pyrazol-1-yl)phenyl)-4-phenylpyrimidin-2-amine was obtained by following procedure E using 2-chloro-4-phenylpyrimidine and 4-(1H-pyrazol-1-yl)aniline. $^1$H NMR (DMSO-d₆, 400 MHz) δ 9.99 (s, 1H), 8.62 (d, 1H), 8.53 (s, 1H), 8.21-8.19 (m, 2H), 8.04 (dd, 2H), 7.72 (dd, 2H), 7.59-7.56 (m, 4H), 7.49 (d, 2H). MS (ESI) 314 (M+H).

Example 45

N-(4-(4-methyl-4H-1,2,4-triazol-3-yl)phenyl)-4-phenylpyrimidin-2-amine

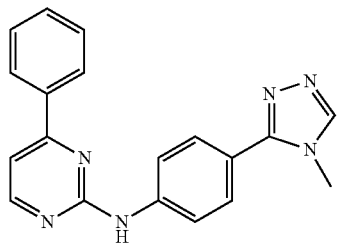 [SMILES: Cn1cnnc1-c1ccc(Nc2nccc(-c3ccccc3)n2)cc1]

N-(4-(4-methyl-4H-1,2,4-triazol-3-yl)phenyl)-4-phenylpyrimidin-2-amine was obtained by following procedure E using 2-chloro-4-phenylpyrimidine and 4-(4-methyl-4H-1,2,4-triazol-3-yl)aniline. $^1$H NMR (DMSO-d₆, 400 MHz) δ 9.69 (s, 1H), 8.49 (d, 1H), 8.12-8.09 (m, 2H), 7.78 (d, 2H), 7.51-7.48 (m, 3H), 7.36 (d, 1H), 7.24 (d, 1H), 6.82-6.78 (m, 1H), 4.20 (s, 1H). MS (ESI) 329 (M+H).

Example 46

2-(4-(4-(3-(Phenylamino)phenyl)pyrimidin-2-ylamino)phenyl)acetamide

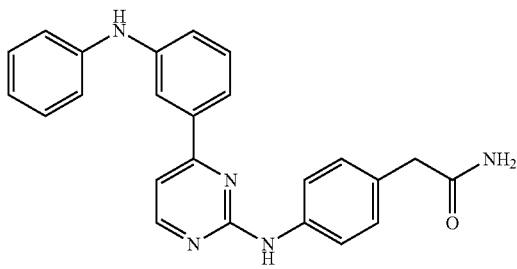 [SMILES: NC(=O)Cc1ccc(Nc2nccc(-c3cccc(Nc4ccccc4)c3)n2)cc1]

2-(4-(4-(3-(Phenylamino)phenyl)pyrimidin-2-ylamino)phenyl)acetamide was obtained by following procedure E using 3-(2-chloropyrimidin-4-yl)-N-phenylaniline and 2-(4-aminophenyl)acetamide MS (ESI) 396 (M+H).

Example 47

N-(4-((1H-1,2,4-triazol-5-yl)methyl)phenyl)-4-(3-(phenylamino)phenyl)pyrimidin-2-amine

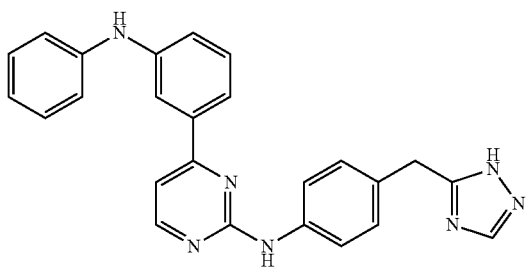 [SMILES: c1ccc(Nc2cccc(-c3ccnc(Nc4ccc(Cc5ncn[nH]5)cc4)n3)c2)cc1]

2-(4-(4-(3-(Phenylamino)phenyl)pyrimidin-2-ylamino)phenyl)acetamide (200 mg, 0.5 mmol) in N,N'-dimethylformamide dimethyl acetal (10 mL) was stirred at 120° C. for 1.5 h. The reaction mixture was cooled to room temperature and concentrated in vacuo. The residue was treated with glacial acetic acid (5 mL) and hydrazine hydrate (1 mL) and was heated at 90° C. for 1.5 h. The reaction mixture was concentrated in vacuo and washed with water to afford N-(4-((1H-1,2,4-triazol-5-yl)methyl)phenyl)-4-(3-(phenylamino)phenyl)pyrimidin-2-amine in 90% yield. MS (ESI) 420 (M+H).

Example 48

N-(4-(1H-pyrazol-5-yl)phenyl)-4-phenylpyrimidin-2-amine

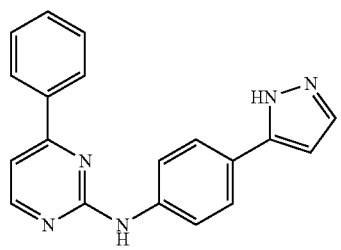 [SMILES: c1ccc(-c2ccnc(Nc3ccc(-c4ccn[nH]4)cc3)n2)cc1]

N-(4-(1H-pyrazol-5-yl)phenyl)-4-phenylpyrimidin-2-amine was obtained by following procedure E using 2-chloro-4-phenylpyrimidine and 4-(1H-pyrazol-5-yl)aniline. $^1$H NMR (DMSO-$d_6$, 400 MHz) δ 9.82 (s, 1H), 8.63 (d, 1H), 8.25-8.23 (m, 2H), 7.95 (d, 2H), 7.80 (d, 2H), 7.71 (d, 1H), 7.63-7.61 (m, 3H), 7.48 (d, 1H), 6.69 (d, 1H). MS (ESI) 314 (M+H).

Example 49

N-(4-(1,2,4-oxadiazol-5-yl)phenyl)-4-phenylpyrimidin-2-amine

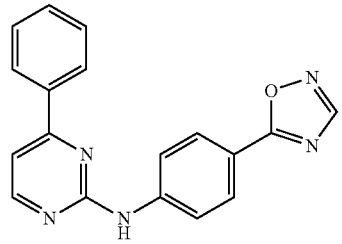 [SMILES: c1ccc(-c2ccnc(Nc3ccc(-c4ncno4)cc3)n2)cc1]

N-(4-(1,2,4-oxadiazol-5-yl)phenyl)-4-phenylpyrimidin-2-amine was obtained by following procedure E using 2-chloro-4-phenylpyrimidine and 4-(1,2,4-oxadiazol-5-yl)aniline. $^1$H NMR (DMSO-$d_6$, 400 MHz) δ 10.17 (s, 1H), 8.65 (d, 1H), 8.28-8.26 (m, 2H), 8.20-7.93 (m, 4H), 7.58-7.54 (m, 4H). MS (ESI) 316 (M+H).

Example 50

N-(4-(1H-1,2,4-triazol-1-yl)phenyl)-4-(3-morpholinophenyl)pyrimidin-2-amine

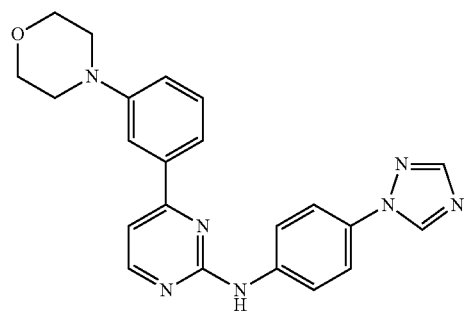 [SMILES: c1cc(-c2ccnc(Nc3ccc(-n4cncn4)cc3)n2)cc(N2CCOCC2)c1]

N-(4-(1H-1,2,4-triazol-1-yl)phenyl)-4-(3-morpholinophenyl)pyrimidin-2-amine was obtained by following procedure E using 4-(1H-1,2,4-triazol-1-yl)aniline and 4-(3-(2-chloropyrimidin-4-yl)phenyl)morpholine which was prepared according procedure B from 4-(3-(4,4,5,5-tetramethyl-1,3,2-dioxaborolan-2-yl)phenyl)morpholine and 2,4-dichloropyrimidine. $^1$H NMR (DMSO-$d_6$, 400 MHz) δ 9.9 (s, 1H), 9.2 (s, 1H), 8.6 (d, 1H), 8.2 (s, 1H), 8.0 (d, 2H), 7.8-7.7 (m, 3H), 7.6 (d, 1H), 7.45 (d, 1H), 7.4 (t, 1H), 7.15 (dd, 1H), 3.8 (m, 4H), 3.2 (m, 4H). MS (ESI) 400 (M+H).

Example 51

N-(4-(4-methyl-4H-1,2,4-triazol-3-yl)phenyl)-4-(3-(phenylamino)phenyl)pyrimidin-2-amine

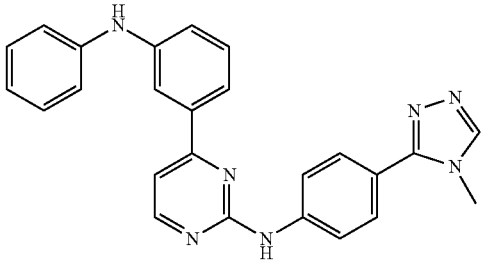 [SMILES: Cn1cnnc1-c1ccc(Nc2nccc(-c3cccc(Nc4ccccc4)c3)n2)cc1]

N-(4-(4-methyl-4H-1,2,4-triazol-3-yl)phenyl)-4-(3-(phenylamino)phenyl)pyrimidin-2-amine was obtained by following procedure E using 3-(2-chloropyrimidin-4-yl)-N-phenylaniline and 4-(4-methyl-4H-1,2,4-triazol-3-yl)aniline. MS (ESI) 420 (M+H).

Example 52

N-(4-(4-methyl-4H-1,2,4-triazol-3-yl)phenyl)-4-(3-morpholinophenyl)pyrimidin-2-amine

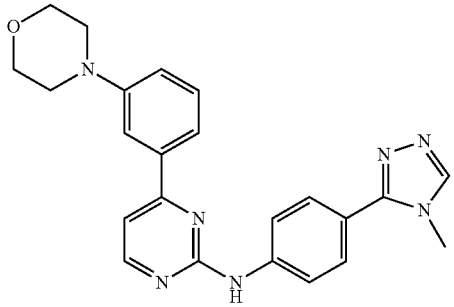 [SMILES: Cn1cnnc1-c1ccc(Nc2nccc(-c3cccc(N4CCOCC4)c3)n2)cc1]

N-(4-(4-methyl-4H-1,2,4-triazol-3-yl)phenyl)-4-(3-morpholinophenyl)pyrimidin-2-amine was obtained by following procedure E using 4-(4-methyl-4H-1,2,4-triazol-3-yl) aniline and 4-(3-(2-chloropyrimidin-4-yl)phenyl) morpholine. $^1$H NMR (MeOH-$d_4$, 400 MHz) δ 9.1 (s, 1H), 8.6 (d, 1H), 8.2 (d, 2H), 7.9 (br s, 1H), 7.8 (d, 2H), 7.7 (d, 1H), 7.5-7.4 (m, 2H), 7.25 (dd, 1H), 4.05 (s, 3H), 3.9 (m, 4H), 3.3 (m, 4H). MS (ESI) 414 (M+H).

Example 53

N-(4-(2-(4-(4-methyl-4H-1,2,4-triazol-3-yl)phenylamino)pyrimidin-4-yl)phenyl)methanesulfonamide

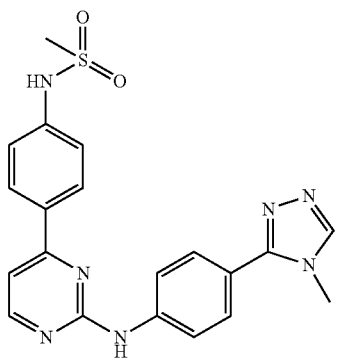 [SMILES: Cn1cnnc1-c1ccc(Nc2nccc(-c3ccc(NS(C)(=O)=O)cc3)n2)cc1]

N-(4-(2-(4-(4-methyl-4H-1,2,4-triazol-3-yl)phenylamino)pyrimidin-4-yl)phenyl)methanesulfonamide was obtained by following procedure E using 4-(4-methyl-4H-1,2,4-triazol-3-yl)aniline and N-(4-(2-chloropyrimidin-4-yl)phenyl)methanesulfonamide which was prepared according procedure B from N-(4-(4,4,5,5-tetramethyl-1,3,2-dioxaborolan-2-yl)phenyl)methanesulfonamide and 2,4-dichloropyrimidine. $^1$H NMR (DMSO-$d_6$, 400 MHz) δ 9.1 (s, 1H), 8.5 (d, 1H), 8.3-8.2 (m, 4H), 7.8 (d, 1H), 7.5-7.4 (m, 4H), 4.0 (s, 3H), 3.1 (s, 3H). MS (ESI) 422 (M+H).

Example 54

4-(4-Chlorophenyl)-N-(4-(4-methyl-4H-1,2,4-triazol-3-yl)phenyl)pyrimidin-2-amine

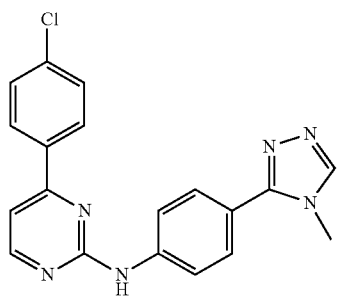 [SMILES: Cn1cnnc1-c1ccc(Nc2nccc(-c3ccc(Cl)cc3)n2)cc1]

4-(4-Chlorophenyl)-N-(4-(4-methyl-4H-1,2,4-triazol-3-yl)phenyl)pyrimidin-2-amine was obtained by following procedure E using 4-(4-methyl-4H-1,2,4-triazol-3-yl)aniline and N-(4-(2-chloropyrimidin-4-yl)phenyl)methanesulfonamide which was prepared according procedure B from 4-chlorophenylboronic acid and 2,4-dichloropyrimidine. $^1$H NMR (CDCl$_3$, 400 MHz) δ 7.65 (d, 1H), 7.38 (s, 1H), 7.43 (br s, 1H), 7.27-7.17 (m, 2H), 7.08-7.05 (m, 2H), 6.87-6.82 (m, 2H), 6.68-6.63 (m, 2H), 6.02 (d, 1H), 3.02 (s, 3H).

Example 55

N-(4-(2H-1,2,3-triazol-2-yl)phenyl)-4-phenylpyrimidin-2-amine

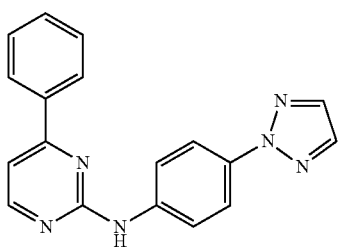 [SMILES: c1ccc(-c2ccnc(Nc3ccc(-n4nccn4)cc3)n2)cc1]

N-(4-(2H-1,2,3-triazol-2-yl)phenyl)-4-phenylpyrimidin-2-amine was obtained by following procedure E using 4-(2H-1,2,3-triazol-2-yl)aniline and 2-chloro-4-phenylpyrimidine. $^1$H NMR (DMSO-$d_6$, 400 MHz) δ 9.97 (s, 1H), 8.61 (d, 1H), 8.22-8.19 (m, 2H), 8.07-8.00 (m, 6H), 7.58-7.57 (m, 3H), 7.48 (d, 1H). MS (ESI) 315 (M+H).

Example 56

2-Chloro-4-(4-phenylpyrimidin-2-ylamino)benzamide

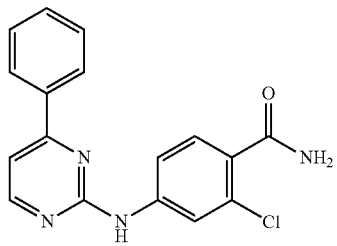 [SMILES: NC(=O)c1ccc(Nc2nccc(-c3ccccc3)n2)cc1Cl]

2-Chloro-4-(4-phenylpyrimidin-2-ylamino)benzamide was obtained by following procedure E using 4-amino-2-chlorobenzamide and 2-chloro-4-phenylpyrimidine except that ethoxylethanol was replaced with diglyme and the mixture was heated at 170° C. overnight. $^1$H NMR (DMSO-$d_6$, 400 MHz) δ 10.05 (s, 1H), 8.64 (d, 1H), 8.22-8.17 (m, 2H), 8.14 (d, 1H), 7.78-7.76 (m, 2H), 7.59-7.56 (m, 3H), 7.52 (d, 1H), 7.48 (s, 1H), 7.46 (s, 1H). MS (ESI) 325 (M+H).

Example 57

N-(4-(1H-1,2,3-triazol-1-yl)phenyl)-4-(4-(methylsulfonyl)phenyl)pyrimidin-2-amine

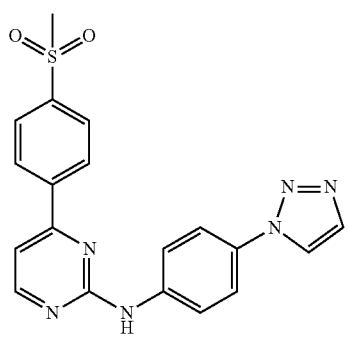 [SMILES: CS(=O)(=O)c1ccc(-c2ccnc(Nc3ccc(-n4ccnn4)cc3)n2)cc1]

N-(4-(1H-1,2,3-triazol-1-yl)phenyl)-4-(4-(methylsulfonyl)phenyl)pyrimidin-2-amine was obtained by following procedure E using 4-(1H-1,2,3-triazol-1-yl)aniline and 2-chloro-4-(4-(methylsulfonyl)phenyl)pyrimidine which was prepared from 2,4-dichloropyrimidine and 4,4,5,5-tetramethyl-2-(4-(methylsulfonyl)phenyl)-1,3,2-dioxaborolane by following procedure B. $^1$H NMR (DMSO-$d_6$, 400 MHz) δ 10.13 (s, 1H), 8.74-8.71 (m, 2H), 8.44 (d, 2H), 8.12 (d, 2H), 8.06 (d, 2H), 7.96 (s, 1H), 7.87 (d, 2H), 7.60 (d, 1H), 3.31 (s, 3H). MS (ESI) 393 (M+H).

Example 58

3-(4-(4-(Methylsulfonyl)phenyl)pyrimidin-2-ylamino)benzamide

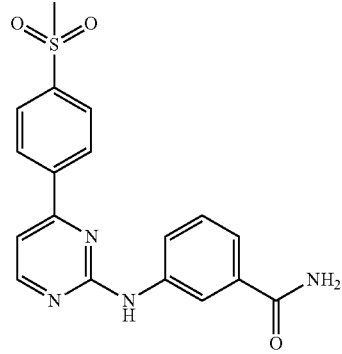 [SMILES: CS(=O)(=O)c1ccc(-c2ccnc(Nc3cccc(C(N)=O)c3)n2)cc1]

3-(4-(4-(Methylsulfonyl)phenyl)pyrimidin-2-ylamino)benzamide was obtained by following procedure E using 3-aminobenzamide and 2-chloro-4-(4-(methylsulfonyl)phenyl)pyrimidine. $^1$H NMR (DMSO-$d_6$, 400 MHz) δ 9.93 (s, 1H), 8.67 (d, 1H), 8.53 (br s, 1H), 8.48 (d, 2H), 8.09 (d, 2H), 7.92 (br s, 1H), 7.88-7.86 (m, 1H), 7.56 (d, 1H), 7.49 (d, 1H), 7.41-7.37 (m, 1H), 7.34 (br s, 1H), 3.30 (s, 3H). MS (ESI) 369 (M+H).

Example 59

N-(4-(4H-1,2,4-triazol-3-yl)phenyl)-4-(4-(methylsulfonyl)phenyl)pyrimidin-2-amine

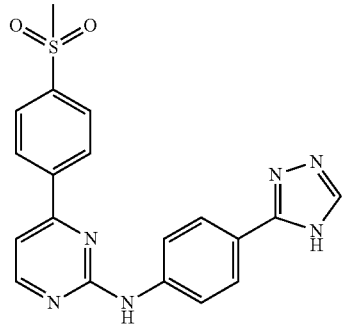 [SMILES: CS(=O)(=O)c1ccc(-c2ccnc(Nc3ccc(-c4nnc[nH]4)cc3)n2)cc1]

N-(4-(4H-1,2,4-triazol-3-yl)phenyl)-4-(4-(methylsulfonyl)phenyl)pyrimidin-2-amine was obtained by following procedure E using 4-(4H-1,2,4-triazol-3-yl)aniline and 2-chloro-4-(4-(methylsulfonyl)phenyl)pyrimidine. $^1$H NMR (DMSO-$d_6$, 400 MHz) δ 10.01 (s, 1H), 8.62 (d, 1H), 8.38-8.36 (m, 2H), 8.08-8.05 (m, 2H), 7.91-7.82 (m, 4H), 7.50 (d, 1H), 3.23 (s, 3H). MS (ESI) 393 (M+H).

Example 60

2-Chloro-4-(4-(4-(methylsulfonyl)phenyl)pyrimidin-2-ylamino)benzamide

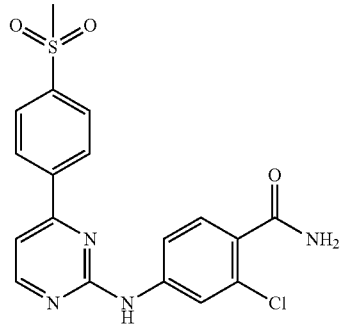 [SMILES: CS(=O)(=O)c1ccc(-c2ccnc(Nc3ccc(C(N)=O)c(Cl)c3)n2)cc1]

2-Chloro-4-(4-(4-(methylsulfonyl)phenyl)pyrimidin-2-ylamino)benzamide was obtained by following procedure E using 4-amino-2-chlorobenzamide and 2-chloro-4-(4-(methylsulfonyl)phenyl)pyrimidine except that ethoxylethanol was replaced with diglyme and the mixture was heated at 170° C. overnight. $^1$H NMR (DMSO-d$_6$, 400 MHz) δ 10.08 (s, 1H), 8.63 (d, 1H), 8.33 (d, 2H), 8.03 (d, 2H), 8.00 (d, 1H), 7.71-7.68 (m, 1H), 7.64 (br s, 1H), 7.53 (d, 1H), 7.38 (d, 2H), 3.22 (s, 3H). MS (ESI) 403 (M+H).

Example 61

4-(4-(Methylsulfonyl)phenyl)-N-phenylpyrimidin-2-amine

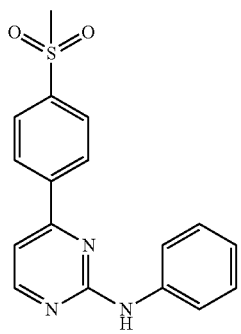 [SMILES: CS(=O)(=O)c1ccc(-c2ccnc(Nc3ccccc3)n2)cc1]

4-(4-(Methylsulfonyl)phenyl)-N-phenylpyrimidin-2-amine was obtained by following procedure E using aniline and 2-chloro-4-(4-(methylsulfonyl)phenyl)pyrimidine. $^1$H NMR (DMSO-d$_6$, 400 MHz) δ 9.80 (s, 1H), 8.64 (d, 1H), 8.41 (d, 2H), 8.11 (d, 2H), 7.85-7.83 (dd, 2H), 7.52 (d, 1H), 7.35-7.31 (m, 2H), 6.99 (t, 1H), 3.30 (s, 3H). MS (ESI) 326 (M+H).

Example 72

2-(4-(4-(4-(Methylsulfonyl)phenyl)pyrimidin-2-ylamino)phenyl)acetamide

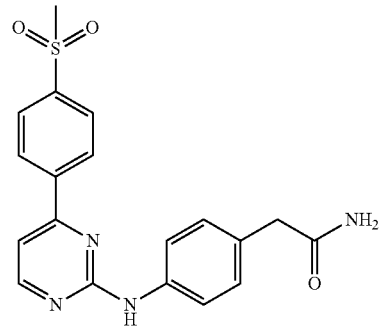 [SMILES: CS(=O)(=O)c1ccc(-c2ccnc(Nc3ccc(CC(N)=O)cc3)n2)cc1]

2-(4-(4-(4-(Methylsulfonyl)phenyl)pyrimidin-2-ylamino)phenyl)acetamide was obtained by following procedure E using 2-(4-aminophenyl)acetamide and 2-chloro-4-(4-(methylsulfonyl)phenyl)pyrimidine. MS (ESI) 383 (M+H).

Example 73

N-(4-(1H-1,2,4-triazol-1-yl)phenyl)-4-(4-(methylsulfonyl)phenyl)pyrimidin-2-amine

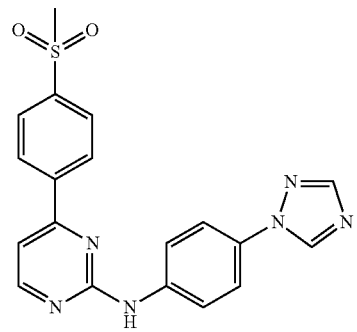 [SMILES: CS(=O)(=O)c1ccc(-c2ccnc(Nc3ccc(-n4cncn4)cc3)n2)cc1]

N-(4-(1H-1,2,4-triazol-1-yl)phenyl)-4-(4-(methylsulfonyl)phenyl)pyrimidin-2-amine was obtained by following procedure E using 4-(1H-1,2,4-triazol-1-yl)aniline and 2-chloro-4-(4-(methylsulfonyl)phenyl)pyrimidine. MS (ESI) 393 (M+H).

Example 74

N-(4-(1H-1,2,3-triazol-1-yl)phenyl)-4-(3-(methylsulfonyl)phenyl)pyrimidin-2-amine

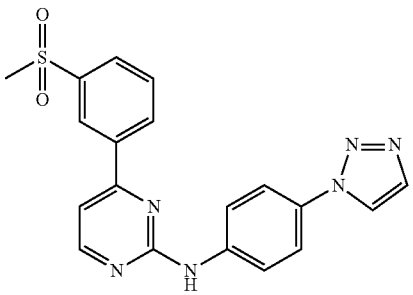 [SMILES: CS(=O)(=O)c1cccc(-c2ccnc(Nc3ccc(-n4ccnn4)cc3)n2)c1]

N-(4-(1H-1,2,3-triazol-1-yl)phenyl)-4-(3-(methylsulfonyl)phenyl)pyrimidin-2-amine was obtained by following procedure E using 4-(1H-1,2,3-triazol-1-yl)aniline and 2-chloro-4-(3-(methylsulfonyl)phenyl)pyrimidine which was prepared from 4,4,5,5-tetramethyl-2-(3-(methylsulfonyl)phenyl)-1,3,2-dioxaborolane and 2,4-dichloropyrimidine by following procedure B. MS (ESI) 393 (M+H).

Example 75

N-(4-(1H-1,2,3-triazol-1-yl)phenyl)-4-(benzo[d][1,3]-dioxol-5-yl)pyrimidin-2-amine

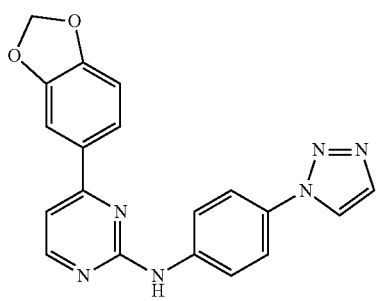 [SMILES: c1cn(-c2ccc(Nc3nccc(-c4ccc5c(c4)OCO5)n3)cc2)nn1]

N-(4-(1H-1,2,3-triazol-1-yl)phenyl)-4-(benzo[d][1,3]dioxol-5-yl)pyrimidin-2-amine was obtained by following procedure E using 4-(1H-1,2,3-triazol-1-yl)aniline and 4-(benzo[d][1,3]dioxol-5-yl)-2-chloropyrimidine which was prepared by following procedure B using 2,4-dichloropyrimidine and 2-(benzo[d][1,3]dioxol-5-yl)-4,4,5,5-tetramethyl-1,3,2-dioxaborolane. MS (ESI) 359 (M+H).

Example 76

N-(4-(1H-1,2,3-triazol-1-yl)phenyl)-4-(3-morpholinophenyl)pyrimidin-2-amine

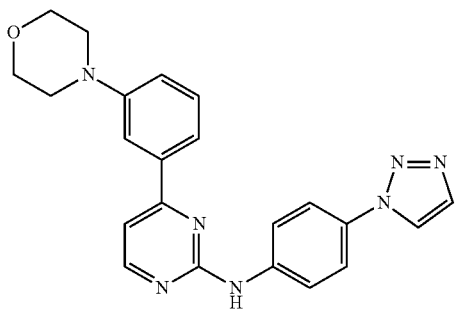 [SMILES: c1cc(-c2ccnc(Nc3ccc(-n4ccnn4)cc3)n2)cc(N2CCOCC2)c1]

N-(4-(1H-1,2,3-triazol-1-yl)phenyl)-4-(3-morpholinophenyl)pyrimidin-2-amine was obtained by following procedure E using 4-(1H-1,2,3-triazol-1-yl)aniline and 4-(3-(2-chloropyrimidin-4-yl)phenyl)morpholine. $^1$H NMR (DMSO-$d_6$, 400 MHz) δ 9.98 (s, 1H), 8.74 (d, 1H), 8.59 (d, 1H), 8.09-8.05 (m, 2H), 7.86 (d, 1H), 7.86-7.82 (m, 2H), 7.76 (s, 1H), 7.65-7.62 (m, 1H), 7.52 (d, 1H), 7.42 (t, 1H), 7.16 (d, 1H), 3.81-3.79 (m, 4H), 3.25-3.23 (m, 4H). MS (ESI) 400 (M+H).

Example 77

N-(4-(1H-1,2,3-triazol-1-yl)phenyl)-4-(3-(piperidin-1-yl)phenyl)pyrimidin-2-amine

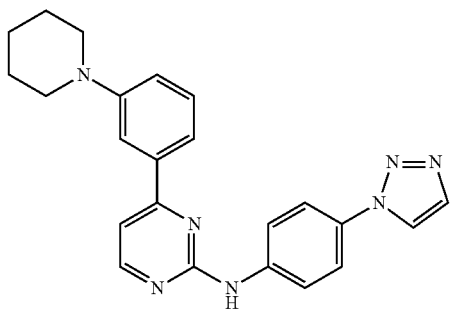 [SMILES: c1cc(-c2ccnc(Nc3ccc(-n4ccnn4)cc3)n2)cc(N2CCCCC2)c1]

N-(4-(1H-1,2,3-triazol-1-yl)phenyl)-4-(3-(piperidin-1-yl)phenyl)pyrimidin-2-amine was obtained by following procedure E using 4-(1H-1,2,3-triazol-1-yl)aniline and 2-chloro-4-(3-(piperidin-1-yl)phenyl)pyrimidine which was prepared from 1-(3-(4,4,5,5-tetramethyl-1,3,2-dioxaborolan-2-yl)phenyl)piperidine and 2,4-dichloropyrimidine by following procedure B. $^1$H NMR (DMSO-$d_6$, 400 MHz) δ 10.02 (s, 1H), 8.74 (d, 1H), 8.64 (d, 1H), 8.08-8.06 (m, 3H), 7.96-7.94 (m, 1H), 7.85-7.79 (m, 3H), 7.55 (t, 1H), 7.51 (s, 1H), 7.45 (s, 1H), 3.49-3.42 (m, 4H), 1.87-1.76 (m, 4H), 1.64-1.60 (m, 2H). MS (ESI) 398 (M+H).

Example 78

2-Chloro-4-(4-(3-(phenylamino)phenyl)pyrimidin-2-ylamino)benzamide

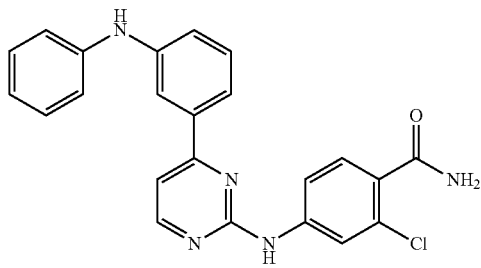 [SMILES: NC(=O)c1ccc(Nc2nccc(-c3cccc(Nc4ccccc4)c3)n2)cc1Cl]

2-Chloro-4-(4-(3-(phenylamino)phenyl)pyrimidin-2-ylamino)benzamide was obtained by following procedure E using 4-amino-2-chlorobenzamide and 3-(2-chloropyrimidin-4-yl)-N-phenylaniline except that ethoxyethanol was replaced with diglyme and the mixture was heated at 170° C. overnight. MS (ESI) 416.2 (M+H).

Example 79 tert-Butyl 4-(4-(4-(methylsulfonyl)phenyl)pyrimidin-2-ylamino)piperidine-1-carboxylate

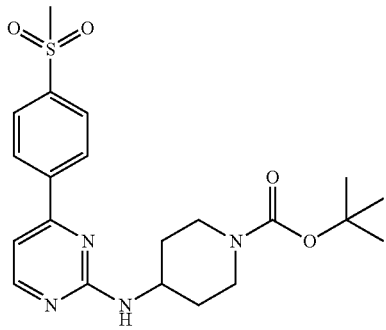 [SMILES: CC(C)(C)OC(=O)N1CCC(Nc2nccc(-c3ccc(S(C)(=O)=O)cc3)n2)CC1]

tert-Butyl 4-(4-(4-(methylsulfonyl)phenyl)pyrimidin-2-ylamino)piperidine-1-carboxylate was obtained by following procedure E using tert-butyl 4-aminopiperidine-1-carboxylate and 2-chloro-4-(4-(methylsulfonyl)phenyl)pyrimidine. MS (ESI) 433 (M+H).

Example 80

4-(4-(Methylsulfonyl)phenyl)-N-(naphthalen-1-yl)pyrimidin-2-amine

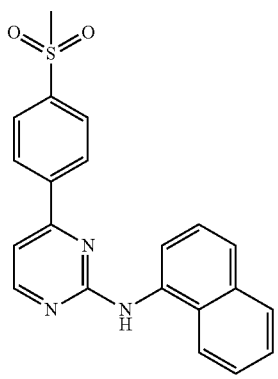 [SMILES: CS(=O)(=O)c1ccc(-c2ccnc(Nc3cccc4ccccc34)n2)cc1]

4-(4-(Methylsulfonyl)phenyl)-N-(naphthalen-1-yl)pyrimidin-2-amine was obtained by following procedure E using naphthalen-1-amine and 2-chloro-4-(4-(methylsulfonyl)phenyl)pyrimidine. MS (ESI) 376 (M+H).

Example 81

(3-(4-(4-(Methylsulfonyl)phenyl)pyrimidin-2-ylamino)cyclohexyl)methanol

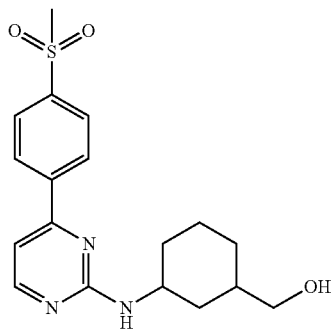 [SMILES: CS(=O)(=O)c1ccc(-c2ccnc(NC3CCCC(CO)C3)n2)cc1]

(3-(4-(4-(Methylsulfonyl)phenyl)pyrimidin-2-ylamino)cyclohexyl)methanol was obtained by following procedure E using (3-aminocyclohexyl)methanol and 2-chloro-4-(4-(methylsulfonyl)phenyl)pyrimidine. MS (ESI) 348 (M+H).

Example 82

N-cyclohexyl-4-(4-(methylsulfonyl)phenyl)pyrimidin-2-amine

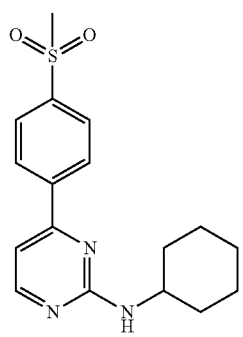 [SMILES: CS(=O)(=O)c1ccc(-c2ccnc(NC3CCCCC3)n2)cc1]

N-cyclohexyl-4-(4-(methylsulfonyl)phenyl)pyrimidin-2-amine was obtained by following procedure E using cyclohexanamine and 2-chloro-4-(4-(methylsulfonyl)phenyl)pyrimidine. MS (ESI) 332 (M+H).

Example 83

N-(4-((1H-1,2,4-triazol-1-yl)methyl)phenyl)-4-(4-(methylsulfonyl)phenyl)pyrimidin-2-amine

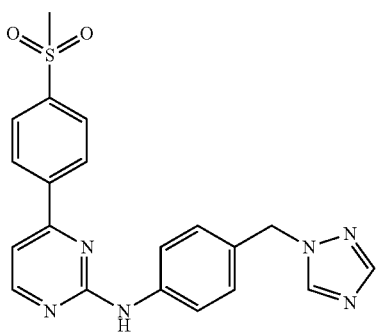 [SMILES: CS(=O)(=O)c1ccc(-c2ccnc(Nc3ccc(Cn4cncn4)cc3)n2)cc1]

N-(4-((1H-1,2,4-triazol-1-yl)methyl)phenyl)-4-(4-(methylsulfonyl)phenyl)pyrimidin-2-amine was obtained by following procedure E using 4-((1H-1,2,4-triazol-1-yl)methyl)aniline and 2-chloro-4-(4-(methylsulfonyl)phenyl)pyrimidine. MS (ESI) 407 (M+H).

Example 84 tert-Butyl 4-(4-(4-(methylsulfonyl)phenyl)pyrimidin-2-ylamino)benzylcarbamate

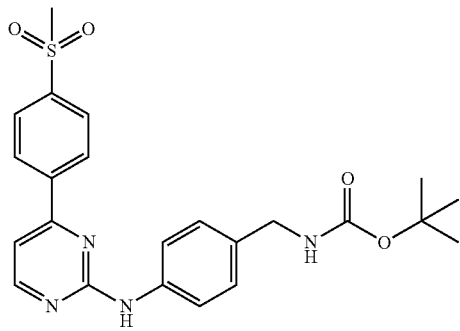 [SMILES: CC(C)(C)OC(=O)NCc1ccc(Nc2nccc(-c3ccc(S(C)(=O)=O)cc3)n2)cc1]

tert-Butyl 4-(4-(4-(methylsulfonyl)phenyl)pyrimidin-2-ylamino)benzylcarbamate was obtained by following procedure E using tert-butyl 4-aminobenzylcarbamate and 2-chloro-4-(4-(methylsulfonyl)phenyl)pyrimidine. MS (ESI) 455 (M+H).

Example 85

N-(3-chloro-2-fluorophenyl)-4-(4-(methylsulfonyl)phenyl)pyrimidin-2-amine

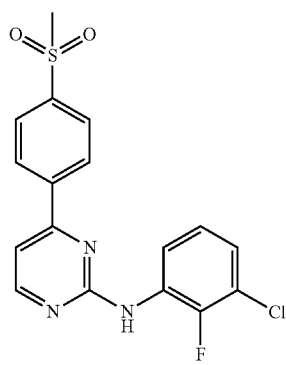 [SMILES: CS(=O)(=O)c1ccc(-c2ccnc(Nc3cccc(Cl)c3F)n2)cc1]

N-(3-chloro-2-fluorophenyl)-4-(4-(methylsulfonyl)phenyl)pyrimidin-2-amine was obtained by following procedure E using 3-chloro-2-fluoroaniline and 2-chloro-4-(4-(methylsulfonyl)phenyl)pyrimidine. MS (ESI) 378 (M+H).

Example 86

N-Cyclopropyl-3-methyl-4-(4-(4-(methylsulfonyl)phenyl)pyrimidin-2-ylamino)benzamide

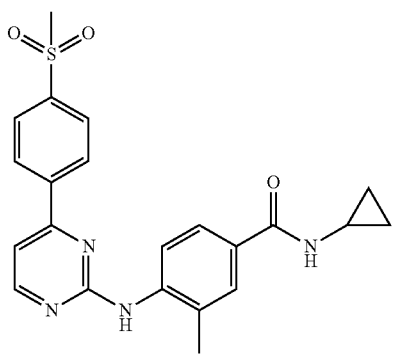 [SMILES: Cc1cc(C(=O)NC2CC2)ccc1Nc1nccc(-c2ccc(S(C)(=O)=O)cc2)n1]

N-Cyclopropyl-3-methyl-4-(4-(4-(methylsulfonyl)phenyl)pyrimidin-2-ylamino)benzamide was obtained by following procedure E using 4-amino-N-cyclopropyl-3-methylbenzamide and 2-chloro-4-(4-(methylsulfonyl)phenyl)pyrimidine. MS (ESI) 423 (M+H).

Example 87

N-(2-Chlorophenyl)-4-(4-(methylsulfonyl)phenyl)pyrimidin-2-amine

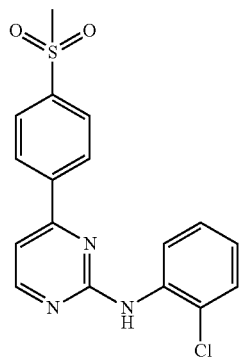 [SMILES: CS(=O)(=O)c1ccc(-c2ccnc(Nc3ccccc3Cl)n2)cc1]

N-(2-Chlorophenyl)-4-(4-(methylsulfonyl)phenyl)pyrimidin-2-amine was obtained by following procedure E using 2-chloroaniline and 2-chloro-4-(4-(methylsulfonyl)phenyl)pyrimidine. MS (ESI) 360.2 (M+H).

Example 88

N-(4-Ethoxyphenyl)-4-(4-(methylsulfonyl)phenyl)pyrimidin-2-amine

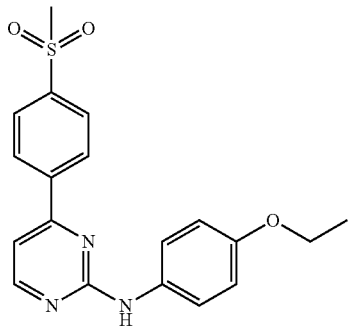 [SMILES: CCOc1ccc(Nc2nccc(-c3ccc(S(C)(=O)=O)cc3)n2)cc1]

N-(4-Ethoxyphenyl)-4-(4-(methylsulfonyl)phenyl)pyrimidin-2-amine was obtained by following procedure E using 4-ethoxyaniline and 2-chloro-4-(4-(methylsulfonyl)phenyl)pyrimidine. MS (ESI) 370.2 (M+H).

Example 89

N-(4-(1H-1,2,3-Triazol-1-yl)phenyl)-4-(3-(1H-pyrazol-5-yl)phenyl)pyrimidin-2-amine

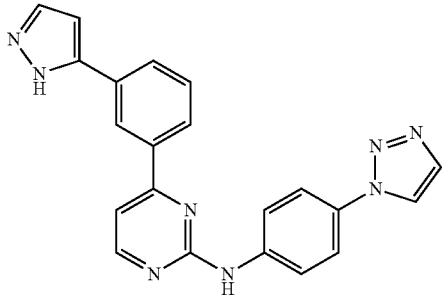 [SMILES: c1cc(-c2ccnc(Nc3ccc(-n4ccnn4)cc3)n2)cc(-c2ccn[nH]2)c1]

N-(4-(1H-1,2,3-Triazol-1-yl)phenyl)-4-(3-(1H-pyrazol-5-yl)phenyl)pyrimidin-2-amine was obtained was obtained by following procedure B using 1H-pyrazol-5-ylboronic acid and N-(4-(1H-1,2,3-triazol-1-yl)phenyl)-4-(3 bromophenyl)pyrimidin-2-amine which was prepared from 4-(3-bromophenyl)-2-chloropyrimidine and 4-(1H-1,2,3-triazol-1-yl)aniline by following procedure E. MS (ESI) 381 (M+H).

Example 90

1-(3-(2-(4-(1H-1,2,3-triazol-1-yl)phenylamino)pyrimidin-4-yl)phenyl)piperidin-4-ol

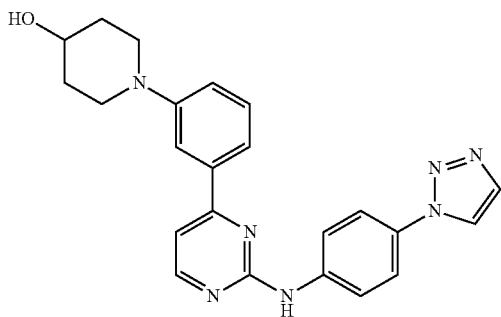 [SMILES: OC1CCN(c2cccc(-c3ccnc(Nc4ccc(-n5ccnn5)cc4)n3)c2)CC1]

Part I 1-(3-(2-Chloropyrimidin-4-yl)phenyl)piperidin-4-ol

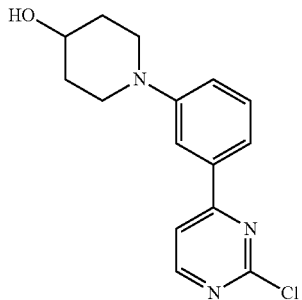 [SMILES: OC1CCN(c2cccc(-c3ccnc(Cl)n3)c2)CC1]

A solution of 1-ethyl-1-methyl-4-oxopiperidinium (3.33 g, 15 mmol) in water (15 mL) was added slowly to a refluxing mixture of 3-bromoanaline (1.1 mL, 10 mmol), $K_2CO_3$ (0.14 g, 1 mmol) and ethanol (10 mL). The mixture was refluxed for 1 h, cooled, and quenched with water (10 mL). The resulting slurry was stirred for 1 h at room temperature and then extracted with ethyl acetate (2×). The combined organics were concentrated in vacuo and the crude residue was purified by chromatography on silica gel (EtOAc/hexanes) to give 1-(3-bromophenyl)piperidin-4-one.

A mixture of 1-(3-bromophenyl)piperidin-4-one (1.5 g, 6.0 mmol), bis(pinacolato)diboron (2.4 g, 9.4 mmol), Pd(dppf) (0.3 g, 0.36 mmol), KOAc (1.74 g, 18 mmol) and DMSO (8 mL) was place in a sealed tube and heated to 100° C. for 2 h. The reaction mixture was cooled, diluted with water and extracted with ether (3×). The combined organics were dried (MgSO$_4$) and concentrated to give 1-(3-(4,4,5,5-tetramethyl-1,3,2-dioxaborolan-2-yl)phenyl)piperidin-4-one which was used for next step without further purification.

1-(3-(2-Chloropyrimidin-4-yl)phenyl)piperidin-4-one was prepared from 1-(3-(4,4,5,5-tetramethyl-1,3,2-dioxaborolan-2-yl)phenyl)piperidin-4-one and 2,4-dichloropyrimidine according to procedure B.

To a 0° C. solution of 1-(3-(2-chloropyrimidin-4-yl)phenyl)piperidin-4-one (200 mg, 0.7 mmol) in methanol (5 mL) was added NaBH$_4$ (53 mg, 1.4 mmol). The reaction mixture was warmed to room temperature and monitored by TLC analysis. When the starting material had been consumed, the reaction was quenched with water and diluted with EtOAc. The layers were separated, and the organics were dried (MgSO$_4$) and concentrated to give 1-(3-(2-chloropyrimidin-4-yl)phenyl)piperidin-4-ol.

Part II 1-(3-(2-(4-(1H-1,2,3-triazol-1-yl)phenylamino)pyrimidin-4-yl)phenyl)piperidin-4-ol was obtained by following procedure E using 4-(1H-1,2,3-triazol-1-yl)aniline and 1-(3-(2-chloropyrimidin-4-yl)phenyl)piperidin-4-ol. MS (ESI) 414 (M+H).

Example 91

4-(4-(Methylsulfonyl)phenyl)-N-(4-(5-phenyl-1H-1,2,3-triazol-1-yl)phenyl)pyrimidin-2-amine

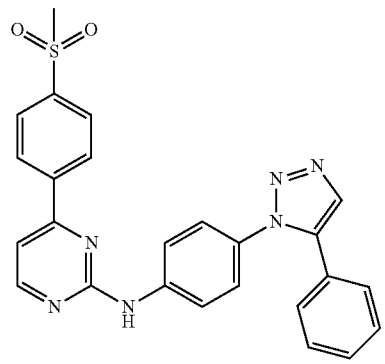 [SMILES: CS(=O)(=O)c1ccc(-c2ccnc(Nc3ccc(-n4nncc4-c4ccccc4)cc3)n2)cc1]

4-(4-(Methylsulfonyl)phenyl)-N-(4-(5-phenyl-1H-1,2,3-triazol-1-yl)phenyl)pyrimidin-2-amine was obtained by following procedure E using 4-(5-phenyl-1H-1,2,3-triazol-1-yl)aniline and 2-chloro-4-(4-(methylsulfonyl)phenyl)pyrimidine. $^1$H NMR (DMSO-d$_6$, 400 MHz) δ 10.2 (s, 1H), 8.8 (d, 1H), 8.5 (d, 2H), 8.25-8.15 (m, 3H), 8.05 (d, 1H), 7.65 (d, 1H), 7.5-7.3 (m, 7H), 3.4 (s, 3H). MS (ESI) 469 (M+H).

Example 92

4-(4-(Methylsulfonyl)phenyl)-N-(4-(4-phenyl-1H-1,2,3-triazol-1-yl)phenyl)pyrimidin-2-amine

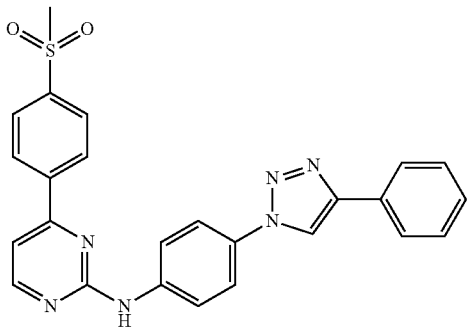 [SMILES: CS(=O)(=O)c1ccc(-c2ccnc(Nc3ccc(-n4cc(-c5ccccc5)nn4)cc3)n2)cc1]

4-(4-(Methylsulfonyl)phenyl)-N-(4-(4-phenyl-1H-1,2,3-triazol-1-yl)phenyl)pyrimidin-2-amine was obtained by following procedure E using 4-(4-phenyl-1H-1,2,3-triazol-1-yl)aniline and 2-chloro-4-(4-(methylsulfonyl)phenyl)pyrimidine. $^1$H NMR (DMSO-d$_6$, 400 MHz) δ 10.2 (s, 1H), 9.2 (s, 1H), 8.7 (d, 1H), 8.45 (d, 2H), 8.15-8.05 (m, 4H), 7.95 (d, 2H), 7.9 (d, 2H), 7.6 (d, 1H), 7.5 (t, 2H), 7.4 (t, 1H), 3.3 (s, 3H).

Example 93

N-(4-(1H-1,2,3-triazol-1-yl)phenyl)-4-(4-(1H-pyrazol-5-yl)phenyl)pyrimidin-2-amine

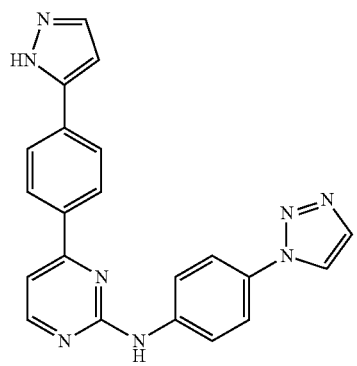 [SMILES: c1cn(-c2ccc(Nc3nccc(-c4ccc(-c5ccn[nH]5)cc4)n3)cc2)nn1]

N-(4-(1H-1,2,3-triazol-1-yl)phenyl)-4-(4-(1H-pyrazol-5-yl)phenyl)pyrimidin-2-amine was obtained was obtained by following procedure B using 1H-pyrazol-5-ylboronic acid and N-(4-(1H-1,2,3-triazol-1-yl)phenyl)-4-(4-bromophenyl)pyrimidin-2-amine which was prepared from 4-(4-bromophenyl)-2-chloropyrimidine and 4-(1H-1,2,3-triazol-1-yl)aniline according to procedure E. MS (ESI) 381 (M+H).

Example 94

N-(4-(2-(4-(3-methyl-1H-1,2,4-triazol-1-yl)phenylamino)pyrimidin-4-yl)phenyl)methanesulfonamide

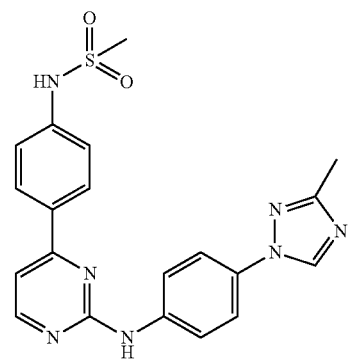 [SMILES: Cc1ncn(-c2ccc(Nc3nccc(-c4ccc(NS(C)(=O)=O)cc4)n3)cc2)n1]

N-(4-(2-(4-(3-methyl-1H-1,2,4-triazol-1-yl)phenylamino)pyrimidin-4-yl)phenyl)methanesulfonamide was obtained by following procedure E using 4-(3-methyl-1H-1,2,4-triazol-1-yl)aniline and N-(4-(2-chloropyrimidin-4-yl)phenyl)methanesulfonamide which was prepared by following procedure B using N-(4-(4,4,5,5-tetramethyl-1,3,2-dioxaborolan-2-yl)phenyl)methanesulfonamide and 2,4-dichloropyrimidine. MS (ESI) 422.1 (M+H).

Example 95

N-(4-(2-(4-(1H-imidazol-1-yl)phenylamino)pyrimidin-4-yl)phenyl)methanesulfonamide

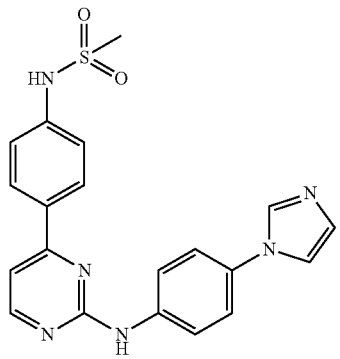 [SMILES: CS(=O)(=O)Nc1ccc(-c2ccnc(Nc3ccc(-n4ccnc4)cc3)n2)cc1]

N-(4-(2-(4-(1H-imidazol-1-yl)phenylamino)pyrimidin-4-yl)phenyl)methanesulfonamide was obtained by following procedure E using 4-(1H-imidazol-1-yl)aniline and N-(4-(2-chloropyrimidin-4-yl)phenyl)methanesulfonamide which was prepared by following procedure B using N-(4-(4,4,5,5-tetramethyl-1,3,2-dioxaborolan-2-yl)phenyl)methanesulfonamide and 2,4-dichloropyrimidine. MS (ESI) 407.1 (M+H).

Example 96

N-(4-(2-(4-(1H-tetrazol-1-yl)phenylamino)pyrimidin-4-yl)phenyl)methanesulfonamide

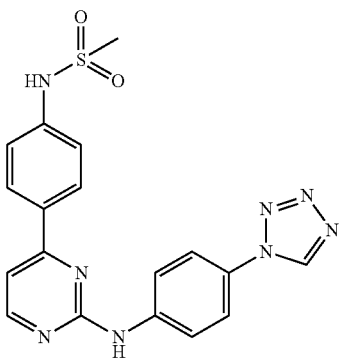 [SMILES: CS(=O)(=O)Nc1ccc(-c2ccnc(Nc3ccc(-n4cnnn4)cc3)n2)cc1]

N-(4-(2-(4-(1H-tetrazol-1-yl)phenylamino)pyrimidin-4-yl)phenyl)methanesulfonamide was obtained by following procedure E using 4-(1H-tetrazol-1-yl)aniline and N-(4-(2-chloropyrimidin-4-yl)phenyl)methanesulfonamide which was prepared by following procedure B using N-(4-(4,4,5,5-tetramethyl-1,3,2-dioxaborolan-2-yl)phenyl)methanesulfonamide and 2,4-dichloropyrimidine. MS (ESI) 408.9 (M+H).

Example 97

N-(4-(2-(4-(2-oxooxazolidin-3-yl)phenylamino)pyrimidin-4-yl)phenyl)methanesulfonamide

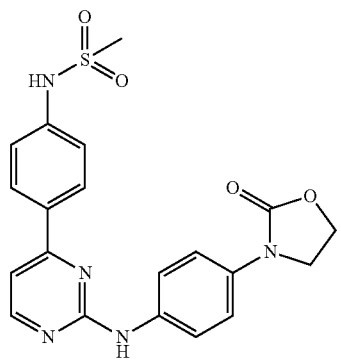 [SMILES: CS(=O)(=O)Nc1ccc(-c2ccnc(Nc3ccc(N4CCOC4=O)cc3)n2)cc1]

N-(4-(2-(4-(2-oxooxazolidin-3-yl)phenylamino)pyrimidin-4-yl)phenyl)methanesulfonamide was obtained by following procedure E using 3-(4-aminophenyl)oxazolidin-2-one and N-(4-(2-chloropyrimidin-4-yl)phenyl)methanesulfonamide which was prepared by following procedure B using N-(4-(4,4,5,5-tetramethyl-1,3,2-dioxaborolan-2-yl)phenyl)methanesulfonamide and 2,4-dichloropyrimidine. MS (ESI) 426.1 (M+H).

Example 98

N-(4-(2-(4-(4H-1,2,4-triazol-4-yl)phenylamino)pyrimidin-4-yl)phenyl)methanesulfonamide

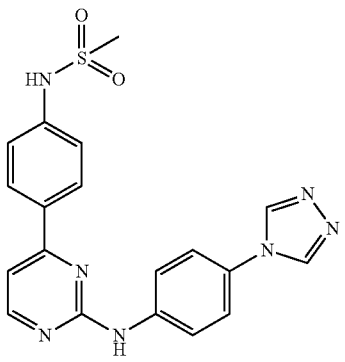 [SMILES: CS(=O)(=O)Nc1ccc(-c2ccnc(Nc3ccc(-n4cnnc4)cc3)n2)cc1]

N-(4-(2-(4-(4H-1,2,4-triazol-4-yl)phenylamino)pyrimidin-4-yl)phenyl)methanesulfonamide was obtained by following procedure E using 4-(4H-1,2,4-triazol-4-yl)aniline and N-(4-(2-chloropyrimidin-4-yl)phenyl)methanesulfonamide which was prepared by following procedure B using N-(4-(4,4,5,5-tetramethyl-1,3,2-dioxaborolan-2-yl)phenyl)methanesulfonamide and 2,4-dichloropyrimidine. MS (ESI) 408.1 (M+H).

Example 99

N-(4-(2-(4-(2H-tetrazol-5-yl)phenylamino)pyrimidin-4-yl)phenyl)methanesulfonamide

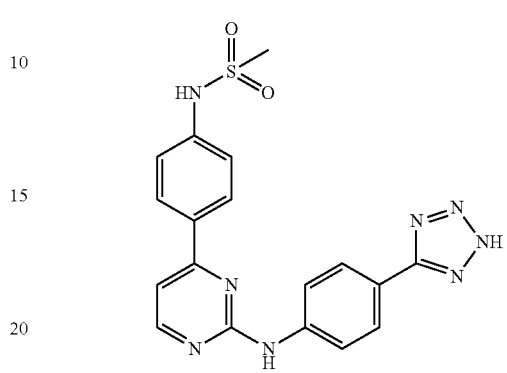

N-(4-(2-(4-(2H-tetrazol-5-yl)phenylamino)pyrimidin-4-yl)phenyl)methanesulfonamide was obtained by following procedure E using 4-(2H-tetrazol-5-yl)aniline and N-(4-(2-chloropyrimidin-4-yl)phenyl)methanesulfonamide which was prepared by following procedure B using N-(4-(4,4,5,5-tetramethyl-1,3,2-dioxaborolan-2-yl)phenyl)methanesulfonamide and 2,4-dichloropyrimidine. MS (ESI) 409.1 (M+H).

Example 100

N-(4-(2-(4-(1,1,1,3,3,3-hexafluoro-2-hydroxypropan-2-yl)phenylamino)pyrimidin-4-yl)phenyl)methanesulfonamide

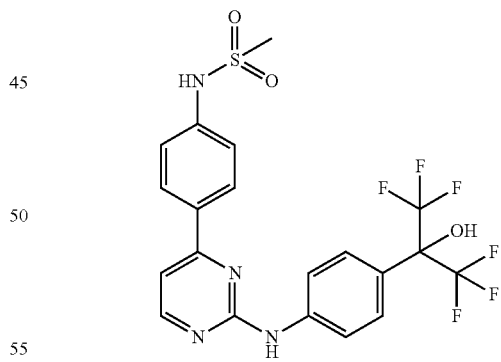

N-(4-(2-(4-(1,1,1,3,3,3-hexafluoro-2-hydroxypropan-2-yl)phenylamino)pyrimidin-4-yl)phenyl)methanesulfonamide was obtained by following procedure E using 2-(4-aminophenyl)-1,1,1,3,3,3-hexafluoropropan-2-ol and N-(4-(2-chloropyrimidin-4-yl)phenyl)methanesulfonamide which was prepared by following procedure B using N-(4-(4,4,5,5-tetramethyl-1,3,2-dioxaborolan-2-yl)phenyl)methanesulfonamide and 2,4-dichloropyrimidine. MS (EST) 507.1 (M+H).

Example 101

N-(4-(2-(4-(5-methyl-1H-1,2,3-triazol-1-yl)phenylamino)pyrimidin-4-yl)phenyl)methanesulfonamide

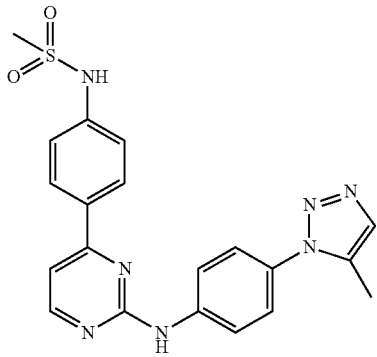 [SMILES: Cc1cnnn1-c1ccc(Nc2nccc(-c3ccc(NS(C)(=O)=O)cc3)n2)cc1]

N-(4-(2-(4-(5-methyl-1H-1,2,3-triazol-1-yl)phenylamino)pyrimidin-4-yl)phenyl)methanesulfonamide was obtained by following procedure E using 4-(5-methyl-1H-1,2,3-triazol-1-yl)aniline and N-(4-(2-chloropyrimidin-4-yl)phenyl)methanesulfonamide which was prepared from 2,4-dichloropyrimidine and N-(4-(4,4,5,5-tetramethyl-1,3,2-dioxaborolan-2-yl)phenyl)methanesulfonamide according to procedure B.

Example 102

3-(4-(4-(3-morpholinophenyl)pyrimidin-2-ylamino)phenyl)oxazolidin-2-one

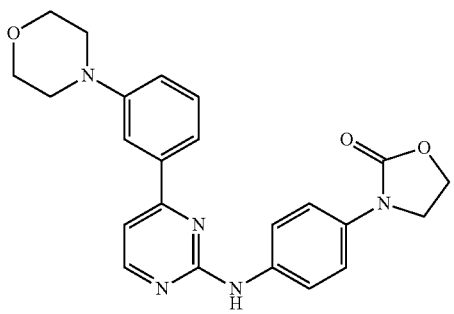 [SMILES: O=C1OCCN1c1ccc(Nc2nccc(-c3cccc(N4CCOCC4)c3)n2)cc1]

3-(4-(4-(3-morpholinophenyl)pyrimidin-2-ylamino)phenyl)oxazolidin-2-one was obtained by following procedure E using 3-(4-aminophenyl)oxazolidin-2-one and 4-(3-(2-chloropyrimidin-4-yl)phenyl)morpholine which was prepared by following procedure B using N-4-(3-(4,4,5,5-tetramethyl-1,3,2-dioxaborolan-2-yl)phenyl)morpholine and 2,4-dichloropyrimidine. MS (ESI) 418.3 (M+H).

Example 103

N-(4-(4H-1,2,4-triazol-4-yl)phenyl)-4-(3-morpholinophenyl)pyrimidin-2-amine

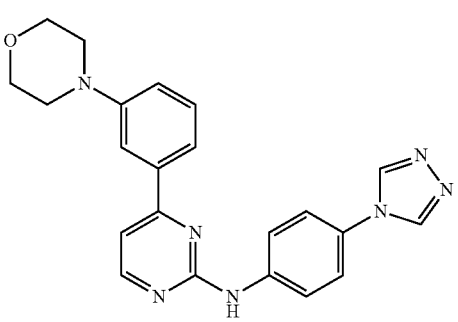 [SMILES: c1cc(-c2ccnc(Nc3ccc(-n4cnnc4)cc3)n2)cc(N2CCOCC2)c1]

N-(4-(4H-1,2,4-triazol-4-yl)phenyl)-4-(3-morpholinophenyl)pyrimidin-2-amine was obtained by following procedure E using 4-(4H-1,2,4-triazol-4-yl)aniline and 4-(3-(2-chloropyrimidin-4-yl)phenyl)morpholine which was prepared by following procedure B using N-4-(3-(4,4,5,5-tetramethyl-1,3,2-dioxaborolan-2-yl)phenyl)morpholine and 2,4-dichloropyrimidine. MS (ESI) 400.3 (M+H).

Example 104

3-(4-(4-(3-fluoro-5-morpholinophenyl)pyrimidin-2-ylamino)phenyl) oxazolidin-2-one

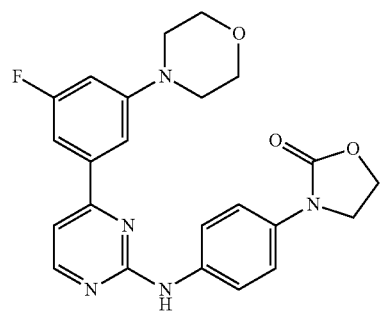 [SMILES: O=C1OCCN1c1ccc(Nc2nccc(-c3cc(F)cc(N4CCOCC4)c3)n2)cc1]

3-(4-(4-(3-fluoro-5-morpholinophenyl)pyrimidin-2-ylamino)phenyl)oxazolidin-2-one was obtained by following procedure E using 3-(4-aminophenyl)oxazolidin-2-one and 4-(3-(2-chloropyrimidin-4-yl)-5-fluorophenyl)morpholine which was prepared by following procedure B using 4-(3-fluoro-5-(4,4,5,5-tetramethyl-1,3,2-dioxaborolan-2-yl)phenyl)morpholine and 2,4-dichloropyrimidine. MS (ESI) 436.3 (M+H).

Example 105

3-(2-(4-(4-methyl-4H-1,2,4-triazol-3-yl)phenylamino)pyrimidin-4-yl)-5-morpholinobenzonitrile

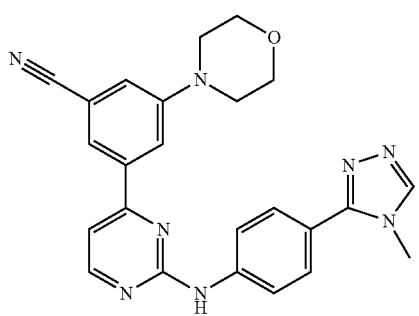 [SMILES: Cn1cnnc1-c1ccc(Nc2nccc(-c3cc(C#N)cc(N4CCOCC4)c3)n2)cc1]

3-(2-(4-(4-methyl-4H-1,2,4-triazol-3-yl)phenylamino)pyrimidin-4-yl)-5-morpholinobenzonitrile was obtained by following procedure E using 4-(4-methyl-4H-1,2,4-triazol-3-yl)aniline and 3-(2-chloropyrimidin-4-yl)-5-morpholinobenzonitrile which was prepared by following procedure B using 3-morpholino-5-(4,4,5,5-tetramethyl-1,3,2-dioxaborolan-2-yl)benzonitrile and 2,4-dichloropyrimidine. MS (ESI) xxx (M+H).

Example 106

4-(3-fluoro-5-morpholinophenyl)-N-(4-(4-methyl-4H-1,2,4-triazol-3-yl)phenyl)pyrimidin-2-amine

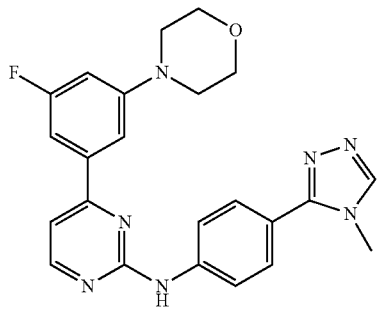 [SMILES: Cn1cnnc1-c1ccc(Nc2nccc(-c3cc(F)cc(N4CCOCC4)c3)n2)cc1]

4-(3-fluoro-5-morpholinophenyl)-N-(4-(4-methyl-4H-1,2,4-triazol-3-yl)phenyl)pyrimidin-2-amine was obtained by following procedure E using 4-(4-methyl-4H-1,2,4-triazol-3-yl)aniline and 4-(3-(2-chloropyrimidin-4-yl)-5-fluorophenyl)morpholine which was prepared by following procedure B using 4-(3-fluoro-5-(4,4,5,5-tetramethyl-1,3,2-dioxaborolan-2-yl)phenyl)morpholine and 2,4-dichloropyrimidine. MS (ESI) 432.3 (M+H).

Example 107

3-(2-(4-(3,5-dimethyl-1H-1,2,4-triazol-1-yl)phenylamino)pyrimidin-4-yl)-5-morpholinobenzonitrile

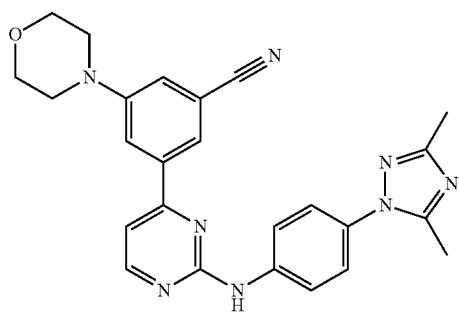 [SMILES: Cc1nc(C)n(-c2ccc(Nc3nccc(-c4cc(C#N)cc(N5CCOCC5)c4)n3)cc2)n1]

3-(2-(4-(3,5-dimethyl-1H-1,2,4-triazol-1-yl)phenylamino)pyrimidin-4-yl)-5-morpholinobenzonitrile was obtained by following procedure E using 4-(3,5-dimethyl-1H-1,2,4-triazol-1-yl)aniline and 3-(2-chloropyrimidin-4-yl)-5-morpholinobenzonitrile which was prepared by following procedure B using 3-morpholino-5-(4,4,5,5-tetramethyl-1,3,2-dioxaborolan-2-yl)benzonitrile and 2,4-dichloropyrimidine. MS (ESI) 453.3 (M+H).

Example 108

3-(2-(4-(5-Methyl-1H-1,2,3-triazol-1-yl)phenylamino)pyrimidin-4-yl)-5-morpholinobenzonitrile

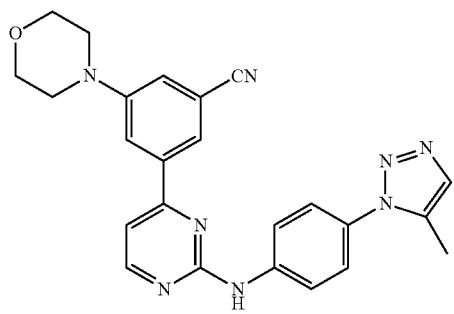 [SMILES: Cc1cnnn1-c1ccc(Nc2nccc(-c3cc(C#N)cc(N4CCOCC4)c3)n2)cc1]

3-(2-(4-(5-Methyl-1H-1,2,3-triazol-1-yl)phenylamino)pyrimidin-4-yl)-5-morpholinobenzonitrile was obtained by following procedure E using 4-(5-methyl-1H-1,2,3-triazol-1-yl)aniline and 3-(2-chloropyrimidin-4-yl)-5-morpholinobenzonitrile which was prepared by following procedure B using 3-morpholino-5-(4,4,5,5-tetramethyl-1,3,2-dioxaborolan-2-yl)benzonitrile and 2,4-dichloropyrimidine. MS (ESI) 439 (M+H).

Example 109

3'3-(2-(4-(4-Methyl-1H-1,2,3-triazol-1-yl)phenylamino)pyrimidin-4-yl)-5-morpholinobenzonitrile

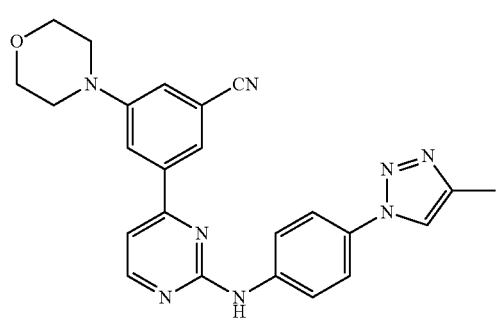 [SMILES: Cc1cn(-c2ccc(Nc3nccc(-c4cc(C#N)cc(N5CCOCC5)c4)n3)cc2)nn1]

Part I 4-(4-Methyl-1H-1,2,3-triazol-1-yl)aniline

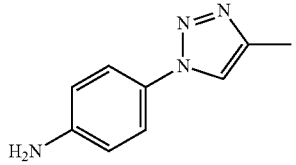

A mixture of 1-azido-4-nitrobenzene (0.5 g, 3.0 mmol), propargyl bromide (80% in toluene) (0.7 mL, 0.6 mmol) and toluene (3 mL) in a sealed tube was heated to 60° C. for 24 h. The reaction mixture was cooled to room temperature and concentrated to give two inseparable isomers 4-(4-(bromomethyl)-1H-1,2,3-triazol-1-yl)aniline and 4-(5-(bromomethyl)-1H-1,2,3-triazol-1-yl)aniline in a 2/1 ratio (as judged by analytical HPLC analysis) which were hydrogenated to afford a mixture of 4-(4-methyl-1H-1,2,3-triazol-1-yl)aniline and 4-(5-methyl-1H-1,2,3-triazol-1-yl)aniline.

Part II

The reaction of 3-(2-chloropyrimidin-4-yl)-5-morpholinobenzonitrile with the mixture of 4-(4-methyl-1H-1,2,3-triazol-1-yl)aniline and 4-(5-methyl-1H-1,2,3-triazol-1-yl)aniline following procedure E gave two isomers which was separated by preparative HPLC to generate the desired 3'3-(2-(4-(4-methyl-1H-1,2,3-triazol-1-yl)phenylamino)pyrimidin-4-yl)-5-morpholinobenzonitrile. $^1$H NMR (DMSO-$d_6$, 400 MHz) δ 9.96 (s, 1H), 8.58 (d, 1H), 8.38 (d, 1H), 7.95-7.91 (m, 4H), 7.73-7.70 (m, 2H), 7.54 (d, 1H), 7.50-7.49 (m, 1H), 3.74-3.69 (m, 4H), 3.28-3.24 (m, 4H), 2.23 (s, 3H). MS (ESI) 439 (M+H).

Example 110

N-(4-(3-methyl-1H-1,2,4-triazol-1-yl)phenyl)-4-(4-(methylsulfonyl)phenyl)pyrimidin-2-amine

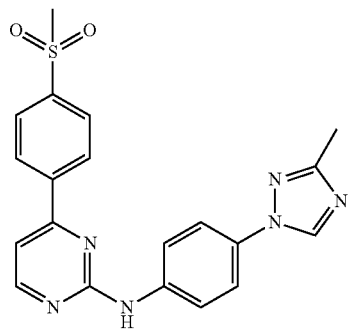 [SMILES: Cc1ncn(-c2ccc(Nc3nccc(-c4ccc(S(C)(=O)=O)cc4)n3)cc2)n1]

N-(4-(3-methyl-1H-1,2,4-triazol-1-yl)phenyl)-4-(4-(methylsulfonyl)phenyl)pyrimidin-2-amine was obtained by following procedure E using 4-(3-methyl-1H-1,2,4-triazol-1-yl)aniline and 2-chloro-4-(4-(methylsulfonyl)phenyl)pyrimidine. MS (ESI) 407 (M+H).

Example 111

N-(4-(1,3,4-oxadiazol-2-yl)phenyl)-4-(3-morpholinophenyl)pyrimidin-2-amine

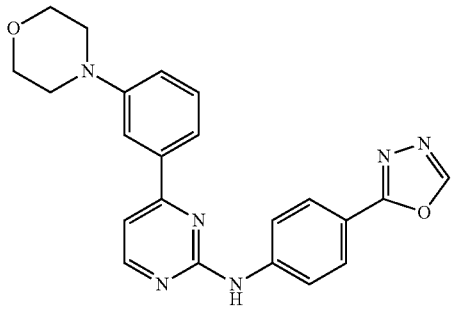 [SMILES: c1cc(-c2ccnc(Nc3ccc(-c4nnco4)cc3)n2)cc(N2CCOCC2)c1]

N-(4-(1,3,4-oxadiazol-2-yl)phenyl)-4-(3 morpholinophenyl)pyrimidin-2-amine was obtained by following procedure E using 4-(1,3,4-oxadiazol-2-yl)aniline and 4-(3-(2-chloropyrimidin-4-yl)phenyl)morpholine. MS (ESI) 401 (M+H).

Example 112

3-(2-(4-(4-Chloro-1H-1,2,3-triazol-1-yl)phenylamino)pyrimidin-4-yl)-5-morpholinobenzonitrile

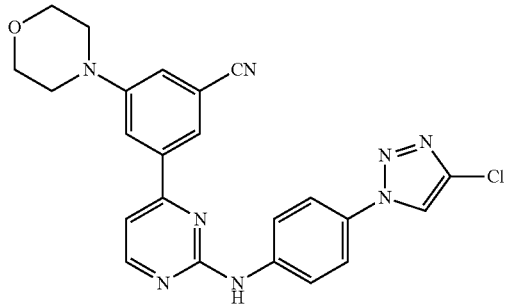 [SMILES: N#Cc1cc(-c2ccnc(Nc3ccc(-n4cc(Cl)nn4)cc3)n2)cc(N2CCOCC2)c1]

Part I 4-(4-Chloro-1H-1,2,3-triazol-1-yl)aniline

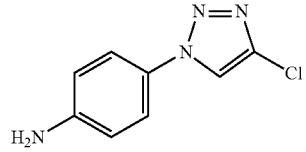 [SMILES: Nc1ccc(-n2cc(Cl)nn2)cc1]

To a mixture of 1-(4-nitrophenyl)-4-(trimethylsilyl)-1H-1,2,3-triazole (0.5 g, 1.9 mmol) and silica gel (2.9 g) in anhydrous $CH_3CN$ (10 mL) was added NCS (1.1 g, 6.7 mmol). The mixture was heated to 80° C. for 24 h. The reaction was cooled, filtered and concentrated in vacuo. The resulting crude residue was purified by chromatography on silica gel (EtOAc/hexanes) to give 4-chloro-1-(4-nitrophenyl)-1H-1,2,3-triazole. $^1$H NMR ($CDCl_3$, 400 MHz) δ 8.39 (dd, 2H), 8.02 (s, 1H), 7.89 (dd, 2H).

To a solution of 4-chloro-1-(4-nitrophenyl)-1H-1,2,3-triazole (0.1 g, 0.45 mmol) in ethanol (3 mL) was added $SnCl_2$ (0.4 g, 1.8 mmol) portionwise. The slurry was warmed up to 85° C. for 2.5 h, then quenched with NaOH (2M), filtered and concentrated. The residue was redissolved in EtOAc and washed with brine. The organic layer was separated, dried ($MgSO_4$), and concentrated to afford 4-(4-chloro-1H-1,2,3-triazol-1-yl)aniline.

Part II 3-(2-(4-(4-Chloro-1H-1,2,3-triazol-1-yl)phenylamino)pyrimidin-4-yl)-5-morpholinobenzonitrile was obtained by following procedure E using 4-(4-chloro-1H-1,2,3-triazol-1-yl)aniline and 3-(2-chloropyrimidin-4-yl)-5-morpholinobenzonitrile. $^1$H NMR (DMSO-$d_6$, 400 MHz) δ 10.10 (s, 1H), 9.05 (s, 1H), 8.72 (d, 1H), 8.23-8.02 (m, 3H), 7.76 (d, 1H), 7.64-7.57 (m, 4H), 4.05-3.80 (m, 4H), 3.33-3.11 (m, 4H). MS (ESI) 459/461 (M+H) (3/1).

Example 113

N-(4-(1H-1,2,3-triazol-1-yl)phenyl)-4-(3-(4-methylpiperazin-1-yl)phenyl)pyrimidin-2-amine

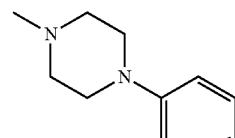

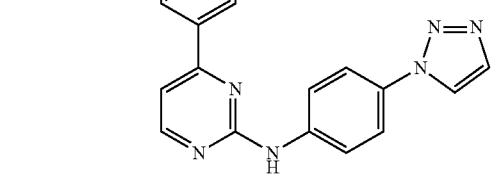

N-(4-(1H-1,2,3-triazol-1-yl)phenyl)-4-(3-(4-methylpiperazin-1-yl)phenyl)pyrimidin-2-amine was obtained by following procedure E using 4-(1H-1,2,3-triazol-1-yl)aniline and 2-chloro-4-(3-(4 methylpiperazin-1-yl)phenyl)pyrimidine which was prepared from 1-methyl-4-(3-(4,4,5,5-tetramethyl-1,3,2-dioxaborolan-2-yl)phenyl)piperazine and 2,4-dichloropyrimidine according to procedure B. MS (ESI) 413 (M+H).

Example 114

3-(2-(4-(3-tert-butyl-1H-1,2,4-triazol-1-yl)phenylamino)pyrimidin-4-yl)-5-morpholinobenzonitrile

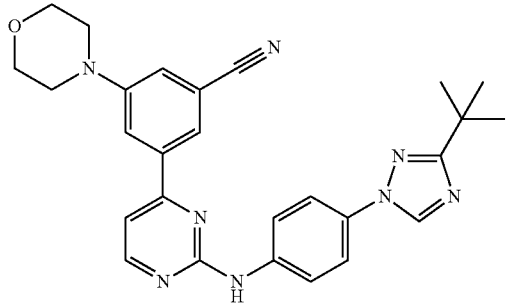 [SMILES: CC(C)(C)c1ncn(-c2ccc(Nc3nccc(-c4cc(C#N)cc(N5CCOCC5)c4)n3)cc2)n1]

3-(2-(4-(3-tert-butyl-1H-1,2,4-triazol-1-yl)phenylamino)pyrimidin-4-yl)-5-morpholinobenzonitrile was obtained by following procedure E using 4-(3-tert-butyl-1H-1,2,4-triazol-1-yl)aniline and 3-(2-chloropyrimidin-4-yl)-5-morpholinobenzonitrile which was prepared by following procedure B from 3-morpholino-5-(4,4,5,5-tetramethyl-1,3,2-dioxaborolan-2-yl)benzonitrile and 2,4-dichloropyrimidine. MS (ESI) 481.4 (M+H).

Example 115

3-Morpholino-5-(2-(4-(5-(trifluoromethyl)-1,3,4-oxadiazol-2-yl)phenylamino)pyrimidin-4-yl)benzonitrile

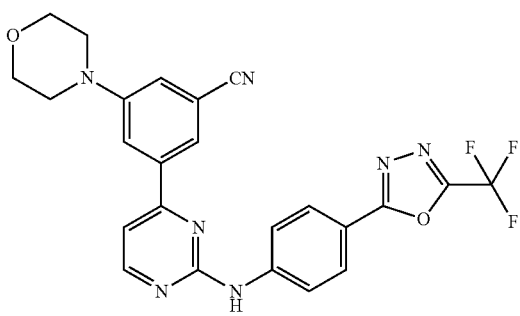 [SMILES: N#Cc1cc(-c2ccnc(Nc3ccc(-c4nnc(C(F)(F)F)o4)cc3)n2)cc(N2CCOCC2)c1]

3-Morpholino-5-(2-(4-(5-(trifluoromethyl)-1,3,4-oxadiazol-2-yl)phenylamino)pyrimidin-4-yl)benzonitrile was obtained by following procedure E using 4-(5-(trifluoromethyl)-1,3,4-oxadiazol-2-yl)aniline and 3-(2-chloropyrimidin-4-yl)-5-morpholinobenzonitrile. MS (ESI) 494 (M+H).

Example 116

3-(2-(4-(2H-tetrazol-5-yl)phenylamino)pyrimidin-4-yl)-5-morpholinobenzonitrile

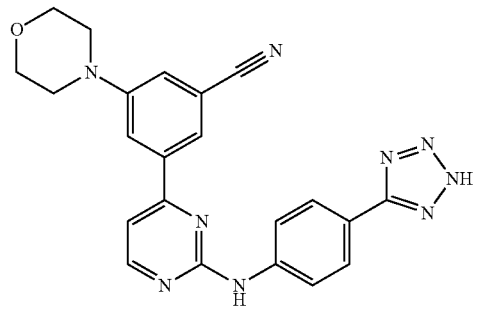 [SMILES: N#Cc1cc(-c2ccnc(Nc3ccc(-c4nn[nH]n4)cc3)n2)cc(N2CCOCC2)c1]

3-(2-(4-(2H-tetrazol-5-yl)phenylamino)pyrimidin-4-yl)-5-morpholinobenzonitrile was obtained by following procedure E using 4-(2H-tetrazol-5-yl)aniline and 3-(2-chloropyrimidin-4-yl)-5-morpholinobenzonitrile which was prepared by following procedure B from 3-morpholino-5-(4,4,5,5-tetramethyl-1,3,2-dioxaborolan-2-yl)benzonitrile and 2,4-dichloropyrimidine. MS (ESI) 426.1 (M+H).

Example 117

N-(4-(5-methyl-1H-1,2,3-triazol-1-yl)phenyl)-4-(3-morpholinophenyl)pyrimidin-2-amine

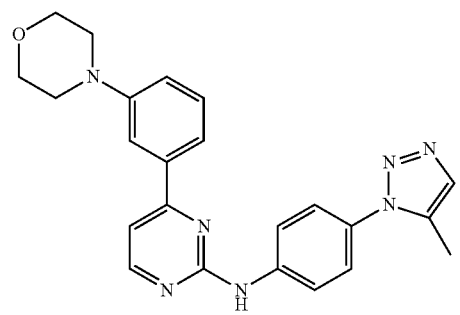 [SMILES: Cc1cnnn1-c1ccc(Nc2nccc(-c3cccc(N4CCOCC4)c3)n2)cc1]

N-(4-(5-methyl-1H-1,2,3-triazol-1-yl)phenyl)-4-(3-morpholinophenyl)pyrimidin-2-amine was obtained by following procedure E using 4-(5-methyl-1H-1,2,3-triazol-1-yl)aniline and 4-(3-(2-chloropyrimidin-4-yl)phenyl)morpholine. MS (ESI) 414 (M+H).

Example 118

N-(3-(2-(4-(1H-1,2,3-triazol-1-yl)phenylamino)pyrimidin-4-yl)-5-morpholinophenyl)acetamide

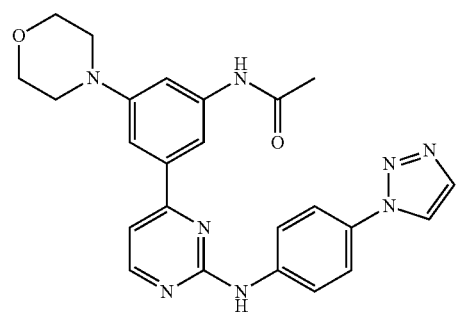 [SMILES: CC(=O)Nc1cc(-c2ccnc(Nc3ccc(-n4ccnn4)cc3)n2)cc(N2CCOCC2)c1]

A solution of acetyl chloride (0.02 mL, 0.28 mmol) in CH₂Cl₂ (1 mL) was added to N-(4-(1H-1,2,3-triazol-1-yl)phenyl)-4-(3-morpholino-5-(phenylamino)phenyl)pyrimidin-2-amine (0.11 g, 0.28 mmol) in CH₂Cl₂ (3 mL) drop wise at 0° C. The reaction was warmed to room temperature, stirred for 30 min, concentrated, and purified by chromatography on silica gel (ethyl acetate/hexanes) to afford N-(3-(2-(4-(1H-1,2,3-triazol-1-yl)phenylamino)pyrimidin-4-yl)-5-morpholinophenyl)acetamide. MS (ESI) 457 (M+H).

Example 119

N-(4-(5-methyl-1,3,4-oxadiazol-2-yl)phenyl)-4-(3-morpholinophenyl)pyrimidin-2-amine

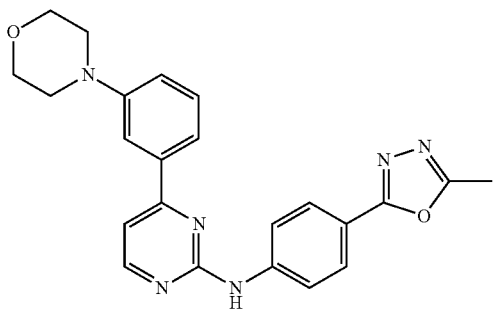 [SMILES: Cc1nnc(-c2ccc(Nc3nccc(-c4cccc(N5CCOCC5)c4)n3)cc2)o1]

N-(4-(5-methyl-1,3,4-oxadiazol-2-yl)phenyl)-4-(3 morpholinophenyl)pyrimidin-2-amine was obtained by following procedure E using 4-(5-methyl-1,3,4-oxadiazol-2-yl)aniline and 4-(3-(2-chloropyrimidin-4-yl)phenyl)morpholine. MS (ESI) 415 (M+H).

Example 120

N-(4-(1H-imidazol-1-yl)phenyl)-4-(3-morpholinophenyl)pyrimidin-2-amine

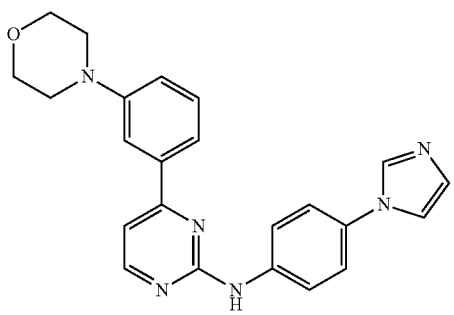 [SMILES: c1cc(-c2ccnc(Nc3ccc(-n4ccnc4)cc3)n2)cc(N2CCOCC2)c1]

N-(4-(1H-imidazol-1-yl)phenyl)-4-(3-morpholinophenyl)pyrimidin-2-amine was obtained by following procedure E using 4-(1H-imidazol-1-yl)aniline and 4-(3-(2-chloropyrimidin-4-yl)phenyl)morpholine which was prepared according procedure B from 4-(3-(4,4,5,5-tetramethyl-1,3,2-dioxaborolan-2-yl)phenyl)morpholine and 2,4-dichloropyrimidine. MS (ESI) 399 (M+H).

Example 121

3-(4-(4-(3-morpholino-5-nitrophenyl)pyrimidin-2-ylamino)phenyl)oxazolidin-2-one

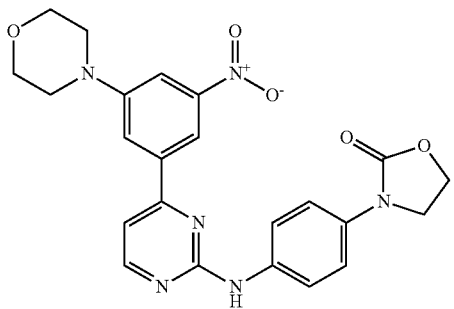 [SMILES: O=C1OCCN1c1ccc(Nc2nccc(-c3cc(N4CCOCC4)cc([N+](=O)[O-])c3)n2)cc1]

3-(4-(4-(3-morpholino-5-nitrophenyl)pyrimidin-2-ylamino)phenyl)oxazolidin-2-one was obtained by following procedure E using 3-(4-aminophenyl)oxazolidin-2-one and 4-(3-(2-chloropyrimidin-4-yl)-5-nitrophenyl)morpholine which was prepared by following procedure B using 4-(3-nitro-5-(4,4,5,5-tetramethyl-1,3,2-dioxaborolan-2-yl)phenyl)morpholine and 2,4-dichloropyrimidine. $^1$H NMR (DMSO-d$_6$, 400 MHz) δ 9.8 (s, 1H), 8.6 (d, 1H), 8.35 (s, 1H), 8.1 (s, 1H), 7.9-7.8 (m, 3H), 7.6 (d, 1H), 7.5 (d, 2H), 4.45 (t, 2H), 4.05 (t, 2H), 3.85-3.75 (m, 4H), 3.45-3.35 (m, 4H). MS (ESI) 463.3 (M+H).

Example 122

N-(4-(1H-1,2,3-triazol-1-yl)phenyl)-4-(3-morpholino-5-(phenylamino)phenyl)pyrimidin-2-amine

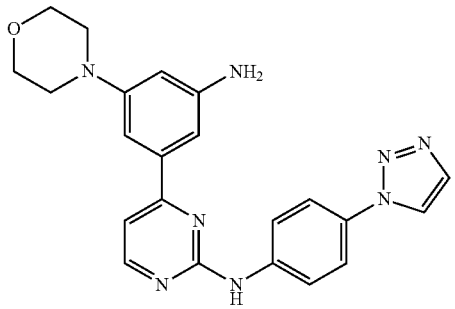

N-(4-(1H-1,2,3-triazol-1-yl)-phenyl)-4-(3-morpholino-5-(phenylamino)phenyl)pyrimidin-2-amine was obtained by hydrogenation of N-(4-(1H-1,2,3-triazol-1-yl)phenyl)-4-(3 morpholino-5-nitrophenyl)pyrimidin-2-amine following general procedure D. MS (ESI) 415 (M+H).

Example 123

3-(5-Fluoro-4-phenylpyrimidin-2-ylamino)benzamide

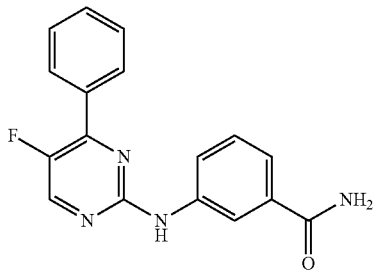 [SMILES: NC(=O)c1cccc(Nc2ncc(F)c(-c3ccccc3)n2)c1]

3-(5-Fluoro-4-phenylpyrimidin-2-ylamino)benzamide was obtained by following procedure E using 3-aminobenzamide and 2-chloro-5-fluoro-4-phenylpyrimidine which was prepared by following procedure B using 2,4-dichloro-5-fluoropyrimidine and phenylboronic acid. $^1$H NMR (DMSO-d$_6$, 400 MHz) δ 10.08 (s, 1H), 8.71 (s, 1H), 8.08-8.05 (m, 2H), 7.91-7.83 (m, 4H), 7.65-7.60 (m, 4H), 7.16 (br s, 1H). MS (ESI) 309 (M+H).

Example 124

4-(5-Fluoro-4-phenylpyrimidin-2-ylamino)benzamide

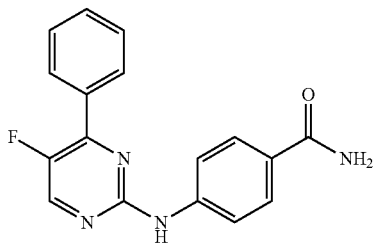 [SMILES: NC(=O)c1ccc(Nc2ncc(F)c(-c3ccccc3)n2)cc1]

4-(5-Fluoro-4-phenylpyrimidin-2-ylamino)benzamide was obtained by following procedure E using 4-aminobenzamide and 2-chloro-5-fluoro-4-phenylpyrimidine. $^1$H NMR (DMSO-d$_6$, 400 MHz) δ 9.88 (s, 1H), 9.13 (s, 1H), 8.53 (d, 1H), 8.14-8.10 (m, 2H), 7.98-7.95 (m, 2H), 7.75-7.72 (m, 2H), 7.52-7.49 (m, 3H), 7.40 (d, 1H). MS (ESI) 309 (M+H).

Example 125

N-(4-(1H-1,2,4-triazol-1-yl)phenyl)-4-phenylpyrimidin-2-amine

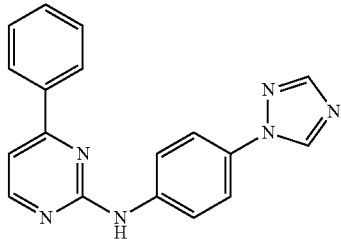 [SMILES: c1ccc(-c2ccnc(Nc3ccc(-n4cncn4)cc3)n2)cc1]

N-(4-(1H-1,2,4-triazol-1-yl)phenyl)-4-phenylpyrimidin-2-amine was obtained by following procedure E using 2-chloro-4-phenylpyrimidine and 4-(1H-1,2,4-triazol-1-yl)aniline. $^1$H NMR (DMSO-d$_6$, 400 MHz) δ 9.77 (s, 1H), 8.52 (dd, 1H), 8.34 (t, 1H), 8.14-8.10 (m, 2H), 7.92-7.88 (m, 2H), 7.73-7.70 (m, 2H), 7.64 (d, 1H), 7.53-7.48 (m, 2H), 7.37 (d, 1H), 6.45 (dd, 1H). MS (ESI) 315 (M+H).

Example 126

2-(4-Hydroxypiperidin-1-yl)-5-(2-(4-(3-(trifluoromethyl)-1H-1,2,4-triazol-1-yl)phenylamino)pyrimidin-4-yl)benzonitrile

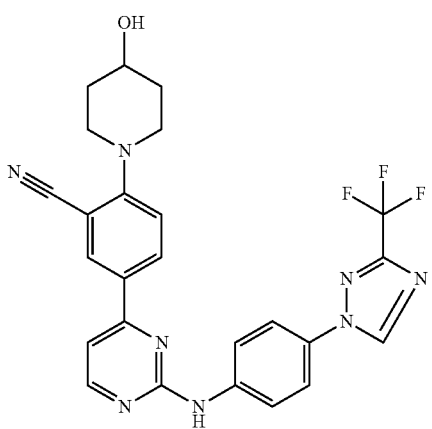

Part I 3-(Trifluoromethyl)-1H-1,2,4-triazole

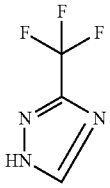

To a solution of hydrazine hydrate (2.7 mL, 48.6 mmol) in EtOH (80 mL) was added ethyl 2,2,2-trifluoroacetate (6.3 mL, 48.6 mmol). The reaction was aged at room temperature for 90 minutes and concentrated in vacuo. To the crude residue was added EtOH (50 mL) and formamidine acetate (5.1 g, 48.6 mmol) and the reaction was warmed to reflux for 3 h. The reaction was cooled, concentrated in vacuo, and taken up in EtOAc and washed with sat. aq. NaHCO$_3$ (2×). The organic layer was dried (MgSO$_4$) and concentrated to give a pale yellow oil which was used without further purification. $^1$H NMR (CDCl$_3$, 400 MHz) δ 13.6 (br s, 1H), 8.5 (s, 1H).

Part II 4-(3-(Trifluoromethyl)-1H-1,2,4-triazol-1-yl)aniline

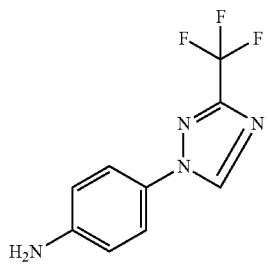 [SMILES: Nc1ccc(-n2cnc(C(F)(F)F)n2)cc1]

4-(3-(Trifluoromethyl)-1H-1,2,4-triazol-1-yl)aniline was obtained by following procedures C and D using 4-fluoro-1-nitrobenzene and 3-(trifluoromethyl)-1H-1,2,4-triazole. $^1$H NMR (CDCl$_3$, 400 MHz) δ 8.5 (s, 1H), 7.50 (d, 2H), 6.80 (d, 2H), 4.0 (br s, 2H).

Part III 2-(4-Hydroxypiperidin-1-yl)-5-(2-(4-(3-(trifluoromethyl)-1H-1,2,4-triazol-1-yl)phenylamino)pyrimidin-4-yl)benzonitrile was obtained by following procedure E using 5-(2-chloropyrimidin-4-yl)-2-(4-hydroxypiperidin-1-yl)benzonitrile and 4-(3-(trifluoromethyl)-1H-1,2,4-triazol-1-yl)aniline. $^1$H NMR (DMSO-d$_6$, 400 MHz) δ 9.91 (s, 1H), 9.37 (s, 1H), 8.48 (d, 1H), 8.37 (d, 1H), 8.26 (dd, 1H), 7.92 (d, 2H), 7.72 (d, 2H), 7.41 (d, 1H), 7.19 (d, 1H), 4.67 (brs, 1H), 3.52 (m, 1H), 3.47 (m, 2H), 3.00 (m, 2H), 1.79 (m, 2H), 1.47 (m, 2H). MS (ESI) 507.30 (M+H).

Example 127

2-(4-Hydroxypiperidin-1-yl)-5-(2-(4-(5-methyl-1H-tetrazol-1-yl)phenylamino)pyrimidin-4-yl)benzonitrile

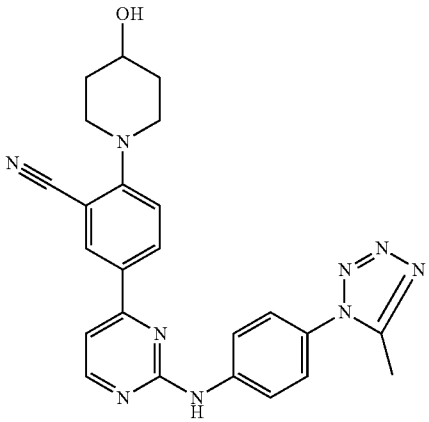 [SMILES: Cc1nnnn1-c1ccc(Nc2nccc(-c3ccc(N4CCC(O)CC4)c(C#N)c3)n2)cc1]

2-(4-Hydroxypiperidin-1-yl)-5-(2-(4-(5-methyl-1H-tetrazol-1-yl)phenylamino)pyrimidin-4-yl)benzonitrile was obtained by following procedure E using 5-(2-chloropyrimidin-4-yl)-2-(4-hydroxypiperidin-1-yl)benzonitrile and 4-(5- methyl-1H-tetrazol-1-yl)aniline. $^1$H NMR (DMSO-d$_6$, 400 MHz) δ 10.10 (s, 1H), 8.60 (d, 1H), 8.50 (d, 1H), 8.38 (dd, 1H), 8.08 (d, 2H), 7.61 (d, 2H), 7.54 (d, 1H), 7.30 (d, 1H), 3.74 (m, 1H), 3.60 (m, 2H), 3.11 (m, 2H), 2.61 (s, 3H), 1.96 (m, 2H), 1.59 (m, 2H). MS (ESI) 454.03 (M+H).

Example 128

5-(2-(4-(2H-Tetrazol-5-yl)phenylamino)pyrimidin-4-yl)-2-(4-hydroxypiperidin-1-yl)benzonitrile

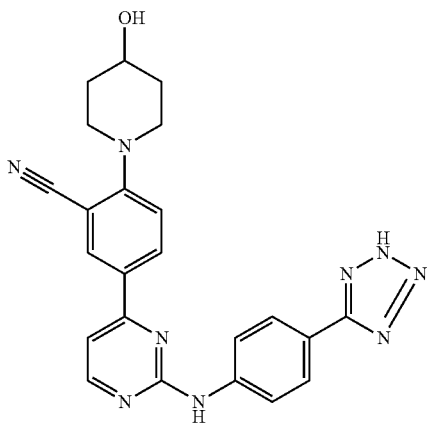 [SMILES: N#Cc1cc(-c2ccnc(Nc3ccc(-c4nn[nH]n4)cc3)n2)ccc1N1CCC(O)CC1]

5-(2-(4-(2H-Tetrazol-5-yl)phenylamino)pyrimidin-4-yl)-2-(4 hydroxypiperidin-1-yl)benzonitrile was obtained by following procedure E using 5-(2-chloropyrimidin-4-yl)-2-(4-hydroxypiperidin-1-yl)benzonitrile and 4-(2H-tetrazol-5-yl)aniline. $^1$H NMR (DMSO-d$_6$, 400 MHz) δ 10.09 (s, 1H), 8.61 (d, 1H), 8.50 (d, 1H), 8.38 (dd, 1H), 8.06 (d, 2H), 8.00 (d, 2H), 7.55 (d, 1H), 7.32 (d, 1H), 3.72 (m, 1H), 3.61 (m, 2H), 3.13 (m, 2H), 1.89 (m, 2H), 1.59 (m, 2H). MS (ESI) 440.10 (M+H).

Example 129

2-(4-Hydroxypiperidin-1-yl)-5-(2-(4-(2-methyl-2H-tetrazol-5-yl)phenylamino)pyrimidin-4-yl)benzonitrile

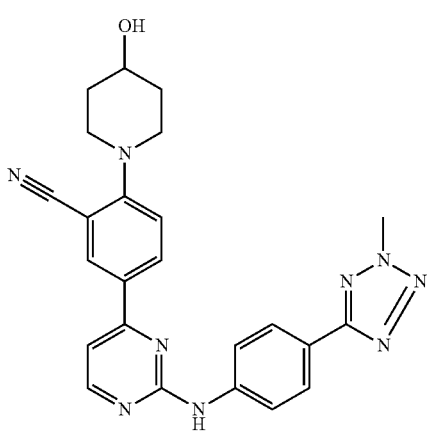 [SMILES: Cn1nnc(-c2ccc(Nc3nccc(-c4ccc(N5CCC(O)CC5)c(C#N)c4)n3)cc2)n1]

Part I 4-(2-Methyl-2H-tetrazol-5-yl)aniline

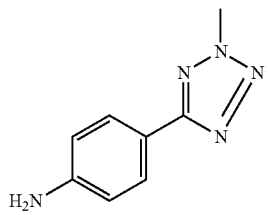

4-(2-Methyl-2H-tetrazol-5-yl)aniline was obtained by following procedure D from 2-methyl-5-(4-nitrophenyl)-2H-tetrazole. $^1$H NMR (CDCl$_3$, 400 MHz) δ 7.95 (d, 2H), 6.78 (d, 2H), 4.38 (s, 3H), 3.91 (br s, 2H).

Part II 2-(4-Hydroxypiperidin-1-yl)-5-(2-(4-(2-methyl-2H-tetrazol-5-yl)phenylamino)pyrimidin-4-yl)benzonitrile was obtained by following procedure E using 5-(2-chloropyrimidin-4-yl)-2-(4-hydroxypiperidin-1-yl)benzonitrile and 4-(2-methyl-2H-tetrazol-5-yl)aniline. $^1$H NMR (MeOH-d$_4$, 400 MHz) δ 8.52 (s, 1H), 8.41 (d, 1H), 8.38 (d, 1H), 8.19 (d, 2H), 7.84 (d, 2H), 7.56 (d, 1H), 7.29 (d, 1H), 4.45 (s, 3H), 3.90 (m, 1H), 3.77 (m, 2H), 3.24 (m, 2H), 2.06 (m, 2H), 1.77 (m, 2H). MS (ESI) 454.14 (M+H).

Example 130

2-(4-Hydroxypiperidin-1-yl)-5-(2-(4-(1-methyl-1H-tetrazol-5-yl)phenylamino)pyrimidin-4-yl)benzonitrile

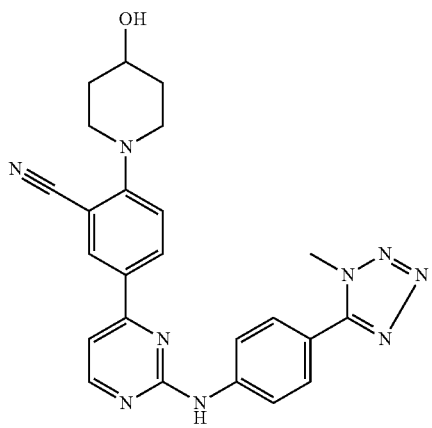 [SMILES: Cn1nnnc1-c1ccc(Nc2nccc(-c3ccc(N4CCC(O)CC4)c(C#N)c3)n2)cc1]

Part I 4-(1-Methyl-1H-tetrazol-5-yl)aniline

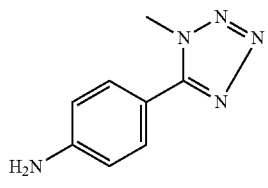

4-(1-Methyl-1H-tetrazol-5-yl)aniline was obtained by following procedure D from 1-methyl-5-(4-nitrophenyl)-1H-tetrazole. $^1$H NMR (CDCl$_3$, 400 MHz) δ 7.59 (d, 2H), 6.82 (d, 2H), 4.18 (s, 3H), 4.07 (br s, 2H).

Part II 2-(4-Hydroxypiperidin-1-yl)-5-(2-(4-(2-methyl-2H-tetrazol-5-yl)phenylamino)pyrimidin-4-yl)benzonitrile was obtained by following procedure E using 5-(2-chloropyrimidin-4-yl)-2-(4-hydroxypiperidin-1-yl)benzonitrile and 4-(1-methyl-1H-tetrazol-5-yl)aniline. $^1$H NMR (DMSO-d$_6$, 400 MHz) δ 10.11 (s, 1H), 8.61 (d, 1H), 8.50 (d, 1H), 8.39 (d, 1H), 8.08 (d, 2H), 7.85 (d, 2H), 7.55 (d, 1H), 7.31 (d, 1H), 4.20 (s, 3H), 3.73 (m, 2H), 3.57 (m, 1H), 3.12 (m, 2H), 1.91 (m, 2H), 1.59 (m, 2H). MS (ESI) 454.16 (M+H).

Example 131

3-(2-(4-(2-Methyl-2H-tetrazol-5-yl)phenylamino)pyrimidin-4-yl)-5-morpholinobenzonitrile

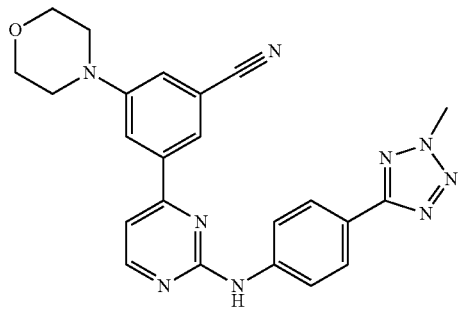 [SMILES: Cn1nnc(-c2ccc(Nc3nccc(-c4cc(C#N)cc(N5CCOCC5)c4)n3)cc2)n1]

3-(2-(4-(2-Methyl-2H-tetrazol-5-yl)phenylamino)pyrimidin-4-yl)-5-morpholinobenzonitrile was obtained by following procedure E using 3-(2-chloropyrimidin-4-yl)-5-morpholinobenzonitrile and 4-(2-methyl-2H-tetrazol-5-yl)aniline. $^1$H NMR (CDCl$_3$, 400 MHz) δ 8.49 (d, 1H), 8.05 (d, 2H), 7.86 (s, 1H), 7.76 (d, 2H), 7.65 (s, 1H), 7.36 (s, 1H), 7.16 (d, 1H), 7.10 (d, 1H), 4.33 (s, 3H), 3.85 (m, 4H), 3.23 (m, 4H). MS (ESI) 440.11 (M+H).

Example 132

3-(2-(4-(1-Methyl-1H-tetrazol-5-yl)phenylamino)pyrimidin-4-yl)-5-morpholinobenzonitrile

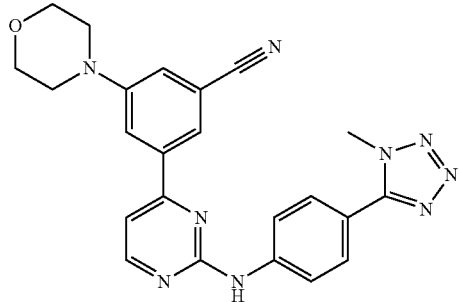 [SMILES: Cn1nnnc1-c1ccc(Nc2nccc(-c3cc(C#N)cc(N4CCOCC4)c3)n2)cc1]

3-(2-(4-(1-Methyl-1H-tetrazol-5-yl)phenylamino)pyrimidin-4-yl)-5-morpholinobenzonitrile was obtained by following procedure E using 3-(2-chloropyrimidin-4-yl)-5-morpholinobenzonitrile and 4-(1-methyl-1H-tetrazol-5-yl)aniline. $^1$H NMR (CDCl$_3$, 400 MHz) δ 8.52 (d, 1H), 7.87 (d, 2H), 7.77 (s, 1H), 7.71 (s, 1H), 7.68 (d, 2H), 7.40 (m, 1H), 7.18 (d, 1H), 7.14 (d, 1H), 4.14 (s, 3H), 3.84 (m, 4H), 3.23 (m, 4H).

Example 133

3-Morpholino-5-(2-(4-(3-(trifluoromethyl)-1H-1,2,4-triazol-1-yl)phenylamino)pyrimidin-4-yl)benzonitrile

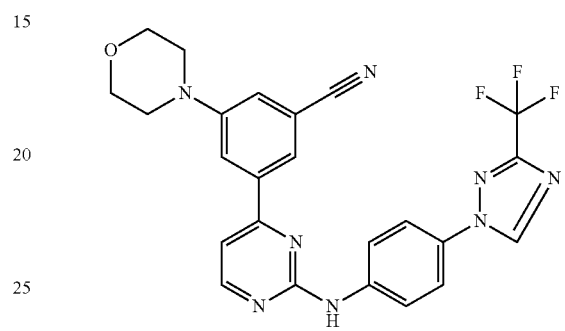

3-Morpholino-5-(2-(4-(3-(trifluoromethyl)-1H-1,2,4-triazol-1-yl)phenylamino)pyrimidin-4-yl)benzonitrile was obtained by following procedure E using 3-(2-chloropyrimidin-4-yl)-5-morpholinobenzonitrile and 4-(3-(trifluoromethyl)-1H-1,2,4-triazol-1-yl)aniline. $^1$H NMR (DMSO-d$_6$, 400 MHz) δ 10.09 (s, 1H), 9.49 (s, 1H), 8.67 (d, 1H), 8.04 (m, 3H), 7.99 (s, 1H), 7.83 (d, 2H), 7.63 (d, 1H), 7.56 (d, 1H), 3.80 (m, 4H), 3.30 (m, 4H). MS (ESI) 493.26 (M+H).

Example 134

3-(2-(4-(3-Bromo-1H-1,2,4-triazol-1-yl)phenylamino)pyrimidin-4-yl)-5-morpholinobenzonitrile

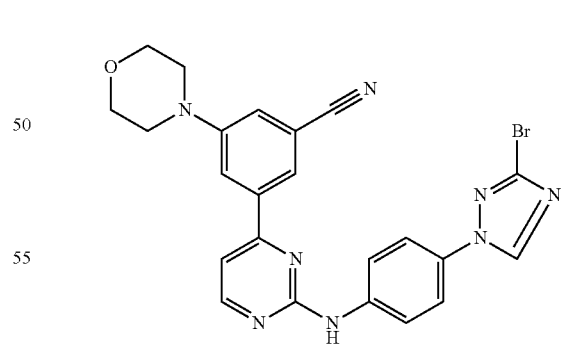

3-(2-(4-(3-Bromo-1H-1,2,4-triazol-1-yl)phenylamino)pyrimidin-4-yl)-5-morpholinobenzonitrile was obtained by following procedure E using 3-(2-chloropyrimidin-4-yl)-5-morpholinobenzonitrile and 4-(3-bromo-1H-1,2,4-triazol-1-yl)aniline. $^1$H NMR (DMSO-d$_6$, 400 MHz) δ 10.04 (s, 1H), 9.23 (s, 1H), 8.66 (d, 1H), 8.00 (m, 4H), 7.76 (d, 2H), 7.62 (d, 1H), 7.58 (s, 1H), 3.80 (m, 4H), 3.30 (m, 4H).

Example 135

3-Morpholino-5-(2-(4-(3-(pyridin-3-yl)-1H-1,2,4-triazol-1-yl)phenylamino)pyrimidin-4-yl)benzonitrile

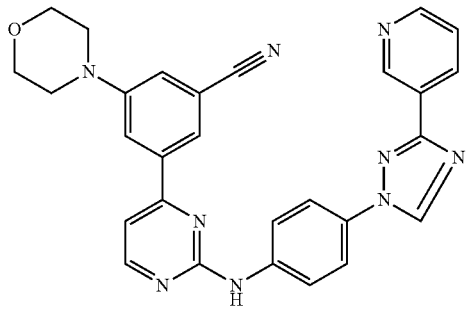 [SMILES: N#Cc1cc(-c2ccnc(Nc3ccc(-n4cnc(-c5cccnc5)n4)cc3)n2)cc(N2CCOCC2)c1]

3-Morpholino-5-(2-(4-(3-(pyridin-3-yl)-1H-1,2,4-triazol-1-yl)phenylamino)pyrimidin-4-yl)benzonitrile was obtained by following procedure K using 3-(2-(4-(3-bromo-1H-1,2,4-triazol-1-yl)phenylamino)pyrimidin-4-yl)-5-morpholinobenzonitrile and pyridin-3-ylboronic acid. $^1$H NMR (CDCl$_3$, 400 MHz) δ 9.38 (s, 1H), 8.59 (s, 1H), 8.51 (s, 1H), 8.49 (s, 1H), 8.40 (d, 1H), 7.83 (d, 2H), 7.81 (s, 1H), 7.68 (d, 2H), 7.65 (s, 1H), 7.36 (m, 2H), 7.19 (d, 1H), 7.12 (d, 1H), 3.85 (m, 4H), 3.23 (m, 4H). MS (ESI) 502.32 (M+H).

Example 136

4-(3-Fluoro-5-morpholinophenyl)-N-(4-(3-methyl-1H-1,2,4-triazol-1-yl)phenyl)pyrimidin-2-amine

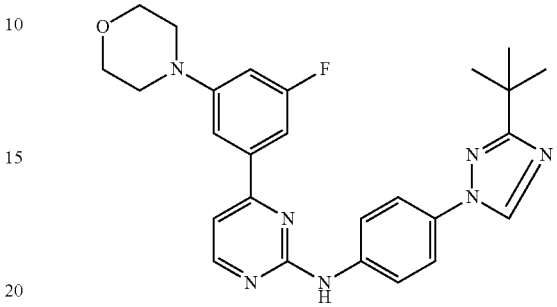

4-(3-Fluoro-5-morpholinophenyl)-N-(4-(3-methyl-1H-1,2,4-triazol-1-yl)phenyl)pyrimidin-2-amine was obtained by following procedure E using 4-(3-(2-chloropyrimidin-4-yl)-5-fluorophenyl)morpholine and 4-(3-methyl-1H-1,2,4-triazol-1-yl)aniline. $^1$H NMR (DMSO-d$_6$, 400 MHz) δ 9.93 (s, 1H), 9.06 (s, 1H), 8.61 (d, 1H), 7.97 (d, 2H), 7.74 (d, 2H), 7.59 (s, 1H), 7.53 (d, 1H), 7.38 (d, 1H), 6.97 (d, 1H), 3.79 (m, 4H), 3.28 (m, 4H), 2.37 (s, 3H). MS (ESI). 432.32 (M+H).

Example 137

N-(4-(3-Tert-butyl-1H-1,2,4-triazol-1-yl)phenyl)-4-(3-fluoro-5-morpholinophenyl)pyrimidin-2-amine N-(4-(3-Tert-butyl-1H-1,2,4-triazol-1-yl)phenyl)-4-(3-fluoro-5-morpholinophenyl)pyrimidin-2-amine was obtained by following procedure E using 4-(3-(2-chloropyrimidin-4-yl)-5-fluorophenyl)morpholine and 4-(3-tert-butyl-1H-1,2,4-triazol-1-yl)aniline. $^1$H NMR (DMSO-d$_6$, 400 MHz) δ 9.78 (s, 1H), 8.90 (s, 1H), 8.48 (d, 1H), 7.84 (d, 2H), 7.61 (d, 2H), 7.49 (s, 1H), 7.40 (d, 1H), 7.26 (d, 1H), 6.85 (d, 1H), 3.66 (m, 4H), 3.15 (m, 4H). MS (ESI) 474.37 (M+H).

Example 138

4-(3-Fluoro-5-morpholinophenyl)-N-(4-(3-(trifluoromethyl)-1H-1,2,4-triazol-1-yl)phenyl)pyrimidin-2-amine

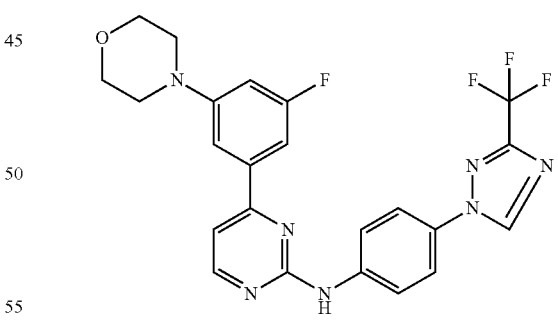

4-(3-Fluoro-5-morpholinophenyl)-N-(4-(3-(trifluoromethyl)-1H-1,2,4-triazol-1-yl)phenyl)pyrimidin-2-amine was obtained by following procedure E using 4-(3-(2-chloropyrimidin-4-yl)-5-fluorophenyl)morpholine and 4-(3-(trifluoromethyl)-1H-1,2,4-triazol-1-yl)aniline. $^1$H NMR (DMSO-d$_6$, 400 MHz) δ 10.05 (s, 1H), 9.49 (s, 1H), 8.64 (d, 1H), 8.05 (d, 2H), 7.83 (d, 2H), 7.60 (s, 1H), 7.56 (d, 1H), 7.39 (d, 1H), 6.99 (dd, 1H), 3.79 (m, 4H), 3.28 (m, 4H). MS (ESI) 486.28 (M+H).

Example 139

N-(4-(3-Bromo-1H-1,2,4-triazol-1-yl)phenyl)-4-(3-fluoro-5-morpholinophenyl)pyrimidin-2-amine

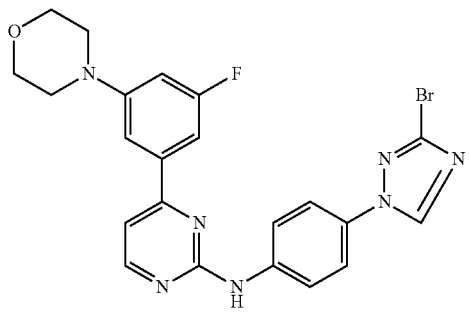 [SMILES: Fc1cc(-c2ccnc(Nc3ccc(-n4cnc(Br)n4)cc3)n2)cc(N2CCOCC2)c1]

N-(4-(3-Bromo-1H-1,2,4-triazol-1-yl)phenyl)-4-(3-fluoro-5-morpholinophenyl)pyrimidin-2-amine was obtained by following procedure E using 4-(3-(2-chloropyrimidin-4-yl)-5-fluorophenyl)morpholine and 4-(3-bromo-1H-1,2,4-triazol-1-yl)aniline. $^1$H NMR (DMSO-$d_6$, 400 MHz) δ 10.00 (s, 1H), 9.23 (s, 1H), 8.62 (d, 1H), 8.01 (d, 2H), 7.75 (d, 2H), 7.59 (s, 1H), 7.55 (d, 1H), 7.39 (m, 1H), 7.00 (m, 1H). MS (ESI) 496.17 & 498.17 (M+H).

Example 140

4-(3-Fluoro-5-morpholinophenyl)-N-(4-(3-(pyridin-4-yl)-1H-1,2,4-triazol-1-yl)phenyl)pyrimidin-2-amine

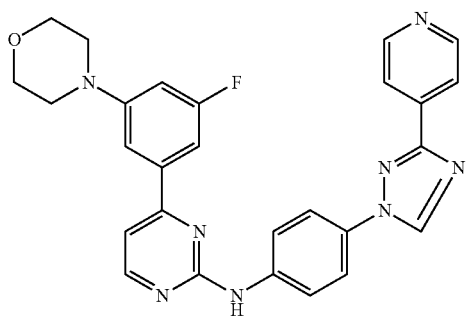 [SMILES: Fc1cc(-c2ccnc(Nc3ccc(-n4cnc(-c5ccncc5)n4)cc3)n2)cc(N2CCOCC2)c1]

4-(3-Fluoro-5-morpholinophenyl)-N-(4-(3-(pyridin-4-yl)-1H-1,2,4-triazol-1-yl)phenyl)pyrimidin-2-amine was obtained by following procedure K using N-(4-(3-bromo-1H-1,2,4-triazol-1-yl)phenyl)-4-(3-fluoro-5-morpholinophenyl)pyrimidin-2-amine and pyridin-4-ylboronic acid. $^1$H NMR (DMSO-$d_6$, 400 MHz) δ 10.01 (s, 1H), 9.38 (s, 1H), 8.74 (d, 2H), 8.63 (d, 1H), 8.04 (m, 4H), 7.88 (d, 2H), 7.61 (d, 1H), 7.56 (d, 1H), 7.40 (d, 1H), 7.01 (d, 1H), 3.80 (m, 4H), 3.29 (m, 4H). MS (ESI) 495.38 (M+H).

Example 141

4-(3-Fluoro-5-morpholinophenyl)-N-(4-(3-morpholino-1H-1,2,4-triazol-1-yl)phenyl)pyrimidin-2-amine

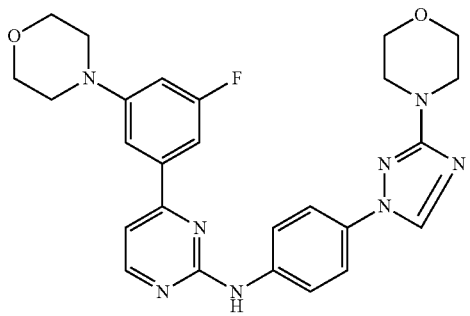 [SMILES: Fc1cc(-c2ccnc(Nc3ccc(-n4cnc(N5CCOCC5)n4)cc3)n2)cc(N2CCOCC2)c1]

Part I 4-(1-(4-Nitrophenyl)-1H-1,2,4-triazol-3-yl)morpholine

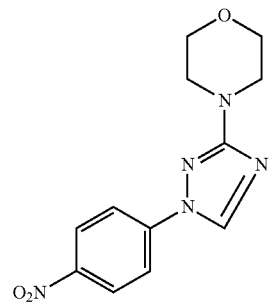

General Procedure M

Substitution of 3-bromo-1-substituted-1,2,4-triazole with secondary amine

A mixture of 3-bromo-1-(4-nitrophenyl)-1H-1,2,4-triazole (1.35 g, 5.0 mmol) and morpholine (8.71 g, 100 mmol) was heated in a sealed tube at 120° C. overnight. The reaction mixture was cooled down to room temperature and diluted with water. The precipitate was filtered, washed with water and dried under air to provide the desired product as a brown solid. $^1$H NMR (CDCl$_3$, 400 MHz) δ 8.40 (s, 1H), 8.34 (d, 2H), 7.80 (d, 2H), 3.84 (m, 4H), 3.54 (m, 4H). MS (ESI) 276.13 (M+H).

Part II 4-(3-Morpholino-1H-1,2,4-triazol-1-yl)aniline

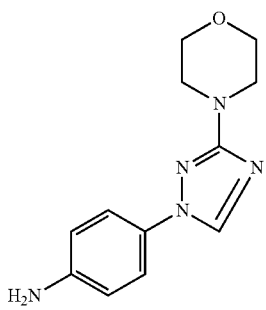 [SMILES: O=[N+]([O-])c1ccc(-n2cnc(N3CCOCC3)n2)cc1]

4-(3-Morpholino-1H-1,2,4-triazol-1-yl)aniline was obtained by following procedure D from 4-(1-(4-nitrophenyl)-1H-1,2,4-triazol-3-yl)morpholine. $^1$H NMR (CDCl$_3$, 400 MHz) δ 8.10 (s, 1H), 7.38 (d, 2H), 6.75 (d, 2H), 3.86 (m, 4H), 3.80 (br s, 2H), 3.51 (m, 4H). MS (ESI) 246.17 (M+H).

Part III 4-(3-Fluoro-5-morpholinophenyl)-N-(4-(3-morpholino-1H-1,2,4-triazol-1-yl)phenyl)pyrimidin-2-amine was obtained by following procedure E using 4-(3-(2-chloropyrimidin-4-yl)-5-fluorophenyl)morpholine and 4-(3-morpholino-1H-1,2,4-triazol-1-yl)aniline. $^1$H NMR (CDCl$_3$, 400 MHz) δ 8.45 (d, 1H), 8.13 (s, 1H), 7.72 (d, 2H), 7.49 (d, 2H), 7.37 (s, 1H), 7.36 (s, 1H), 7.14 (d, 1H), 7.07 (d, 1H), 6.65 (d, 1H), 3.82 (m, 4H), 3.78 (m, 4H), 3.44 (m, 4H), 3.18 (m, 4H). MS (ESI) 503.31 (M+H).

Example 142

1-(1-(4-(4-(3-Fluoro-5-morpholinophenyl)pyrimidin-2-ylamino)phenyl)-1H-1,2,4-triazol-3-yl)piperidin-4-ol

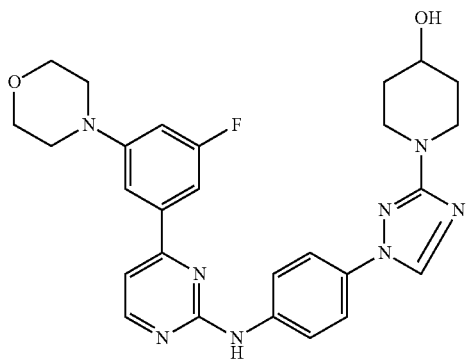 [SMILES: OC1CCN(c2ncn(-c3ccc(Nc4nccc(-c5cc(F)cc(N6CCOCC6)c5)n4)cc3)n2)CC1]

Part I 1-(1-(4-Nitrophenyl)-1H-1,2,4-triazol-3-yl)piperidin-4-ol

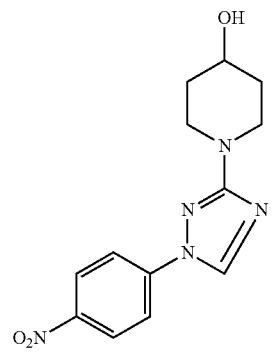 [SMILES: O=[N+]([O-])c1ccc(-n2cnc(N3CCC(O)CC3)n2)cc1]

1-(1-(4-Nitrophenyl)-1H-1,2,4-triazol-3-yl)piperidin-4-ol was obtained by following procedure M from 3-bromo-1-(4-nitrophenyl)-1H-1,2,4-triazole and piperidin-4-ol. $^1$H NMR (CDCl$_3$, 400 MHz) δ 8.40 (s, 1H), 8.36 (d, 2H), 7.82 (d, 2H), 4.04 (m, 2H), 3.95 (m, 1H), 3.24 (m, 2H), 2.03 (m, 2H), 1.68 (m, 2H), 1.49 (d, 1H). MS (ESI) 290.07 (M+H).

Part II 1-(1-(4-Aminophenyl)-1H-1,2,4-triazol-3-yl)piperidin-4-ol

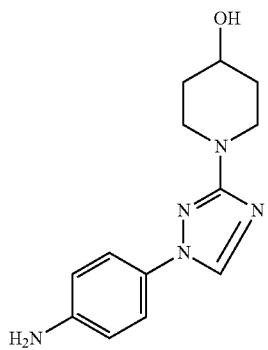

1-(1-(4-Aminophenyl)-1H-1,2,4-triazol-3-yl)piperidin-4-ol was obtained by following procedure D from 1-(1-(4-nitrophenyl)-1H-1,2,4-triazol-3-yl)piperidin-4-ol. $^1$H NMR (CDCl$_3$, 400 MHz) δ 8.13 (s, 1H), 7.43 (d, 2H), 6.80 (d, 2H), 4.06 (m, 2H), 3.95 (m, 1H), 3.83 (brs, 2H), 3.20 (m, 2H), 2.06 (m, 2H), 1.73 (m, 2H), 1.51 (d, 1H). MS (ESI) 260.14 (M+H).

Part III 1-(1-(4-(4-(3-Fluoro-5-morpholinophenyl)pyrimidin-2-ylamino)phenyl)-1H-1,2,4-triazol-3-yl)piperidin-4-ol was obtained by following procedure E using 4-(3-(2-chloropyrimidin-4-yl)-5-fluorophenyl)morpholine and 1-(1-(4-aminophenyl)-1H-1,2,4-triazol-3-yl)piperidin-4-ol. $^1$H NMR (CDCl$_3$, 400 MHz) δ 11.20 (brs, 1H), 8.31 (s, 1H), 8.25 (d, 1H), 7.79 (d, 2H), 7.56 (d, 2H), 7.37 (s, 1H), 7.18 (s, 1H), 7.14 (d, 1H), 6.74 (d, 1H), 3.91 (m, 2H), 3.82 (m, 4H), 3.19 (m, 4H), 3.13 (m, 2H), 1.93 (m, 2H), 1.59 (m, 2H). MS (ESI) 517.26 (M+H).

Example 143

4-(3-Fluoro-5-morpholinophenyl)-N-(4-(3-(4-methylpiperazin-1-yl)-1H-1,2,4-triazol-1-yl)phenyl)pyrimidin-2-amine

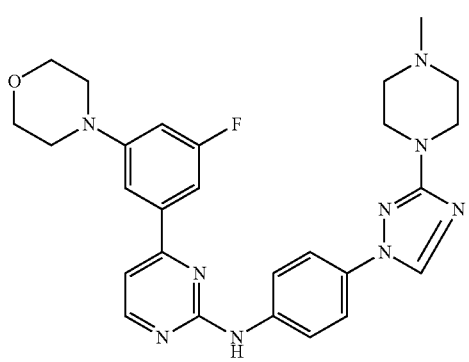 [SMILES: CN1CCN(c2ncn(-c3ccc(Nc4nccc(-c5cc(F)cc(N6CCOCC6)c5)n4)cc3)n2)CC1]

4-(3-Fluoro-5-morpholinophenyl)-N-(4-(3-(4-methylpiperazin-1-yl)-1H-1,2,4-triazol-1-yl)phenyl)pyrimidin-2-amine was obtained by following procedure M from N-(4-(3-bromo-1H-1,2,4-triazol-1-yl)phenyl)-4-(3-fluoro-5-morpholinophenyl)pyrimidin-2-amine and 1-methylpiperazine in the presence of $K_2CO_3$ with DMSO as the solvent at 190° C. overnight. The desired product was purified by Prep. HPLC as a yellow solid. $^1$H NMR (CDCl$_3$, 400 MHz) δ 10.70 (brs, 1H), 8.28 (d, 1H), 8.19 (s, 1H), 7.78 (d, 2H), 7.52 (d, 2H), 7.34 (s, 1H), 7.17 (d, 1H), 7.13 (d, 1H), 6.73 (dd, 1H), 4.17 (m, 2H), 3.81 (m, 4H), 3.56 (m, 2H), 3.49 (m, 2H), 3.18 (m, 4H), 2.88 (m, 2H), 2.79 (s, 3H). MS (ESI) 516.34 (M+H).

Example 144

N-(4-(3-(Dimethylamino)-1H-1,2,4-triazol-1-yl)phenyl)-4-(3-fluoro-5-morpholinophenyl)pyrimidin-2-amine

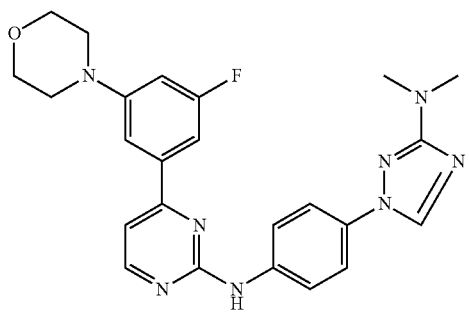 [SMILES: CN(C)c1ncn(-c2ccc(Nc3nccc(-c4cc(F)cc(N5CCOCC5)c4)n3)cc2)n1]

N-(4-(3-(Dimethylamino)-1H-1,2,4-triazol-1-yl)phenyl)-4-(3-fluoro-5-morpholinophenyl)pyrimidin-2-amine was obtained by following procedure M from N-(4-(3-bromo-1H-1,2,4-triazol-1-yl)phenyl)-4-(3-fluoro-5-morpholinophenyl)pyrimidin-2-amine and dimethylamine (THF solution) in the presence of $K_2CO_3$ with DMSO as the solvent at 190° C. overnight. The desired product was purified by Prep. HPLC. $^1$H NMR (CDCl$_3$, 400 MHz) δ 10.40 (brs, 1H), 8.26 (s, 1H), 7.78 (d, 2H), 7.56 (d, 2H), 7.38 (s, 1H), 7.16 (d, 1H), 7.12 (s, 1H), 6.72 (d, 1H), 3.82 (m, 4H), 3.19 (m, 4H), 3.02 (s, 6H). MS (ESI) 461.28 (M+H).

Example 145

N-(4-(2H-Tetrazol-5-yl)phenyl)-4-(3-morpholinophenyl)pyrimidin-2-amine

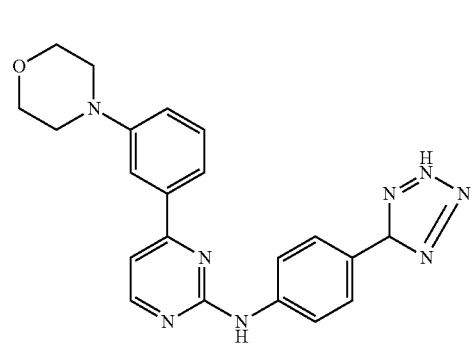

N-(4-(2H-Tetrazol-5-yl)phenyl)-4-(3-morpholinophenyl)pyrimidin-2-amine was obtained by following procedure E using 4-(3-(2-chloropyrimidin-4-yl)phenyl)morpholine and 4-(2H-tetrazol-5-yl)aniline. $^1$H NMR (DMSO-d$_6$, 400 MHz) δ 10.09 (s, 1H), 8.62 (d, 1H), 8.10 (d, 2H), 7.99 (d, 2H), 7.78 (s, 1H), 7.63 (d, 1H), 7.53 (d, 1H), 7.43 (t, 1H), 7.18 (dd, 1H).

Example 146

N-(4-(2-Methyl-2H-tetrazol-5-yl)phenyl)-4-(3-morpholinophenyl)pyrimidin-2-amine

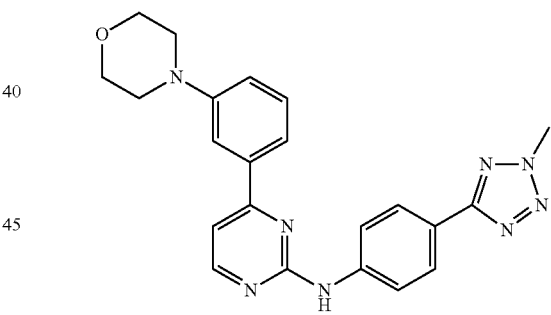

N-(4-(1-Methyl-1H-tetrazol-5-yl)phenyl)-4-(3-morpholinophenyl)pyrimidin-2-amine

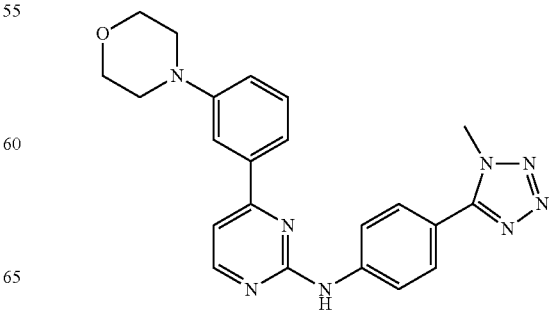

General Procedure N

Alkylation of 5-substituted-1(2)H-tetrazole

A mixture of N-(4-(2H-tetrazol-5-yl)phenyl)-4-(3-morpholinophenyl)pyrimidin-2-amine (0.20 g, 0.50 mmol), MeI (0.71 g, 5.0 mmol) and $K_2CO_3$ (0.35 g, 2.50 mmol) in acetone (5 mL) was stirred at room temperature overnight. The reaction mixture was diluted with water, extracted with EtOAc (3×). The combined organic solution was dried over anhydrous $MgSO_4$ and concentrated in vacuo to give a solid. Purification of this material by column chromatography on silica gel (40% EtOAc/hexane) provided N-(4-(2-methyl-2H-tetrazol-5-yl)phenyl)-4-(3 morpholinophenyl)pyrimidin-2-amine as the major product. $^1$H NMR (DMSO-$d_6$, 400 MHz) δ 10.00 (s, 1H), 8.60 (d, 1H), 8.05 (d, 2H), 8.00 (d, 2H), 7.78 (s, 1H), 7.65 (d, 1H), 7.50 (d, 1H), 7.42 (t, 1H), 7.18 (dd, 1H), 4.42 (s, 3H), 3.80 (m, 4H), 3.24 (m, 4H). MS (ESI) 415.13 (M+H).

Further elution with 60% EtOAc/hexane provided N-(4-(1-methyl-1H-tetrazol-5-yl)phenyl)-4-(3-morpholinophenyl)pyrimidin-2-amine as the minor product. $^1$H NMR (DMSO-$d_6$, 400 MHz) δ 10.11 (s, 1H), 8.62 (d, 1H), 8.12 (d, 2H), 7.84 (d, 2H), 7.78 (s, 1H), 7.64 (d, 1H), 7.54 (d, 1H), 7.43 (t, 1H), 7.18 (dd, 1H), 4.21 (s, 3H), 3.80 (m, 4H), 3.24 (m, 4H). MS (ESI) 415.15 (M+H).

Example 147

N-(4-(2-Ethyl-2H-tetrazol-5-yl)phenyl)-4-(3-morpholinophenyl)pyrimidin-2-amine

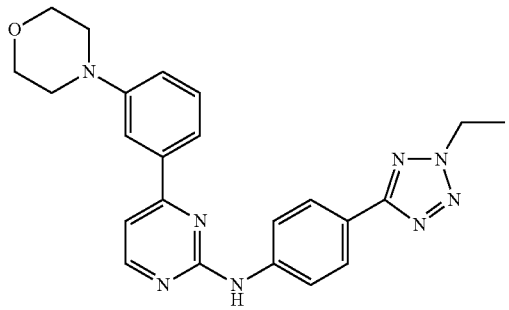 [SMILES: CCn1nnc(-c2ccc(Nc3nccc(-c4cccc(N5CCOCC5)c4)n3)cc2)n1]

N-(4-(2-Ethyl-2H-tetrazol-5-yl)phenyl)-4-(3-morpholinophenyl)pyrimidin-2-amine was obtained by following procedure N as the major product using N-(4-(2H-tetrazol-5-yl)phenyl)-4-(3-morpholinophenyl)pyrimidin-2-amine and ethyl iodide. $^1$H NMR (CDCl$_3$, 400 MHz) δ 8.51 (d, 1H), 8.12 (d, 2H), 8.87 (d, 2H), 7.75 (d, 1H), 7.61 (d, 1H), 7.53 (d, 1H), 7.41 (t, 1H), 7.21 (d, 1H), 7.07 (dd, 1H).

Example 148

N-(4-(1-Ethyl-1H-tetrazol-5-yl)phenyl)-4-(3-morpholinophenyl)pyrimidin-2-amine

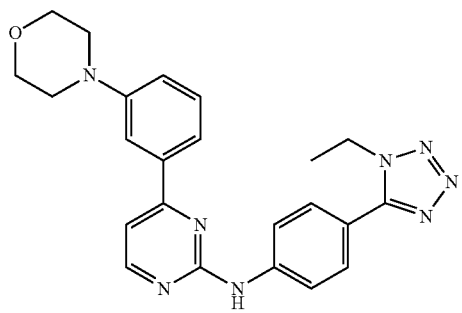 [SMILES: CCn1nnnc1-c1ccc(Nc2nccc(-c3cccc(N4CCOCC4)c3)n2)cc1]

N-(4-(1-Ethyl-1H-tetrazol-5-yl)phenyl)-4-(3 morpholinophenyl)pyrimidin-2-amine was obtained by following procedure N as the minor product using N-(4-(2H-tetrazol-5-yl)phenyl)-4-(3-morpholinophenyl)pyrimidin-2-amine and ethyl iodide. $^1$H NMR (CDCl$_3$, 400 MHz) δ 8.46 (d, 1H), 7.89 (d, 2H), 7.62 (m, 3H), 7.46 (d, 1H), 7.43 (s, 1H), 7.35 (t, 1H), 7.17 (d, 1H), 7.01 (dd, 1H).

Example 149

N-(4-(2-Benzyl-2H-tetrazol-5-yl)phenyl)-4-(3-morpholinophenyl)pyrimidin-2-amine

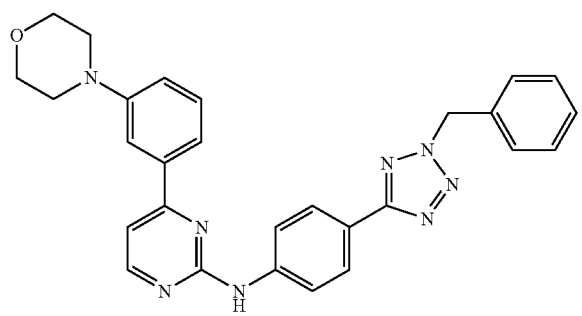 [SMILES: c1ccc(Cn2nnc(-c3ccc(Nc4nccc(-c5cccc(N6CCOCC6)c5)n4)cc3)n2)cc1]

N-(4-(2-Benzyl-2H-tetrazol-5-yl)phenyl)-4-(3-morpholinophenyl)pyrimidin-2-amine was obtained by following procedure N as the major product using N-(4-(2H-tetrazol-5-yl)phenyl)-4-(3-morpholinophenyl)pyrimidin-2-amine and benzyl bromide. $^1$H NMR (CDCl$_3$, 400 MHz) δ 8.51 (d, 1H), 8.12 (d, 2H), 7.86 (d, 2H), 7.74 (s, 1H), 7.44 (d, 1H), 7.40 (m, 7H), 7.27 (d, 1H), 7.20 (dd, 1H), 5.81 (s, 2H), 3.92 (m, 4H), 3.28 (m, 4H). MS (ESI) 491.14 (M+H).

Example 150

N-(4-(1-Benzyl-1H-tetrazol-5-yl)phenyl)-4-(3-morpholinophenyl)pyrimidin-2-amine

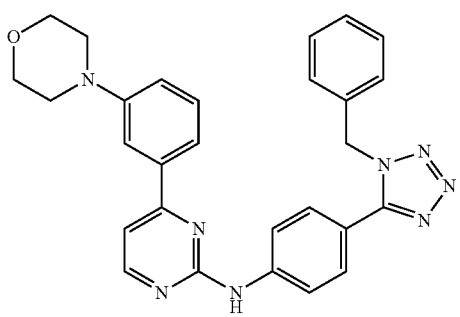 [SMILES: c1ccc(Cn2nnnc2-c2ccc(Nc3nccc(-c4cccc(N5CCOCC5)c4)n3)cc2)cc1]

N-(4-(1-Benzyl-1H-tetrazol-5-yl)phenyl)-4-(3-morpholinophenyl)pyrimidin-2-amine was obtained by following procedure N as the minor product using N-(4-(2H-tetrazol-5-yl)phenyl)-4-(3-morpholinophenyl)pyrimidin-2-amine and benzyl bromide. $^1$H NMR (CDCl$_3$, 400 MHz) δ 8.45 (m, 1H), 7.79 (m, 2H), 7.63 (m, 1H), 7.61 (m, 2H), 7.53 (m, 2H), 7.33 (m, 5H), 7.18 (m, 2H), 7.00 (m, 1H), 5.58 (d, 2H), 3.81 (m, 4H), 3.18 (m, 4H). MS (ESI) 491.16 (M+H).

Example 151

N-(4-(3-Methyl-1H-1,2,4-triazol-1-yl)phenyl)-4-(3-morpholinophenyl)pyrimidin-2-amine

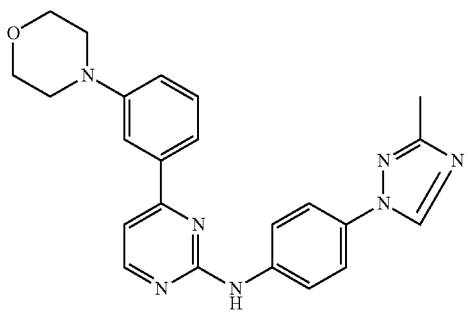 [SMILES: Cc1ncn(-c2ccc(Nc3nccc(-c4cccc(N5CCOCC5)c4)n3)cc2)n1]

N-(4-(3-methyl-1H-1,2,4-triazol-1-yl)phenyl)-4-(3-morpholinophenyl)pyrimidin-2-amine was obtained by following procedure E using 4-(3-(2-chloropyrimidin-4-yl)phenyl)morpholine and 4-(3-methyl-1H-1,2,4-triazol-1-yl)aniline. ¹H NMR (CDCl₃, 400 MHz) δ 8.42 (d, 1H), 8.31 (s, 1H), 7.80 (d, 2H), 7.67 (s, 1H), 7.59 (d, 2H), 7.46 (d, 1H), 7.34 (t, 1H), 7.13 (d, 1H), 7.01 (d, 1H), 3.85 (m, 4H), 3.20 (m, 4H), 2.44 (s, 3H).

Example 152

N-(4-(5-Methyl-1H-1,2,4-triazol-1-yl)phenyl)-4-(3-morpholinophenyl)pyrimidin-2-amine

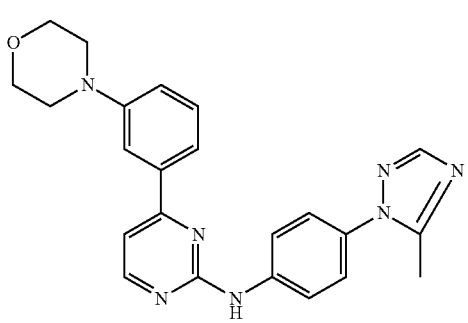 [SMILES: Cc1ncnn1-c1ccc(Nc2nccc(-c3cccc(N4CCOCC4)c3)n2)cc1]

4-(5-Methyl-1H-1,2,4-triazol-1-yl)aniline 4-(5-Methyl-1H-1,2,4-triazol-1-yl)aniline was obtained by following procedure D from 5-methyl-1-(4-nitrophenyl)-1H-1,2,4-triazole. ¹H NMR (CDCl₃, 400 MHz) δ 7.95 (s, 1H), 7.22 (d, 2H), 6.78 (d, 2H), 2.52 (s, 3H).

N-(4-(5-Methyl-1H-1,2,4-triazol-1-yl)phenyl)-4-(3 morpholinophenyl)pyrimidin-2-amine was obtained by following procedure E using 4-(3-(2-chloropyrimidin-4-yl)phenyl)morpholine and 4-(5-methyl-1H-1,2,4-triazol-1-yl)aniline. ¹H NMR (CDCl₃, 400 MHz) δ 8.53 (d, 1H), 7.97 (s, 1H), 7.92 (d, 2H), 7.70 (s, 1H), 7.54 (d, 1H), 7.44 (m, 3H), 7.27 (d, 1H), 7.12 (m, 1H).

Example 153

N-(4-(3-Chloro-1H-1,2,4-triazol-1-yl)phenyl)-4-(3-morpholinophenyl)pyrimidin-2-amine

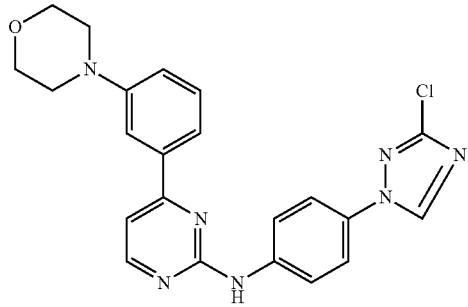 [SMILES: Clc1ncn(-c2ccc(Nc3nccc(-c4cccc(N5CCOCC5)c4)n3)cc2)n1]

Part I

3-Chloro-1-(4-nitrophenyl)-1H-1,2,4-triazole

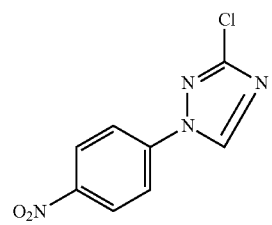

3-Chloro-1-(4-nitrophenyl)-1H-1,2,4-triazole was obtained as a single product by following procedure C using 3-chloro-1H-1,2,4-triazole and 4-fluoro-1-nitrobenzene and no purification was necessary. ¹H NMR (CDCl₃, 400 MHz) δ 8.53 (s, 1H), 7.35 (d, 2H), 7.82 (d, 2H).

Part II 4-(3-Chloro-1H-1,2,4-triazol-1-yl)aniline

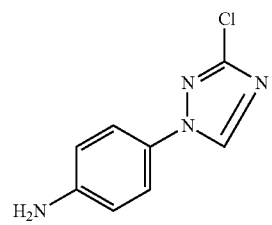 [SMILES: O=[N+]([O-])c1ccc(-n2cnc(Cl)n2)cc1]

4-(3-Chloro-1H-1,2,4-triazol-1-yl)aniline was obtained by following procedure J from 3-chloro-1-(4-nitrophenyl)-1H-

1,2,4-triazole. ¹H NMR (CDCl₃, 400 MHz) δ 8.20 (s, 1H), 7.30 (d, 2H), 6.69 (d, 2H), 3.81 (br s, 2H).

Part III

N-(4-(3-Chloro-1H-1,2,4-triazol-1-yl)phenyl)-4-(3-morpholinophenyl)pyrimidin-2-amine was obtained by following procedure E using 4-(3-(2-chloropyrimidin-4-yl)phenyl)morpholine and 4-(3-chloro-1H-1,2,4-triazol-1-yl)aniline. ¹H NMR (CDCl₃, 400 MHz) δ 8.43 (d, 1H), 8.33 (s, 1H), 7.82 (d, 2H), 7.66 (s, 1H), 7.54 (d, 2H), 7.47 (d, 1H), 7.36 (t, 1H), 7.16 (d, 1H), 7.04 (d, 1H).

Example 154

N-(4-(3-Tert-butyl-1H-1,2,4-triazol-1-yl)phenyl)-4-(3-morpholinophenyl)pyrimidin-2-amine

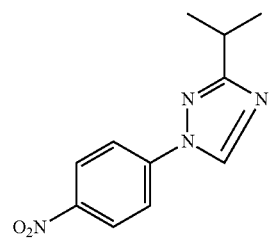

N-(4-(3-Tert-butyl-1H-1,2,4-triazol-1-yl)phenyl)-4-(3-morpholinophenyl)pyrimidin-2-amine was obtained by following procedure E using 4-(3-(2-chloropyrimidin-4-yl)phenyl)morpholine and 4-(3-tert-butyl-1H-1,2,4-triazol-1-yl)aniline. ¹H NMR (CDCl₃, 400 MHz) δ 8.41 (d, 1H), 8.31 (s, 1H), 7.78 (d, 2H), 7.64 (s, 1H), 7.54 (d, 2H), 7.46 (d, 1H), 7.35 (t, 1H), 7.14 (d, 1H), 7.02 (d, 1H), 3.85 (m, 4H), 3.21 (m, 4H), 1.37 (s, 9H).

Example 155

N-(4-(3-Isopropyl-1H-1,2,4-triazol-1-yl)phenyl)-4-(3-morpholinophenyl)pyrimidin-2-amine

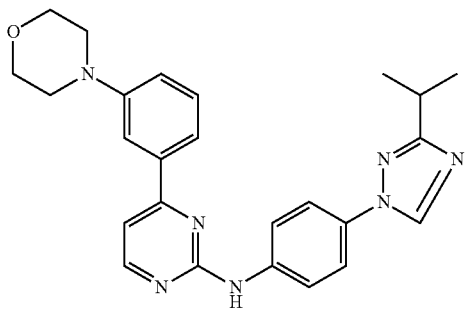 [SMILES: CC(C)c1ncn(-c2ccc(Nc3nccc(-c4cccc(N5CCOCC5)c4)n3)cc2)n1]

Part I

3-Isopropyl-1H-1,2,4-triazole

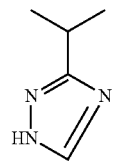

3-Isopropyl-1H-1,2,4-triazole was obtained by following procedure H using thiosemicarbazide, isobutyryl chloride and nitric acid. ¹H NMR (CDCl₃, 400 MHz) δ 7.92 (s, 1H), 3.10 (m, 1H), 1.32 (d, 6H).

Part II

3-Isopropyl-1-(4-nitrophenyl)-1H-1,2,4-triazole

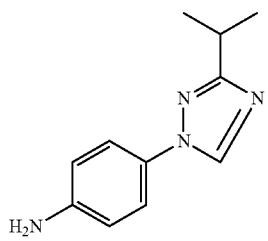

3-Isopropyl-1-(4 nitrophenyl)-1H-1,2,4-triazole was obtained as a single product by following procedure C using 3-isopropyl-1H-1,2,4-triazole and 4-fluoro-1-nitrobenzene and no purification was necessary. ¹H NMR (CDCl₃, 400 MHz) δ 8.61 (s, 1H), 8.40 (d, 2H), 7.91 (d, 2H), 3.21 (m, 1H), 1.43 (d, 6H). MS (ESI) 233.15 (M+H).

Part III 4-(3-Isopropyl-1H-1,2,4-triazol-1-yl)aniline 4-(3-Isopropyl-1H-1,2,4-triazol-1-yl)aniline was obtained by following procedure D from 3-isopropyl-1-(4-nitrophenyl)-1H-1,2,4-triazole. ¹H NMR (CDCl₃, 400 MHz) δ 8.30 (s, 1H), 7.41 (d, 2H), 6.76 (d, 2H), 3.20 (m, 1H), 1.41 (d, 6H).

Part IV

N-(4-(3-Isopropyl-1H-1,2,4-triazol-1-yl)phenyl)-4-(3-morpholinophenyl)pyrimidin-2-amine was obtained by following procedure E using 4-(3-(2-chloropyrimidin-4-yl)phenyl)morpholine and 4-(3-isopropyl-1H-1,2,4-triazol-1-yl)aniline. $^1$H NMR (CDCl$_3$, 400 MHz) δ 8.42 (d, 1H), 8.31 (s, 1H), 7.76 (d, 2H), 7.61 (s, 1H), 7.56 (s, 1H), 7.52 (d, 2H), 7.45 (d, 1H), 7.33 (t, 1H), 7.12 (d, 1H), 6.98 (dd, 1H), 3.83 (m, 4H), 3.18 (m, 4H), 3.10 (m, 1H), 1.33 (d, 6H).

Example 156

N-(4-(5-Methyl-1H-tetrazol-1-yl)phenyl)-4-(3-morpholinophenyl)pyrimidin-2-amine

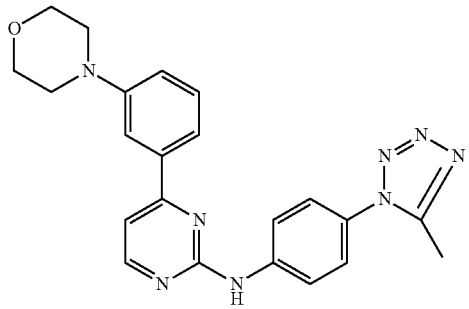 [SMILES: Cc1nnnn1-c1ccc(Nc2nccc(-c3cccc(N4CCOCC4)c3)n2)cc1]

N-(4-(5-Methyl-1H-tetrazol-1-yl)phenyl)-4-(3-morpholinophenyl)pyrimidin-2-amine was obtained by following procedure E using 4-(3-(2-chloropyrimidin-4-yl)phenyl)morpholine and 4-(5-methyl-1H-tetrazol-1-yl)aniline. $^1$H NMR (DMSO-d$_6$, 400 MHz) δ 10.09 (s, 1H), 8.61 (d, 1H), 8.11 (d, 2H), 7.75 (s, 1H), 7.61 (m, 3H), 7.53 (d, 1H), 7.42 (t, 1H), 7.18 (dd, 1H), 3.79 (m, 4H), 3.23 (m, 4H), 2.56 (s, 3H). MS (ESI) 415.05 (M+H).

Example 157

1,1,1,3,3,3-Hexafluoro-2-(4-(4-(3-morpholinophenyl)pyrimidin-2-ylamino)phenyl)propan-2-ol

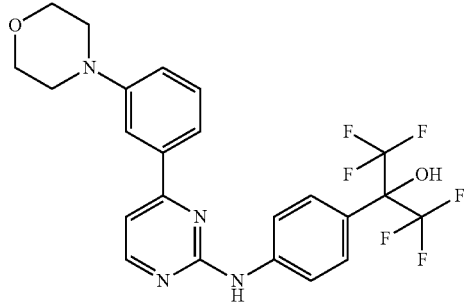 [SMILES: OC(c1ccc(Nc2nccc(-c3cccc(N4CCOCC4)c3)n2)cc1)(C(F)(F)F)C(F)(F)F]

1,1,1,3,3,3-Hexafluoro-2-(4-(4-(3 morpholinophenyl)pyrimidin-2-ylamino)phenyl)propan-2-ol was obtained by following procedure E using 4-(3-(2-chloropyrimidin-4-yl)phenyl)morpholine and 2-(4-aminophenyl)-1,1,1,3,3,3-hexafluoropropan-2-ol. $^1$H NMR (CDCl$_3$, 400 MHz) δ 8.52 (d, 1H), 7.86 (d, 2H), 7.84 (s, 1H), 7.77 (d, 2H), 7.53 (d, 1H), 7.45 (t, 1H), 7.34 (s, 1H), 7.24 (d, 1H), 7.09 (dd, 1H), 3.93 (m, 4H), 3.29 (m, 4H).

Example 158

N-(4-(2H-Tetrazol-2-yl)phenyl)-4-(3-morpholinophenyl)pyrimidin-2-amine

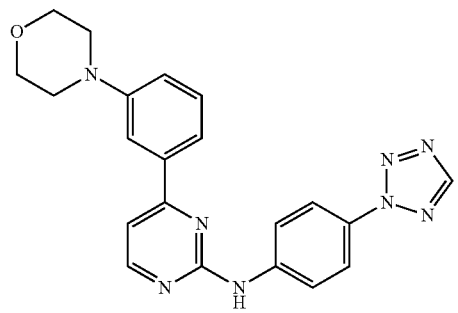 [SMILES: c1cc(-c2ccnc(Nc3ccc(-n4ncnn4)cc3)n2)cc(N2CCOCC2)c1]

N-(4-(2H-Tetrazol-2-yl)phenyl)-4-(3-morpholinophenyl)pyrimidin-2-amine was obtained by following procedure E using 4-(3-(2-chloropyrimidin-4-yl)phenyl)morpholine and 4-(2H-tetrazol-2-yl)aniline. $^1$H NMR (CDCl$_3$, 400 MHz) δ 8.67 (s, 1H), 8.55 (d, 1H), 8.14 (d, 2H), 7.98 (d, 2H), 7.74 (s, 1H), 7.56 (d, 1H), 7.45 (t, 1H), 7.42 (s, 1H), 7.27 (d, 1H), 7.11 (dd, 1H). MS (ESI) 401.01 (M+H).

Example 159

N-(4-(1H-Tetrazol-1-yl)phenyl)-4-(3-morpholinophenyl)pyrimidin-2-amine

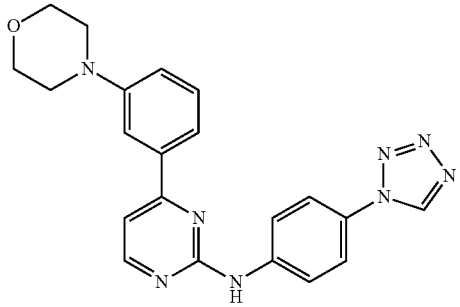 [SMILES: c1cc(-c2ccnc(Nc3ccc(-n4cnnn4)cc3)n2)cc(N2CCOCC2)c1]

N-(4-(1H-Tetrazol-1-yl)phenyl)-4-(3-morpholinophenyl)pyrimidin-2-amine was obtained by following procedure E using 4-(3-(2-chloropyrimidin-4-yl)phenyl)morpholine and 4-(1H-tetrazol-1-yl)aniline. $^1$H NMR (CDCl$_3$, 400 MHz) δ 8.87 (s, 1H), 8.46 (d, 1H), 7.90 (d, 2H), 7.59 (m, 3H), 7.45 (dd, 1H), 7.36 (d, 1H), 7.34 (s, 1H), 7.18 (s, 1H), 7.02 (dd, 1H). MS (ESI) 401.03 (M+H).

Example 160

N-(4-(3-Ethyl-1H-1,2,4-triazol-1-yl)phenyl)-4-(3-morpholinophenyl)pyrimidin-2-amine

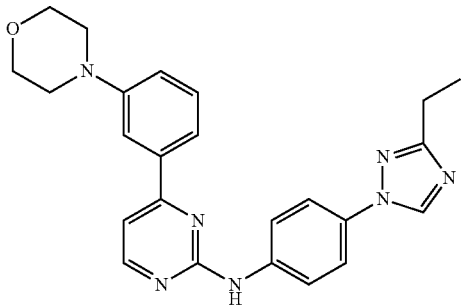 [SMILES: CCc1ncn(-c2ccc(Nc3nccc(-c4cccc(N5CCOCC5)c4)n3)cc2)n1]

Part I

3-Ethyl-1-(4-nitrophenyl)-1H-1,2,4-triazole

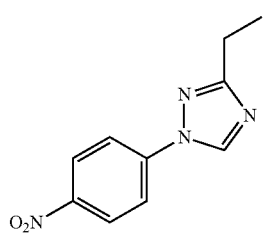

5-Ethyl-1-(4-nitrophenyl)-1H-1,2,4-triazole

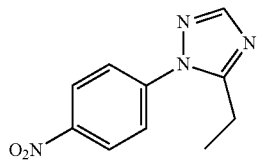

3-Ethyl-1-(4 nitrophenyl)-1H-1,2,4-triazole was obtained by following procedure C as the major product from 4-fluoro-1-nitrobenzene and 3-ethyl-1H-1,2,4-triazole. $^1$H NMR (CDCl$_3$, 400 MHz) δ 8.61 (s, 1H), 8.41 (d, 2H), 7.90 (d, 2H), 2.89 (q, 2H), 1.42 (t, 3H).

5-Ethyl-1-(4-nitrophenyl)-1H-1,2,4-triazole was obtained by following procedure C as the minor product from 4-fluoro-1-nitrobenzene and 3-ethyl-1H-1,2,4-triazole. $^1$H NMR (CDCl$_3$, 400 MHz) δ 8.34 (d, 2H), 7.94 (s, 1H), 7.63 (d, 2H), 2.85 (q, 2H), 1.34 (t, 3H).

Part II 4-(3-Ethyl-1H-1,2,4-triazol-1-yl)aniline

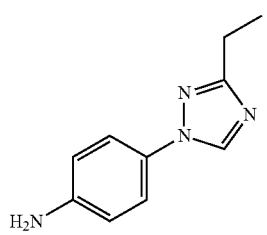 [SMILES: CCc1ncn(-c2ccc([N+](=O)[O-])cc2)n1]

4-(3-Ethyl-1H-1,2,4-triazol-1-yl)aniline was obtained by following procedure D from 3-ethyl-1-(4-nitrophenyl)-1H-1,2,4-triazole. $^1$H NMR (CDCl$_3$, 400 MHz) δ 8.32 (s, 1H), 7.41 (d, 2H), 6.77 (d, 2H), 2.86 (q, 2H), 1.40 (t, 3H).

Part III

N-(4-(3-Ethyl-1H-1,2,4-triazol-1-yl)phenyl)-4-(3 morpholinophenyl)pyrimidin-2-amine was obtained by following procedure E using 4-(3-(2-chloropyrimidin-4-yl)phenyl)morpholine and 4-(3-ethyl-1H-1,2,4-triazol-1-yl)aniline. $^1$H NMR (CDCl$_3$, 400 MHz) δ 8.51 (d, 1H), 8.42 (s, 1H), 7.88 (d, 2H), 7.72 (s, 1H), 7.65 (d, 2H), 7.56 (d, 1H), 7.44 (t, 1H), 7.24 (d, 1H), 7.12 (d, 1H), 3.94 (m, 4H), 3.30 (m, 4H), 2.89 (q, 2H), 1.42 (t, 3H). MS (ESI) 428.30 (M+H).

Example 161

N-(4-(5-Ethyl-1H-1,2,4-triazol-1-yl)phenyl)-4-(3-morpholinophenyl)pyrimidin-2-amine

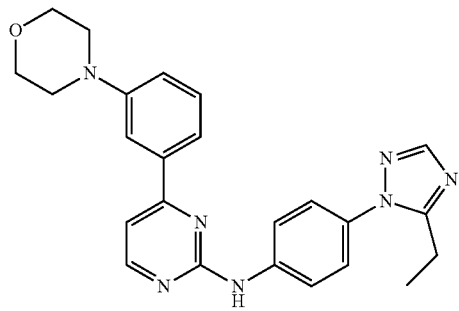 [SMILES: CCc1ncnn1-c1ccc(Nc2nccc(-c3cccc(N4CCOCC4)c3)n2)cc1]

4-(5-Ethyl-1H-1,2,4-triazol-1-yl)aniline

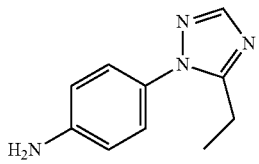

4-(5-Ethyl-1H-1,2,4-triazol-1-yl)aniline was obtained by following procedure D from 5-ethyl-1-(4-nitrophenyl)-1H-1,2,4-triazole. $^1$H NMR (CDCl$_3$, 400 MHz) δ 7.82 (s, 1H), 7.06 (dd, 2H), 6.58 (dd, 2H), 2.66 (q, 2H), 1.20 (t, 3H). MS (ESI) 189.20 (M+H).

N-(4-(5-Ethyl-1H-1,2,4-triazol-1-yl)phenyl)-4-(3-morpholinophenyl)pyrimidin-2-amine was obtained by following procedure E using 4-(3-(2-chloropyrimidin-4-yl)phenyl)morpholine and 4-(5-ethyl-1H-1,2,4-triazol-1-yl)aniline. $^1$H NMR (CDCl$_3$, 400 MHz) δ 8.44 (d, 1H), 7.89 (s, 1H), 7.82 (d, 2H), 7.63 (s, 1H), 7.60 (d, 1H), 7.52 (d, 1H), 7.46 (d, 1H), 7.33 (d, 2H), 7.15 (d, 1H), 7.05 (dd, 1H), 3.84 (m, 4H), 3.20 (m, 4H), 2.76 (q, 2H), 1.28 (t, 3H). MS (ESI) 428.29 (M+H).

Example 162

N-(4-(3-Bromo-1H-1,2,4-triazol-1-yl)phenyl)-4-(3-morpholinophenyl)pyrimidin-2-amine

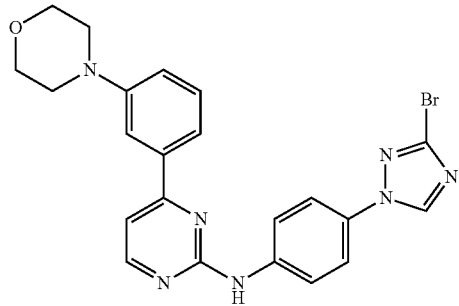 [SMILES: Brc1ncn(-c2ccc(Nc3nccc(-c4cccc(N5CCOCC5)c4)n3)cc2)n1]

N-(4-(3-Bromo-1H-1,2,4-triazol-1-yl)phenyl)-4-(3-morpholinophenyl)pyrimidin-2-amine was obtained by following procedure E using 4-(3-(2-chloropyrimidin-4-yl)phenyl)morpholine and 4-(3-bromo-1H-1,2,4-triazol-1-yl)aniline. ¹H NMR (CDCl₃, 400 MHz) δ 8.53 (d, 1H), 8.40 (s, 1H), 7.92 (d, 2H), 7.69 (s, 1H), 7.62 (d, 2H), 7.55 (d, 1H), 7.44 (t, 1H), 7.37 (s, 1H), 7.24 (s, 1H), 7.12 (d, 1H), 3.94 (m, 4H), 3.30 (m, 4H).

Example 163

4-(3-Morpholinophenyl)-N-(4-(3-vinyl-1-1H-1,2,4-triazol-1-yl)phenyl)pyrimidin-2-amine

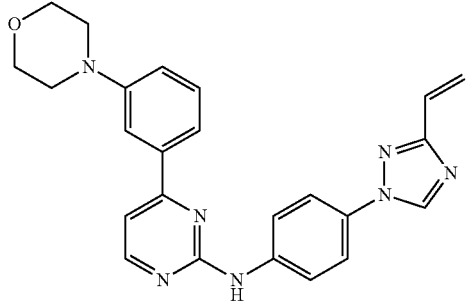 [SMILES: C=Cc1ncn(-c2ccc(Nc3nccc(-c4cccc(N5CCOCC5)c4)n3)cc2)n1]

A mixture of N-(4-(3-bromo-1H-1,2,4-triazol-1-yl)phenyl)-4-(3-morpholinophenyl)pyrimidin-2-amine (0.024 g, 0.05 mmol), tributyl(vinyl)stannane (0.032 g, 0.10 mmol), Pd(PPh₃)₄ (0.012 g, 0.01 mmol), toluene (0.4 mL) and DMF (0.1 mL) was heated in a sealed tube at 120° C. with microwave irradiation for 1 h. The reaction mixture was cooled down to room temperature. Purification of this material by column chromatography on silica gel (40% EtOAc/hexane) provided the desired product as a white solid. ¹H NMR (CDCl₃, 400 MHz) δ 8.43 (d, 1H), 8.36 (s, 1H), 7.80 (d, 2H), 7.59 (d, 2H), 7.37 (m, 4H), 7.14 (d, 1H), 7.01 (dd, 1H), 6.75 (dd, 1H), 6.27 (d, 1H), 5.51 (d, 1H), 3.84 (m, 4H), 3.20 (m, 4H). MS (ESI) 426.29 (M+H).

Example 164

4-(3-Morpholinophenyl)-N-(4-(3-phenyl-1H-1,2,4-triazol-1-yl)phenyl)pyrimidin-2-amine

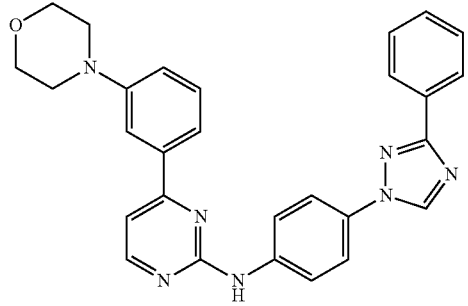

4-(3-Morpholinophenyl)-N-(4-(3-phenyl-1H-1,2,4-triazol-1-yl)phenyl)pyrimidin-2-amine was obtained by following procedure K using N-(4-(3-bromo-1H-1,2,4-triazol-1-yl)phenyl)-4-(3-morpholinophenyl)pyrimidin-2-amine and phenylboronic acid. ¹H NMR (CDCl₃, 400 MHz) δ 8.44 (s, 1H), 8.42 (d, 1H), 8.12 (d, 2H), 7.78 (d, 2H), 7.67 (s, 1H), 7.59 (m, 3H), 7.45 (d, 1H), 7.35 (m, 4H), 7.12 (d, 1H), 6.95 (dd, 1H).

Example 165

4-(3-Morpholinophenyl)-N-(4-(3-(pyridin-3-yl)-1H-1,2,4-triazol-1-yl)phenyl)pyrimidin-2-amine

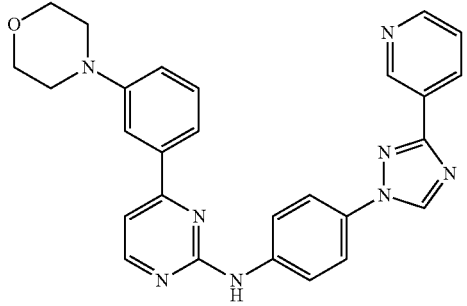

4-(3-Morpholinophenyl)-N-(4-(3-(pyridin-3-yl)-1H-1,2,4-triazol-1-yl)phenyl)pyrimidin-2-amine was obtained by following procedure K using N-(4-(3-bromo-1H-1,2,4-triazol-1-yl)phenyl)-4-(3-morpholinophenyl)pyrimidin-2-amine and pyridin-3-ylboronic acid. ¹H NMR (CDCl₃, 400 MHz) δ 9.37 (br s, 1H), 8.60 (brs, 1H), 8.48 (s, 1H), 8.44 (d, 1H), 8.39 (d, 1H), 7.83 (d, 2H), 7.62 (m, 3H), 7.50 (s, 1H), 7.46 (d, 1H), 7.34 (m, 2H), 7.14 (d, 1H), 7.00 (dd, 1H), 3.83 (m, 4H), 3.19 (m, 4H). MS (ESI) 477.34 (M+H).

Example 166

4-(3-Morpholinophenyl)-N-(4-(3-(pyridin-4-yl)-1H-1,2,4-triazol-1-yl)phenyl)pyrimidin-2-amine

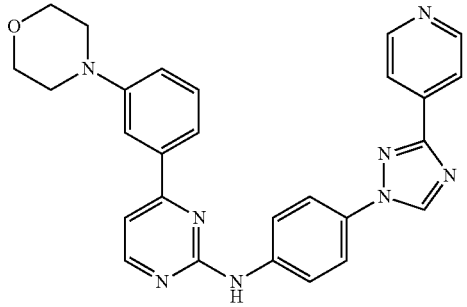 [SMILES: c1ccc(-c2ncn(-c3ccc(Nc4nccc(-c5cccc(N6CCOCC6)c5)n4)cc3)n2)cc1]

4-(3-Morpholinophenyl)-N-(4-(3-(pyridin-4-yl)-1H-1,2,4-triazol-1-yl)phenyl)pyrimidin-2-amine was obtained by following procedure K using N-(4-(3-bromo-1H-1,2,4-triazol-1-yl)phenyl)-4-(3-morpholinophenyl)pyrimidin-2-amine and pyridin-4-ylboronic acid. ¹H NMR (CDCl₃, 400 MHz) δ 8.67 (br s, 2H), 8.50 (s, 1H), 8.44 (d, 1H), 8.00 (d, 2H), 7.85 (d, 2H), 7.63 (m, 3H), 7.47 (d, 1H), 7.46 (d, 1H), 7.43 (s, 1H), 7.36 (t, 1H), 7.19 (d, 1H), 7.15 (d, 1H), 3.84 (m, 4H), 3.20 (m, 4H). MS (ESI) 477.36 (M+H).

Example 167

N-(4-(3-(6-Methylpyridin-3-yl)-1H-1,2,4-triazol-1-yl)phenyl)-4-(3-morpholinophenyl)pyrimidin-2-amine

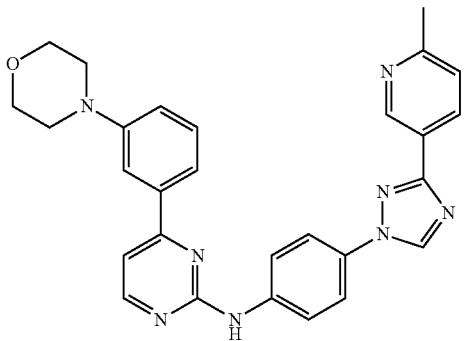 [SMILES: Cc1ccc(-c2ncn(-c3ccc(Nc4nccc(-c5cccc(N6CCOCC6)c5)n4)cc3)n2)cn1]

N-(4-(3-(6-Methylpyridin-3-yl)-1H-1,2,4-triazol-1-yl)phenyl)-4-(3-morpholinophenyl)pyrimidin-2-amine was obtained by following procedure K using N-(4-(3-bromo-1H-1,2,4-triazol-1-yl)phenyl)-4-(3-morpholinophenyl)pyrimidin-2-amine and 2-methyl-5-(4,4,5,5-tetramethyl-1,3,2-dioxaborolan-2-yl)pyridine. $^1$H NMR (CDCl$_3$, 400 MHz) δ 9.24 (s, 1H), 8.47 (s, 1H), 8.42 (d, 1H), 8.27 (dd, 1H), 7.82 (d, 2H), 7.63 (m, 3H), 7.47 (d, 1H), 7.42 (s, 1H), 7.35 (t, 1H), 7.21 (d, 1H), 7.14 (d, 1H), 7.01 (dd, 1H), 3.84 (m, 4H), 3.20 (m, 4H), 2.55 (s, 3H). MS (ESI) 491.34 (M+H).

Example 168

N-(4-(3-(2-Methylpyridin-4-yl)-1H-1,2,4-triazol-1-yl)phenyl)-4-(3-morpholinophenyl)pyrimidin-2-amine

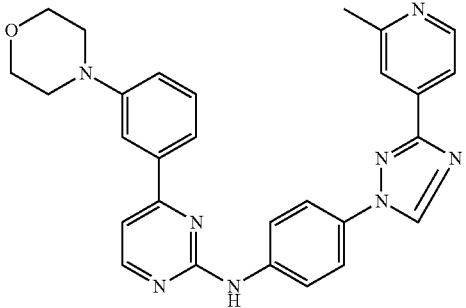 [SMILES: Cc1cc(-c2ncn(-c3ccc(Nc4nccc(-c5cccc(N6CCOCC6)c5)n4)cc3)n2)ccn1]

N-(4-(3-(2-Methylpyridin-4-yl)-1H-1,2,4-triazol-1-yl)phenyl)-4-(3-morpholinophenyl)pyrimidin-2-amine was obtained by following procedure K using N-(4-(3-bromo-1H-1,2,4-triazol-1-yl)phenyl)-4-(3-morpholinophenyl)pyrimidin-2-amine and 2-methyl-4-(4,4,5,5-tetramethyl-1,3,2-dioxaborolan-2-yl)pyridine. $^1$H NMR (CDCl$_3$, 400 MHz) δ 8.54 (d, 1H), 8.49 (s, 1H), 8.44 (d, 1H), 7.88 (s, 1H), 7.83 (d, 2H), 7.79 (d, 1H), 7.61 (m, 3H), 7.55 (s, 1H), 7.46 (d, 1H), 7.34 (t, 1H), 7.14 (d, 1H), 7.00 (dd, 1H), 3.83 (m, 4H), 3.19 (m, 4H), 2.58 (s, 3H). MS (ESI) 491.38 (M+H).

Example 169

N-(4-(3-(6-Methoxypyridin-3-yl)-1H-1,2,4-triazol-1-yl)phenyl)-4-(3-morpholinophenyl)pyrimidin-2-amine

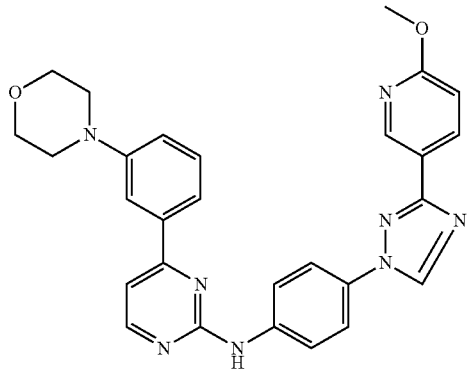 [SMILES: COc1ccc(-c2ncn(-c3ccc(Nc4nccc(-c5cccc(N6CCOCC6)c5)n4)cc3)n2)cn1]

N-(4-(3-(6-Methoxypyridin-3-yl)-1H-1,2,4-triazol-1-yl)phenyl)-4-(3-morpholinophenyl)pyrimidin-2-amine was obtained by following procedure K using N-(4-(3-bromo-1H-1,2,4-triazol-1-yl)phenyl)-4-(3-morpholinophenyl)pyrimidin-2-amine and 6-methoxypyridin-3-ylboronic acid. $^1$H NMR (CDCl$_3$, 400 MHz) δ 8.92 (s, 1H), 8.43 (s, 1H), 8.42 (s, 1H), 8.26 (d, 1H), 7.81 (d, 2H), 7.61 (m, 3H), 7.48 (s, 1H), 7.46 (d, 1H), 7.34 (t, 1H), 7.13 (d, 1H), 7.00 (dd, 1H), 6.76 (d, 1H), 3.93 (s, 1H), 3.83 (m, 4H), 3.19 (m, 4H). MS (ESI) 507.32 (M+H).

Example 170

4-(3-Bromophenyl)-N-(4-(3-methyl-1H-1,2,4-triazol-1-yl)phenyl)pyrimidin-2-amine

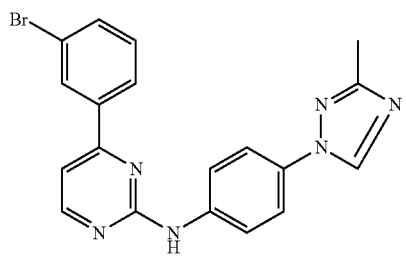 [SMILES: Cc1ncn(-c2ccc(Nc3nccc(-c4cccc(Br)c4)n3)cc2)n1]

4-(3-Bromophenyl)-2-chloropyrimidine

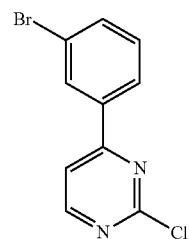 [SMILES: Clc1nccc(-c2cccc(Br)c2)n1]

4-(3-Bromophenyl)-2-chloropyrimidine was obtained by following procedure B using 3-bromophenylboronic acid and 2,4-dicholorrpyrimidine. $^1$H NMR (CDCl$_3$, 400 MHz) δ 8.61 (d, 1H), 8.19 (d, 1H), 7.94 (dd, 1H), 7.60 (dd, 1H), 7.57 (d, 1H), 7.33 (t, 1H).

4-(3-Bromophenyl)-N-(4-(3-methyl-1H-1,2,4-triazol-1-yl)phenyl)pyrimidin-2-amine was obtained by following procedure E using 4-(3-bromophenyl)-2-chloropyrimidine and 4-(3-methyl-1H-1,2,4-triazol-1-yl)aniline. $^1$H NMR (CDCl$_3$, 400 MHz) δ 8.55 (d, 1H), 8.42 (s, 1H), 8.25 (s, 1H), 8.00 (d, 1H), 7.86 (d, 2H), 7.64 (m, 3H), 7.42 (m, 2H), 7.21 (d, 1H), 2.53 (s, 3H).

Example 171

N-(4-(1-amino-2,2,2-trifluoroethyl)phenyl)-4-phenylpyrimidin-2-amine

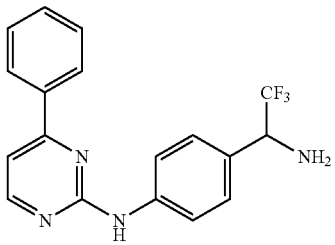 [SMILES: NC(c1ccc(Nc2nccc(-c3ccccc3)n2)cc1)C(F)(F)F]

General Procedure O

Microwave Assisted Buchward Amination

A mixture of 4-phenylpyrimidin-2-amine (70 mg, 0.4 mmol), tert-butyl 1-(4-bromophenyl)-2,2,2-trifluoroethylcarbamate (160 mg, 0.45 mmol), Xantphos (20 mg, 0.03 mmol), Pd2(dba)$_3$ (20 mg, 0.02 mmol), Cs$_2$CO$_3$ (160 mg, 0.5 mmol) and DME (1.0 mL) was placed in a sealed tube and heated up to 100° C. in a microwave (Biotage, Model: Initiator) for 30 min. The reaction mixture was filtered through a pad of Celite, washed with ethyl acetate, and concentrated in vacuo. The resulting crude residue was purified by chromatography on silica gel (ethyl acetate/hexanes) to give tert-butyl 2,2,2-trifluoro-1-(4-(4-phenylpyrimidin-2-ylamino)phenyl)ethylcarbamate. $^1$H NMR (CDCl$_3$, 400 MHz) δ 8.41 (dd, 1H), 8.01-7.98 (m, 2H), 7.70 (d, 2H), 7.46-7.42 (m, 3H), 7.28 (d, 2H), 7.12 (d, 1H). MS (ESI) 445 (M+H).

The carbamate was hydrolyzed in a mixture of CH$_2$Cl$_2$ (5 mL) and trifluoroacetic acid (5 mL) to generate the title compound N-(4-(1-amino-2,2,2-trifluoroethyl)phenyl)-4-phenylpyrimidin-2-amine. MS (ESI) 345 (M+H).

Example 172

N-methyl-1-(4-(4-phenylpyrimidin-2-ylamino)phenyl)methanesulfonamide

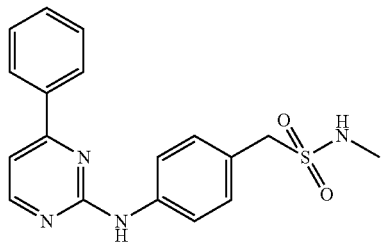 [SMILES: CNS(=O)(=O)Cc1ccc(Nc2nccc(-c3ccccc3)n2)cc1]

N-methyl-1-(4-(4-phenylpyrimidin-2-ylamino)phenyl)methanesulfonamide was obtained by following procedure O using 2-chloro-4-phenylpyrimidine and 1-(4-aminophenyl)-N-methylmethanesulfonamide. $^1$H NMR (DMSO-d$_6$, 400 MHz) δ 9.69 (s, 1H), 8.49 (d, 1H), 8.12-8.09 (m, 2H), 7.78 (d, 2H), 7.51-7.48 (m, 3H), 7.36 (d, 1H), 7.24 (d, 2H), 6.81 (dd, 1H), 4.19 (s, 2H), 2.50 (d, 3H). MS (ESI) 355 (M+H).

Example 173

N-(4-(1-amino-2,2,2-trifluoroethyl)phenyl)-4-(3-(phenylamino)phenyl)pyrimidin-2-amine

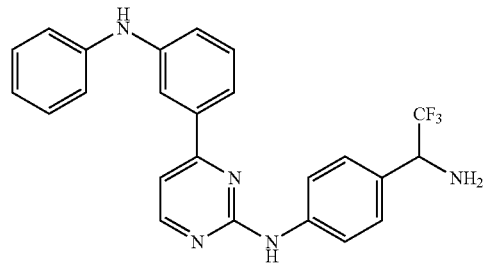 [SMILES: NC(c1ccc(Nc2nccc(-c3cccc(Nc4ccccc4)c3)n2)cc1)C(F)(F)F]

N-(4-(1-amino-2,2,2-trifluoroethyl)phenyl)-4-(3-(phenylamino)phenyl)pyrimidin-2-amine was obtained by following procedure O using 3-(2-chloropyrimidin-4-yl)-N-phenylaniline and tert-butyl 1-(4-bromophenyl)-2,2,2-trifluoroethylcarbamate. $^1$H NMR (DMSO-d$_6$, 400 MHz) δ 9.95 (s, 1H), 9.33 (br s, 2H), 8.58 (d, 1H), 8.40 (s, 1H), 7.98 (d, 2H), 7.89 (t, 1H), 7.57 (d, 2H), 7.50-7.37 (m, 2H), 7.30-7.22 (m, 3H), 7.16 (d, 2H), 6.90 (t, 1H). (MS (ESI) 436 (M+H).

Example 174

5-Fluoro-N-(4-(4-methyl-4H-1,2,4-triazol-3-yl)phenyl)-4-phenylpyrimidin-2-amine

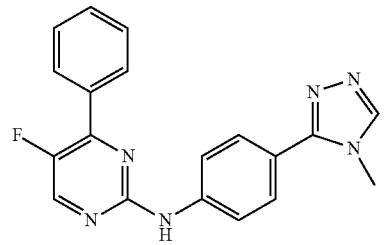 [SMILES: Cn1cnnc1-c1ccc(Nc2ncc(F)c(-c3ccccc3)n2)cc1]

5-Fluoro-N-(4-(4-methyl-4H-1,2,4-triazol-3-yl)phenyl)-4-phenylpyrimidin-2-amine was obtained by following procedure O using 4-(4-methyl-4H-1,2,4-triazol-3-yl)aniline and 2-chloro-5-fluoro-4-phenylpyrimidine. $^1$H NMR (DMSO-d$_6$, 400 MHz) δ 10.25 (s, 1H), 9.03 (s, 1H), 8.73 (d, 1H), 8.09-8.03 (m, 4H), 7.78 (d, 2H), 7.62-7.60 (m, 3H), 3.86 (s, 3H). MS (ESI) 347 (M+H).

Example 175

3-Chloro-4-(4-phenylpyrimidin-2-ylamino)benzamide

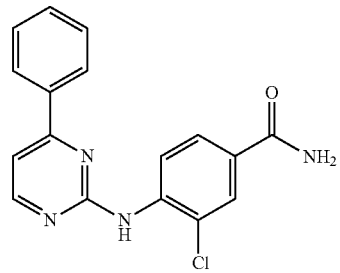 [SMILES: NC(=O)c1ccc(Nc2nccc(-c3ccccc3)n2)c(Cl)c1]

121

Part I

Methyl 3-chloro-4-(4-phenylpyrimidin-2-ylamino)benzoate

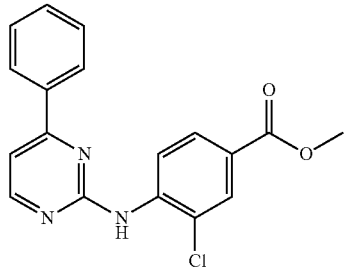 [SMILES: COC(=O)c1ccc(Nc2nccc(-c3ccccc3)n2)c(Cl)c1]

Methyl 3-chloro-4-(4 phenylpyrimidin-2-ylamino)benzoate was obtained by following procedure O using 2-chloro-4-phenylpyrimidine and methyl 4-amino-3-chlorobenzoate.

Part II

Trimethylaluminum (0.8 mL, 2.0 mmol, 2.5M in hexanes) was slowly added to a solution of ammonia in dioxane (4 mL, 0.5 mmol) under argon at room temperature. After stirring for 15 min at room temperature, 3-chloro-4-(4-phenylpyrimidin-2-ylamino)benzoate (0.67 g, 2.0 mmol) in $CH_2Cl_2$ was added slowly. The mixture was stirred at room temperature until the ester had been consumed as judged by analytical HPLC analysis. The reaction was quenched with 1 N HCl and the layers were separated. The aqueous layer was extracted with $CH_2Cl_2$ (2×), and the combined organics were dried ($MgSO_4$) and concentrated to afford (3-chloro-4-(4 phenylpyrimidin-2-ylamino)benzamide. MS (ESI) 325 (M+H).

Example 176

N-(4-(1H-1,2,3-triazol-1-yl)phenyl)-4-(3-(4-(1H-1,2,3-triazol-1-yl)phenylamino)phenyl)pyrimidin-2-amine

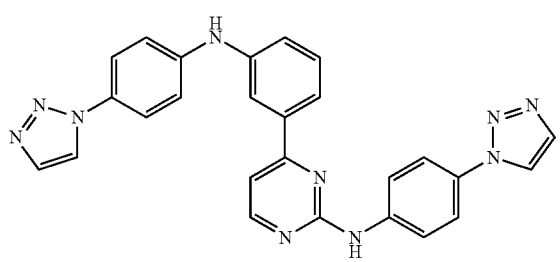 [SMILES: c1cc(Nc2ccc(-n3ccnn3)cc2)cc(-c2ccnc(Nc3ccc(-n4ccnn4)cc3)n2)c1]

N-(4-(1H-1,2,3-triazol-1-yl)phenyl)-4-(3-(4-(1H-1,2,3-triazol-1-yl)phenylamino)phenyl)pyrimidin-2-amine was obtained by following procedure O using -(1H-1,2,3-triazol-1-yl)aniline and 4-(3-bromophenyl)-2-chloropyrimidine. MS (ESI) 473 (M+H).

122

Example 177

4-(4-(Dimethylamino)phenyl)-N-(4-(4-methyl-4H-1,2,4-triazol-3-yl)phenyl)pyrimidin-2-amine

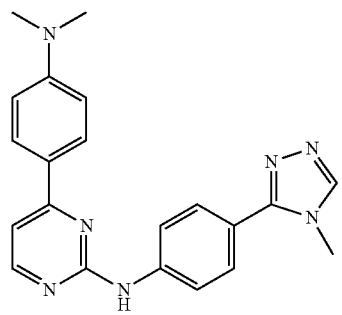 [SMILES: CN(C)c1ccc(-c2ccnc(Nc3ccc(-c4nncn4C)cc3)n2)cc1]

General Procedure P

Modified Microwave Assisted Buchward Amination

A mixture of 4-(2-chloropyrimidin-4-yl)-N,N-dimethylaniline (50 mg, 0.2 mmol) [obtained from 4-(dimethylamino)phenylboronic acid and 2,4-dicholorpyrimidine by following procedure B], 4-(4-methyl-4H-1,2,4-triazol-3-yl)aniline (45 mg, 0.25 mmol), Davephos (3 mg, 0.006 mmol), $Pd_2(dba)_3$ (2 mg, 0.002 mmol), NaO$^t$Bu (30 mg, 0.28 mmol) and DME (1.0 mL) was placed in a sealed tube and heated to 140° C. in a microwave for 30 min. The reaction mixture was cooled, filtered through a pad of Celite, washed with ethyl acetate and concentrated in vacuo. The crude residue was purified by chromatography on silica gel (ethyl acetate/hexanes) to afford 4-(4-(dimethylamino)phenyl)-N-(4-(4-methyl-4H-1,2,4-triazol-3-yl)phenyl)pyrimidin-2-amine. $^1$H NMR (DMSO-$d_6$, 400 MHz) δ 10.00 (s, 1H), 9.06 (s, 1H), 8.47 (d, 1H), 8.12-8.08 (m, 4H), 8.78 (d, 2H), 7.38 (d, 1H), 6.84 (d, 2H), 3.88 (s, 3H), 3.03 (s, 6H). MS (ESI) 372 (M+H).

Example 178

N-(4-(4-methyl-4H-1,2,4-triazol-3-yl)phenyl)-4-p-tolylpyrimidin-2-amine

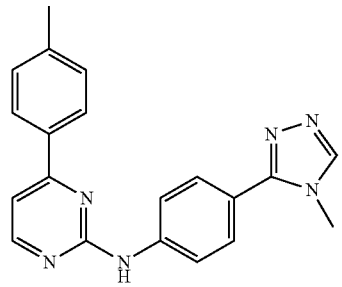 [SMILES: Cc1ccc(-c2ccnc(Nc3ccc(-c4nncn4C)cc3)n2)cc1]

N-(4-(4-methyl-4H-1,2,4-triazol-3-yl)phenyl)-4-p-tolylpyrimidin-2-amine was obtained by following procedure P using 4-(4-methyl-4H-1,2,4-triazol-3-yl)aniline and 2-chloro-4-p-tolylpyrimidine which was prepared from p-tolylboronic acid and 2,4-dicholorpyrimidine by following procedure B. $^1$H NMR (DMSO-$d_6$, 400 MHz) δ 9.97 (s, 1H), 8.58 (d, 1H), 8.54 (s, 1H), 8.10 (d, 2H), 8.04 (d, 2H), 7.71 (dd, 2H), 7.45 (d, 1H), 7.38 (d, 2H), 3.77 (s, 3H), 2.40 (s, 3H). MS (ESI) 343 (M+H).

Example 179

N-(4-(1-amino-2,2,2-trifluoroethyl)phenyl)-4-(4-(methylsulfonyl)phenyl)pyrimidin-2-amine

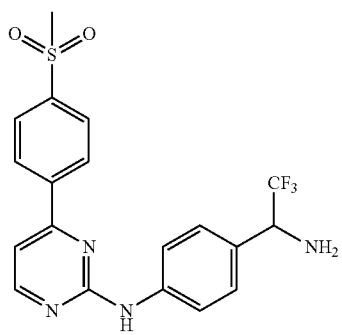 [SMILES: CS(=O)(=O)c1ccc(-c2ccnc(Nc3ccc(C(N)C(F)(F)F)cc3)n2)cc1]

N-(4-(1-amino-2,2,2-trifluoroethyl)phenyl)-4-(4-(methylsulfonyl)phenyl)pyrimidin-2-amine was obtained by following procedure O using 2-chloro-4-(4-(methylsulfonyl)phenyl)pyrimidine and tert-butyl 1-(4-bromophenyl)-2,2,2-trifluoroethylcarbamate. MS (ESI) 423 (M+H).

Example 180

N-(4-(1H-1,2,3-triazol-1-yl)phenyl)-4-(3-morpholino-5-nitrophenyl)pyrimidin-2-amine

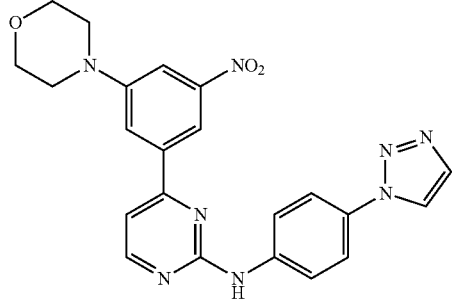 [SMILES: O=[N+]([O-])c1cc(-c2ccnc(Nc3ccc(-n4ccnn4)cc3)n2)cc(N2CCOCC2)c1]

Part I 4-(3-(2-Chloropyrimidin-4-yl)-5-nitrophenyl)morpholine

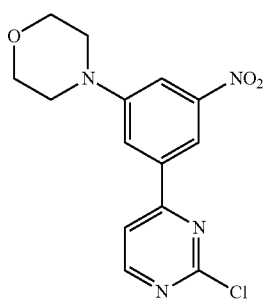 [SMILES: O=[N+]([O-])c1cc(-c2ccnc(Cl)n2)cc(N2CCOCC2)c1]

4-(3-nitro-5-(4,4,5,5-tetramethyl-1,3,2-dioxaborolan-2-yl)phenyl)morpholine was prepared from 4-(3-bromo-5-nitrophenyl)morpholine and bis(pinacolato)diboron by following procedure A in 90% yield.

4-(3-(2-Chloropyrimidin-4-yl)-5-nitrophenyl)morpholine was prepared from 4-(3-nitro-5-(4,4,5,5-tetramethyl-1,3,2-dioxaborolan-2-yl)phenyl)morpholine and 2,4-dicholorpyrimidine by following procedure B.

Part II

N-(4-(1H-1,2,3-triazol-1-yl)phenyl)-4-(3-morpholino-5-nitrophenyl)pyrimidin-2-amine was obtained by following procedure E using 4-(3-(2-chloropyrimidin-4-yl)-5-nitrophenyl)morpholine and 4-(1H-1,2,3-triazol-1-yl)aniline. $^1$H NMR (DMSO, 400 MHz) δ 10.1 (s, 1H), 8.75 (s, 1H), 8.7 (s, 1H), 8.4 (br s, 1H), 8.1 (br s, 1H), 8.05 (d, 2H), 7.95 (s, 1H), 7.9-7.8 (m, 3H), 7.7 (d, 1H), 3.8 (m, 4H), 3.4 (m, 4H). MS (ESI) 445 (M+H).

Example 181

N-(4-(1H-1,2,3-triazol-1-yl)phenyl)-4-(3-morpholino-5-(phenylamino)phenyl)pyrimidin-2-amine

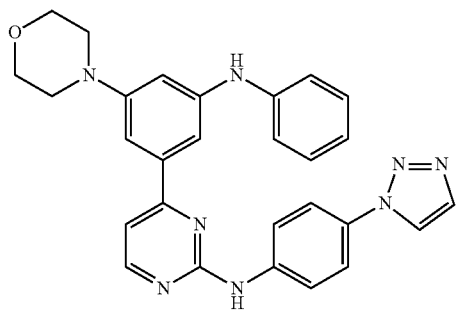 [SMILES: c1ccc(Nc2cc(-c3ccnc(Nc4ccc(-n5ccnn5)cc4)n3)cc(N3CCOCC3)c2)cc1]

N-(4-(1H-1,2,3-triazol-1-yl)phenyl)-4-(3-morpholino-5-(phenylamino)phenyl)pyrimidin-2-amine was obtained by following procedure O using N-(4-(1H-1,2,3-triazol-1-yl)phenyl)-4-(3-morpholino-5-(phenylamino)phenyl)pyrimidin-2-amine and iodobenzene. MS (ESI) 491 (M+H).

Example 182

3-(2-(4-(1,3,4-Oxadiazol-2-yl)phenylamino)pyrimidin-4-yl)-5-morpholinobenzonitrile

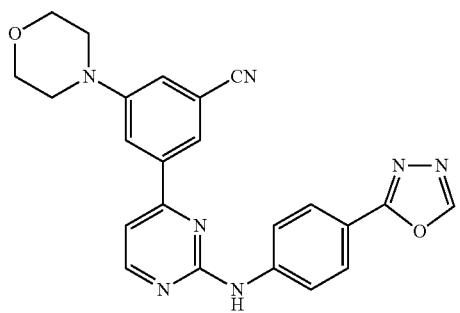 [SMILES: N#Cc1cc(-c2ccnc(Nc3ccc(-c4nnco4)cc3)n2)cc(N2CCOCC2)c1]

Part I

3-(2-Chloropyrimidin-4-yl)-5-morpholinobenzonitrile

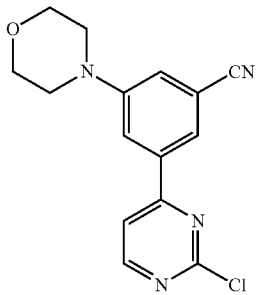 [SMILES: N#Cc1cc(-c2ccnc(Cl)n2)cc(N2CCOCC2)c1]

3-bromo-5-morpholinobenzonitrile was prepared according procedure M from 3-bromo-5-fluorobenzonitrile and morpholine in 81% yield.

3-(2-Chloropyrimidin-4-yl)-5-morpholinobenzonitrile was prepared according procedure B from 2,4-dichloropyrimidine and 3-morpholino-5-(4,4,5,5-tetramethyl-1,3,2-dioxaborolan-2-yl)benzonitrile which was synthesized by following procedure A using 3-bromo-5-morpholinobenzonitrile and bis(pinacolato)diboron.

Part II 3-(2-(4-(1,3,4-oxadiazol-2-yl)phenylamino)pyrimidin-4-yl)-5-morpholinobenzonitrile was obtained by following procedure E using 4-(1,3,4-oxadiazol-2-yl)aniline and 3-(2-chloropyrimidin-4-yl)-5-morpholinobenzonitrile. MS (ESI) 426 (M+H).

Example 183

N-(4-(3-methyl-1H-1,2,4-triazol-1-yl)phenyl)-3'-morpholino-5'-(trifluoromethoxy)biphenyl-3-amine

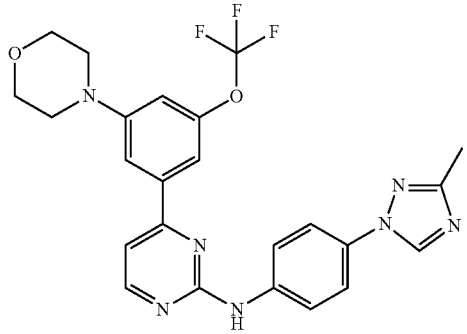 [SMILES: Cc1ncn(-c2ccc(Nc3nccc(-c4cc(OC(F)(F)F)cc(N5CCOCC5)c4)n3)cc2)n1]

Part I

4-(3-Bromo-5-(trifluoromethoxy)phenyl)morpholine

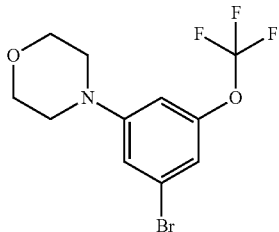 [SMILES: FC(F)(F)Oc1cc(Br)cc(N2CCOCC2)c1]

4-(3-Bromo-5-(trifluoromethoxy)phenyl)morpholine was obtained by following procedure F using 1-bromo-3-fluoro-5-(trifluoromethoxy)benzene and morpholine.

Part II

N-(4-(3-methyl-1H-1,2,4-triazol-1-yl)phenyl)-4-(3-morpholino-5-(trifluoromethoxy)phenyl)pyrimidin-2-amine was obtained by following general procedure G using 4-(3-Bromo-5-(trifluoromethoxy)phenyl)morpholine and N-(4-(3-methyl-1H-1,2,4-triazol-1-yl)phenyl)-4-(trimethylstannyl)pyrimidin-2-amine. MS (ESI) 498 (M+H).

Example 184

N-(4-(3-methyl-1H-1,2,4-triazol-1-yl)phenyl)-4-(3-morpholino-5-(trifluoromethyl)phenyl)pyrimidin-2-amine

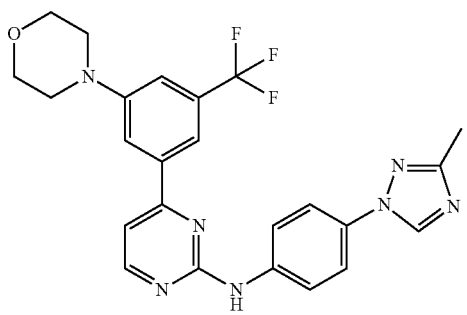 [SMILES: Cc1ncn(-c2ccc(Nc3nccc(-c4cc(N5CCOCC5)cc(C(F)(F)F)c4)n3)cc2)n1]

N-(4-(3-methyl-1H-1,2,4-triazol-1-yl)phenyl)-4-(3-morpholino-5-(trifluoromethyl)phenyl)pyrimidin-2-amine was obtained by following procedure G using N-(4-(3-methyl-1H-1,2,4-triazol-1-yl)phenyl)-4-(trimethylstannyl)pyrimidin-2-amine and 4-(3-bromo-5-(trifluoromethyl)phenyl)morpholine which was prepared from 1-bromo-3-fluoro-5-(trifluoromethyl)benzene and morpholine according to general procedure F. MS (ESI) 482 (M+H).

Example 185

3-(Dimethylamino)-5-(2-(4-(3-methyl-1H-1,2,4-triazol-1-yl)phenylamino)pyrimidin-4-yl)benzonitrile

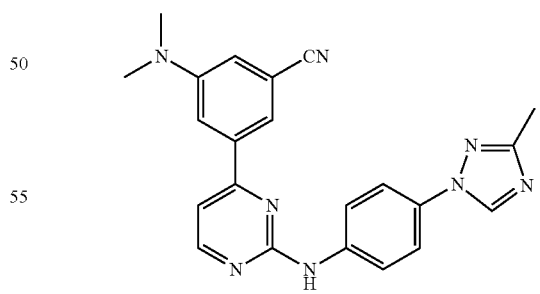

3-(Dimethylamino)-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(dimethylamino)benzonitrile which was prepared from 3-bromo-5-fluorobenzonitrile and dimethylamine (THF solution) according to procedure F. MS (ESI) 397 (M+H).

Example 186

3-(2-(4-(3-Methyl-1H-1,2,4-triazol-1-yl)phenylamino)pyrimidin-4-yl)-5-morpholinobenzonitrile

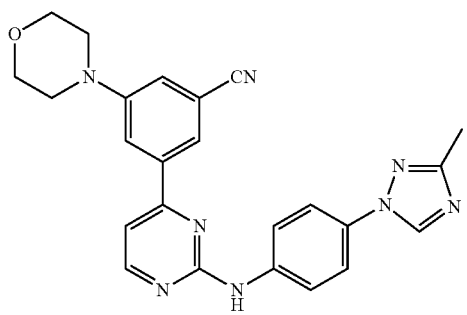 [SMILES: Cc1ncn(-c2ccc(Nc3nccc(-c4cc(C#N)cc(N5CCOCC5)c4)n3)cc2)n1]

3-(2-(4-(3-Methyl-1H-1,2,4-triazol-1-yl)phenylamino)pyrimidin-4-yl)-5-morpholinobenzonitrile was obtained by following procedure G using 3-bromo-5-morpholinobenzonitrile and N-(4-(3-methyl-1H-1,2,4-triazol-1-yl)phenyl)-4-(trimethylstannyl)pyrimidin-2-amine. MS (ESI) 439 (M+H).

Example 187

N-(4-(1H-1,2,3-triazol-1-yl)phenyl)-4-(3-fluoro-5-morpholinophenyl)pyrimidin-2-amine

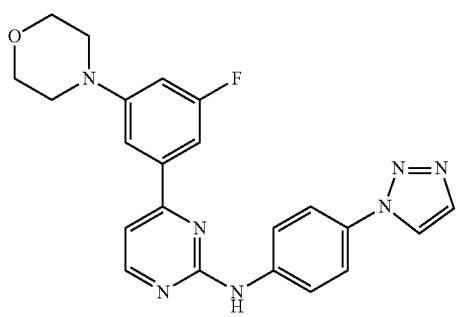 [SMILES: Fc1cc(-c2ccnc(Nc3ccc(-n4ccnn4)cc3)n2)cc(N2CCOCC2)c1]

N-(4-(1H-1,2,3-triazol-1-yl)phenyl)-4-(3-fluoro-5-morpholinophenyl)pyrimidin-2-amine was obtained by following procedure E using 4-(1H-1,2,3-triazol-1-yl)aniline and 4-(3-(2-chloropyrimidin-4-yl)-5-fluorophenyl)morpholine which was prepared from 2,4-dicholorrpyrimidine and 4-(3-fluoro-5-(4,4,5,5-tetramethyl-1,3,2-dioxaborolan-2-yl)phenyl)morpholine according to procedure B. The 4-(3-fluoro-5-(4,4,5,5-tetramethyl-1,3,2-dioxaborolan-2-yl)phenyl)morpholine was synthesized by following procedure A from bis(pinacolato)diboron and 4-(3-bromo-5-fluorophenyl)morpholine which was prepared from 1-bromo-3,5-difluorobenzene and morpholine according to procedure F. MS (ESI) 418 (M+H).

Example 188

N-(4-(1H-1,2,3-triazol-1-yl)phenyl)-4-(3-morpholino-5-(naphthalen-1-ylamino)phenyl)pyrimidin-2-amine

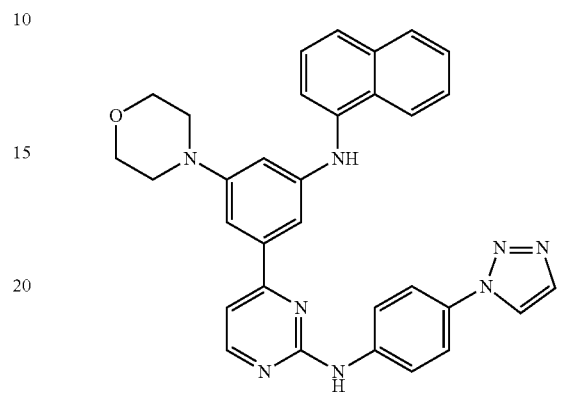

N-(4-(1H-1,2,3-triazol-1-yl)phenyl)-4-(3-morpholino-5-(naphthalen-1-ylamino)phenyl)pyrimidin-2-amine was obtained by following procedure O using N-(4-(1H-1,2,3-triazol-1-yl)phenyl)-4-(3-morpholino-5-(phenylamino)phenyl)pyrimidin-2-amine and 1-bromonaphthalene. MS (ESI) 541 (M+H).

Example 189

3-(4-Allylpiperazin-1-yl)-5-(2-(4-(3-methyl-1H-1,2,4-triazol-1-yl)phenylamino)pyrimidin-4-yl)benzonitrile

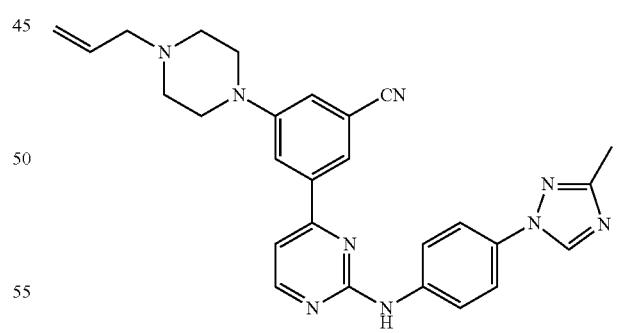

3-(4-Allylpiperazin-1-yl)-5-(2-(4-(3-methyl-1H-1,2,4-triazol-1-yl)phenylamino)pyrimidin-4-yl)benzonitrile was obtained by following procedure G utilizing N-(4-(3-methyl-1H-1,2,4-triazol-1-yl)phenyl)-4-(trimethylstannyl)pyrimidin-2-amine and 3-(4-allylpiperazin-1-yl)-5-bromobenzonitrile which was prepared by following procedure F using 1-allylpiperazine and 3-bromo-5-fluorobenzonitrile. MS (ESI) 478 (M+H).

Example 190

3-(2-(4-(3-Methyl-1H-1,2,4-triazol-1-yl)phenylamino)pyrimidin-4-yl)-5-(1-methylpiperidin-4-ylamino)benzonitrile

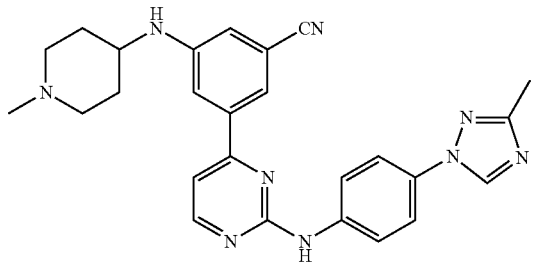

3-(2-(4-(3-Methyl-1H-1,2,4-triazol-1-yl)phenylamino)pyrimidin-4-yl)-5-(1-methylpiperidin-4-ylamino)benzonitrile was obtained by following procedure G using N-(4-(3-methyl-1H-1,2,4-triazol-1-yl)phenyl)-4-(trimethylstannyl)pyrimidin-2-amine and 3-bromo-5-(1 methylpiperidin-4-ylamino)benzonitrile which was prepared by following procedure F using 1-methylpiperidin-4-amine and 3-bromo-5-fluorobenzonitrile. MS (ESI) 466 (M+H).

Example 191

3-(2-Methoxyethylamino)-5-(2-(4-(3-methyl-1H-1,2,4-triazol-1-yl)phenylamino)pyrimidin-4-yl)benzonitrile

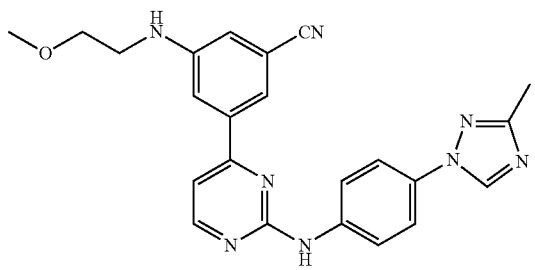

3-(2-Methoxyethylamino)-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(2-methoxyethylamino)benzonitrile which was prepared by following general procedure F using 2-methoxyethanamine and 3-bromo-5-fluorobenzonitrile. MS (ESI) 427 (M+H).

Example 192

3-(Cyclohexylamino)-5-(2-(4-(3-methyl-1H-1,2,4-triazol-1-yl)phenylamino)pyrimidin-4-yl)benzonitrile

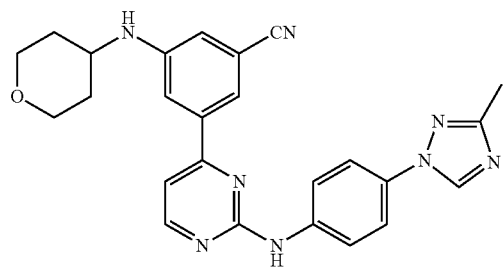 [SMILES: Cc1ncn(-c2ccc(Nc3nccc(-c4cc(C#N)cc(NC5CCOCC5)c4)n3)cc2)n1]

3-(Cyclohexylamino)-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(cyclohexylamino)benzonitrile which was prepared by following general procedure F using cyclohexanamine and 3-bromo-5-fluorobenzonitrile. MS (ESI) 451 (M+H).

Example 193

3-(2-(4-(3-Methyl-1H-1,2,4-triazol-1-yl)phenylamino)pyrimidin-4-yl)-5-(tetrahydro-2H-pyran-4-ylamino)benzonitrile

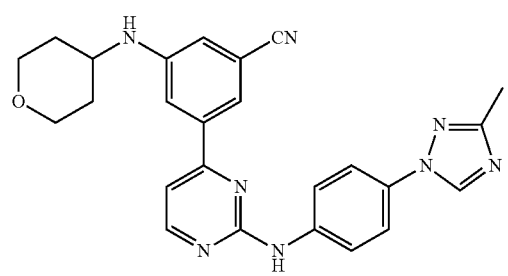 [SMILES: Cc1ncn(-c2ccc(Nc3nccc(-c4cc(C#N)cc(NC5CCOCC5)c4)n3)cc2)n1]

3-(2-(4-(3-Methyl-1H-1,2,4-triazol-1-yl)phenylamino)pyrimidin-4-yl)-5-(tetrahydro-2H-pyran-4-ylamino)benzonitrile was obtained by following procedure G using N-(4-(3-methyl-1H-1,2,4-triazol-1-yl)phenyl)-4-(trimethylstannyl)pyrimidin-2-amine and 3-bromo-5-(tetrahydro-2H-pyran-4-ylamino)benzonitrile which was prepared by following general procedure F using tetrahydro-2H-pyran-4-amine and 3-bromo-5-fluorobenzonitrile. MS (ESI) 453 (M+H).

Example 194

3-(Isopropylamino)-5-(2-(4-(3-methyl-1H-1,2,4-triazol-1-yl)phenylamino)pyrimidin-4-yl)benzonitrile

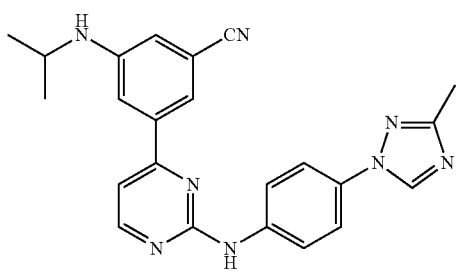 [SMILES: Cc1ncn(-c2ccc(Nc3nccc(-c4cc(C#N)cc(NC(C)C)c4)n3)cc2)n1]

3-(Isopropylamino)-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(isopropylamino)benzonitrile which was prepared by following general procedure F using propan-2-amine and 3-bromo-5-fluorobenzonitrile. MS (ESI) 411 (M+H).

Example 195

N-(4-(3-methyl-1H-1,2,4-triazol-1-yl)phenyl)-4-(2-(methylsulfonyl)-5-morpholinophenyl)pyrimidin-2-amine

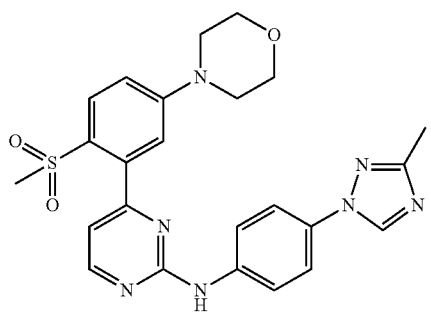 [SMILES: Cc1ncn(-c2ccc(Nc3nccc(-c4cc(N5CCOCC5)ccc4S(C)(=O)=O)n3)cc2)n1]

Part I 4-(3-bromo-4-(methylsulfonyl)phenyl)morpholine

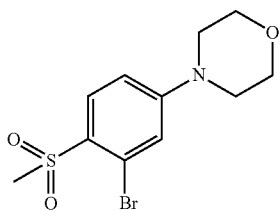 [SMILES: CS(=O)(=O)c1ccc(N2CCOCC2)cc1Br]

A mixture of 2,4-dibromo-1-fluorobenzene (1.0 g, 4.0 mmol), NaSMe (0.33 g, 4.8 mmol), triethylamine (0.52 mL, 4.0 mmol) and dimethylacetamide (3 mL) in a sealed tube was heated up to 100° C. for 12 hr. The reaction mixture was cooled, diluted with EtOAc and washed with brine. The organic layer was separated, dried (MgSO$_4$) and concentrated to give a crude residue which was purified by chromatography on silica gel (EtOAc/hexanes) to afford (2,4-dibromophenyl)(methyl)sulfane.

4-(3-bromo-4-(methylsulfonyl)phenyl)morpholine was obtained by following procedure O utilizing morpholine and 2,4-dibromo-1-(methylsulfonyl)benzene which was prepared from (2,4-dibromophenyl)(methyl)sulfane following the protocol as described for Example 43.

Part II

N-(4-(3-methyl-1H-1,2,4-triazol-1-yl)phenyl)-4-(2-(methylsulfonyl)-5-morpholinophenyl)pyrimidin-2-amine was obtained by following procedure G using N-(4-(3-methyl-1H-1,2,4-triazol-1-yl)phenyl)-4-(trimethylstannyl)pyrimidin-2-amine and 4-(3-bromo-4-(methylsulfonyl)phenyl)morpholine. MS (ESI) 492 (M+H).

Example 196

N-(4-(3-methyl-1H-1,2,4-triazol-1-yl)phenyl)-4'-(methylsulfonyl)-3'-morpholinobiphenyl-3-amine

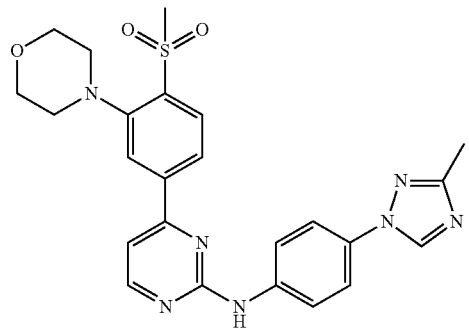 [SMILES: Cc1ncn(-c2ccc(Nc3nccc(-c4ccc(S(C)(=O)=O)c(N5CCOCC5)c4)n3)cc2)n1]

Part I 4-(5-bromo-2-(methylsulfonyl)phenyl)morpholine

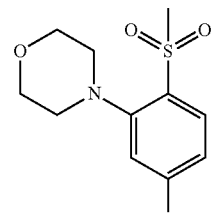

A mixture of 2,4-dibromo-1-(methylsulfonyl)benzene (0.3 g, 0.96 mmol) and morpholine (0.25 g, 2.9 mmol) in DME was heated at 90° C. for 16 h, cooled, and concentrated in vacuo. The crude residue was dissolved in EtOAc and washed with brine (2×). The organic layer was dried (MgSO$_4$), concentrated to give a near colorless solid which was ~1:1 mixture of regioisomers by analytical HPLC and LC/MS analysis. This residue was purified by chromatography on silica gel (EtOAc/hexanes) to afford 4-(5-bromo-2-(methylsulfonyl)phenyl)morpholine as a near colorless solid. $^1$H NMR (DMSO-d$_6$, 400 MHz) δ 8.2 (d, 1H), 7.8 (s, 1H), 7.7 (d, 1H), 3.8-3.6 (m, 4H), 3.4 (s, 3H), 3.1-2.9 (m, 4H). MS (ESI) 322.1, 320.1 (M+H).

Part II

N-(4-(3-methyl-1H-1,2,4-triazol-1-yl)phenyl)-4'-(methylsulfonyl)-3'-morpholinobiphenyl-3-amine was obtained by following procedure G using N-(4-(3-methyl-1H-1,2,4-triazol-1-yl)phenyl)-4-(trimethylstannyl)pyrimidin-2-amine and 4-(5-bromo-2-(methylsulfonyl)phenyl)morpholine. MS (ESI) 492 (M+H).

Example 197

5-(2-(4-(3-Methyl-1H-1,2,4-triazol-1-yl)phenylamino)pyrimidin-4-yl)biphenyl-3-carbonitrile

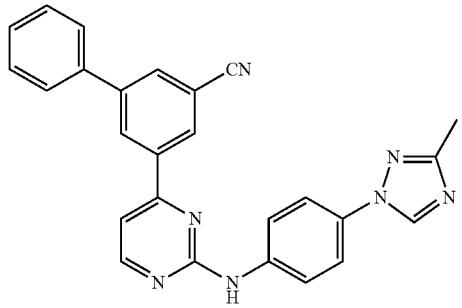 [SMILES: Cc1ncn(-c2ccc(Nc3nccc(-c4cc(C#N)cc(-c5ccccc5)c4)n3)cc2)n1]

Part I

5-Bromobiphenyl-3-carbonitrile

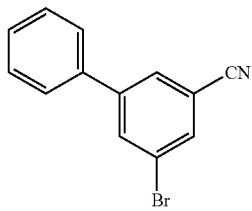 [SMILES: N#Cc1cc(Br)cc(-c2ccccc2)c1]

General Procedure Q

Suzuki reaction of 3,5-dibromobenzonitrile

A mixture of 3,5-dibromobenzonitrile (0.58 g, 2.2 mmol), phenylboronic acid (0.24 g, 2.0 mmol), Pd(PPh$_3$)$_4$ (0.23 g, 0.1 mmol), K$_2$CO$_3$ (3 mL 2 M aqueous solution) and DME (3 mL) was degassed and heated to 95° C. for 12 hr under argon. The reaction mixture was diluted with EtOAc and washed with water. The aqueous layer was extracted with ethyl acetate (2×). The combined organics were dried (MgSO$_4$) and concentrated to give the crude product which was purified with chromatography on silica gel (EtOAc/hexanes) to afford 5-bromobiphenyl-3-carbonitrile.

Part II 5-(2-(4-(3-Methyl-1H-1,2,4-triazol-1-yl)phenylamino)pyrimidin-4-yl)biphenyl-3-carbonitrile was obtained by following procedure G using N-(4-(3-methyl-1H-1,2,4-triazol-1-yl)phenyl)-4-(trimethylstannyl)pyrimidin-2-amine and 5-bromobiphenyl-3-carbonitrile. MS (ESI) 430 (M+H).

Example 198

3-(2-(4-(3-Methyl-1H-1,2,4-triazol-1-yl)phenylamino)pyrimidin-4-yl)-5-(piperidin-1-yl)benzonitrile

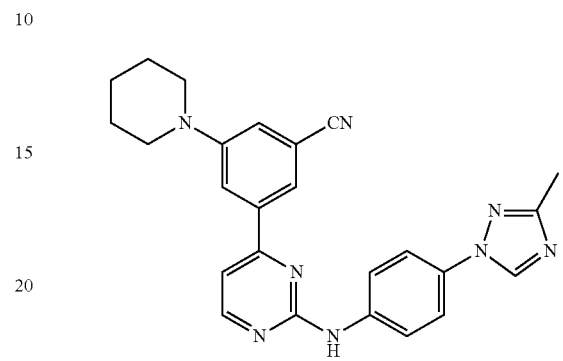

3-(2-(4-(3-Methyl-1H-1,2,4-triazol-1-yl)phenylamino)pyrimidin-4-yl)-5-(piperidin-1-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(piperidin-1-yl)benzonitrile which was prepared by following general procedure F using piperidine and 3-bromo-5-fluorobenzonitrile. MS (ESI) 437 (M+H).

Example 199

3-(2-(4-(3-Methyl-1H-1,2,4-triazol-1-yl)phenylamino)pyrimidin-4-yl)-5-(pyrrolidin-1-yl)benzonitrile

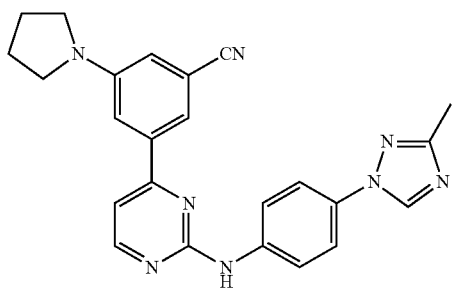 [SMILES: Cc1ncn(-c2ccc(Nc3nccc(-c4cc(C#N)cc(N5CCCC5)c4)n3)cc2)n1]

3-(2-(4-(3-Methyl-1H-1,2,4-triazol-1-yl)phenylamino)pyrimidin-4-yl)-5-(pyrrolidin-1-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(pyrrolidin-1-yl)benzonitrile which was prepared by following general procedure F using pyrrolidine and 3-bromo-5-fluorobenzonitrile. MS (ESI) 423 (M+H).

Example 200

3-Cyclopropyl-5-(2-(4-(3-methyl-1H-1,2,4-triazol-1-yl)phenylamino)pyrimidin-4-yl)benzonitrile

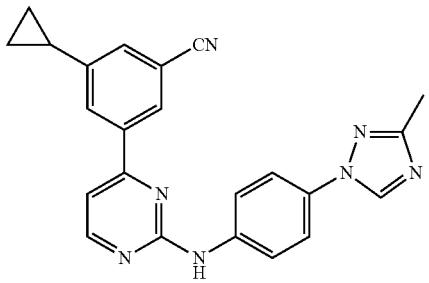 [SMILES: Cc1ncn(-c2ccc(Nc3nccc(-c4cc(C#N)cc(C5CC5)c4)n3)cc2)n1]

3-Cyclopropyl-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-cyclopropylbenzonitrile which was prepared by following the general procedure Q using 3,5-dibromobenzonitrile and cyclopropylboronic acid. MS (ESI) 394 (M+H).

Example 201

3'3-(2-(4-(3-Methyl-1H-1,2,4-triazol-1-yl)phenylamino)pyrimidin-4-yl)-5-(pyridin-2-ylamino)benzonitrile

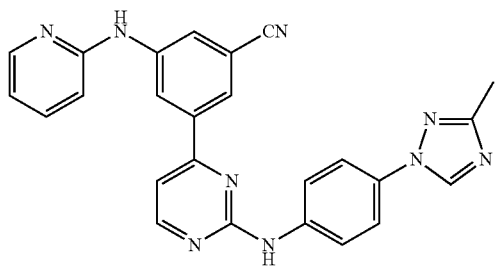 [SMILES: Cc1ncn(-c2ccc(Nc3nccc(-c4cc(C#N)cc(Nc5ccccn5)c4)n3)cc2)n1]

3'3-(2-(4-(3-Methyl-1H-1,2,4-triazol-1-yl)phenylamino)pyrimidin-4-yl)-5-(pyridin-2-ylamino)benzonitrile was obtained by following procedure G using N-(4-(3-methyl-1H-1,2,4-triazol-1-yl)phenyl)-4-(trimethylstannyl)pyrimidin-2-amine and 3-bromo-5-(pyridin-2-ylamino)benzonitrile which was prepared by following the general procedure O using 3,5-dibromobenzonitrile and pyridin-2-amine. MS (ESI) 446 (M+H).

Example 202

3-(2-(4-(3-Methyl-1H-1,2,4-triazol-1-yl)phenylamino)pyrimidin-4-yl)-5-(pyridin-4-ylamino)benzonitrile

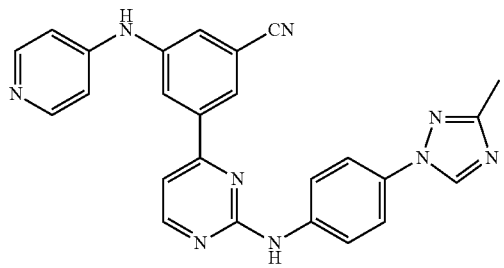 [SMILES: Cc1ncn(-c2ccc(Nc3nccc(-c4cc(C#N)cc(Nc5ccncc5)c4)n3)cc2)n1]

3-(2-(4-(3-Methyl-1H-1,2,4-triazol-1-yl)phenylamino)pyrimidin-4-yl)-5-(pyridin-4-ylamino)benzonitrile was obtained by following procedure G using N-(4-(3-methyl-1H-1,2,4-triazol-1-yl)phenyl)-4-(trimethylstannyl)pyrimidin-2-amine and 3-bromo-5-(pyridin-4-ylamino)benzonitrile which was prepared by following the general procedure O using 3,5-dibromobenzonitrile and pyridin-4-amine. MS (ESI) 446 (M+H).

Example 203

3-(2-(4-(3-Methyl-1H-1,2,4-triazol-1-yl)phenylamino)pyrimidin-4-yl)-5-(phenylamino)benzonitrile

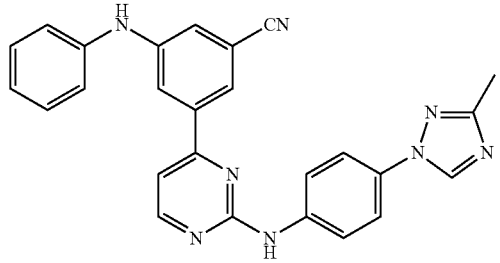 [SMILES: Cc1ncn(-c2ccc(Nc3nccc(-c4cc(C#N)cc(Nc5ccccc5)c4)n3)cc2)n1]

3-(2-(4-(3-Methyl-1H-1,2,4-triazol-1-yl)phenylamino)pyrimidin-4-yl)-5-(phenylamino)benzonitrile was obtained by following procedure G using N-(4-(3-methyl-1H-1,2,4-triazol-1-yl)phenyl)-4-(trimethylstannyl)pyrimidin-2-amine and 3-bromo-5-(phenylamino)benzonitrile which was prepared by following the general procedure O using 3,5-dibromobenzonitrile and aniline. MS (ESI) 445 (M+H).

Example 204

3-(4-Fluorophenoxy)-5-(2-(4-(3-methyl-1H-1,2,4-triazol-1-yl)phenylamino)pyrimidin-4-yl)benzonitrile

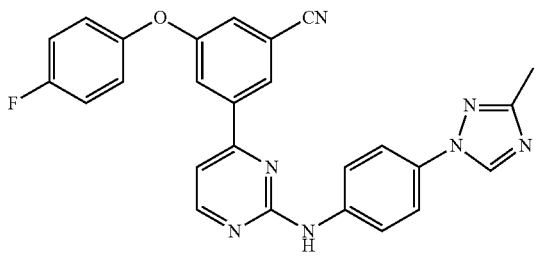 [SMILES: Cc1ncn(-c2ccc(Nc3nccc(-c4cc(C#N)cc(Oc5ccc(F)cc5)c4)n3)cc2)n1]

Part I

3-Bromo-5-(4-fluorophenoxy)benzonitrile

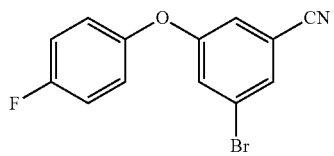 [SMILES: N#Cc1cc(Br)cc(Oc2ccc(F)cc2)c1]

A mixture of 4-fluorophenol (0.3 g, 2.7 mmol), 3-bromo-5-fluorobenzonitrile (0.53 g, 2.7 mmol), $K_2CO_3$ (1.1 g, 8.0 mmol) in N,N-dimethylacetamide (3 mL) was heated to 160° C. for 3 hr. The reaction mixture was cooled to room temperature and diluted with EtOAc and water. The organic layer was separated, dried ($MgSO_4$), concentrated, and purified by chromatography on silica gel (EtOAc/hexanes) to afford 3-bromo-5-(4-fluorophenoxy)benzonitrile.

Part II 3-(4-Fluorophenoxy)-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(4-fluorophenoxy)benzonitrile. MS (ESI) 464 (M+H).

Example 205

3-(Diethylamino)-5-(2-(4-(3-methyl-1H-1,2,4-triazol-1-yl)phenylamino)pyrimidin-4-yl)benzonitrile

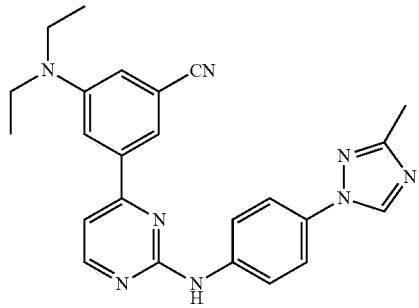 [SMILES: CCN(CC)c1cc(C#N)cc(-c2ccnc(Nc3ccc(-n4cnc(C)n4)cc3)n2)c1]

3-(Diethylamino)-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(diethylamino)benzonitrile which was prepared by following general procedure F using diethylamine and 3-bromo-5-fluorobenzonitrile. MS (ESI) 425 (M+H).

Example 206

3-(4-Hydroxypiperidin-1-yl)-5-(2-(4-(3-methyl-1H-1,2,4-triazol-1-yl)phenylamino)pyrimidin-4-yl)benzonitrile

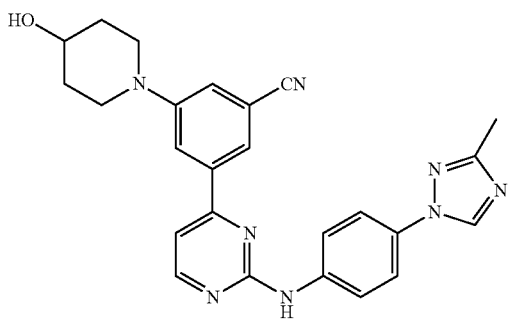 [SMILES: Cc1ncn(-c2ccc(Nc3nccc(-c4cc(C#N)cc(N5CCC(O)CC5)c4)n3)cc2)n1]

3-(4-Hydroxypiperidin-1-yl)-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(4 hydroxypiperidin-1-yl)benzonitrile which was prepared by following general procedure F using piperidin-4-ol and 3-bromo-5-fluorobenzonitrile. MS (ESI) 453 (M+H).

Example 207

3-(3-Hydroxypiperidin-1-yl)-5-(2-(4-(3-methyl-1H-1,2,4-triazol-1-yl)phenylamino)pyrimidin-4-yl)benzonitrile

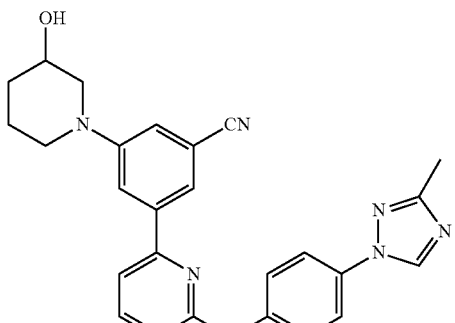

3-(3-Hydroxypiperidin-1-yl)-5-(2-(4-(3-methyl-1H-1,2,4-triazol-1-yl)phenylamino)pyrimidin-4-yl)benzonitrile was obtained by following procedure G using N-(4-(3-methyl-1H-1,2,4-triazol-1-yl)phenyl)-4-(trimethylstannyl)pyrimidin-2-amine and 3-bromo-5-(3 hydroxypiperidin-1-yl)benzonitrile which was prepared by following general procedure F using piperidin-3-ol and 3-bromo-5-fluorobenzonitrile. MS (ESI) 453 (M+H).

Example 208

1-(3-Cyano-5-(2-(4-(3-methyl-1H-1,2,4-triazol-1-yl)phenylamino)pyrimidin-4-yl) phenyl) piperidine-4-carboxylic acid

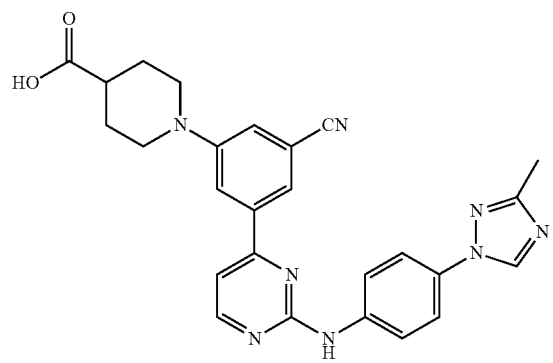 [SMILES: Cc1ncn(-c2ccc(Nc3nccc(-c4cc(C#N)cc(N5CCC(C(=O)O)CC5)c4)n3)cc2)n1]

Part I 1-(3-Bromo-5-cyanophenyl)piperidine-4-carboxylic acid

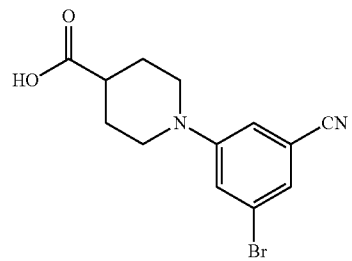 [SMILES: N#Cc1cc(Br)cc(N2CCC(C(=O)O)CC2)c1]

A mixture of 3-bromo-5-fluorobenzonitrile (1.6 g, 7.8 mmol), piperidine-4-carboxylic acid (2.6 g, 12.0 mmol), triethylamine (4.0 mL, 28.5 mmol) and N,N-dimethylacetamide (1.5 mL) in a sealed tube was heated to 130° C. for 48 hr. The reaction mixture was diluted with EtOAc and water. The organic layer was separated, dried (MgSO$_4$), and concentrated to give a crude reside which was purified by chromatography on silica gel (CH$_2$Cl$_2$/MeOH) to afford 1-(3-bromo-5-cyanophenyl)piperidine-4-carboxylic acid.

Part II 1-(3-Cyano-5-(2-(4-(3-methyl-1H-1,2,4-triazol-1-yl)phenylamino)pyrimidin-4-yl)phenyl)piperidine-4-carboxylic acid was obtained by following procedure G using N-(4-(3-methyl-1H-1,2,4-triazol-1-yl)phenyl)-4-(trimethylstannyl)pyrimidin-2-amine and 1-(3-bromo-5-cyanophenyl)piperidine-4-carboxylic acid. MS (ESI) 481 (M+H).

Example 209

Methyl 1-(3-cyano-5-(2-(4-(3-methyl-1H-1,2,4-triazol-1-yl) phenylamino)pyrimidin-4-yl)phenyl)piperidine-4-carboxylate

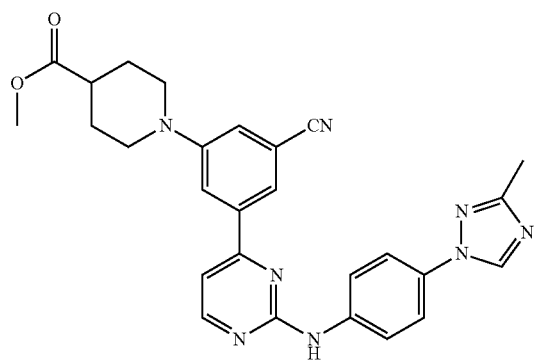 [SMILES: COC(=O)C1CCN(c2cc(C#N)cc(-c3ccnc(Nc4ccc(-n5cnc(C)n5)cc4)n3)c2)CC1]

Part I

Methyl 1-(3-bromo-5-cyanophenyl)piperidine-4-carboxylate

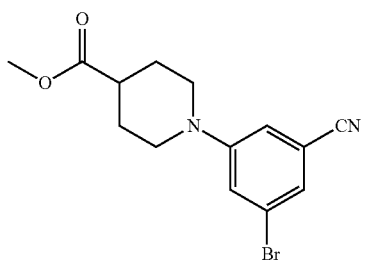 [SMILES: COC(=O)C1CCN(c2cc(Br)cc(C#N)c2)CC1]

To a solution of 1-(3-bromo-5-cyanophenyl)piperidine-4-carboxylic acid (1.1 g, 3.6 mmol) in toluene (4 mL) and methanol (2 mL) was added TMSCHN$_2$ (2 M in Et$_2$O, 3.5 mL, 7.0 mmol) dropwise at room temperature. After 1 h, the reaction was quenched with acetic acid (~0.1 mL), diluted with EtOAc and washed with saturated aqueous NaHCO$_3$. The organic layer was separated, dried (MgSO$_4$), and concentrated to give methyl 1-(3-bromo-5-cyanophenyl)piperidine-4-carboxylate in ~100% yield.

Part II

Methyl 1-(3-cyano-5-(2-(4-(3-methyl-1H-1,2,4-triazol-1-yl)phenylamino)pyrimidin-4-yl)phenyl)piperidine-4-carboxylate was obtained by following procedure G using N-(4-(3-methyl-1H-1,2,4-triazol-1-yl)phenyl)-4-(trimethylstannyl)pyrimidin-2-amine and methyl 1-(3-bromo-5-cyanophenyl)piperidine-4-carboxylate. MS (ESI) 495 (M+H).

Example 210

4-(3,4-Difluoro-5-morpholinophenyl)-N-(4-(3-methyl-1H-1,2,4-triazol-1-yl)phenyl)pyrimidin-2-amine

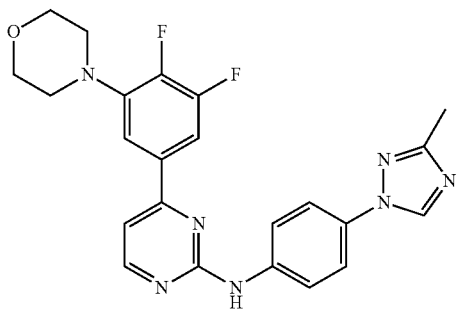 [SMILES: Cc1ncn(-c2ccc(Nc3nccc(-c4cc(F)c(F)c(N5CCOCC5)c4)n3)cc2)n1]

Part I 4-(5-Bromo-2,3-difluorophenyl)morpholine

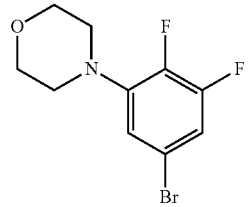 [SMILES: Fc1cc(Br)cc(N2CCOCC2)c1F]

A mixture of 5-bromo-1,2,3-trifluorobenzene (2.5 g, 11.8 mmol), morpholine (1.0 mL, 11.8 mmol), K$_2$CO$_3$ (1.6 g, 11.8 mmol) and DMSO (2 mL) in a sealed tube was heated up to 90° C. for 2.5 h. The reaction mixture was cooled to room temperature and diluted with water. The resulting colorless precipitate was filtered, washed with water, and dried in vacuo to afford 4-(5-bromo-2,3-difluorophenyl)morpholine in 76% yield. $^1$H NMR (CDCl$_3$, 400 MHz) δ 6.91-6.87 (m, 1H), 6.75-6.72 (m, 1H), 3.80-3.78 (m, 4H), 3.04-3.02 (m, 4H).

Part II 4-(3,4-Difluoro-5-morpholinophenyl)-N-(4-(3-methyl-1H-1,2,4-triazol-1-yl)phenyl)pyrimidin-2-amine was obtained by following procedure G using N-(4-(3-methyl-1H-1,2,4-triazol-1-yl)phenyl)-4-(trimethylstannyl)pyrimidin-2-amine and 5-bromo-1,2,3-trifluorobenzene. MS (ESI) 450 (M+H).

Example 211

2-Fluoro-4-(2-(4-(3-methyl-1H-1,2,4-triazol-1-yl)phenylamino)pyrimidin-4-yl)-6-morpholinobenzonitrile

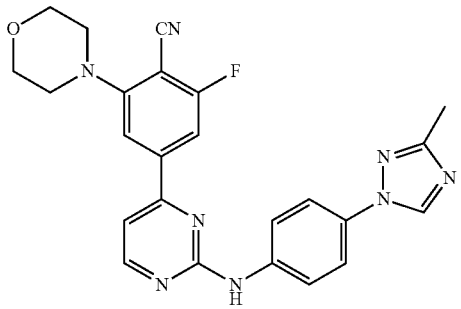 [SMILES: Cc1ncn(-c2ccc(Nc3nccc(-c4cc(F)c(C#N)c(N5CCOCC5)c4)n3)cc2)n1]

2-Fluoro-4-(2-(4-(3-methyl-1H-1,2,4-triazol-1-yl)phenylamino)pyrimidin-4-yl)-6-morpholinobenzonitrile was obtained by following procedure G using N-(4-(3-methyl-1H-1,2,4-triazol-1-yl)phenyl)-4-(trimethylstannyl)pyrimidin-2-amine and 4-bromo-2-fluoro-6-morpholinobenzonitrile which was prepared following the procedure as described in Example 210 using morpholine and 4-bromo-2,6-difluorobenzonitrile. MS (ESI) 457 (M+H).

Example 212

4-(3-fluoro-5-(methylsulfinyl)phenyl)-N-(4-(3-methyl-1H-1,2,4-triazol-1-yl)phenyl)pyrimidin-2-amine

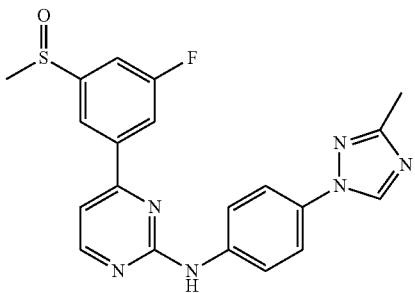 [SMILES: Cc1ncn(-c2ccc(Nc3nccc(-c4cc(F)cc(S(C)=O)c4)n3)cc2)n1]

4-(3-fluoro-5-(methylsulfinyl)phenyl)-N-(4-(3-methyl-1H-1,2,4-triazol-1-yl)phenyl)pyrimidin-2-amine was obtained by following procedure E using 2-chloro-4-(3-fluoro-5-(methylsulfinyl)phenyl)pyrimidine and 4-(3-methyl-1H-1,2,4-triazol-1-yl)aniline. MS (ESI) 409.1 (M+H).

Example 213

4-(3-fluoro-5-(methylsulfinyl)phenyl)-N-(4-(3-(6-methylpyridin-3-yl)-1H-1,2,4-triazol-1-yl)phenyl)pyrimidin-2-amine

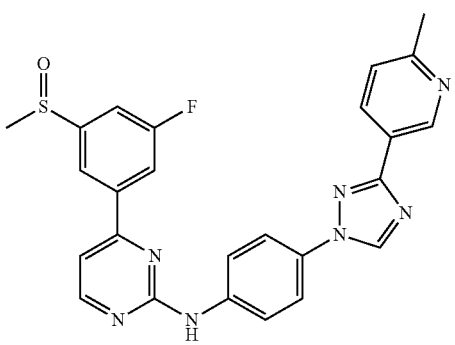 [SMILES: Cc1ccc(-c2ncn(-c3ccc(Nc4nccc(-c5cc(F)cc(S(C)=O)c5)n4)cc3)n2)cn1]

4-(3-fluoro-5-(methylsulfinyl)phenyl)-N-(4-(3-(6-methylpyridin-3-yl)-1H-1,2,4-triazol-1-yl)phenyl)pyrimidin-2-amine was obtained by following procedure E using 2-chloro-4-(3-fluoro-5-(methylsulfinyl)phenyl)pyrimidine and 4-(3-(6-methylpyridin-3-yl)-1H-1,2,4-triazol-1-yl)aniline. MS (ESI) 486.2 (M+H).

Example 214

1-(1-(4-(4-(3-fluoro-5-(methylsulfinyl)phenyl)pyrimidin-2-ylamino)phenyl)-1H-1,2,4-triazol-3-yl)piperidin-3-ol

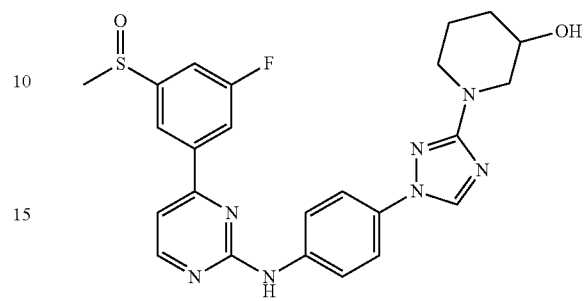

1-(1-(4-(4-(3-fluoro-5-(methylsulfinyl)phenyl)pyrimidin-2-ylamino)phenyl)-1H-1,2,4-triazol-3-yl)piperidin-3-ol was obtained by following procedure E using 2-chloro-4-(3-fluoro-5-(methylsulfinyl)phenyl)pyrimidine and 1-(1-(4-aminophenyl)-1H-1,2,4-triazol-3-yl)piperidin-3-ol. MS (ESI) 494.2 (M+H).

Example 215

1-(3-fluoro-5-(2-(4-(3-(pyridin-2-yl)-1H-1,2,4-triazol-1-yl)phenylamino)pyrimidin-4-yl)phenyl)piperidin-4-ol

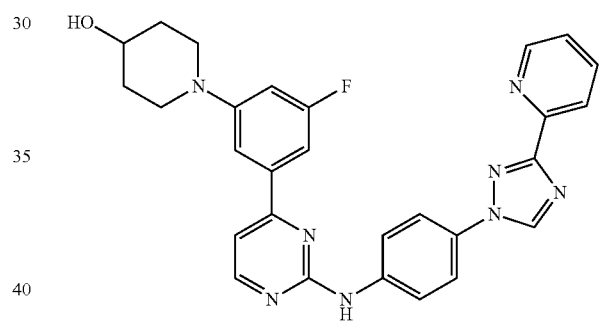

1-(3-fluoro-5-(2-(4-(3-(pyridin-2-yl)-1H-1,2,4-triazol-1-yl)phenylamino)pyrimidin-4-yl)phenyl)piperidin-4-ol was obtained by following procedure E using 1-(3-(2-chloropyrimidin-4-yl)-5-fluorophenyl)piperidin-4-ol and 4-(3-(pyridin-2-yl)-1H-1,2,4-triazol-1-yl)aniline. MS (ESI) 509.3 (M+H).

Example 216

3-(3-hydroxypiperidin-1-yl)-5-(2-(4-(3-(pyridin-2-yl)-1H-1,2,4-triazol-1-yl)phenylamino)pyrimidin-4-yl)benzonitrile

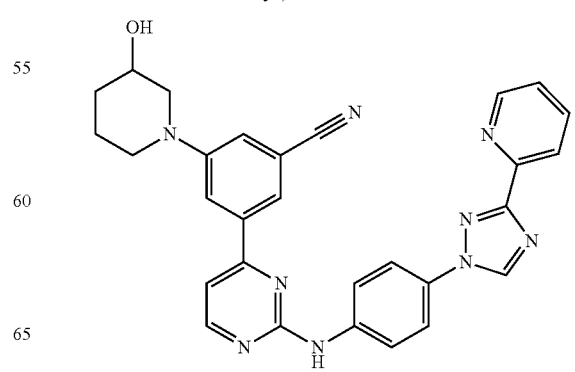

3-(3-hydroxypiperidin-1-yl)-5-(2-(4-(3-(pyridin-2-yl)-1H-1,2,4-triazol-1-yl)phenylamino)pyrimidin-4-yl)benzonitrile was obtained by following procedure E using 3-(2-chloropyrimidin-4-yl)-5-(3-hydroxypiperidin-1-yl)benzonitrile and 4-(3-(pyridin-2-yl)-1H-1,2,4-triazol-1-yl)aniline. MS (ESI) 516.3 (M+H).

Example 217

3-(dimethylamino)-5-(2-(4-(3-(4-methoxypiperidin-1-yl)-1H-1,2,4-triazol-1-yl)phenylamino)pyrimidin-4-yl)benzonitrile

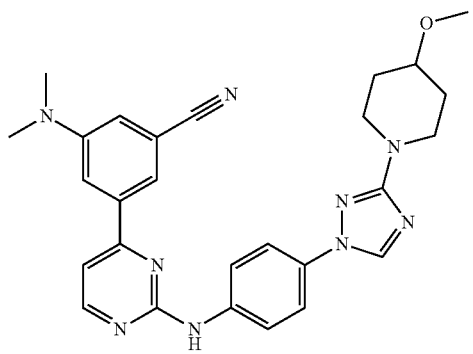

3-(dimethylamino)-5-(2-(4-(3-(4-methoxypiperidin-1-yl)-1H-1,2,4-triazol-1-yl)phenylamino)pyrimidin-4-yl)benzonitrile was obtained by following procedure E using 3-(2-chloropyrimidin-4-yl)-5-(dimethylamino)benzonitrile and 4-(3-(4-methoxypiperidin-1-yl)-1H-1,2,4-triazol-1-yl)aniline. MS (ESI) 496.2 (M+H).

Example 218

3-(dimethylamino)-5-(2-(4-(3-morpholino-1H-1,2,4-triazol-1-yl)phenylamino)pyrimidin-4-yl)benzonitrile

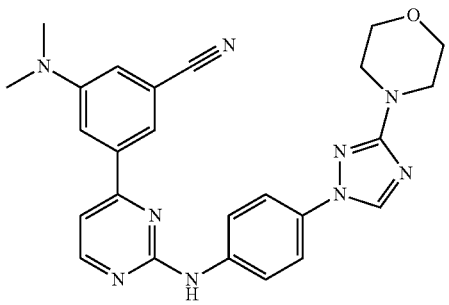 [SMILES: CN(C)c1cc(C#N)cc(-c2ccnc(Nc3ccc(-n4cnc(N5CCOCC5)n4)cc3)n2)c1]

3-(dimethylamino)-5-(2-(4-(3-morpholino-1H-1,2,4-triazol-1-yl)phenylamino)pyrimidin-4-yl)benzonitrile was obtained by following procedure E using 3-(2-chloropyrimidin-4-yl)-5-(3-hydroxypiperidin-1-yl)benzonitrile and 4-(3-morpholino-1H-1,2,4-triazol-1-yl)aniline. MS (ESI) 468.3 (M+H).

Example 219

N-(4-(2-(4-(3-(6-methylpyridin-3-yl)-1H-1,2,4-triazol-1-yl)phenylamino)pyrimidin-4-yl)phenyl)methanesulfonamide

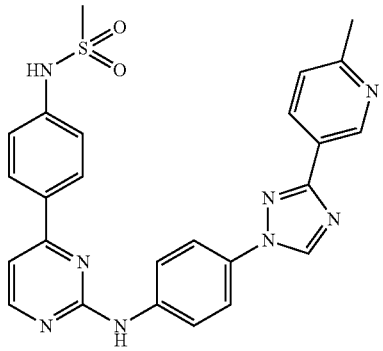 [SMILES: Cc1ccc(-c2ncn(-c3ccc(Nc4nccc(-c5ccc(NS(C)(=O)=O)cc5)n4)cc3)n2)cn1]

N-(4-(2-(4-(3-(6-methylpyridin-3-yl)-1H-1,2,4-triazol-1-yl)phenylamino)pyrimidin-4-yl)phenyl)methanesulfonamide was obtained by following procedure E using N-(4-(2-chloropyrimidin-4-yl)phenyl)methanesulfonamide and 4-(3-(6-methylpyridin-3-yl)-1H-1,2,4-triazol-1-yl)aniline. MS (ESI) 499.2 (M+H).

Example 220

N-(4-(3-(6-methylpyridin-3-yl)-1H-1,2,4-triazol-1-yl)phenyl)-4-(3-(methylsulfonyl)phenyl)pyrimidin-2-amine

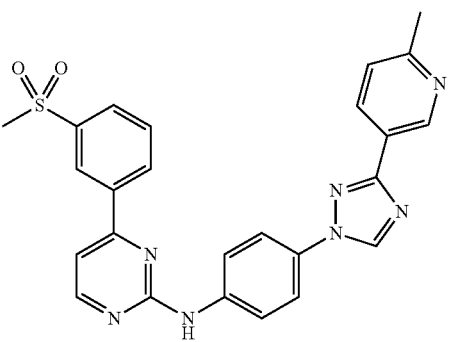 [SMILES: Cc1ccc(-c2ncn(-c3ccc(Nc4nccc(-c5cccc(S(C)(=O)=O)c5)n4)cc3)n2)cn1]

N-(4-(3-(6-methylpyridin-3-yl)-1H-1,2,4-triazol-1-yl)phenyl)-4-(3-(methylsulfonyl)phenyl)pyrimidin-2-amine was obtained by following procedure E using 2-chloro-4-(3-(methylsulfonyl)phenyl)pyrimidine and 4-(3-(pyridin-2-yl)-1H-1,2,4-triazol-1-yl)aniline. MS (ESI) 484.3 (M+H).

Example 221

1-(1-(4-(4-(3-(methylsulfonyl)phenyl)pyrimidin-2-ylamino)phenyl)-1H-1,2,4-triazol-3-yl)piperidin-4-ol

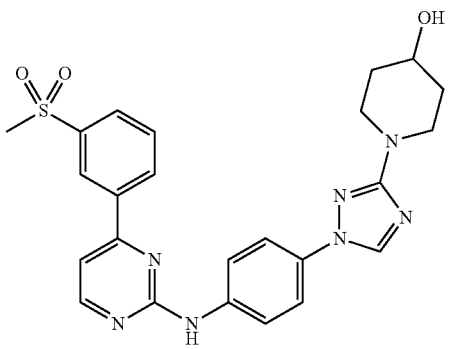 [SMILES: CS(=O)(=O)c1cccc(-c2ccnc(Nc3ccc(-n4cnc(N5CCC(O)CC5)n4)cc3)n2)c1]

1-(1-(4-(4-(3-(methylsulfonyl)phenyl)pyrimidin-2-ylamino)phenyl)-1H-1,2,4-triazol-3-yl)piperidin-4-ol was obtained by following procedure E using 3-(2-chloropyrimidin-4-yl)-5-(3-hydroxypiperidin-1-yl)benzonitrile and 1-(1-(4-aminophenyl)-1H-1,2,4-triazol-3-yl)piperidin-4-ol. MS (ESI) 492.2 (M+H).

Example 222

N-(4-(3,5-dimethyl-1H-1,2,4-triazol-1-1/1)phenyl)-4-phenylpyrimidin-2-amine

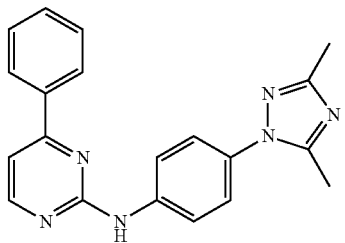 [SMILES: Cc1nc(C)n(-c2ccc(Nc3nccc(-c4ccccc4)n3)cc2)n1]

N-(4-(3,5-dimethyl-1H-1,2,4-triazol-1-yl)phenyl)-4-phenylpyrimidin-2-amine was obtained by following procedure E using 4-phenylpyrimidin-2-amine and 4-phenylpyrimidin-2-amine. MS (ESI) 343.3 (M+H).

Example 223

N-(4-(3,5-dimethyl-1H-1,2,4-triazol-1-yl)phenyl)-4-(3-morpholinophenyl)pyrimidin-2-amine

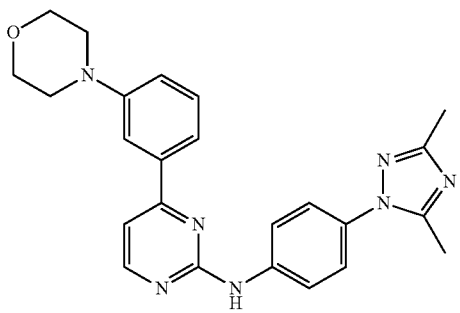 [SMILES: Cc1nc(C)n(-c2ccc(Nc3nccc(-c4cccc(N5CCOCC5)c4)n3)cc2)n1]

N-(4-(3,5-dimethyl-1H-1,2,4-triazol-1-yl)phenyl)-4-(3-morpholinophenyl)pyrimidin-2-amine was obtained by following procedure E using 4-(3-(2-chloropyrimidin-4-yl)phenyl) morpholine and 4-(3-(pyridin-2-yl)-1H-1,2,4-triazol-1-yl)aniline. MS (ESI) 428.3 (M+H).

Example 224

4-(benzo[d][1,3]-dioxol-5-yl)-N-(4-(3-(trifluoromethyl)-1H-1,2,4-triazol-1-yl)phenyl)pyrimidin-2-amine

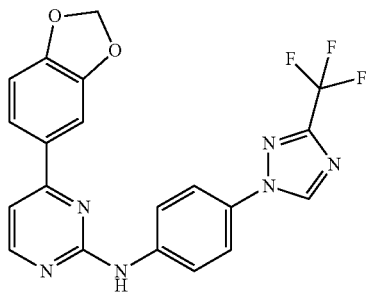 [SMILES: FC(F)(F)c1ncn(-c2ccc(Nc3nccc(-c4ccc5c(c4)OCO5)n3)cc2)n1]

4-(benzo[d][1,3]dioxol-5-yl)-N-(4-(3-(trifluoromethyl)-1H-1,2,4-triazol-1-yl)phenyl)pyrimidin-2-amine was obtained by following procedure E using 4-(benzo[d][1,3]dioxol-5-yl)-2-chloropyrimidine and 4-(3-(trifluoromethyl)-1H-1,2,4-triazol-1-yl)aniline. MS (ESI) 427.3 (M+H).

Example 225

4-(benzo[d][1,3]-dioxol-5-yl)-N-(4-(3,5-dimethyl-1H-1,2,4-triazol-1-yl)phenyl)pyrimidin-2-amine

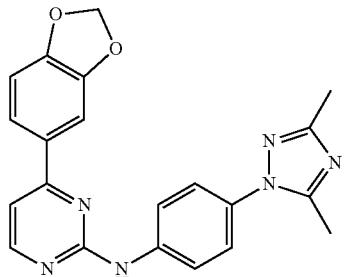

4-(benzo[d][1,3]dioxol-5-yl)-N-(4-(3,5-dimethyl-1H-1,2,4-triazol-1-yl)phenyl)pyrimidin-2-amine was obtained by following procedure E using 4-(benzo[d][1,3]dioxol-5-yl)-2-chloropyrimidine and 4-(3-(pyridin-2-yl)-1H-1,2,4-triazol-1-yl)aniline. MS (ESI) 387.3 (M+H).

Example 226

N-(4-(4H-1,2,4-triazol-3-yl)phenyl)-4-(benzo[d][1,3]dioxol-5-yl)pyrimidin-2-amine

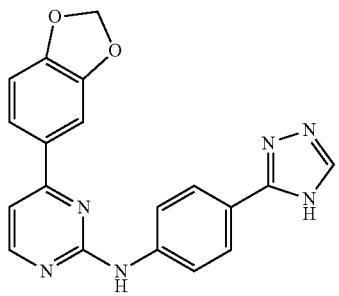 [SMILES: c1cc(-c2ccc3c(c2)OCO3)nc(Nc2ccc(-c3nnc[nH]3)cc2)n1]

N-(4-(4H-1,2,4-triazol-3-yl)phenyl)-4-(benzo[d][1,3]dioxol-5-yl)pyrimidin-2-amine was obtained by following procedure E using 4-(benzo[d][1,3]dioxol-5-yl)-2-chloropyrimidine and 4-(4H-1,2,4-triazol-3-yl)aniline. MS (ESI) 359.1 (M+H).

Example 227

N-(4-(4H-1,2,4-triazol-3-yl)phenyl)-4-(3-fluoro-5-morpholinophenyl)pyrimidin-2-amine

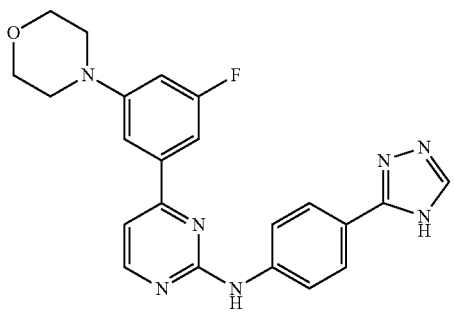 [SMILES: Fc1cc(-c2ccnc(Nc3ccc(-c4nnc[nH]4)cc3)n2)cc(N2CCOCC2)c1]

N-(4-(4H-1,2,4-triazol-3-yl)phenyl)-4-(3-fluoro-5-morpholinophenyl)pyrimidin-2-amine was obtained by following procedure E using 4-(3-(2-chloropyrimidin-4-yl)-5-fluorophenyl)morpholine and 4-(4H-1,2,4-triazol-3-yl)aniline. MS (ESI) 418.1 (M+H).

Example 228

4-(3-morpholino-5-(trifluoromethyl)phenyl)-N-(4-(3-(trifluoromethyl)-1H-1,2,4-triazol-1-yl)phenyl)pyrimidin-2-amine

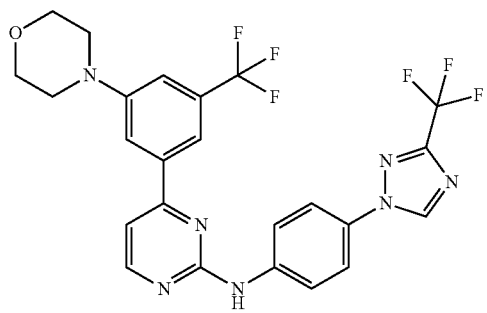 [SMILES: FC(F)(F)c1cc(-c2ccnc(Nc3ccc(-n4cnc(C(F)(F)F)n4)cc3)n2)cc(N2CCOCC2)c1]

4-(3-morpholino-5-(trifluoromethyl)phenyl)-N-(4-(3-(trifluoromethyl)-1H-1,2,4-triazol-1-yl)phenyl)pyrimidin-2-amine was obtained by following procedure E using 4-(3-(2-chloropyrimidin-4-yl)-5-(trifluoromethyl)phenyl)morpholine and 4-(3-(trifluoromethyl)-1H-1,2,4-triazol-1-yl)aniline. MS (ESI) 536.1 (M+H).

Example 229

N-(4-(3,5-dimethyl-1H-1,2,4-triazol-1-yl)phenyl)-4-(3-morpholino-5-(trifluoromethyl)phenyl)pyrimidin-2-amine

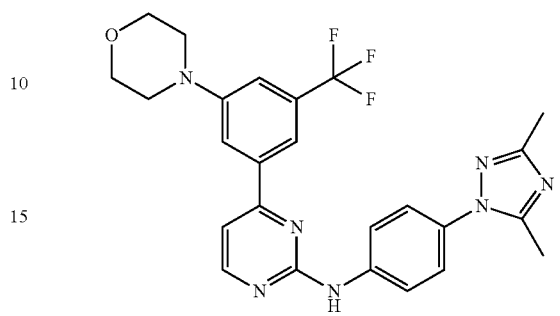

N-(4-(3,5-dimethyl-1H-1,2,4-triazol-1-yl)phenyl)-4-(3-morpholino-5-(trifluoromethyl)phenyl)pyrimidin-2-amine was obtained by following procedure E using 4-(3-(2-chloropyrimidin-4-yl)-5-(trifluoromethyl)phenyl)morpholine and 4-(3,5-dimethyl-1H-1,2,4-triazol-1-yl)aniline. MS (ESI) 496.2 (M+H).

Example 230 tert-butyl 4-(3-fluoro-5-(2-(4-(3-(trifluoromethyl)-1H-1,2,4-triazol-1-yl)phenylamino)pyrimidin-4-yl)phenyl)piperazine-1-carboxylate

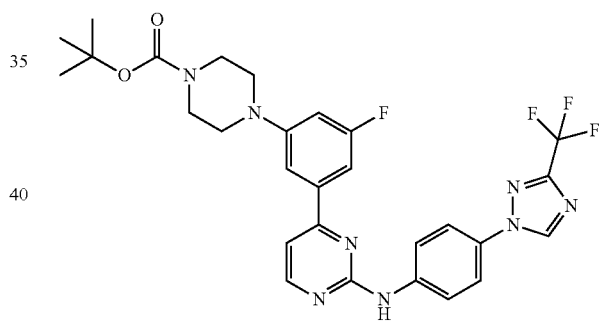

Part I tert-Butyl 4-(3-bromo-5-fluorophenyl)piperazine-1-carboxylate

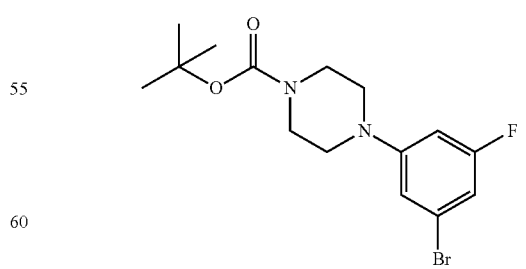

tert-Butyl 4-(3-bromo-5-fluorophenyl)piperazine-1-carboxylate was obtained by following general procedure X using (Boc)$_2$O and 1-(3-bromo-5-fluorophenyl)piperazine which was prepared from 1-bromo-3,5-difluorobenzene and piperazine by following general procedure F.

Part II tert-Butyl 4-(3-fluoro-5-(4,4,5,5-tetramethyl-1,3,2-dioxaborolan-2-yl)phenyl)piperazine-1-carboxylate

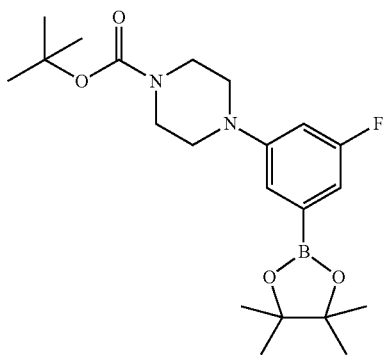 [SMILES: CC(C)(C)OC(=O)N1CCN(c2cc(F)cc(B3OC(C)(C)C(C)(C)O3)c2)CC1]

tert-Butyl 4-(3-fluoro-5-(4,4,5,5-tetramethyl-1,3,2-dioxaborolan-2-yl)phenyl)piperazine-1-carboxylate was obtained by following general procedure A using tert-butyl 4-(3-bromo-5-fluorophenyl)piperazine-1-carboxylate and bis(pinacolato)diboron.

Part III tert-Butyl 4-(3-(2-chloropyrimidin-4-yl)-5-fluorophenyl)piperazine-1-carboxylate

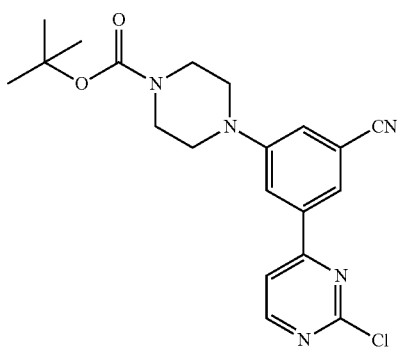 [SMILES: CC(C)(C)OC(=O)N1CCN(c2cc(C#N)cc(-c3ccnc(Cl)n3)c2)CC1]

tert-Butyl 4-(3-(2-chloropyrimidin-4-yl)-5-fluorophenyl)piperazine-1-carboxylate was obtained by following general procedure B using tert-butyl 4-(3-fluoro-5-(4,4,5,5-tetramethyl-1,3,2-dioxaborolan-2-yl)phenyl)piperazine-1-carboxylate and dichloropyrimidine.

Part IV tert-butyl 4-(3-fluoro-5-(2-(4-(3-(trifluoromethyl)-1H-1,2,4-triazol-1-yl)phenylamino)pyrimidin-4-yl)phenyl)piperazine-1-carboxylate was obtained by following procedure O using tert-butyl 4-(3-(2-chloropyrimidin-4-yl)-5-fluorophenyl)piperazine-1-carboxylate and 4-(3-(trifluoromethyl)-1H-1,2,4-triazol-1-yl)aniline. MS (ESI) 585.2 (M+H).

Example 231

N-(4-(3,5-dimethyl-1H-1,2,4-triazol-1-yl)phenyl)-4-(3-fluoro-5-(4-isopropylpiperazin-1-yl)phenyl)pyrimidin-2-amine

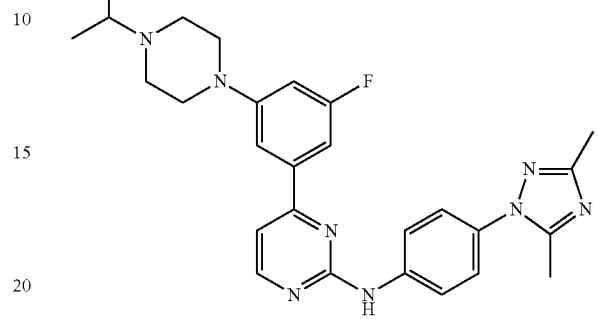

2-chloro-4-(3-fluoro-5-(4-isopropylpiperazin-1-yl)phenyl)pyrimidine

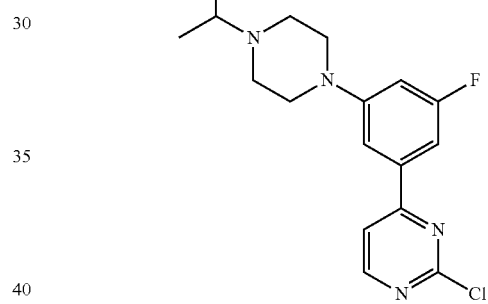

Part I

To a solution of tert-butyl 4-(3-(2-chloropyrimidin-4-yl)-5-fluorophenyl)piperazine-1-carboxylate (210 mg, 0.54 mmol) in $CH_2Cl_2$ (2 mL) was added TFA (2 mL). The reaction was aged at room temperature for 2 h, and then concentrated in vacuo.

The crude residue was taken up in $CH_2Cl_2$ and acetone (313 mg, 5.4 mmol) was added followed by $NaBH(OAc)_3$ (172 mg, 0.81 mmol). After stifling at room temperature for 18 h, more acetone (313 mg) and borohydride (172 mg) were added. After an additional 4 h, the starting material is consumed as judged by reverse-phase analytical HPLC. The reaction is diluted with EtOAc and sat. aq. $NaHCO_3$ and the layers are separated. The organic layer is dried ($MgSO_4$) and concentrated to give the title compound which was used without further purification. MS (ESI) 335.1 (M+H

Part II

N-(4-(3,5-dimethyl-1H-1,2,4-triazol-1-yl)phenyl)-4-(3-fluoro-5-(4 isopropylpiperazin-1-yl)phenyl)pyrimidin-2-amine was obtained by following procedure O using 2-chloro-4-(3-fluoro-5-(4 isopropylpiperazin-1-yl)phenyl) pyrimidine and 4-(3,5-dimethyl-1H-1,2,4-triazol-1-yl) aniline. MS (ESI) 487.2 (M+H).

Example 232

4-(3-fluoro-5-(4-isopropylpiperazin-1-yl)phenyl)-N-(4-(3-(6-methoxypyridin-3-yl)-1H-1,2,4-triazol-1-yl)phenyl)pyrimidin-2-amine

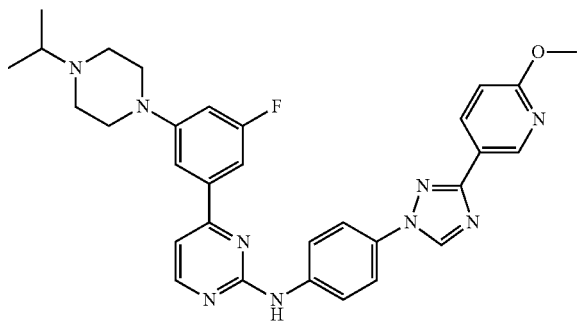 [SMILES: COc1ccc(-c2ncn(-c3ccc(Nc4nccc(-c5cc(F)cc(N6CCN(C(C)C)CC6)c5)n4)cc3)n2)cn1]

4-(3-fluoro-5-(4-isopropylpiperazin-1-yl)phenyl)-N-(4-(3-(6-methoxypyridin-3-yl)-1H-1,2,4-triazol-1-yl)phenyl)pyrimidin-2-amine was obtained by following procedure O using 2-chloro-4-(3-fluoro-5-(4-isopropylpiperazin-1-yl)phenyl)pyrimidine and 4-(3-(6-methoxypyridin-3-yl)-1H-1,2,4-triazol-1-yl)aniline. MS (ESI) 566.2 (M+H).

Example 233

4-(3-fluoro-5-(piperazin-1-yl) phenyl)-N-(4-(3-(trifluoromethyl)-1H-1,2,4-triazol-1-yl)phenyl)pyrimidin-2-amine

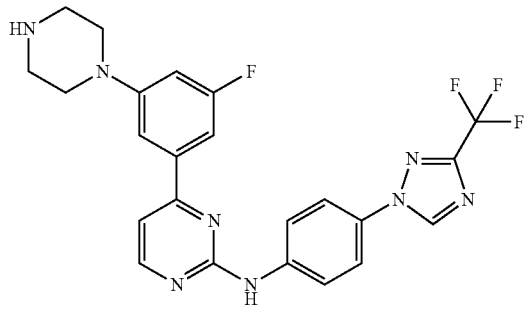 [SMILES: Fc1cc(-c2ccnc(Nc3ccc(-n4cnc(C(F)(F)F)n4)cc3)n2)cc(N2CCNCC2)c1]

To a solution of the product from Example 230 in CH$_2$Cl$_2$ was added TFA. The reaction was aged at room temperature for 2 h, and then concentrated in vacuo to give the title compound as the TFA salt. MS (ESI) 485.1 (M+H).

Example 234

3-(5-fluoro-2-(4-(3-(trifluoromethyl)-1H-1,2,4-triazol-1-yl) phenylamino)pyrimidin-4-yl)-5-morpholinobenzonitrile

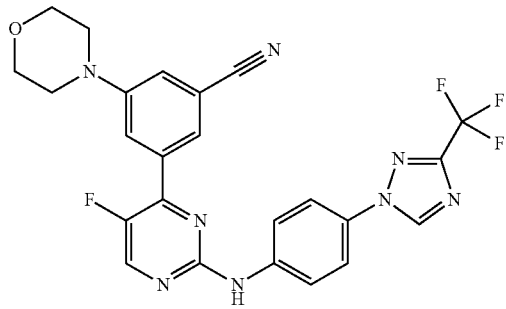 [SMILES: N#Cc1cc(-c2nc(Nc3ccc(-n4cnc(C(F)(F)F)n4)cc3)ncc2F)cc(N2CCOCC2)c1]

3-(5-fluoro-2-(4-(3-(trifluoromethyl)-1H-1,2,4-triazol-1-yl)phenylamino)pyrimidin-4-yl)-5-morpholinobenzonitrile was obtained by following procedure O using 4-(3-(trifluoromethyl)-1H-1,2,4-triazol-1-yl)aniline and 3-(2-chloro-5-fluoropyrimidin-4-yl)-5-morpholinobenzonitrile which was prepared from 2,4-dichloro-5-fluoropyrimidine and 3-morpholino-5-(4,4,5,5-tetramethyl-1,3,2-dioxaborolan-2-yl)benzonitrile according to procedure B. MS (ESI) 511.1 (M+H).

Example 235

3-(2-(4-(3,5-dimethyl-1H-1,2,4-triazol-1-yl)phenylamino)-5-fluoropyrimidin-4-yl)-5-morpholinobenzonitrile

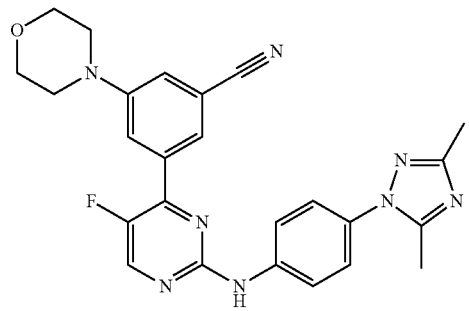 [SMILES: Cc1nc(C)n(-c2ccc(Nc3ncc(F)c(-c4cc(C#N)cc(N5CCOCC5)c4)n3)cc2)n1]

3-(2-(4-(3,5-dimethyl-1H-1,2,4-triazol-1-yl)phenylamino)-5-fluoropyrimidin-4-yl)-5-morpholinobenzonitrile was obtained by following procedure O using 3-(2-chloro-5-fluoropyrimidin-4-yl)-5-morpholinobenzonitrile and 4-(3,5-dimethyl-1H-1,2,4-triazol-1-yl)aniline. MS (ESI) 471.2 (M+H).

Example 236

3-(2-(4-(3-(dimethylamino)-1H-1,2,4-triazol-1-yl)phenylamino)pyrimidin-4-yl)-5-morpholinobenzonitrile

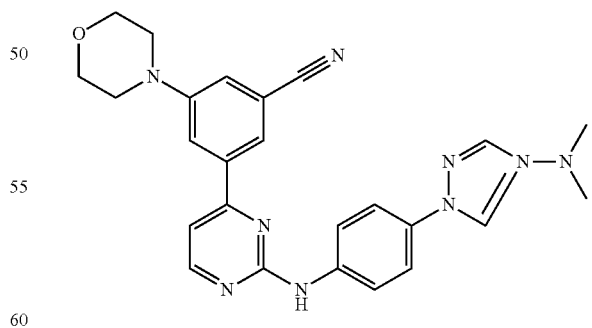

3-(2-(4-(3-(dimethylamino)-1H-1,2,4-triazol-1-yl)phenylamino)pyrimidin-4-yl)-5-morpholinobenzonitrile was obtained by following procedure E using 3-(2-chloropyrimidin-4-yl)-5-morpholinobenzonitrile and 1-(4-aminophenyl)-N,N-dimethyl-1H-1,2,4-triazol-3-amine. MS (ESI) 468.3 (M+H).

Example 237

N-(4-(3-(dimethylamino)-1H-1,2,4-triazol-1-yl)phenyl)-4-(3-morpholino-5-(trifluoromethyl)phenyl)pyrimidin-2-amine

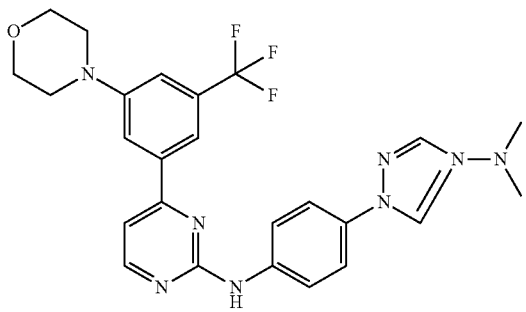

N-(4-(3-(dimethylamino)-1H-1,2,4-triazol-1-yl)phenyl)-4-(3-morpholino-5-(trifluoromethyl)phenyl)pyrimidin-2-amine was obtained by following procedure E using 4-(3-(2-chloropyrimidin-4-yl)-5-(trifluoromethyl)phenyl)morpholine and 1-(4-aminophenyl)-N,N-dimethyl-1H-1,2,4-triazol-3-amine. MS (ESI) 511.3 (M+H).

Example 238

3-(2-(4-(6-methoxypyridin-3-yl)phenylamino)pyrimidin-4-yl)-5-morpholinobenzonitrile

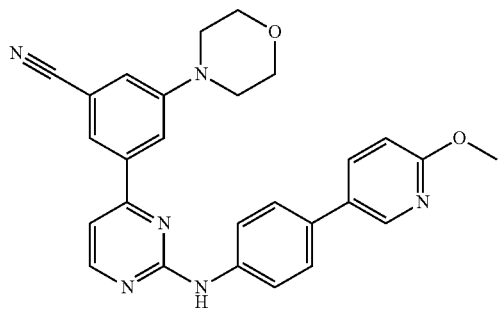 [SMILES: COc1ccc(-c2ccc(Nc3nccc(-c4cc(C#N)cc(N5CCOCC5)c4)n3)cc2)cn1]

Part I 3-(2-(4-bromophenylamino)pyrimidin-4-yl)-5-morpholinobenzonitrile

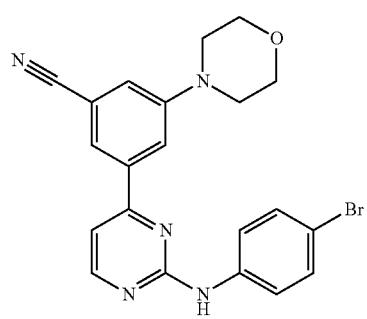 [SMILES: N#Cc1cc(-c2ccnc(Nc3ccc(Br)cc3)n2)cc(N2CCOCC2)c1]

3-(2-(4-bromophenylamino)pyrimidin-4-yl)-5-morpholinobenzonitrile was obtained by following procedure E using 3-(2-chloropyrimidin-4-yl)-5-morpholinobenzonitrile and 4-bromoaniline.

Part II 3-(2-(4-(6-methoxypyridin-3-yl)phenylamino)pyrimidin-4-yl)-5-morpholinobenzonitrile was obtained by following procedure B using 34244-bromophenylamino)pyrimidin-4-yl)-5-morpholinobenzonitrile and 6-methoxypyridin-3-ylboronic acid. MS (ESI) 465.2 (M+H).

Example 239

4-(3,5-dichlorophenyl)-N-(4-(3-methyl-1H-1,2,4-triazol-1-yl)phenyl)pyrimidin-2-amine

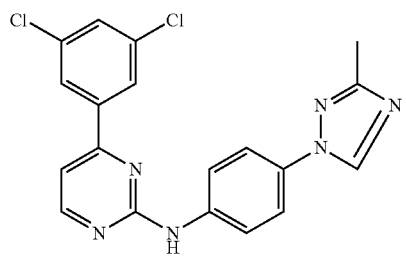 [SMILES: Cc1ncn(-c2ccc(Nc3nccc(-c4cc(Cl)cc(Cl)c4)n3)cc2)n1]

General Procedure R

Suzuki Coupling of Substituted Chloropyrimidine with Boronic Acid

A mixture of 4-chloro-N-(4-(3-methyl-1H-1,2,4-triazol-1-yl)phenyl)pyrimidin-2-amine (0.050 g, 0.17 mmol), 3,5-dichlorophenylboronic acid (0.037 g, 0.17 mmol) and Pd(PPh$_3$)$_4$ (0.035 g, 0.03 mmol), 2M K$_2$CO$_3$ (0.52 mL) in DME (2 mL) was heated in a microwave at 110° C. for 1 h. The reaction mixture was cooled down to room temperature and the organic phase was separated and evaporated. Purification of this material by column chromatography on silica gel (85% EtOAc/hexane) provided the desired product as a yellow solid. $^1$H NMR (DMSO-d$_6$, 400 MHz) δ 10.0 (s, 1H), 9.05 (s, 1H), 8.65 (d, 1H), 8.22 (d, 2H), 7.96 (d, 2H), 7.82 (m, 1H), 7.73 (d, 2H), 7.60 (m, 1H), 2.37 (s, 3H). MS (ESI) 397.30 (M+H).

Example 240

4-(3-fluoro-4-methoxyphenyl)-N-(4-(3-methyl-1H-1,2,4-triazol-1-yl)phenyl)pyrimidin-2-amine

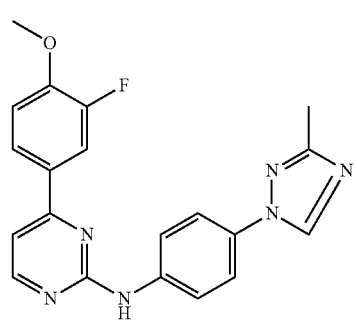 [SMILES: COc1ccc(-c2ccnc(Nc3ccc(-n4cnc(C)n4)cc3)n2)cc1F]

4-(3-fluoro-4-methoxyphenyl)-N-(4-(3-methyl-1H-1,2,4-triazol-1-yl)phenyl)pyrimidin-2-amine was obtained by following procedure R using 3-fluoro-4-methoxy-phenylboronic acid. ¹H NMR (DMSO-d₆, 400 MHz) δ 9.89 (s, 1H), 9.04 (s, 1H), 8.55 (d, 2H), 8.04 (m, 2H), 7.97 (d, 2H), 7.74 (d, 2H), 7.46 (d, 1H), 7.38 (m, 1H), 3.94 (s, 3H), 2.35 (s, 3H). MS (ESI) 377.15 (M+H).

Example 241

4-(benzo[d][1,3]-dioxol-5-yl)-N-(4-(3-methyl-1H-1,2,4-triazol-1-yl)phenyl)pyrimidin-2-amine

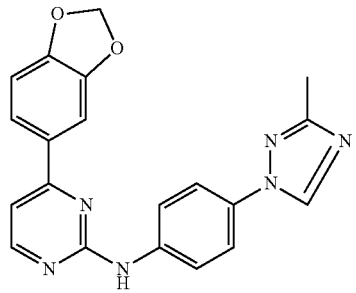 [SMILES: Cc1ncn(-c2ccc(Nc3nccc(-c4ccc5c(c4)OCO5)n3)cc2)n1]

4-(benzo[d][1,3]dioxol-5-yl)-N-(4-(3-methyl-1H-1,2,4-triazol-1-yl)phenyl)pyrimidin-2-amine was obtained by following procedure R using benzo[d][1,3]dioxol-5-ylboronic acid. ¹H NMR (DMSO-d₆, 400 MHz) δ 9.84 (s, 1H), 9.15 (s, 1H), 8.53 (d, 1H), 7.95 (m, 2H), 7.80 (m, 1H), 7.76 (m, 3H), 7.40 (d, 1H), 7.11 (d, 1H), 6.14 (s, 2H), 2.34 (s, 3H). MS (ESI) 373. (M+H).

Example 242

5-(2-(4-(3-methyl-1H-1,2,4-triazol-1-yl)phenylamino)pyrimidin-4-yl)picolinonitrile

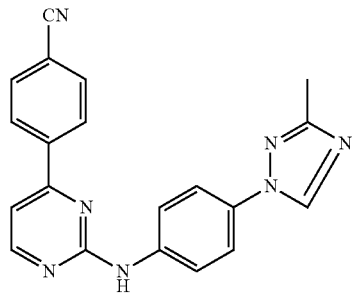 [SMILES: Cc1ncn(-c2ccc(Nc3nccc(-c4ccc(C#N)cc4)n3)cc2)n1]

5-(2-(4-(3-methyl-1H-1,2,4-triazol-1-yl)phenylamino)pyrimidin-4-yl)picolinonitrile was obtained by following procedure R using 6-cyanopyridin-3-ylboronic acid. ¹H NMR (DMSO-d₆, 400 MHz) δ 10.05 (s, 1H), 9.38 (m, 1H), 9.05 (s, 1H), 8.70 (m, 1H), 8.26 (s, 1H), 8.22 (d, 1H), 7.99 (m, 2H), 7.78 (m, 2H), 7.62 (d, 1H), 2.37 (s, 3H). MS (ESI) 355.20 (M+H).

Example 243

N-(4-(3,5-Dimethyl-1H-1,2,4-triazol-1-yl)phenyl)-4-(3-(4-ethylpiperazin-1-yl)-5-fluorophenyl)pyrimidin-2-amine

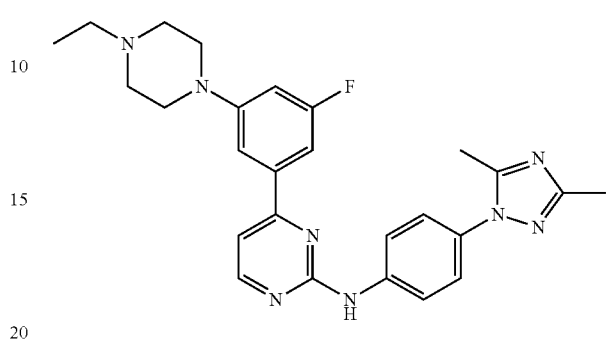

Part I 1-(3-Bromo-5-fluorophenyl)piperazine

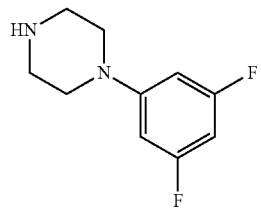 [SMILES: Fc1cc(F)cc(N2CCNCC2)c1]

(1-(3-Bromo-5-fluorophenyl)piperazine was obtained by following general procedure F using 1-bromo-3,5-difluorobenzene and piperazine.

Part II tert-Butyl 4-(3-bromo-5-fluorophenyl)piperazine-1-carboxylate

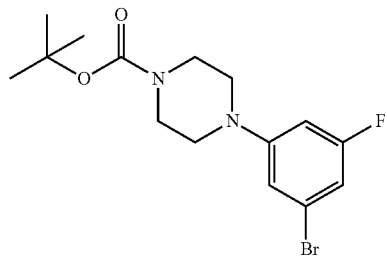 [SMILES: CC(C)(C)OC(=O)N1CCN(c2cc(F)cc(Br)c2)CC1]

General Procedure S

Boc Protection of Piperazine (Boc)₂O (10.7 g, 49 mmol) was added to the mixture of (1-(3-bromo-5-fluorophenyl)piperazine (12.7 g, 49 mmol) in CH₃CN (30 mL) at 0° C. The resulting mixture was warmed up to room temperature and stirred for 1 h. Removing CH₃CN in vacuo gave desired product tert-butyl 4-(3-bromo-5-fluorophenyl)piperazine-1-carboxylate in quantitative yield.

Part III tert-Butyl 4-(3-fluoro-5-(4,4,5,5-tetramethyl-1,3,2-dioxaborolan-2-yl)phenyl)piperazine-1-carboxylate

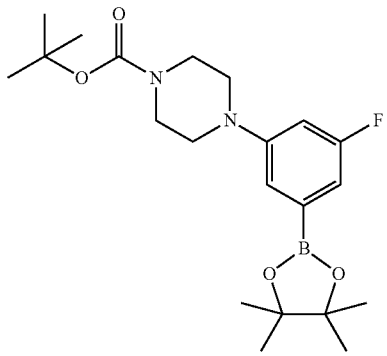 [SMILES: CC(C)(C)OC(=O)N1CCN(c2cc(F)cc(B3OC(C)(C)C(C)(C)O3)c2)CC1]

tert-Butyl 4-(3-fluoro-5-(4,4,5,5-tetramethyl-1,3,2-dioxaborolan-2-yl)phenyl)piperazine-1-carboxylate was obtained by following general procedure A using tert-butyl 4-(3-bromo-5-fluorophenyl)piperazine-1-carboxylate and bis(pinacolato)diboron.

Part IV tert-Butyl 4-(3-(2-chloropyrimidin-4-yl)-5-fluorophenyl)piperazine-1-carboxylate

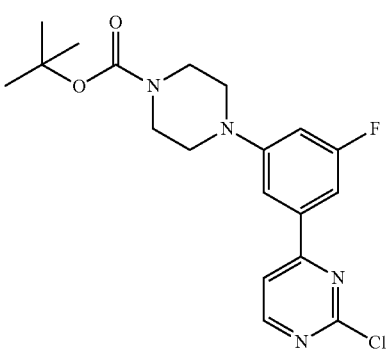 [SMILES: CC(C)(C)OC(=O)N1CCN(c2cc(F)cc(-c3ccnc(Cl)n3)c2)CC1]

tert-Butyl 4-(3-(2-chloropyrimidin-4-yl)-5-fluorophenyl)piperazine-1-carboxylate was obtained by following general procedure B using tert-butyl 4-(3-fluoro-5-(4,4,5,5-tetramethyl-1,3,2-dioxaborolan-2-yl)phenyl)piperazine-1-carboxylate and dichloropyrimidine.

Part V

2-Chloro-4-(3-fluoro-5-(piperazin-1-yl)phenyl)pyrimidine

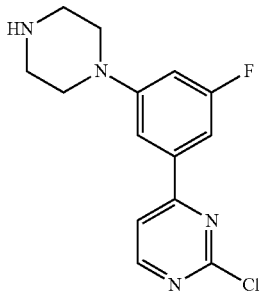 [SMILES: Fc1cc(-c2ccnc(Cl)n2)cc(N2CCNCC2)c1]

General Procedure T

Deprotection of Boc Group

The carbamate tert-butyl 4-(3-fluoro-5-(4,4,5,5-tetramethyl-1,3,2-dioxaborolan-2-yl)phenyl)piperazine-1-carboxylate (0.58 g, 2 mmol) in a mixture of $CH_2Cl_2$ (5 mL) and trifluoroacetic acid (5 mL) was stirred at room temperature overnight. The reaction mixture was concentrated in vacuo and basified with saturated aqueous $NaHCO_3$. The aqueous solution was extracted with EtOAc which was separated, dried with anhydrous $MgSO_4$ and concentrated in vacuo to generate the title compound 2-chloro-4-(3-fluoro-5-(piperazin-1-yl)phenyl)pyrimidine.

Part V

2-Chloro-4-(3-(4-ethylpiperazin-1-yl)-5-fluorophenyl)pyrimidine

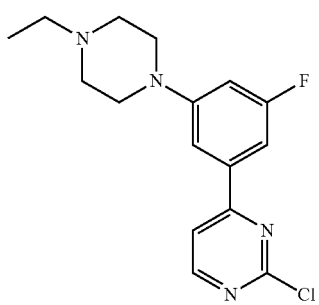 [SMILES: CCN1CCN(c2cc(F)cc(-c3ccnc(Cl)n3)c2)CC1]

General Procedure U

Reductive Amination of 2-chloro-4-(3-fluoro-5-(piperazin-1-yl)phenyl)pyrimidine with ethyl aldehyde 2-Cloro-4-(3-fluoro-5-(piperazin-1-yl)phenyl)pyrimidine (0.29 g, 1 mmol) and ethyl aldehyde (0.13 g, 3 mmol) were mixed in dichloroethane (10 mL) and then added with $NaBH(OAc)_3$ (0.64 g, 3 mmol). After stirring at room temperature under argon for overnight, the reaction mixture was quenched with saturated $NaHCO_3$ and extracted with EtOAc. The organic layer was separated, dried with anhydrous $MgSO_4$ and concentrated in vacuo to give desired product 2-Chloro-4-(3-(4-ethylpiperazin-1-yl)-5-fluorophenyl)pyrimidine.

N-(4-(3,5-dimethyl-1H-1,2,4-triazol-1-yl)phenyl)-4-(3-(4-ethylpiperazin-1-yl)-5-fluorophenyl)pyrimidin-2-amine was obtained by following general procedure O using 2-chloro-4-(3-(4 ethylpiperazin-1-yl)-5-fluorophenyl)pyrimidine and 4-(3,5-dimethyl-1H-1,2,4-triazol-1-yl)aniline. $^1$H NMR (DMSO-$d_6$, 400 MHz) d9.72 (br s, 1H), 8.64 (d, 1H), 8.02-7.98 (m, 2H), 7.62 (s, 1H), 7.56 (d, 1H), 7.52-7.48 (m, 2H), 7.47-7.45 (m, 1H), 7.13-7.09 (m, 1H), 4.09-4.06 (m, 2H), 3.63-3.61 (m, 2H), 3.25-3.20 (m, 2H), 3.15-3.10 (m, 2H), 2.43 (s, 3H), 2.29 (s, 3H), 1.28 (t, 3H). MS (ESI) 473 (M+H).

Example 244

4-(3-(4-Ethylpiperazin-1-yl)-5-fluorophenyl)-N-(4-(3-(trifluoromethyl)-1H-1,2,4-triazol-1-yl)phenyl)pyrimidin-2-amine

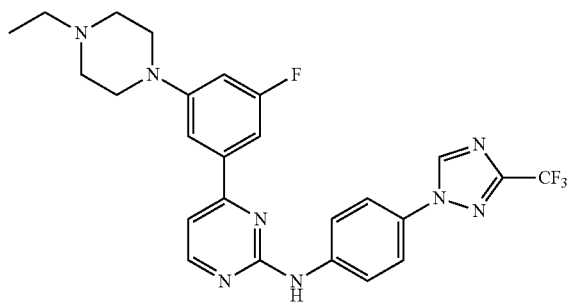 [SMILES: CCN1CCN(c2cc(F)cc(-c3ccnc(Nc4ccc(-n5cnc(C(F)(F)F)n5)cc4)n3)c2)CC1]

4-(3-(4-Ethylpiperazin-1-yl)-5-fluorophenyl)-N-(4-(3-(trifluoromethyl)-1H-1,2,4-triazol-1-yl)phenyl)pyrimidin-2-amine was obtained by following general procedure O from 2-chloro-4-(3-(4 ethylpiperazin-1-yl-5-fluorophenyl)pyrimidine and 4-(3-(trifluoromethyl)-1H-1,2,4-triazol-1-yl)aniline. $^1$H NMR (DMSO-$d_6$, 400 MHz) δ 9.75 (br s, 1H), 9.41 (d, 1H), 8.59 (d, 1H), 8.00-7.96 (m, 2H), 7.78-7.75 (m, 2H), 7.55 (s, 1H), 7.49 (d, 1H), 7.40-7.35 (m, 1H), 7.06-7.02 (m, 1H), 4.42-4.19 (m, 2H), 3.56-3.54 (m, 2H), 3.18-3.13 (m, 2H), 3.08-3.03 (m, 4H), 1.21 (t, 3H). MS (ESI) 513 (M+H).

Example 245

4-(3-(4-Ethylpiperazin-1-yl)-5-fluorophenyl)-N-(4-(3-(6-methoxypyridin-3-1H)-1H-1,2,4-triazol-1-yl)phenyl)pyrimidin-2-amine

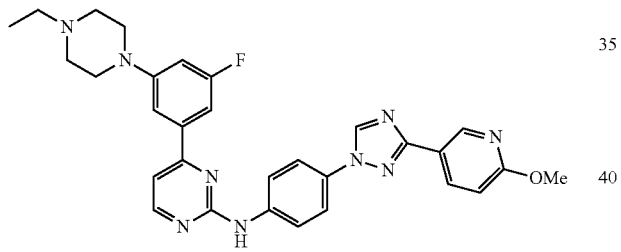

4-(3-(4-Ethylpiperazin-1-yl)-5-fluorophenyl)-N-(4-(3-(6-methoxypyridin-3-yl)-1H-1,2,4-triazol-1-yl-phenyl)pyrimidin-2-amine was obtained by following general procedure O from 2-chloro-4-(3-(4-ethylpiperazin-1-yl)-5-fluorophenyl)pyrimidine and 4-(3-(6-methoxypyridin-3-yl)-1H-1,2,4-triazol-1-yl)aniline. MS (ESI) 552 (M+H).

Example 246

4-(3-Fluoro-5-(piperazin-1-yl)phenyl)-N-(4-(3-(6-methoxypyridin-3-yl)-1H-1,2,4-triazol-1-yl)phenyl)pyrimidin-2-amine

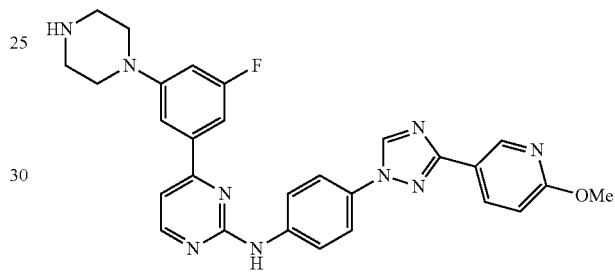

Part I tert-Butyl 4-(3-fluoro-5-(2-(4-(3-(6-methoxypyridin-3-yl)-1H-1,2,4-triazol-1-yl)phenylamino)pyrimidin-4-yl)phenyl)piperazine-1-carboxylate

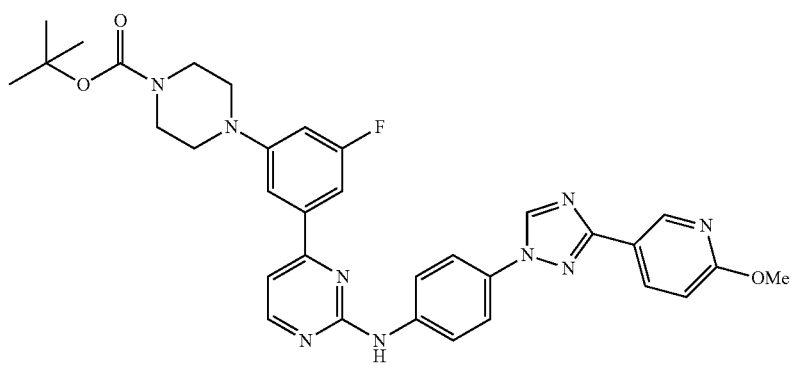 [SMILES: COc1ccc(-c2ncn(-c3ccc(Nc4nccc(-c5cc(F)cc(N6CCN(C(=O)OC(C)(C)C)CC6)c5)n4)cc3)n2)cn1]

tert-Butyl 4-(3-fluoro-5-(2-(4-(3-(6 methoxypyridin-3-yl)-1H-1,2,4-triazol-1-yl)phenylamino)pyrimidin-4-yl)phenyl)piperazine-1-carboxylate was obtained by following general procedure O using tert-butyl 4-(3-(2-chloropyrimidin-4-yl)-5-fluorophenyl)piperazine-1-carboxylate and 4-(3-(6-methoxypyridin-3-yl)-1H-1,2,4-triazol-1-yl)aniline.

The resulting carbamate was deprotected by following general procedure X to generate the title compound 4-(3-Fluoro-5-(piperazin-1-yl)phenyl)-N-(4-(3-(6-methoxypyridin-3-yl)-1H-1,2,4-triazol-1-yl)phenyl)pyrimidin-2-amine. MS (ESI) 524 (M+H).

Example 247

3-(piperazin-1-yl)-5-(2-(4-(3-(trifluoromethyl)-1H-1,2,4-triazol-1-yl)phenylamino)pyrimidin-4-yl)benzonitrile

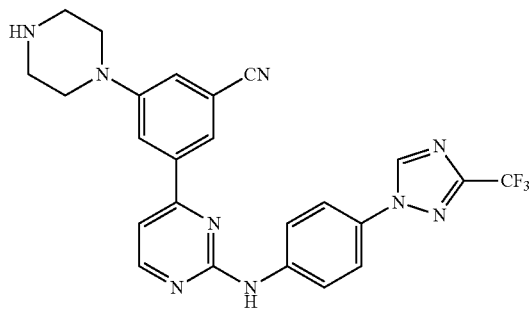 [SMILES: N#Cc1cc(-c2ccnc(Nc3ccc(-n4cnc(C(F)(F)F)n4)cc3)n2)cc(N2CCNCC2)c1]

Part I

3-Bromo-5-(piperazin-1-yl)benzonitrile

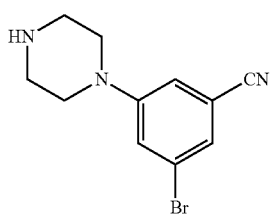 [SMILES: N#Cc1cc(Br)cc(N2CCNCC2)c1]

3-Bromo-5-(piperazin-1-yl)benzonitrile was obtained by following general procedure F using piperazine and 1-bromo-3-fluorobenzonitrile.

Part II tert-Butyl 4-(3-bromo-5-cyanophenyl)piperazine-1-carboxylate

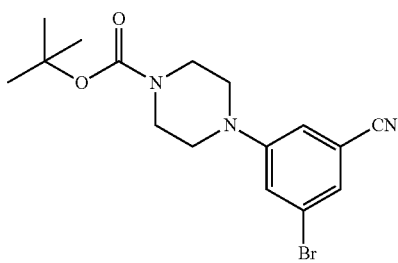 [SMILES: CC(C)(C)OC(=O)N1CCN(c2cc(Br)cc(C#N)c2)CC1]

tert-Butyl 4-(3-bromo-5-cyanophenyl)piperazine-1-carboxylate was obtained by following general procedure S using (Boc)₂O and 1-bromo-3-fluorobenzonitrile.

Part III tert-Butyl 4-(3-cyano-5-(4,4,5,5-tetramethyl-1,3,2-dioxaborolan-2-yl)phenyl)piperazine-1-carboxylate

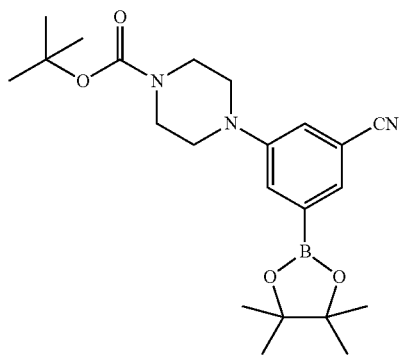 [SMILES: CC(C)(C)OC(=O)N1CCN(c2cc(C#N)cc(B3OC(C)(C)C(C)(C)O3)c2)CC1]

tert-Butyl 4-(3-cyano-5-(4,4,5,5-tetramethyl-1,3,2-dioxaborolan-2-yl)phenyl)piperazine-1-carboxylate was obtained by following general procedure A using tert-butyl 4-(3-bromo-5-cyanophenyl)piperazine-1-carboxylate and bis(pinacolato)diboron.

Part IV tert-Butyl 4-(3-(2-chloropyrimidin-4-yl)-5-cyanophenyl)piperazine-1-carboxylate

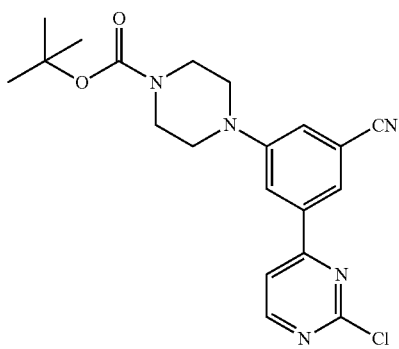 [SMILES: CC(C)(C)OC(=O)N1CCN(c2cc(C#N)cc(-c3ccnc(Cl)n3)c2)CC1]

tert-Butyl 4-(3-(2-chloropyrimidin-4-yl)-5-cyanophenyl)piperazine-1-carboxylate was obtained by following general procedure B using tert-butyl 4-(3-cyano-5-(4,4,5,5-tetramethyl-1,3,2-dioxaborolan-2-yl)phenyl)piperazine-1-carboxylate and dichloropyrimidine.

Part V tert-Butyl 4-(3-cyano-5-(2-(4-(3-(trifluoromethyl)-1H-1,2,4-triazol-1-yl)phenylamino)pyrimidin-4-yl)phenyl)piperazine-1-carboxylate

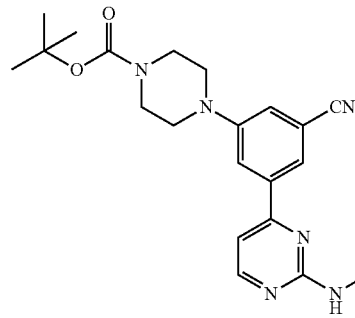

tert-Butyl 4-(3-cyano-5-(2-(4-(3-(trifluoromethyl)-1H-1,2,4-triazol-1-yl)phenylamino)pyrimidin-4-yl)phenyl)piperazine-1-carboxylate was obtained by following general procedure O using tert-butyl 4-(3-(2-chloropyrimidin-4-yl)-5-cyanophenyl)piperazine-1-carboxylate and 4-(3-(trifluoromethyl)-1H-1,2,4-triazol-1-yl)aniline.

The resulting carbamate was deprotected by following general procedure X to generate the compound 3-(piperazin-1-yl)-5-(2-(4-(3-(trifluoromethyl)-1H-1,2,4-triazol-1-yl)phenylamino)pyrimidin-4-yl)benzonitrile. $^1$H NMR (DMSO-d$_6$, 400 MHz) δ 9.48 (s, 1H), 8.86 (br s, 2H), 8.69 (d, 1H), 8.06-8.04 (m, 4H), 7.85-7.82 (m, 2H), 7.66-7.60 (m, 2H), 3.61-3.58 (m, 4H), 3.33-3.28 (m, 4H). MS (ESI) 492 (M+H).

Example 248

3-(2-(4-(3-(6-Methoxypyridin-3-yl)-1H-1,2,4-triazol-1-yl)phenylamino)pyrimidin-4-yl)-5-(piperazin-1-yl)benzonitrile

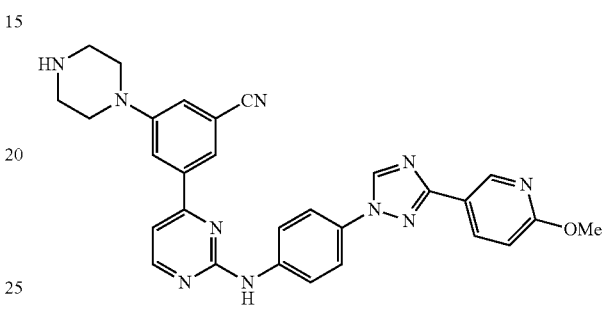

Part I tert-Butyl 4-(3-cyano-5-(2-(4-(3-(6-methoxypyridin-3-yl)-1H-1,2,4-triazol-1-yl)phenylamino)pyrimidin-4-yl)phenyl)piperazine-1-carboxylate

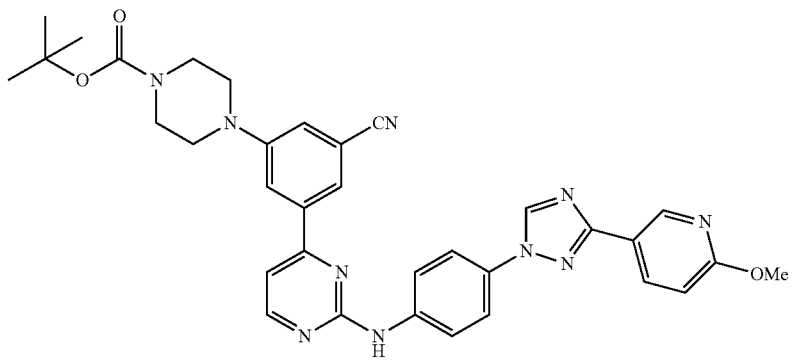 [SMILES: COc1ccc(-c2ncn(-c3ccc(Nc4nccc(-c5cc(C#N)cc(N6CCN(C(=O)OC(C)(C)C)CC6)c5)n4)cc3)n2)cn1]

tert-Butyl 4-(3-cyano-5-(2-(4-(3-(6-methoxypyridin-3-yl)-1H-1,2,4-triazol-1-yl)phenylamino)pyrimidin-4-yl)phenyl)piperazine-1-carboxylate was obtained by following general procedure O using tert-butyl 4-(3-(2-chloropyrimidin-4-yl)-5-cyanophenyl)piperazine-1-carboxylate and 4-(3-(6-methoxypyridin-3-yl)-1H-1,2,4-triazol-1-yl)aniline.

The resulting carbamate was deprotected by following general procedure X to generate the title compound 3-(2-(4-(3-(6-methoxypyridin-3-yl)-1H-1,2,4-triazol-1-yl)phenylamino)pyrimidin-4-yl-5-(piperazin-1-yl)benzonitrile. $^1$H NMR (DMSO-d$_6$, 400 MHz) δ 9.20 (s, 1H), 8.85 (br s, 2H), 8.81-8.80 (m, 1H), 8.60 (d, 1H), 8.27-8.18 (m, 2H), 7.99-7.94 (m, 4H), 7.79 (d, 2H), 7.59 (d, 1H), 7.54 (d, 1H), 6.93-6.90 (m, 1H), 3.86 (s, 3H), 3.54-3.51 (m, 4H), 3.26-3.21 (m, 4H). MS (ESI) 531 (M+H).

Example 249

3-(2-(4-(3,5-Dimethyl-1H-1,2,4-triazol-1-yl)-3-fluorophenylamino)pyrimidin-4-yl)-5-morpholinobenzonitrile

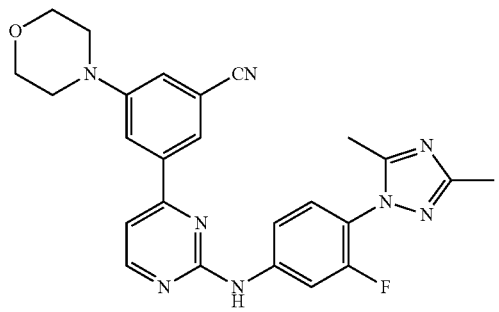 [SMILES: Cc1nc(C)n(-c2ccc(Nc3nccc(-c4cc(C#N)cc(N5CCOCC5)c4)n3)cc2F)n1]

3-(2-(4-(3,5-Dimethyl-1H-1,2,4-triazol-1-yl)-3-fluorophenylamino)pyrimidin-4-yl)-5-morpholinobenzonitrile was obtained by following general procedure O using 3-(2-chloropyrimidin-4-yl)-5-morpholinobenzonitrile and 4-(3,5-dimethyl-1H-1,2,4-triazol-1-yl)-3-fluoroaniline. $^1$H NMR (DMSO-d$_6$, 400 MHz) δ 8.51 (d, 1H), 8.20-8.16 (m, 1H), 7.88-7.87 (m, 1H), 7.64-7.63 (m, 1H), 7.56 (s, 1H), 7.35-7.29 (m, 1H), 7.16 (s, 1H), 3.87-3.82 (m, 4H), 3.26-3.23 (m, 4H), 2.37 (s, 3H), 2.33 (s, 3H). MS (ESI) 471 (M+H).

Example 250

N-(4-(3,5-dimethyl-1H-1,2,4-triazol-1-yl)-3-fluorophenyl)-4-(3-fluoro-5-morpholinophenyl)pyrimidin-2-amine

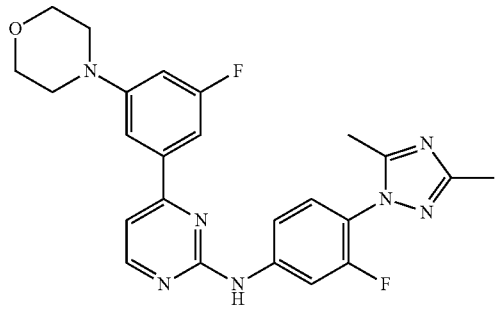 [SMILES: Cc1nc(C)n(-c2ccc(Nc3nccc(-c4cc(F)cc(N5CCOCC5)c4)n3)cc2F)n1]

N-(4-(3,5-dimethyl-1H-1,2,4-triazol-1-yl)-3-fluorophenyl)-4-(3-fluoro-5-morpholinophenyl)pyrimidin-2-amine was obtained by following general procedure O using 4-(3-(2-chloropyrimidin-4-yl)-5-fluorophenyl)morpholine and 4-(3,5-dimethyl-1H-1,2,4-triazol-1-yl)-3-fluoroaniline. $^1$H NMR (DMSO-d$_6$, 400 MHz) δ 8.44 (d, 1H), 8.22-8.18 (m, 2H), 7.45 (s, 1H), 7.35-7.31 (m, 1H), 7.28-7.23 (m, 1H), 7.17 (s, 1H), 7.12-7.09 (m, 1H), 6.71-6.67 (m, 1H), 3.83-3.81 (m, 4H), 3.22-3.20 (m, 4H), 2.39 (s, 3H), 2.36 (s, 3H). MS (ESI) 464 (M+H).

Example 251

N-(4-(3,5-dimethyl-1H-1,2,4-triazol-1-yl)-3-fluorophenyl)-4-(3-morpholino-5-(trifluoromethyl)phenyl)pyrimidin-2-amine

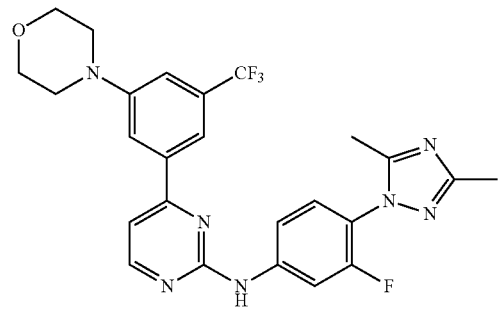

N-(4-(3,5-dimethyl-1H-1,2,4-triazol-1-yl)-3-fluorophenyl)-4-(3-morpholino-5-(trifluoromethyl)phenyl)pyrimidin-2-amine was obtained by following general procedure O using 4-(3-(2-chloropyrimidin-4-yl)-5-(trifluoromethyl)phenyl)morpholine and 4-(3,5-dimethyl-1H-1,2,4-triazol-1-yl)-3-fluoroaniline. MS (ESI) 514 (M+H).

Example 252

3-(3-hydroxypiperidin-1-yl)-5-(2-(4-(2-methyl-2H-tetrazol-5-yl)phenylamino)pyrimidin-4-yl)benzonitrile

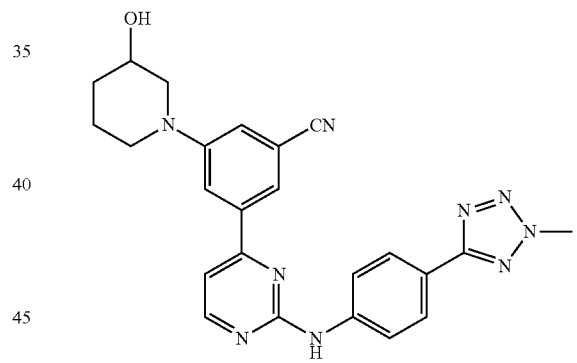

Part I

3-Bromo-5-(3-hydroxypiperidin-1-yl)benzonitrile

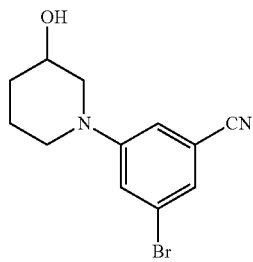 [SMILES: N#Cc1cc(Br)cc(N2CCCC(O)C2)c1]

3-Bromo-5-(3-hydroxypiperidin-1-yl)benzonitrile was obtained by following general procedure F using 1-bromo-3-fluorobenzonitrile and piperidin-3-ol.

167

Part II 3-(3-Hydroxypiperidin-1-yl)-5-(4,4,5,5-tetramethyl-1,3,2-dioxaborolan-2-yl)benzonitrile

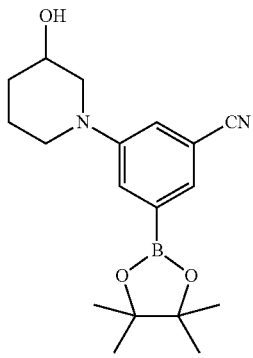 [SMILES: CC1(C)OB(c2cc(C#N)cc(N3CCCC(O)C3)c2)OC1(C)C]

3-(3-Hydroxypiperidin-1-yl)-5-(4,4,5,5-tetramethyl-1,3,2-dioxaborolan-2-yl)benzonitrile was obtained by following general procedure A using 3-Bromo-5-(3-hydroxypiperidin-1-yl)benzonitrile and bis(pinacolato)diboron.

Part III 3-(2-Chloropyrimidin-4-yl)-5-(3-hydroxypiperidin-1-yl)benzonitrile

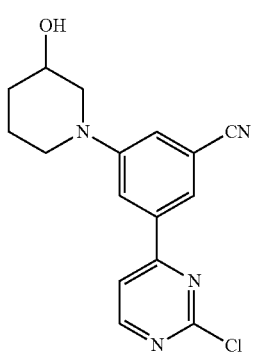 [SMILES: N#Cc1cc(-c2ccnc(Cl)n2)cc(N2CCCC(O)C2)c1]

3-(2-Chloropyrimidin-4-yl)-5-(3 hydroxypiperidin-1-yl)benzonitrile was obtained by following general procedure B using 3-(3-hydroxypiperidin-1-yl)-5-(4,4,5,5-tetramethyl-1,3,2-dioxaborolan-2-yl)benzonitrile and dichloropyrimidine.

3-(3-Hydroxypiperidin 1-yl)-5-(2-(4-(2-methyl-2H-tetrazol-5-yl)phenylamino)pyrimidin-4-yl)benzonitrile was obtained by following general procedure E using 3-(2-chloropyrimidin-4-yl)-5-(3 hydroxypiperidin-1-yl)benzonitrile and 4-(2-methyl-2H-tetrazol-5-yl)aniline. MS (ESI) 454 (M+H).

168

Example 253

3-(3-Hydroxypiperidin-1-yl)-5-(2-(4-(3-morpholino-1H-1,2,4-triazol-1-yl)phenylamino)pyrimidin-4-yl)benzonitrile

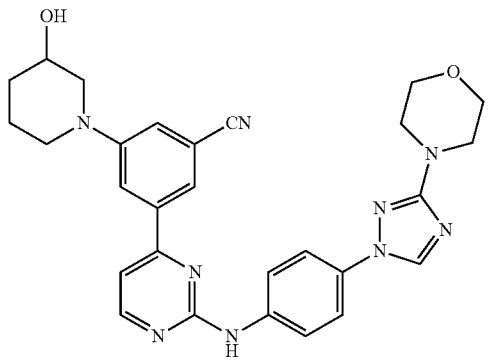 [SMILES: N#Cc1cc(-c2ccnc(Nc3ccc(-n4cnc(N5CCOCC5)n4)cc3)n2)cc(N2CCCC(O)C2)c1]

3-(3-Hydroxypiperidin-1-yl)-5-(2-(4-(3 morpholino-1H-1,2,4-triazol-1-yl)phenylamino)pyrimidin-4-yl)benzonitrile was obtained by following general procedure E using 3-(2-chloropyrimidin-4-yl)-5-(3-hydroxypiperidin-1-yl)benzonitrile and 4-(3-morpholino-1H-1,2,4-triazol-1-yl)aniline. MS (ESI) 524 (M+H).

Example 254

3-(4-Hydroxypiperidin-1-yl)-5-(2-(4-(3-(4-methylpiperazin-1-yl)-1H-1,2,4-triazol-1-yl)phenylamino)pyrimidin-4-yl)benzonitrile

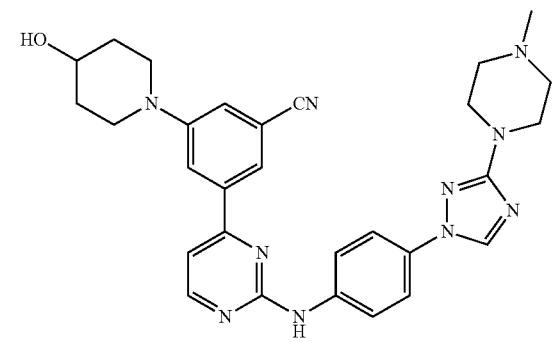 [SMILES: CN1CCN(c2ncn(-c3ccc(Nc4nccc(-c5cc(C#N)cc(N6CCC(O)CC6)c5)n4)cc3)n2)CC1]

Part I

3-Bromo-5-(4-hydroxypiperidin-1-yl)benzonitrile

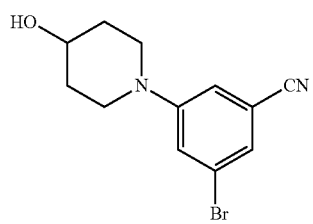 [SMILES: N#Cc1cc(Br)cc(N2CCC(O)CC2)c1]

3-Bromo-5-(4-hydroxypiperidin-1-yl)benzonitrile was obtained by following general procedure F using 1-bromo-3-fluorobenzonitrile and piperidin-4-ol.

Part II

3-(4-Hydroxypiperidin-1-yl)-5-(4,4,5,5-tetramethyl-1,3,2-dioxaborolan-2-yl)benzonitrile

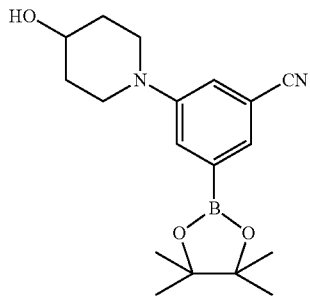 [SMILES: CC1(C)OB(c2cc(C#N)cc(N3CCC(O)CC3)c2)OC1(C)C]

3-(4-Hydroxypiperidin-1-yl)-5-(4,4,5,5-tetramethyl-1,3,2-dioxaborolan-2-yl)benzonitrile was obtained by following general procedure A using 3-Bromo-5-(4-hydroxypiperidin-1-yl)benzonitrile and bis(pinacolato)diboron.

Part III

3-(2-Chloropyrimidin-4-yl)-5-(4-hydroxypiperidin-1-ylbenzonitrile

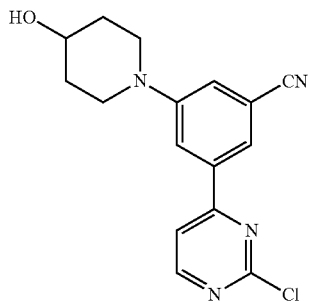 [SMILES: N#Cc1cc(-c2ccnc(Cl)n2)cc(N2CCC(O)CC2)c1]

3-(2-Chloropyrimidin-4-yl)-5-(4-hydroxypiperidin-1-yl)benzonitrile was obtained by following general procedure B using 3-(3-hydroxypiperidin-1-yl)-5-(4,4,5,5-tetramethyl-1,3,2-dioxaborolan-2-yl)benzonitrile and dichloropyrimidine.

3-(4-Hydroxypiperidin-1-yl)-5-(2-(4-(3-(4 methylpiperazin-1-yl)-1H-1,2,4-triazol-1-yl)phenylamino)pyrimidin-4-yl)benzonitrile was obtained by following general procedure E using 3-(2-chloropyrimidin-4-yl)-5-(4 hydroxypiperidin-1-yl)benzonitrile and 4-(3-(4-methylpiperazin-1-yl)-1H-1,2,4-triazol-1-yl)aniline. MS (ESI) 537 (M+H).

Example 255

1-(3-Fluoro-5-(2-(4-(3-(4-methylpiperazin-1-yl)-1H-1,2,4-triazol-1-yl)phenylamino)pyrimidin-4-yl)phenyl)piperidin-4-ol

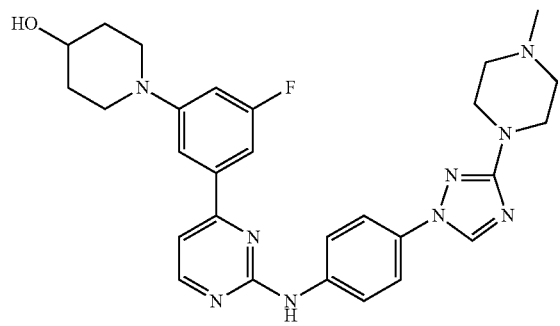 [SMILES: CN1CCN(c2ncn(-c3ccc(Nc4nccc(-c5cc(F)cc(N6CCC(O)CC6)c5)n4)cc3)n2)CC1]

Part I

1-(3-Bromo-5-fluorophenyl)piperidin-4-ol

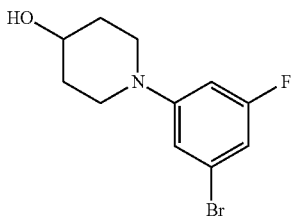 [SMILES: OC1CCN(c2cc(F)cc(Br)c2)CC1]

1-(3-Bromo-5-fluorophenyl)piperidin-4-ol was obtained by following general procedure F using 1-bromo-3,5-difluorobenzene and piperidin-4-ol.

Part II

1-(3-Fluoro-5-(4,4,5,5-tetramethyl-1,3,2-dioxaborolan-2-yl)phenyl)piperidin-4-ol

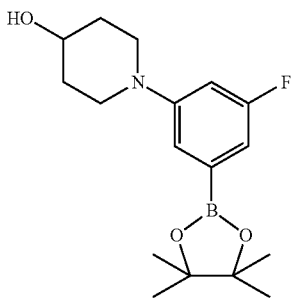 [SMILES: CC1(C)OB(c2cc(F)cc(N3CCC(O)CC3)c2)OC1(C)C]

1-(3-Fluoro-5-(4,4,5,5-tetramethyl-1,3,2-dioxaborolan-2-yl)phenyl)piperidin-4-ol was obtained by following general procedure A using 3-Bromo-5-(4 hydroxypiperidin-1-yl)benzonitrile and bis(pinacolato)diboron.

Part III

1-(3-(2-Chloropyrimidin-4-yl)-5-fluorophenyl)piperidin-4-ol

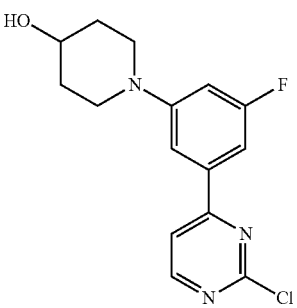 [SMILES: OC1CCN(c2cc(F)cc(-c3ccnc(Cl)n3)c2)CC1]

1-(3-(2-Chloropyrimidin-4-yl)-5-fluorophenyl)piperidin-4-ol was obtained by following general procedure B using 3-(3-hydroxypiperidin-1-yl)-5-(4,4,5,5-tetramethyl-1,3,2-dioxaborolan-2-yl)benzonitrile and dichloropyrimidine.

1-(3-Fluoro-5-(2-(4-(3-(4 methylpiperazin-1-yl)-1H-1,2,4-triazol-1-yl)phenylamino)pyrimidin-4-yl)phenyl)piperidin-4-ol was obtained by following general procedure using 1-(3-(2-Chloropyrimidin-4-yl)-5-fluorophenyl)piperidin-4-ol and 4-(3-(4-methylpiperazin-1-yl)-1H-1,2,4-triazol-1-yl)aniline. MS (ESI) 530 (M+H).

Example 256

4-(3-(Dimethylamino)-5-fluorophenyl)-N-(4-(3-(4-methylpiperazin-1-yl)-1H-1,2,4-triazol-1-yl)phenyl)pyrimidin-2-amine

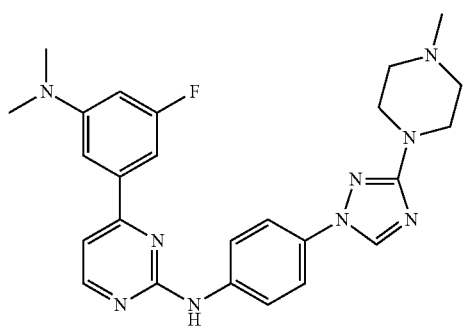 [SMILES: CN1CCN(c2ncn(-c3ccc(Nc4nccc(-c5cc(F)cc(N(C)C)c5)n4)cc3)n2)CC1]

Part I

3-Bromo-5-fluoro-N,N-dimethylaniline

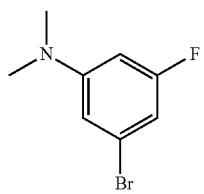

3-Bromo-5-fluoro-N,N-dimethylaniline was obtained by following general procedure F using 1-bromo-3,5-difluorobenzene and dimethyl amine.

Part II

3-Fluoro-N,N-dimethyl-5-(4,4,5,5-tetramethyl-1,3,2-dioxaborolan-2-yl)aniline

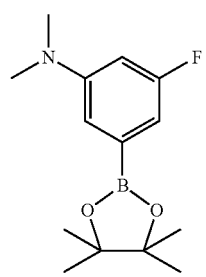 [SMILES: CN(C)c1cc(F)cc(B2OC(C)(C)C(C)(C)O2)c1]

3-Fluoro-N,N-dimethyl-5-(4,4,5,5-tetramethyl-1,3,2-dioxaborolan-2-yl)aniline was obtained by following general procedure A 3-bromo-5-fluoro-N,N-dimethylaniline and bis(pinacolato)diboron.

Part III 3-(2-Chloropyrimidin-4-yl)-5-fluoro-N,N-dimethylaniline

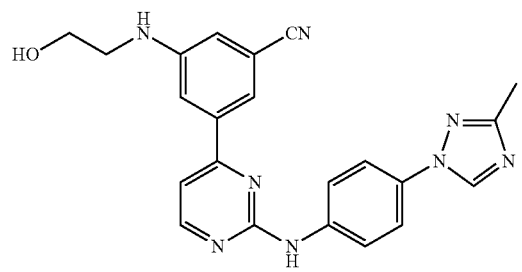 [SMILES: Cc1ncn(-c2ccc(Nc3nccc(-c4cc(C#N)cc(NCCO)c4)n3)cc2)n1]

3-(2-Chloropyrimidin-4-yl)-5-fluoro-N,N-dimethylaniline was obtained by following general procedure B using 3-fluoro-N,N-dimethyl-5-(4,4,5,5-tetramethyl-1,3,2-dioxaborolan-2-yl) aniline and dichloropyrimidine.

4-(3-(Dimethylamino)-5-fluorophenyl)-N-(4-(3-(4-methylpiperazin-1-yl)-1H-1,2,4-triazol-1-yl)phenyl)pyrimidin-2-amine was obtained by following general procedure using 3-(2-chloropyrimidin-4-yl)-5-fluoro-N,N-dimethylaniline and 4-(3-(4-methylpiperazin-1-yl)-1H-1,2,4-triazol-1-yl)aniline. MS (ESI) 474 (M+H).

Example 257

3-(2-Hydroxyethylamino)-5-(2-(4-(3-methyl-1H-1,2,4-triazol-1-yl)phenylamino)pyrimidin-4-yl)benzonitrile

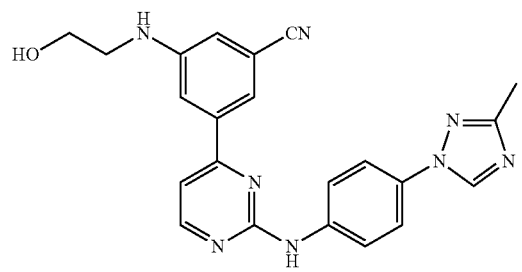 [SMILES: Cc1ncn(-c2ccc(Nc3nccc(-c4cc(C#N)cc(NCCO)c4)n3)cc2)n1]

Part I 2-(3-Bromo-5-fluorophenylamino)ethanol

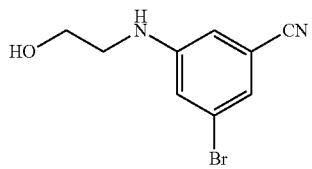 [SMILES: N#Cc1cc(Br)cc(NCCO)c1]

2-(3-Bromo-5-fluorophenylamino)ethanol was obtained by following general procedure F using 1-bromo-3-fluorobenzonitrile and 2-aminoethanol.

3-(2-Hydroxyethylamino)-5-(2-(4-(3-methyl-1H-1,2,4-triazol-1-yl)phenylamino)pyrimidin-4-yl)benzonitrile was obtained by following general procedure G using 2-(3-Bromo-5-fluorophenylamino)ethanol and N-(4-(3-methyl-1H-1,2,4-triazol-1-yl)phenyl)-4-(trimethylstannyl)pyrimidin-2-amine. NMR (DMSO-$d_6$, 400 MHz) δ 9.87 (s, 1H), 8.95 (s, 1H), 8.54 (d, 1H), 7.93-7.90 (m, 2H), 7.69-7.67 (m, 2H), 7.62-7.59 (m, 2H), 7.37 (d, 1H), 7.05-7.04 (m, 1H), 6.37 (br s, 1H), 3.54 (t, 2H), 3.17 (t, 2H), 2.29 (s, 3H). MS (ESI) 413 (M+H).

Example 258

4-(3-(4-Cyclopropylpiperazin-1-yl)-5-fluorophenyl)-N-(4-(3-(trifluoromethyl)-1H-1,2,4-triazol-1-yl)phenyl)pyrimidin-2-amine

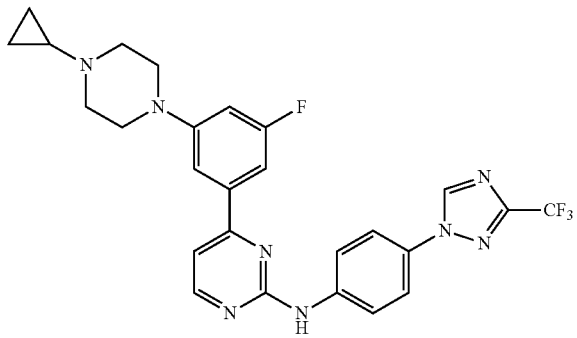 [SMILES: Fc1cc(-c2ccnc(Nc3ccc(-n4cnc(C(F)(F)F)n4)cc3)n2)cc(N2CCN(C3CC3)CC2)c1]

Part I 1-(3-Bromo-5-fluorophenyl)-4-cyclopropylpiperazine

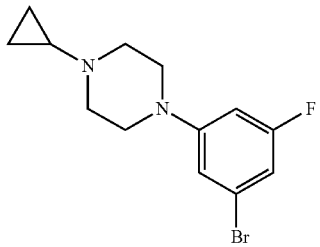 [SMILES: Fc1cc(Br)cc(N2CCN(C3CC3)CC2)c1]

To mixture of 1-(3-bromo-5-fluorophenyl)piperazine (2.91 g, 11 mmol) in MeOH (50 mL) was added (1-ethoxycyclopropoxy)trimethylsilane (13.5 mL, 67.2 mmol), acetic acid (6.5 mL, 112 mmol) and NaBCNH$_4$ (1.0 M in THF) (51 mL, 50.4 mmol). The resulting mixture was heated to 70 C overnight and concentrated in vacuuo to give crude residue which was diluted with EtOAc and washed with 1 N NaOH followed by brine. The organic layer was separated, dried with anhydrous MgSO$_4$, filtered and concentrated in vacuuo to give desired 1-(3-bromo-5-fluorophenyl)-4-cyclopropylpiperazine in quantitative yield.

Part II

1-Cyclopropyl-4-(3-fluoro-5-(4,4,5,5-tetramethyl-1,3,2-dioxaborolan-2-yl)phenyl) piperazine

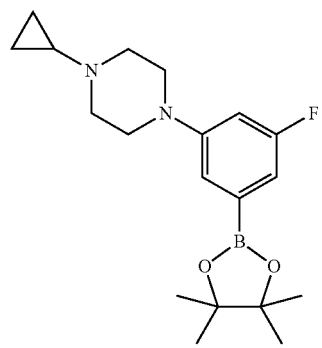 [SMILES: CC1(C)OB(c2cc(F)cc(N3CCN(C4CC4)CC3)c2)OC1(C)C]

1-Cyclopropyl-4-(3-fluoro-5-(4,4,5,5-tetramethyl-1,3,2-dioxaborolan-2-yl)phenyl)piperazine was obtained by following general procedure A using 1-(3-bromo-5-fluorophenyl)-4-cyclopropylpiperazine and bis(pinacolato)diboron.

Part III

2-Chloro-4-(3-(4-cyclopropylpiperazin-1-yl)-5-fluorophenyl)pyrimidine

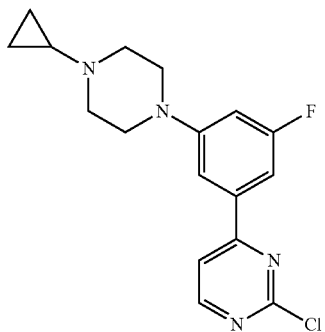 [SMILES: Fc1cc(-c2ccnc(Cl)n2)cc(N2CCN(C3CC3)CC2)c1]

2-Chloro-4-(3-(4-cyclopropylpiperazin-1-yl)-5-fluorophenyl)pyrimidine was obtained by following general procedure B using 1-cyclopropyl-4-(3-fluoro-5-(4,4,5,5-tetramethyl-1,3,2-dioxaborolan-2-yl)phenyl)piperazine and dichloropyrimidine.

The titled product 4-(3-(4-cyclopropylpiperazin-1-yl)-5-fluorophenyl)-N-(4-(3-(trifluoromethyl)-1H-1,2,4-triazol-1-yl)phenyl)pyrimidin-2-amine was obtained by following general procedure O 2-chloro-4-(3-(4-cyclopropylpiperazin-1-yl)-5-fluorophenyl)pyrimidine and 4-(3-(trifluoromethyl)-1H-1,2,4-triazol-1-yl)aniline. NMR (DMSO-$d_6$, 400 MHz) δ 9.41 (s, 1H), 8.58 (d, 1H), 7.99-7.96 (m, 2H), 7.78-7.75 (m, 2H), 7.55 (s, 1H), 7.50 (d, 1H), 7.42-7.37 (m, 1H), 7.05-6.99 (m, 1H), 4.20-4.15 (m, 1H), 3.43-3.35 (m, 4H), 3.10-2.89 (m, 4H), 0.92-0.85 (m, 2H), 0.79-0.77 (m, 2H). MS (ESI) 525 (M+H).

Example 259

4-(3-(4-Cyclopropylpiperazin-1-yl)-5-fluorophenyl)-N-(4-(3,5-dimethyl-1H-1,2,4-triazol-1-yl)phenyl)pyrimidin-2-amine

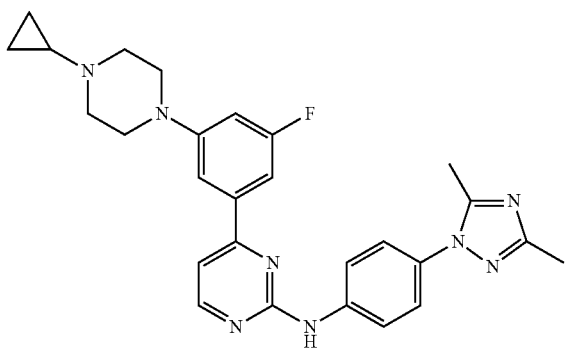 [SMILES: Cc1nc(C)n(-c2ccc(Nc3nccc(-c4cc(F)cc(N5CCN(C6CC6)CC5)c4)n3)cc2)n1]

4-(3-(4-Cyclopropylpiperazin-1-yl)-5-fluorophenyl)-N-(4-(3,5-dimethyl-1H-1,2,4-triazol-1-yl)phenyl)pyrimidin-2-amine was obtained by following general procedure O 2-chloro-4-(3-(4-cyclopropylpiperazin-1-yl)-5-fluorophenyl)pyrimidine and 4-(3,5-dimethyl-1H-1,2,4-triazol-1-yl)aniline. NMR (DMSO-$d_6$, 400 MHz) δ, 8.64 (d, 1H), 8.02-7.98 (m, 2H), 7.62 (s, 1H), 7.56 (d, 1H), 7.51-7.41 (m, 2H), 7.46-7.44 (m, 1H), 7.13-7.09 (m, 1H), 4.07-4.00 (m, 2H), 3.75-2.91 (m, 7H), 2.40 (s, 3H), 2.30 (s, 3H), 1.06-0.96 (m, 2H), 0.90-0.85 (m, 2H). MS (ESI) 485 (M+H).

Example 260

4-(3-fluoro-5-morpholinophenyl)-N-(4-(3-(5-methylpyridin-2-yl)-1H-1,2,4-triazol-1-yl)phenyl)pyrimidin-2-amine

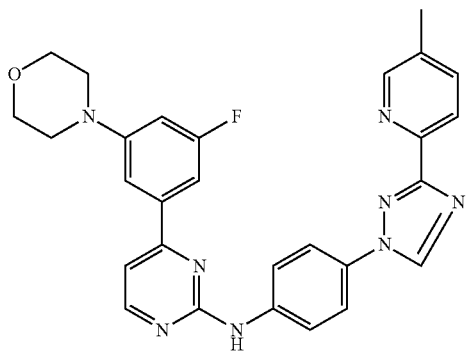 [SMILES: Cc1ccc(-c2ncn(-c3ccc(Nc4nccc(-c5cc(F)cc(N6CCOCC6)c5)n4)cc3)n2)nc1]

General Procedure V one-pot Stille reaction of 3-bromo-1-Substituted-1,2,4-triazole with bromopyridines A mixture of 2-bromo-5-methylpyridine (0.034 g, 0.20 mmol), hexamethylditin (0.066 g, 0.20 mmol), Pd(PPh$_3$)$_4$ (0.023 g, 0.04 mmol) and toluene (0.40 mL) was heated in a sealed tube at 130° C. for 1 h. The reaction mixture was cooled down to room temperature, added with N-(4-(3-bromo-1H-1,2,4-triazol-1-yl)phenyl)-4-(3-fluoro-5-morpholinophenyl)pyrimidin-2-amine (0.060 g, 0.12 mmol) and Pd(PPh$_3$)$_4$ (0.023 g, 0.04 mmol), re-heated in the sealed tube at 150° C. for 2.5 h. The reaction mixture was cooled down to room temperature and filtered. The filtrate was concentrated to a brown oil. Purification of this material by column chromatography on silica gel (40% EtOAc/hexane) provided the desired product as a white solid. MS (ESI) 509.39 (M+H).

Example 261

1-(5-(2-(4-(3-methyl-1H-1,2,4-triazol-1-yl)phenylamino)pyrimidin-4-yl)-2-(methylsulfonyl)phenyl)piperidin-3-ol

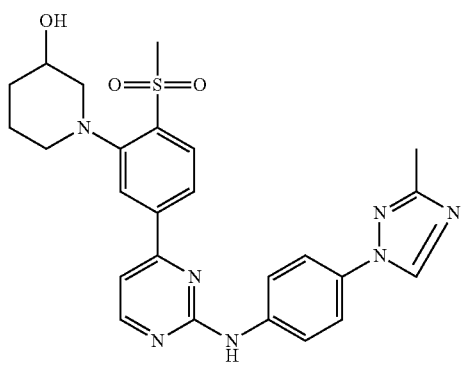 [SMILES: Cc1ncn(-c2ccc(Nc3nccc(-c4ccc(S(C)(=O)=O)c(N5CCCC(O)C5)c4)n3)cc2)n1]

1-(5-(2-(4-(3-methyl-1H-1,2,4-triazol-1-yl)phenylamino)pyrimidin-4-yl)-2-(methylsulfonyl)phenyl)piperidin-3-ol was obtained by following procedure G using 1-(5-bromo-2-(methylsulfonyl)phenyl)piperidin-3-ol and N-(4-(3-methyl-1H-1,2,4-triazol-1-yl)phenyl)-4-(trimethylstannyl)pyrimidin-2-amine. MS (ESI) 506.20 (M+H).

Example 262

3-(2-(4-(3-(4-ethylpiperazin-1-yl)-1H-1,2,4-triazol-1-yl)phenylamino)pyrimidin-4-yl)-5-morpholinobenzonitrile

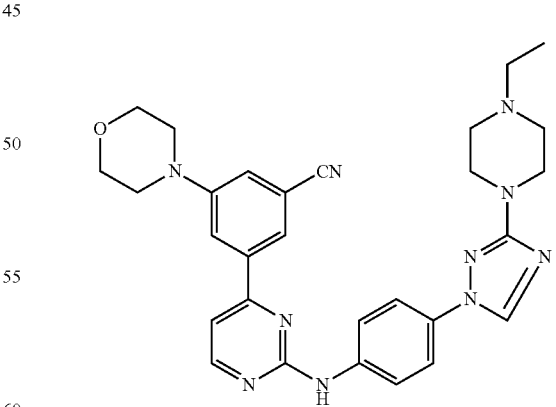

3-(2-(4-(3-(4-ethylpiperazin-1-yl)-1H-1,2,4-triazol-1-yl)phenylamino)pyrimidin-4-yl)-5-morpholinobenzonitrile was obtained by following procedure N using 3-morpholino-5-(2-(4-(3-(piperazin-1-yl)-1H-1,2,4-triazol-1-yl)phenylamino)pyrimidin-4-yl)benzonitrile and ethyl iodide with DMF as the solvent. MS (ESI) 537.29 (M+H).

Example 263

1-(5-(2-(4-(3-(3-hydroxypiperidin-1-yl)-1H-1,2,4-triazol-1-yl)phenylamino)pyrimidin-4-yl-2-(methylsulfonyl)phenyl)piperidin-3-ol

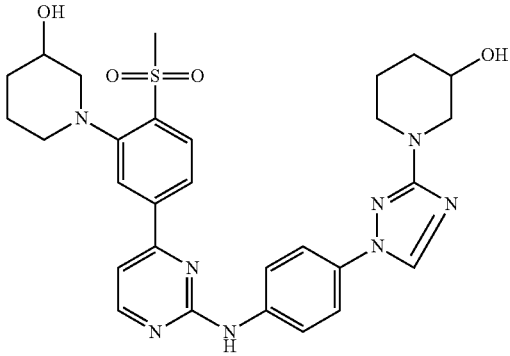 [SMILES: CS(=O)(=O)c1ccc(-c2ccnc(Nc3ccc(-n4cnc(N5CCCC(O)C5)n4)cc3)n2)cc1N1CCCC(O)C1]

1-(5-(2-(4-(3-(3-hydroxypiperidin-1-yl)-1H-1,2,4-triazol-1-yl)phenylamino)pyrimidin-4-yl)-2-(methylsulfonyl)phenyl)piperidin-3-ol was obtained by following procedure E using 1-(5-(2-chloropyrimidin-4-yl)-2-(methylsulfonyl)phenyl)piperidin-3-ol and 1-(1-(4-aminophenyl)-1H-1,2,4-triazol-3-yl)piperidin-3-ol. MS (ESI) 591.26 (M+H).

Example 264

1-(5-(2-(4-(3-(6-methylpyridin-3-yl)-1H-1,2,4-triazol-1-yl)phenylamino)pyrimidin-4-yl)-2-(methylsulfonyl)phenyl)piperidin-3-ol

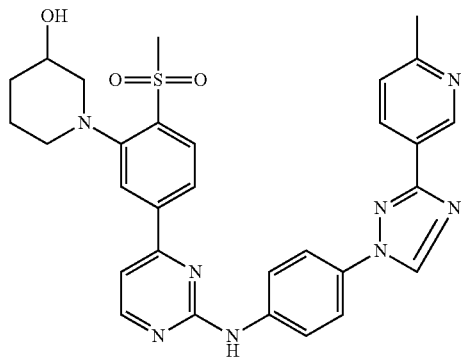 [SMILES: Cc1ccc(-c2ncn(-c3ccc(Nc4nccc(-c5ccc(S(C)(=O)=O)c(N6CCCC(O)C6)c5)n4)cc3)n2)cn1]

1-(5-(2-(4-(3-(6-methylpyridin-3-yl)-1H-1,2,4-triazol-1-yl)phenylamino)pyrimidin-4-yl)-2-(methylsulfonyl)phenyl)piperidin-3-ol was obtained by following procedure E using 1-(5-(2-chloropyrimidin-4-yl)-2-(methylsulfonyl)phenyl)piperidin-3-ol and 4-(3-(6-methylpyridin-3-yl)-1H-1,2,4-triazol-1-yl)aniline. MS (ESI) 583.25 (M+H).

Example 265

4-(3-morpholinophenyl)-N-(4-(3-(pyridin-2-yl)-1H-1,2,4-triazol-1-yl)phenyl)pyrimidin-2-amine

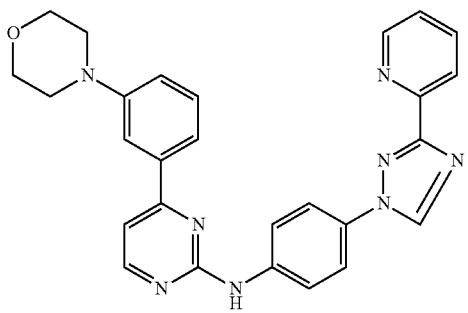 [SMILES: c1ccc(-c2ncn(-c3ccc(Nc4nccc(-c5cccc(N6CCOCC6)c5)n4)cc3)n2)nc1]

4-(3-morpholinophenyl)-N-(4-(3-(pyridin-2-yl)-1H-1,2,4-triazol-1-yl)phenyl)pyrimidin-2-amine was obtained by following procedure E using 4-(3-(2-chloropyrimidin-4-yl)phenyl)morpholine and 4-(3-(pyridin-2-yl)-1H-1,2,4-triazol-1-yl)aniline. MS (ESI) 477.39 (M+H).

Example 266

3-morpholino-5-(2-(4-(3-(pyridin-2-yl)-1H-1,2,4-triazol-1-yl)phenylamino)pyrimidin-4-yl)benzonitrile

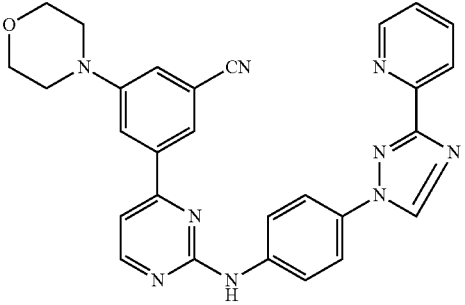 [SMILES: N#Cc1cc(-c2ccnc(Nc3ccc(-n4cnc(-c5ccccn5)n4)cc3)n2)cc(N2CCOCC2)c1]

3-morpholino-5-(2-(4-(3 (pyridin-2-yl)-1H-1,2,4-triazol-1-yl)phenylamino)pyrimidin-4-yl)benzonitrile was obtained by following procedure E using 3-(2-chloropyrimidin-4-yl)-5-morpholinobenzonitrile and 4-(3-(pyridin-2-yl)-1H-1,2,4-triazol-1-yl)aniline. MS (ESI) 502.38 (M+H).

Example 267

4-(3-fluoro-5-morpholinophenyl)-N-(4-(3-(6-methoxypyridin-2-yl)-1H-1,2,4-triazol-1-yl)phenyl)pyrimidin-2-amine

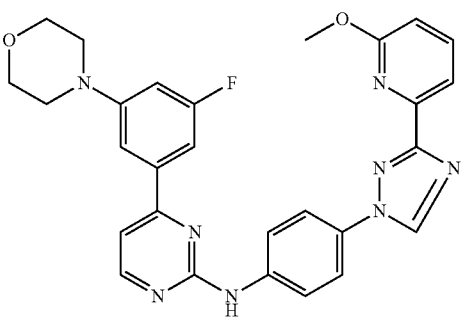 [SMILES: COc1cccc(-c2ncn(-c3ccc(Nc4nccc(-c5cc(F)cc(N6CCOCC6)c5)n4)cc3)n2)n1]

4-(3-fluoro-5-morpholinophenyl)-N-(4-(3-(6-methoxypyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-6-methoxypyridine. MS (ESI) 525.34 (M+H).

Example 268

4-(3-fluoro-5-morpholinophenyl)-N-(4-(3-(3-methoxypyridin-2-yl)-1H-1,2,4-triazol-1-yl)phenyl)pyrimidin-2-amine

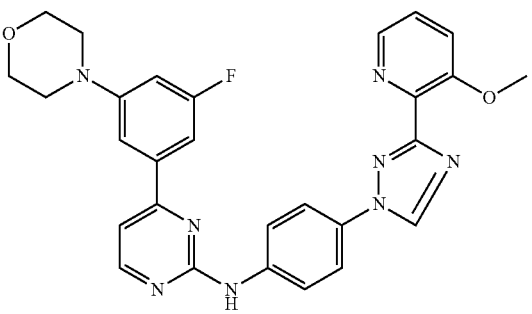 [SMILES: COc1cccnc1-c1ncn(-c2ccc(Nc3nccc(-c4cc(F)cc(N5CCOCC5)c4)n3)cc2)n1]

4-(3-fluoro-5-morpholinophenyl)-N-(4-(3-(3-methoxy-pyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-3-methoxypyridine. MS (ESI) 525.30 (M+H).

Example 269

N-(4-(3-methyl-1H-1,2,4-triazol-1-yl)phenyl)-4-(3-(methylsulfonyl)-5-morpholinophenyl)pyrimidin-2-amine

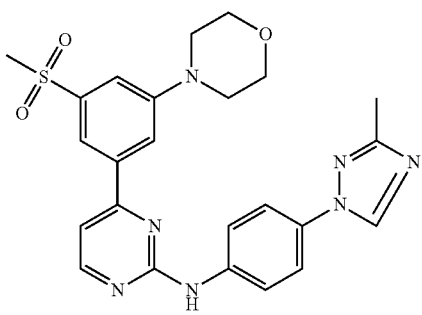 [SMILES: Cc1ncn(-c2ccc(Nc3nccc(-c4cc(N5CCOCC5)cc(S(C)(=O)=O)c4)n3)cc2)n1]

N-(4-(3-methyl-1H-1,2,4-triazol-1-yl)phenyl)-4-(3-(methylsulfonyl)-5-morpholinophenyl)pyrimidin-2-amine was obtained by following procedure E using 4-(3-(2-chloropyrimidin-4-yl)-5-(methylsulfonyl)phenyl)morpholine and 4-(3-methyl-1H-1,2,4-triazol-1-yl)aniline. MS (ESI) 492.30 (M+H).

Example 270

1-(1-(4-(4-(3-(methylsulfonyl)-5-morpholinophenyl)pyrimidin-2-ylamino)phenyl)-1H-1,2,4-triazol-3-yl)piperidin-3-ol

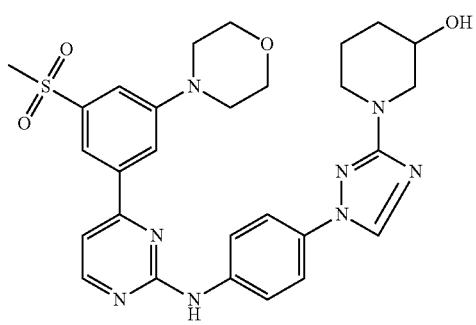 [SMILES: CS(=O)(=O)c1cc(-c2ccnc(Nc3ccc(-n4cnc(N5CCCC(O)C5)n4)cc3)n2)cc(N2CCOCC2)c1]

1-(1-(4-(4-(3-(methylsulfonyl)-5-morpholinophenyl)pyrimidin-2-ylamino)phenyl)-1H-1,2,4-triazol-3-yl)piperidin-3-ol was obtained by following procedure E using 4-(3-(2-chloropyrimidin-4-yl)-5-(methylsulfonyl)phenyl) morpholine and 1-(1-(4-aminophenyl)-1H-1,2,4-triazol-3-yl)piperidin-3-ol. MS (ESI) 577.24 (M+H).

Example 271

4-(3-(methylsulfonyl)-5-morpholinophenyl)-N-(4-(3-(pyridin-2-yl)-1H-1,2,4-triazol-1-yl)phenyl)pyrimidin-2-amine

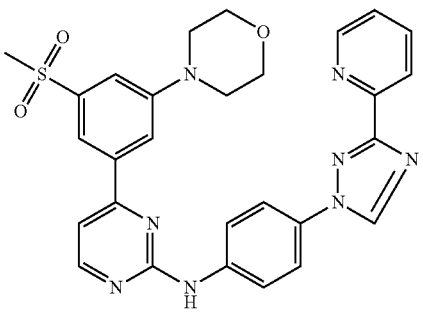 [SMILES: CS(=O)(=O)c1cc(-c2ccnc(Nc3ccc(-n4cnc(-c5ccccn5)n4)cc3)n2)cc(N2CCOCC2)c1]

4-(3-(methylsulfonyl)-5-morpholinophenyl)-N-(4-(3-(pyridin-2-yl)-1H-1,2,4-triazol-1-yl)phenyl)pyrimidin-2-amine was obtained by following procedure E using 4-(3-(2-chloropyrimidin-4-yl)-5-(methylsulfonyl)phenyl)morpholine and 4-(3-(pyridin-2-yl)-1H-1,2,4-triazol-1-yl)aniline. MS (ESI) 555.31 (M+H).

Example 272

N-(4-(3-(6-methylpyridin-3-yl)-1H-1,2,4-triazol-1-yl)phenyl)-4-(3-(methylsulfonyl)-5-morpholinophenyl)pyrimidin-2-amine

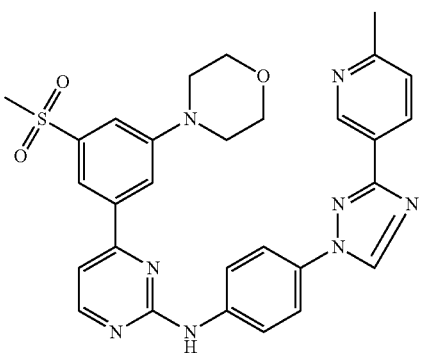 [SMILES: Cc1ccc(-c2ncn(-c3ccc(Nc4nccc(-c5cc(N6CCOCC6)cc(S(C)(=O)=O)c5)n4)cc3)n2)cn1]

N-(4-(3-(6-methylpyridin-3-yl)-1H-1,2,4-triazol-1-yl)phenyl)-4-(3-(methylsulfonyl)-5-morpholinophenyl)pyrimidin-2-amine was obtained by following procedure E using 4-(3-(2-chloropyrimidin-4-yl)-5-(methylsulfonyl)phenyl)morpholine and 4-(3-(6-methylpyridin-3-yl)-1H-1,2,4-triazol-1-yl)aniline. MS (ESI) 569.32 (M+H).

Example 273

6-(1-(4-(4-(3-fluoro-5-morpholinophenyl)pyrimidin-2-ylamino)phenyl)-1H-1,2,4-triazol-3-yl)nicotinonitrile

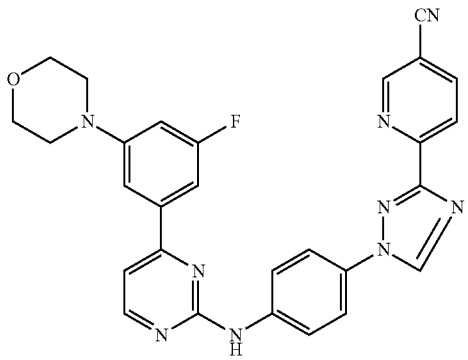 [SMILES: N#Cc1ccc(-c2ncn(-c3ccc(Nc4nccc(-c5cc(F)cc(N6CCOCC6)c5)n4)cc3)n2)nc1]

6-(1-(4-(4-(3-fluoro-5-morpholinophenyl)pyrimidin-2-ylamino)phenyl)-1H-1,2,4-triazol-3-yl)nicotinonitrile was obtained by following procedure V using N-(4-(3-bromo-1H-1,2,4-triazol-1-yl)phenyl)-4-(3-fluoro-5-morpholinophenyl)pyrimidin-2-amine and 6-bromonicotinonitrile. MS (ESI) 520.28 (M+H).

Example 274

4-(3-fluoro-5-morpholinophenyl)-N-(4-(3-(5-(trifluoromethyl)pyridin-2-yl)-1H-1,2,4-triazol-1-yl)phenyl)pyrimidin-2-amine

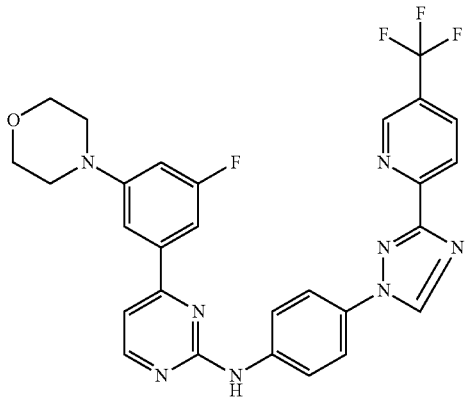 [SMILES: Fc1cc(-c2ccnc(Nc3ccc(-n4cnc(-c5ccc(C(F)(F)F)cn5)n4)cc3)n2)cc(N2CCOCC2)c1]

4-(3-fluoro-5-morpholinophenyl)-N-(4-(3-(5-(trifluoromethyl)pyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-5-(trifluoromethyl)pyridine. MS (ESI) 563.31 (M+H).

Example 275

1-(1-(4-(4-(3-morpholinophenyl)pyrimidin-2-ylamino)phenyl)-1H-1,2,4-triazol-3-yl)piperidin-4-ol

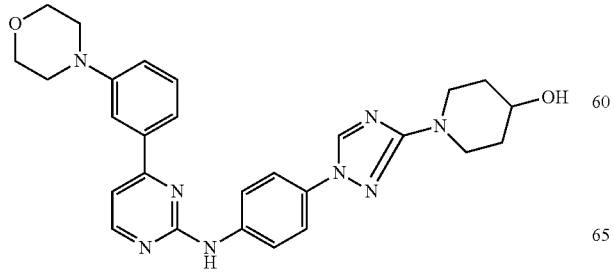

1-(1-(4-(4-(3-morpholinophenyl)pyrimidin-2-ylamino)phenyl)-1H-1,2,4-triazol-3-yl)piperidin-4-ol was obtained by following procedure E using 4-(3-(2-chloropyrimidin-4-yl)phenyl)morpholine and 1-(1-(4-aminophenyl)-1H-1,2,4-triazol-3-yl)piperidin-4-ol. MS (ESI) 499.32 (M+H).

Example 276

4-(3-fluoro-5-morpholinophenyl)-N-(4-(3-(5-fluoropyridin-2-yl)-1H-1,2,4-triazol-1-yl)phenyl)pyrimidin-2-amine

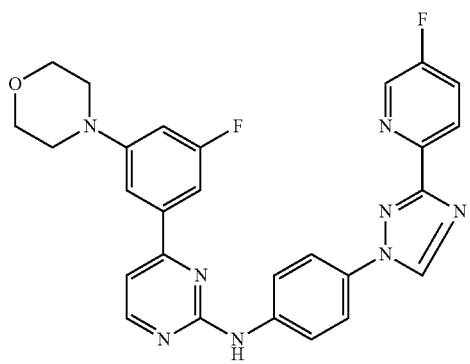 [SMILES: Fc1ccc(-c2ncn(-c3ccc(Nc4nccc(-c5cc(F)cc(N6CCOCC6)c5)n4)cc3)n2)nc1]

4-(3-fluoro-5-morpholinophenyl)-N-(4-(3-(5-fluoropyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-5-fluoropyridine. MS (ESI) 513.32 (M+H).

Example 277

4-(3-fluoro-5-morpholinophenyl)-N-(4-(3-(4-methoxypyridin-2-yl)-1H-1,2,4-triazol-1-yl)phenyl)pyrimidin-2-amine

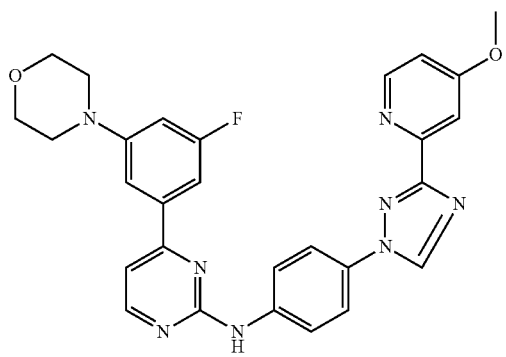 [SMILES: COc1ccnc(-c2ncn(-c3ccc(Nc4nccc(-c5cc(F)cc(N6CCOCC6)c5)n4)cc3)n2)c1]

4-(3-fluoro-5-morpholinophenyl)-N-(4-(3-(4-methoxypyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-4-methoxypyridine. MS (ESI) 525.38 (M+H).

Example 278

N-(4-(3-(3-chloropyridin-2-yl)-1H-1,2,4-triazol-1-yl)phenyl)-4-(3-fluoro-5-morpholinophenyl)pyrimidin-2-amine

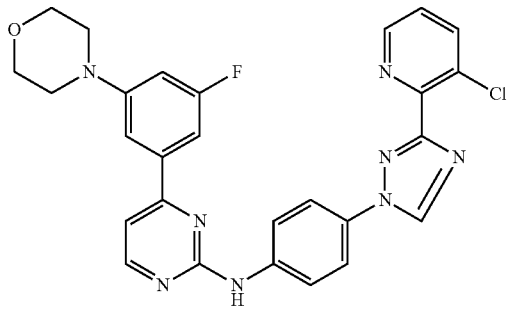 [SMILES: Fc1cc(-c2ccnc(Nc3ccc(-n4cnc(-c5ncccc5Cl)n4)cc3)n2)cc(N2CCOCC2)c1]

N-(4-(3-(3-chloropyridin-2-yl)-1H-1,2,4-triazol-1-yl)phenyl)-4-(3-fluoro-5-morpholinophenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-3-chloropyridine. MS (ESI) 529.32 (M+H).

Example 279

4-(3-fluoro-5-morpholinophenyl)-N-(4-(3-(4-fluoropyridin-2-yl)-1H-1,2,4-triazol-1-yl)phenyl)pyrimidin-2-amine

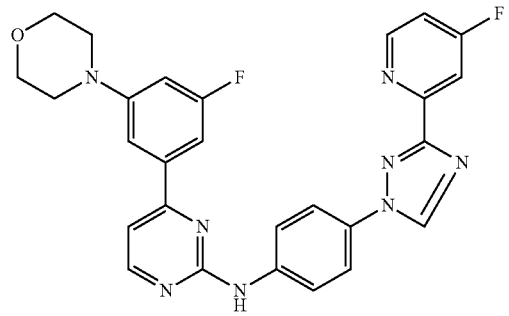 [SMILES: Fc1cc(-c2ccnc(Nc3ccc(-n4cnc(-c5cc(F)ccn5)n4)cc3)n2)cc(N2CCOCC2)c1]

4-(3-fluoro-5-morpholinophenyl)-N-(4-(3-(4-fluoropyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-chloro-4-fluoropyridine. MS (ESI) 513.35 (M+H).

Example 280

4-(3-fluoro-5-morpholinophenyl)-N-(4-(3-(3-fluoropyridin-2-yl)-1H-1,2,4-triazol-1-yl)phenyl)pyrimidin-2-amine

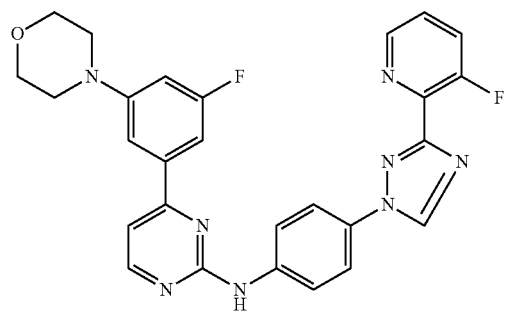 [SMILES: Fc1cc(-c2ccnc(Nc3ccc(-n4cnc(-c5ncccc5F)n4)cc3)n2)cc(N2CCOCC2)c1]

4-(3-fluoro-5-morpholinophenyl)-N-(4-(3-(3-fluoropyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-chloro-3-fluoropyridine. MS (ESI) 513.32 (M+H).

Example 281

1-(1-(4-(4-(3-fluoro-5-morpholinophenyl)pyrimidin-2-ylamino)phenyl)-1H-1,2,4-triazol-3-yl)piperidin-4-ol

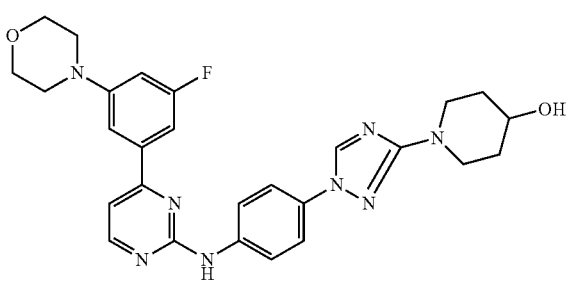 [SMILES: OC1CCN(c2ncn(-c3ccc(Nc4nccc(-c5cc(F)cc(N6CCOCC6)c5)n4)cc3)n2)CC1]

1-(1-(4-(4-(3-fluoro-5-morpholinophenyl)pyrimidin-2-ylamino)phenyl)-1H-1,2,4-triazol-3-yl)piperidin-4-ol was obtained by following procedure E using 4-(3-(2-chloropyrimidin-4-yl)-5-fluorophenyl)morpholine and 1-(1-(4-aminophenyl)-1H-1,2,4-triazol-3-yl)piperidin-4-ol. MS (ESI) 517.29 (M+H).

Example 282

(6-(1-(4-(4-(3-fluoro-5-morpholinophenyl)pyrimidin-2-ylamino)phenyl)-1H-1,2,4-triazol-3-yl)pyridin-3-yl)methanol

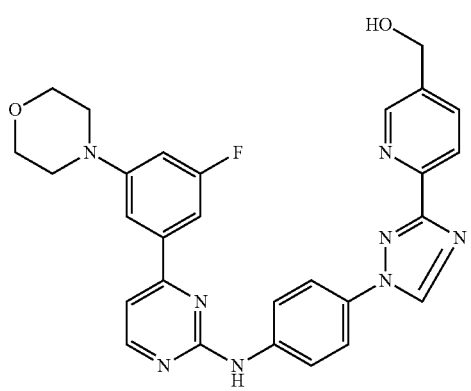 [SMILES: OCc1ccc(-c2ncn(-c3ccc(Nc4nccc(-c5cc(F)cc(N6CCOCC6)c5)n4)cc3)n2)nc1]

(6-(1-(4-(4-(3-fluoro-5-morpholinophenyl)pyrimidin-2-ylamino)phenyl)-1H-1,2,4-triazol-3-yl)pyridin-3-yl)methanol was obtained by following procedure V using N-(4-(3-bromo-1H-1,2,4-triazol-1-yl)phenyl)-4-(3-fluoro-5-morpholinophenyl)pyrimidin-2-amine and (6-chloropyridin-3-yl)methanol. MS (ESI) 525.37 (M+H).

Example 283

4-(3-fluoro-5-morpholinophenyl)-N-(4-(3-(4-(trifluoromethyl)pyridin-2-yl)-1H-1,2,4-triazol-1-yl)phenyl)pyrimidin-2-amine

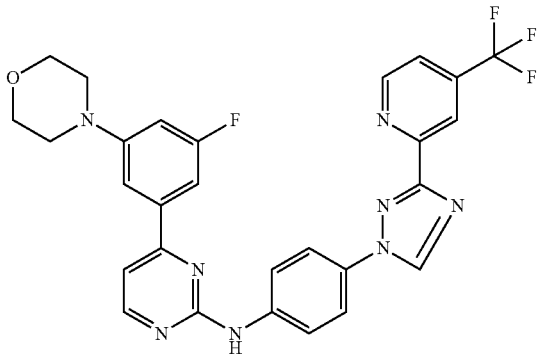 [SMILES: Fc1cc(-c2ccnc(Nc3ccc(-n4cnc(-c5cc(C(F)(F)F)ccn5)n4)cc3)n2)cc(N2CCOCC2)c1]

4-(3-fluoro-5-morpholinophenyl)-N-(4-(3-(4-(trifluoromethyl)pyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-chloro-4-(trifluoromethyl)pyridine. MS (ESI) 563.29 (M+H).

Example 284

N-(4-(3-(5-chloropyridin-2-yl)-1H-1,2,4-triazol-1-yl)phenyl)-4-(3-fluoro-5-morpholinophenyl)pyrimidin-2-amine

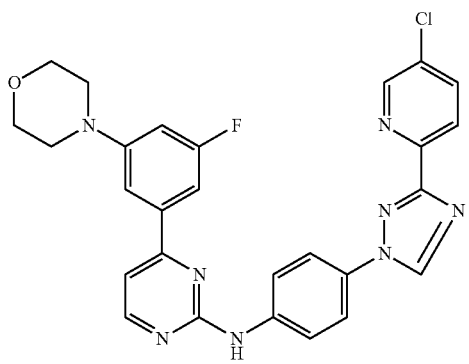 [SMILES: Fc1cc(-c2ccnc(Nc3ccc(-n4cnc(-c5ccc(Cl)cn5)n4)cc3)n2)cc(N2CCOCC2)c1]

N-(4-(3-(5-chloropyridin-2-yl)-1H-1,2,4-triazol-1-yl)phenyl)-4-(3-fluoro-5-morpholinophenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-5-chloropyridine. MS (ESI) 529.28 (M+H).

Example 285

3-(2-(4-(3-(4-hydroxypiperidin-1-yl)-1H-1,2,4-triazol-1-yl)phenylamino)pyrimidin-4-yl)-5-morpholinobenzonitrile

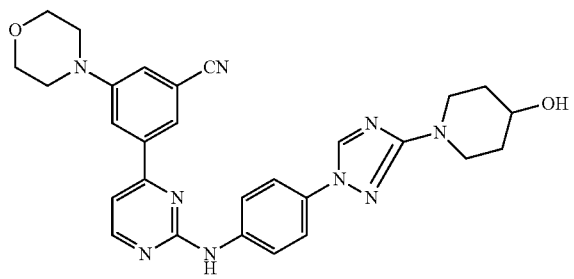 [SMILES: N#Cc1cc(-c2ccnc(Nc3ccc(-n4cnc(N5CCC(O)CC5)n4)cc3)n2)cc(N2CCOCC2)c1]

3-(2-(4-(3-(4-hydroxypiperidin-1-yl)-1H-1,2,4-triazol-1-yl)phenylamino)pyrimidin-4-yl)-5-morpholinobenzonitrile was obtained by following procedure E using 3-(2-chloropyrimidin-4-yl)-5-morpholinobenzonitrile and 1-(1-phenyl-1H-1,2,4-triazol-3-yl)piperidin-4-ol. MS (ESI) 524.23 (M+H).

Example 286

2-(4-hydroxypiperidin-1-yl)-5-(2-(4-(3-(4-hydroxypiperidin-1-yl)-1H-1,2,4-triazol-1-yl)phenylamino)pyrimidin-4-yl)benzonitrile

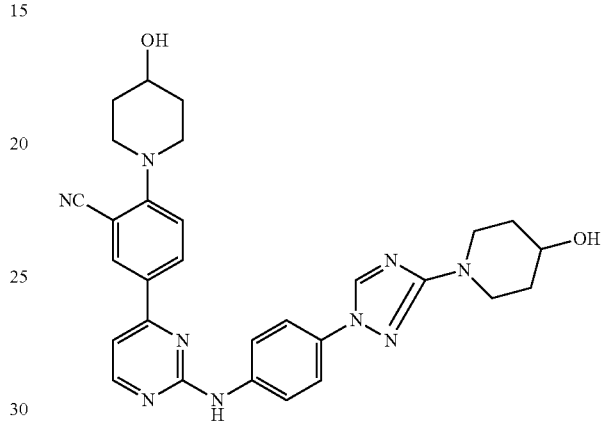

2-(4-hydroxypiperidin-1-yl)-5-(2-(4-(3-(4-hydroxypiperidin-1-yl)-1H-1,2,4-triazol-1-yl)phenylamino)pyrimidin-4-yl)benzonitrile was obtained by following procedure E using 5-(2-chloropyrimidin-4-yl)-2-(4-hydroxypiperidin-1-yl)benzonitrile and 1-(1-(4-aminophenyl)-1H-1,2,4-triazol-3-yl)piperidin-4-ol. MS (ESI) 538.27 (M+H).

Example 287

4-(3-fluoro-5-morpholinophenyl)-N-(4-(3-(6-methylpyridin-3-yl)-1H-1,2,4-triazol-1-yl)phenyl)pyrimidin-2-amine

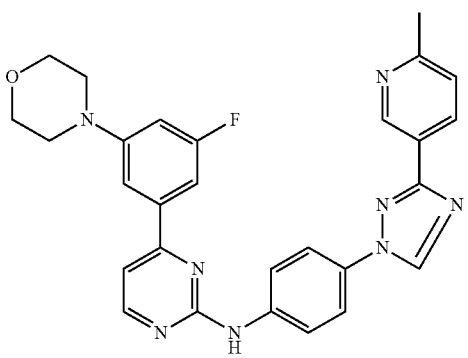 [SMILES: Cc1ccc(-c2ncn(-c3ccc(Nc4nccc(-c5cc(F)cc(N6CCOCC6)c5)n4)cc3)n2)cn1]

4-(3-fluoro-5-morpholinophenyl)-N-(4-(3-(6-methylpyridin-3-yl)-1H-1,2,4-triazol-1-yl)phenyl)pyrimidin-2-amine was obtained by following procedure E using 4-(3-(2-chloropyrimidin-4-yl)-5-fluorophenyl)morpholine and 4-(3-(6-methylpyridin-3-yl)-1H-1,2,4-triazol-1-yl)aniline. MS (ESI) 509.42 (M+H).

Example 288

N-(4-(3-morpholino-1H-1,2,4-triazol-1-yl)phenyl)-4-(3-morpholinophenyl)pyrimidin-2-amine

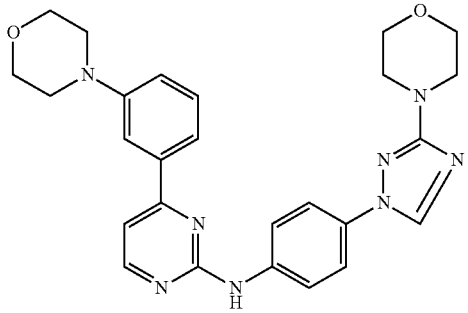 [SMILES: c1cc(-c2ccnc(Nc3ccc(-n4cnc(N5CCOCC5)n4)cc3)n2)cc(N2CCOCC2)c1]

N-(4-(3-morpholino-1H-1,2,4-triazol-1-yl)phenyl)-4-(3-morpholinophenyl)pyrimidin-2-amine was obtained by following procedure E using 4-(3-(2-chloropyrimidin-4-yl)phenyl)morpholine and 4-(3-morpholino-1H-1,2,4-triazol-1-yl)aniline. MS (ESI) 485.32 (M+H).

Example 289

4-(3-fluoro-5-morpholinophenyl)-N-(4-(3-morpholino-1H-1,2,4-triazol-1-yl)phenyl)pyrimidin-2-amine

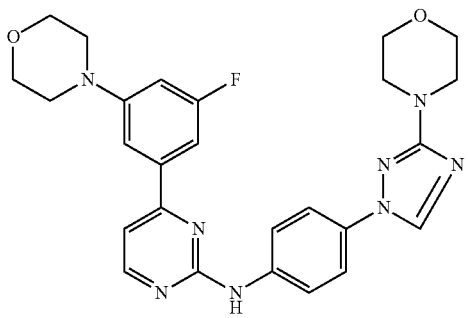 [SMILES: Fc1cc(-c2ccnc(Nc3ccc(-n4cnc(N5CCOCC5)n4)cc3)n2)cc(N2CCOCC2)c1]

4-(3-fluoro-5-morpholinophenyl)-N-(4-(3-morpholino-1H-1,2,4-triazol-1-yl)phenyl)pyrimidin-2-amine was obtained by following procedure E using 4-(3-(2-chloropyrimidin-4-yl)-5-fluorophenyl)morpholine and 4-(3-morpholino-1H-1,2,4-triazol-1-yl)aniline. MS (ESI) 503.30 (M+H).

Example 290

3-morpholino-5-(2-(4-(3-morpholino-1H-1,2,4-triazol-1-yl)phenylamino)pyrimidin-4-yl)benzonitrile

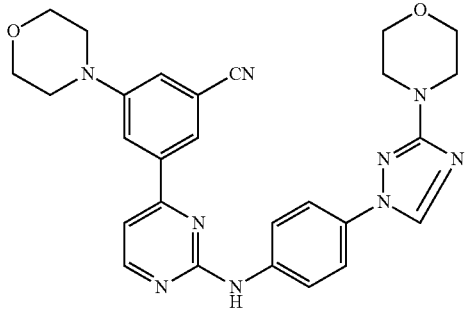 [SMILES: N#Cc1cc(-c2ccnc(Nc3ccc(-n4cnc(N5CCOCC5)n4)cc3)n2)cc(N2CCOCC2)c1]

3-morpholino-5-(2-(4-(3-morpholino-1H-1,2,4-triazol-1-yl)phenylamino)pyrimidin-4-yl)benzonitrile was obtained by following procedure E using 3-(2-chloropyrimidin-4-yl)-5-morpholinobenzonitrile and 4-(3-morpholino-1H-1,2,4-triazol-1-yl)aniline. MS (ESI) 510.26 (M+H).

Example 291

2-(4-hydroxypiperidin-1-yl)-5-(2-(4-(3-morpholino-1H-1,2,4-triazol-1-yl)phenylamino)pyrimidin-4-yl)benzonitrile

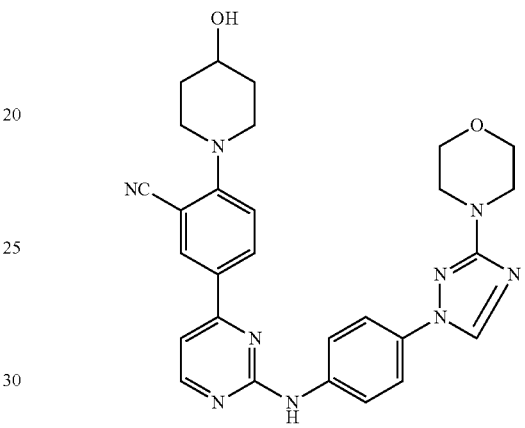

2-(4-hydroxypiperidin-1-yl)-5-(2-(4-(3-morpholino-1H-1,2,4-triazol-1-yl)phenylamino)pyrimidin-4-yl)benzonitrile was obtained by following procedure E using 5-(2-chloropyrimidin-4-yl)-2-(4-hydroxypiperidin-1-yl)benzonitrile and 4-(3-morpholino-1H-1,2,4-triazol-1-yl)aniline. MS (ESI) 524.29 (M+H).

Example 292

1-(1-(4-(4-(3-morpholinophenyl)pyrimidin-2-ylamino)phenyl)-1H-1,2,4-triazol-3-yl)piperidin-3-ol

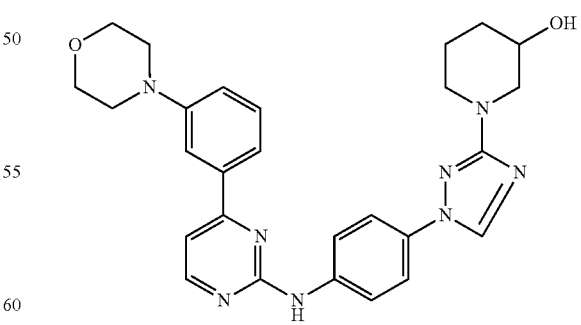

1-(1-(4-(4-(3-morpholinophenyl)pyrimidin-2-ylamino)phenyl)-1H-1,2,4-triazol-3-yl)piperidin-3-ol was obtained by following procedure E using 4-(3-(2-chloropyrimidin-4-yl)phenyl)morpholine and 1-(1-(4-aminophenyl)-1H-1,2,4-triazol-3-yl)piperidin-3-ol. MS (ESI) 499.28 (M+H).

Example 293

1-(1-(4-(4-(3-fluoro-5-morpholinophenyl)pyrimidin-2-ylamino)phenyl)-1H-1,2,4-triazol-3-yl)piperidin-3-ol

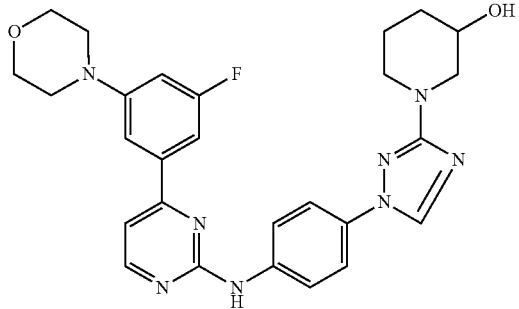 [SMILES: OC1CCCN(c2ncn(-c3ccc(Nc4nccc(-c5cc(F)cc(N6CCOCC6)c5)n4)cc3)n2)C1]

1-(1-(4-(4-(3-fluoro-5-morpholinophenyl)pyrimidin-2-ylamino)phenyl)-1H-1,2,4-triazol-3-yl)piperidin-3-ol was obtained by following procedure E using 4-(3-(2-chloropyrimidin-4-yl)-5-fluorophenyl)morpholine and 1-(1-(4-aminophenyl)-1H-1,2,4-triazol-3-yl)piperidin-3-ol. MS (ESI) 517.27 (M+H).

Example 294

3-(2-(4-(3-(3-hydroxypiperidin-1-yl)-1H-1,2,4-triazol-1-yl)phenylamino)pyrimidin-4-yl)-5-morpholinobenzonitrile

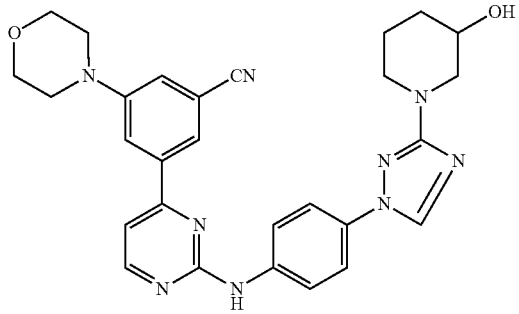 [SMILES: N#Cc1cc(-c2ccnc(Nc3ccc(-n4cnc(N5CCCC(O)C5)n4)cc3)n2)cc(N2CCOCC2)c1]

3-(2-(4-(3-(3-hydroxypiperidin-1-yl)-1H-1,2,4-triazol-1-yl)phenylamino)pyrimidin-4-yl)-5-morpholinobenzonitrile was obtained by following procedure E using 3-(2-chloropyrimidin-4-yl)-5-morpholinobenzonitrile and 1-(1-(4-aminophenyl)-1H-1,2,4-triazol-3-yl)piperidin-3-ol. MS (ESI) 524.23 (M+H).

Example 295

2-(4-hydroxypiperidin-1-yl)-5-(2-(4-(3-(3-hydroxypiperidin-1-yl)-1H-1,2,4-triazol-1-yl)phenylamino)pyrimidin-4-yl)benzonitrile

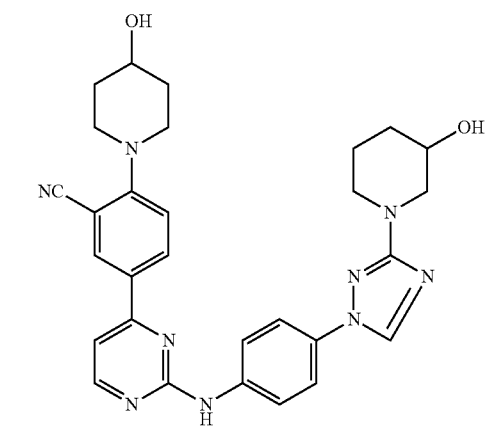 [SMILES: N#Cc1cc(-c2ccnc(Nc3ccc(-n4cnc(N5CCCC(O)C5)n4)cc3)n2)ccc1N1CCC(O)CC1]

2-(4-hydroxypiperidin-1-yl)-5-(2-(4-(3-(3-hydroxypiperidin-1-yl)-1H-1,2,4-triazol-1-yl)phenylamino)pyrimidin-4-yl)benzonitrile was obtained by following procedure E using 5-(2-chloropyrimidin-4-yl)-2-(4-hydroxypiperidin-1-yl)benzonitrile and 1-(1-(4-aminophenyl)-1H-1,2,4-triazol-3-yl)piperidin-3-ol. MS (ESI) 538.63 (M+H).

Example 296

4-(3-morpholinophenyl)-N-(4-(2-(pyridin-3-yl)-2H-tetrazol-5-yl)phenyl)pyrimidin-2-amine

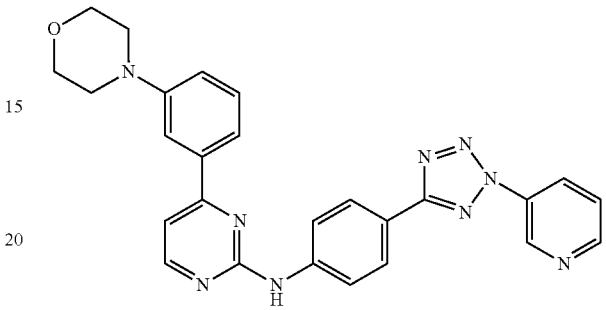

4-(3-morpholinophenyl)-N-(4-(2-(pyridin-3-yl)-2H-tetrazol-5-yl)phenyl)pyrimidin-2-amine was obtained by following procedure O using 4-(3-(2-chloropyrimidin-4-yl)phenyl)morpholine and 4-(2-(pyridin-3-yl)-2H-tetrazol-5-yl)aniline. MS (ESI) 478.00 (M+H).

Example 297

4-(3-fluoro-5-morpholinophenyl)-N-(4-(2-(pyridin-3-yl)-2H-tetrazol-5-yl)phenyl)pyrimidin-2-amine

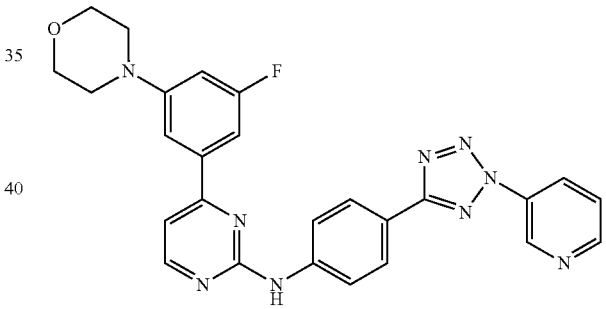

4-(3-fluoro-5-morpholinophenyl)-N-(4-(2-(pyridin-3-yl)-2H-tetrazol-5-yl)phenyl)pyrimidin-2-amine was obtained by following procedure O using 4-(3-(2-chloropyrimidin-4-yl)-5-fluorophenyl)morpholine and 4-(2-(pyridin-3-yl)-2H-tetrazol-5-yl)aniline. MS (ESI) 496.06 (M+H).

Example 298

3-morpholino-5-(2-(4-(2-(pyridin-3-yl)-2H-tetrazol-5-yl)phenylamino)pyrimidin-4-yl)benzonitrile

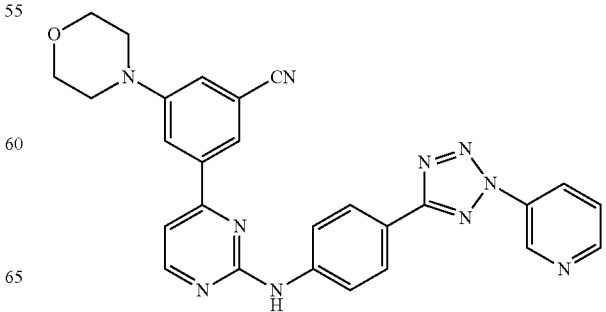

3-morpholino-5-(2-(4-(2-(pyridin-3-yl)-2H-tetrazol-5-yl)phenylamino)pyrimidin-4-yl)benzonitrile was obtained by following procedure O using 3-(2-chloropyrimidin-4-yl)-5-morpholinobenzonitrile and 4-(2-(pyridin-3-yl)-2H-tetrazol-5-yl)aniline. MS (ESI) 503.04 (M+H).

Example 299

3-(3-hydroxypiperidin-1-yl)-5-(2-(4-(3-(pyridin-4-yl)-1H-1,2,4-triazol-1-yl)phenylamino)pyrimidin-4-yl)benzonitrile

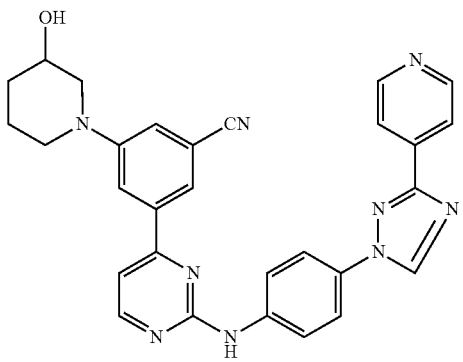 [SMILES: N#Cc1cc(-c2ccnc(Nc3ccc(-n4cnc(-c5ccncc5)n4)cc3)n2)cc(N2CCCC(O)C2)c1]

3-(3-hydroxypiperidin-1-yl)-5-(2-(4-(3-(pyridin-4-yl)-1H-1,2,4-triazol-1-yl)phenylamino)pyrimidin-4-yl)benzonitrile was obtained by following procedure O using 3-(2-chloropyrimidin-4-yl)-5-(3-hydroxypiperidin-1-yl)benzonitrile and 4-(3-(pyridin-4-yl)-1H-1,2,4-triazol-1-yl)aniline. MS (ESI) 516.37 (M+H).

Example 300

3-(2-(4-(3-(6-methylpyridin-3-yl)-1H-1,2,4-triazol-1-yl)phenylamino)pyrimidin-4-yl)-5-morpholinobenzonitrile

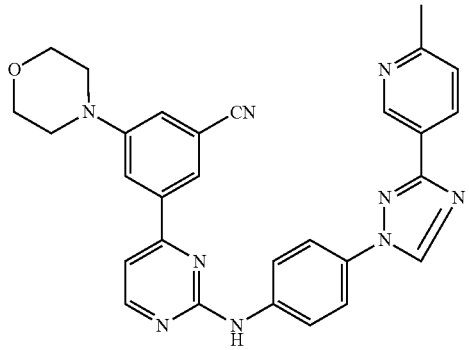 [SMILES: Cc1ccc(-c2ncn(-c3ccc(Nc4nccc(-c5cc(C#N)cc(N6CCOCC6)c5)n4)cc3)n2)cn1]

3-(2-(4-(3-(6-methylpyridin-3-yl)-1H-1,2,4-triazol-1-yl)phenylamino)pyrimidin-4-yl)-5-morpholinobenzonitrile was obtained by following procedure E using 3-(2-chloropyrimidin-4-yl)-5-morpholinobenzonitrile and 4-(3-(6-methylpyridin-3-yl)-1H-1,2,4-triazol-1-yl)aniline. MS (ESI) 516.41 (M+H).

Example 301

3-morpholino-5-(2-(4-(3-(piperazin-1-yl)-1H-1,2,4-triazol-1-yl)phenylamino)pyrimidin-4-yl)benzonitrile

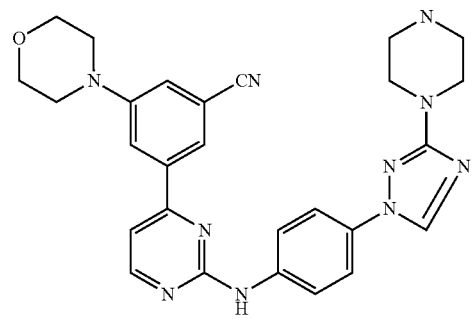 [SMILES: N#Cc1cc(-c2ccnc(Nc3ccc(-n4cnc(N5CCNCC5)n4)cc3)n2)cc(N2CCOCC2)c1]

3-morpholino-5-(2-(4-(3-(piperazin-1-yl)-1H-1,2,4-triazol-1-yl)phenylamino)pyrimidin-4-yl)benzonitrile was obtained by following procedure E using 3-(2-chloropyrimidin-4-yl)-5-morpholinobenzonitrile and 4-(3-(4-methylpiperazin-1-yl)-1H-1,2,4-triazol-1-yl)aniline in which the methyl group was lost in situ. MS (ESI) 509.26 (M+H).

Example 302

3-(2-(4-(3-(4-methoxypiperidin-1-yl)-1H-1,2,4-triazol-1-yl)phenylamino)pyrimidin-4-yl)-5-morpholinobenzonitrile

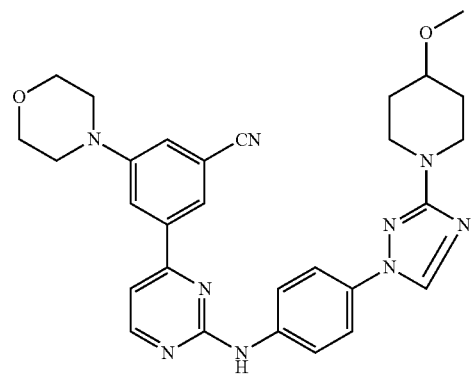 [SMILES: COC1CCN(c2ncn(-c3ccc(Nc4nccc(-c5cc(C#N)cc(N6CCOCC6)c5)n4)cc3)n2)CC1]

3-(2-(4-(3-(4-methoxypiperidin-1-yl)-1H-1,2,4-triazol-1-yl)phenylamino)pyrimidin-4-yl-5-morpholinobenzonitrile was obtained by following procedure E using 3-(2-chloropyrimidin-4-yl)-5-morpholinobenzonitrile and 4-(3-(4-methoxypiperidin-1-yl)-1H-1,2,4-triazol-1-yl)aniline. MS (ESI) 538.23 (M+H).

Example 303

4-(3-fluoro-5-morpholinophenyl)-N-(4-(3-(4-methoxypiperidin-1-yl)-1H-1,2,4-triazol-1-yl)phenyl)pyrimidin-2-amine

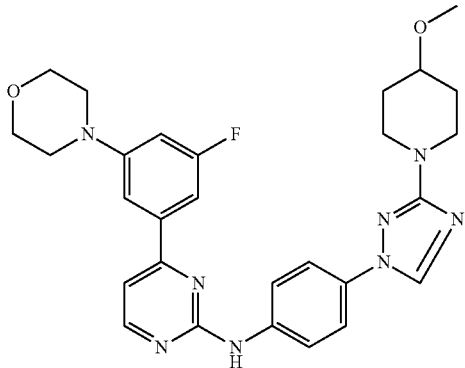 [SMILES: COC1CCN(c2ncn(-c3ccc(Nc4nccc(-c5cc(F)cc(N6CCOCC6)c5)n4)cc3)n2)CC1]

4-(3-fluoro-5-morpholinophenyl)-N-(4-(3-(4-methoxypiperidin-1-yl)-1H-1,2,4-triazol-1-yl)phenyl)pyrimidin-2-amine was obtained by following procedure E using 4-(3-(2-chloropyrimidin-4-yl)-5-fluorophenyl)morpholine and 4-(3-(4-methoxypiperidin-1-yl)-1H-1,2,4-triazol-1-yl)aniline. MS (ESI) 531.24 (M+H).

Example 304

4-(3-morpholinophenyl)-N-(4-(3-(piperazin-1-yl)-1H-1,2,4-triazol-1-yl)phenyl)pyrimidin-2-amine

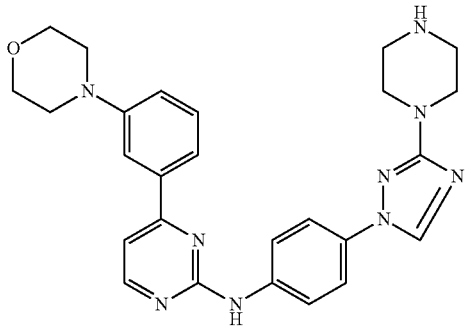 [SMILES: c1cc(-c2ccnc(Nc3ccc(-n4cnc(N5CCNCC5)n4)cc3)n2)cc(N2CCOCC2)c1]

4-(3-morpholinophenyl)-N-(4-(3-(piperazin-1-yl)-1H-1,2,4-triazol-1-yl)phenyl)pyrimidin-2-amine was obtained by following procedure E using 4-(3-(2-chloropyrimidin-4-yl)phenyl)morpholine and 4-(3-(4-methylpiperazin-1-yl)-1H-1,2,4-triazol-1-yl)aniline in which the methyl group was lost in situ. MS (ESI) 484.28 (M+H).

Example 305

3-(4-methoxypiperidin-1-yl)-5-(2-(4-(3-methyl-1H-1,2,4-triazol-1-yl)phenylamino)pyrimidin-4-yl)benzonitrile

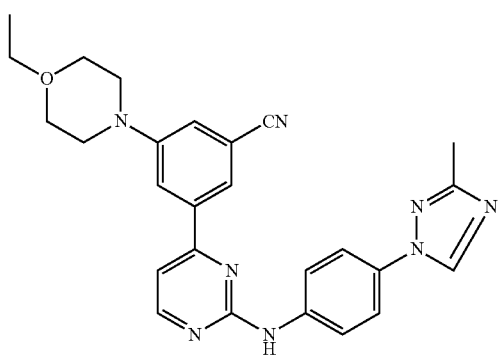

3-(4-methoxypiperidin-1-yl)-5-(2-(4-(3 methyl-1H-1,2,4-triazol-1-yl)phenylamino)pyrimidin-4-yl)benzonitrile was obtained by following procedure G using 3-bromo-5-(4-methoxypiperidin-1-yl)benzonitrile and N-(4-(3-methyl-1H-1,2,4-triazol-1-yl)phenyl)-4-(trimethylstannyl)pyrimidin-2-amine. MS (ESI) 467.23 (M+H).

Example 306

3-(dimethylamino)-5-(2-(4-(3-(6-methylpyridin-3-yl)-1H-1,2,4-triazol-1-yl)phenylamino)pyrimidin-4-yl)benzonitrile

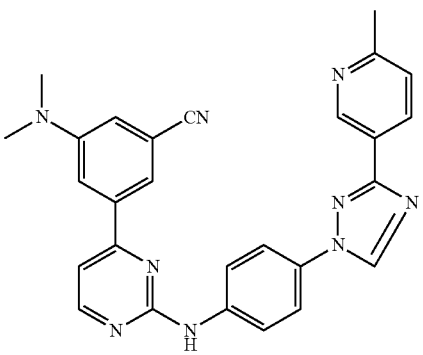 [SMILES: Cc1ccc(-c2ncn(-c3ccc(Nc4nccc(-c5cc(C#N)cc(N(C)C)c5)n4)cc3)n2)cn1]

3-(dimethylamino)-5-(2-(4-(3-(6-methylpyridin-3-yl)-1H-1,2,4-triazol-1-yl)phenylamino)pyrimidin-4-yl)benzonitrile was obtained by following procedure E using 3-(2-chloropyrimidin-4-yl)-5-(dimethylamino)benzonitrile and 4-(3-(6-methylpyridin-3-yl)-1H-1,2,4-triazol-1-yl)aniline. MS (ESI) 474.35 (M+H).

Example 307

3-(3-hydroxypiperidin-1-yl)-5-(2-(4-(3-(6-methylpyridin-3-yl)-1H-1,2,4-triazol-1-yl)phenylamino)pyrimidin-4-yl)benzonitrile

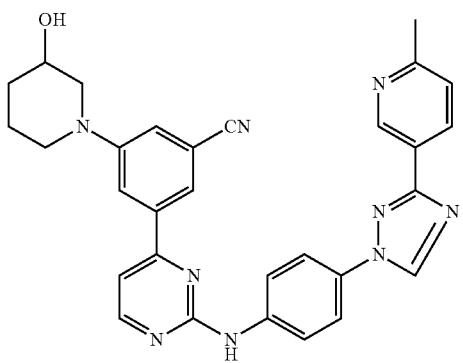 [SMILES: Cc1ccc(-c2ncn(-c3ccc(Nc4nccc(-c5cc(C#N)cc(N6CCCC(O)C6)c5)n4)cc3)n2)cn1]

3-(3-hydroxypiperidin-1-yl)-5-(2-(4-(3-(6-methylpyridin-3-yl)-1H-1,2,4-triazol-1-yl)phenylamino)pyrimidin-4-yl)benzonitrile was obtained by following procedure O using 3-(2-chloropyrimidin-4-yl)-5-(3-hydroxypiperidin-1-yl)benzonitrile and 4-(3-(6-methylpyridin-3-yl)-1H-1,2,4-triazol-1-yl)aniline. MS (ESI) 530.35 (M+H).

Example 308

N-(4-(3-(4-methylpiperazin-1-yl)-1H-1,2,4-triazol-1-yl)phenyl)-4-(3-morpholinophenyl)pyrimidin-2-amine

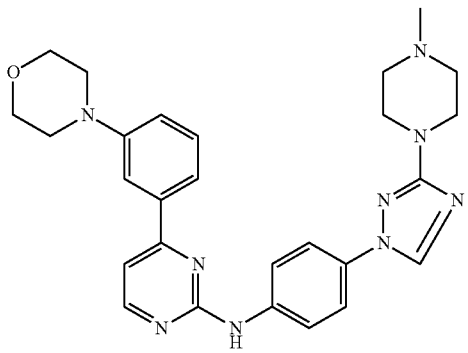 [SMILES: CN1CCN(c2ncn(-c3ccc(Nc4nccc(-c5cccc(N6CCOCC6)c5)n4)cc3)n2)CC1]

N-(4-(3-(4-methylpiperazin-1-yl)-1H-1,2,4-triazol-1-yl)phenyl)-4-(3-morpholinophenyl)pyrimidin-2-amine was obtained by following procedure O using 4-(3-(2-chloropyrimidin-4-yl)phenyl)morpholine and 4-(3-(4-methylpiperazin-1-yl)-1H-1,2,4-triazol-1-yl)aniline. MS (ESI) 498.30 (M+H).

Example 309

3-(2-(4-(3-(4-methylpiperazin-1-yl)-1H-1,2,4-triazol-1-yl)phenylamino)pyrimidin-4-yl)-5-morpholinobenzonitrile

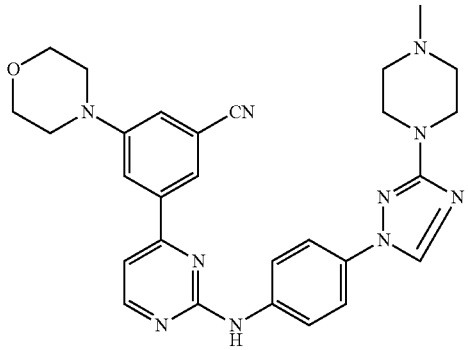

3-(2-(4-(3-(4-methylpiperazin-1-yl)-1H-1,2,4-triazol-1-yl)phenylamino)pyrimidin-4-yl)-5-morpholinobenzonitrile was obtained by following procedure O using 3-(2-chloropyrimidin-4-yl)-5-morpholinobenzonitrile and 4-(3-(4-methylpiperazin-1-yl)-1H-1,2,4-triazol-1-yl)aniline. MS (ESI) 523.34 (M+H).

Example 310

3-(dimethylamino)-5-(2-(4-(3-(4-methylpiperazin-1-yl)-1H-1,2,4-triazol-1-yl)phenylamino)pyrimidin-4-yl)benzonitrile

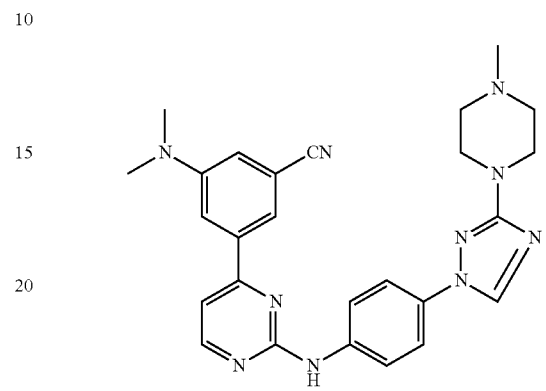

3-(dimethylamino)-5-(2-(4-(3-(4-methylpiperazin-1-yl)-1H-1,2,4-triazol-1-yl)phenylamino)pyrimidin-4-yl)benzonitrile was obtained by following procedure O using 3-(2-chloropyrimidin-4-yl)-5-(dimethylamino)benzonitrile and 4-(3-(4-methylpiperazin-1-yl)-1H-1,2,4-triazol-1-yl)aniline. MS (ESI) 481.31 (M+H).

Example 311

3-(3-hydroxypiperidin-1-yl)-5-(2-(4-(3-(6-methylpyridin-3-yl)-1H-1,2,4-triazol-1-yl)phenylamino)pyrimidin-4-yl)benzonitrile

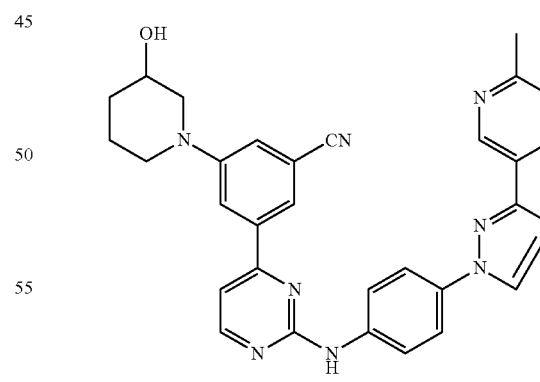

3-(3-hydroxypiperidin-1-yl)-5-(2-(4-(3-(6-methylpyridin-3-yl)-1H-1,2,4-triazol-1-yl)phenylamino)pyrimidin-4-yl)benzonitrile was obtained by following procedure E using 3-(2-chloropyrimidin-4-yl)-5-(3-hydroxypiperidin-1-yl)benzonitrile and 4-(3-(6-methylpyridin-3-yl)-1H-1,2,4-triazol-1-yl)aniline. MS (ESI) 530.33 (M+H).

Example 312

4-(3-(dimethylamino)-5-fluorophenyl)-N-(4-(3-morpholino-1H-1,2,4-triazol-1-yl)phenyl)pyrimidin-2-amine

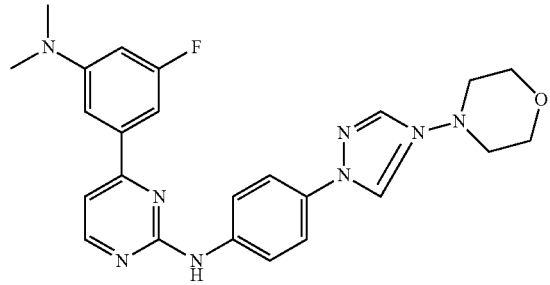

4-(3-(dimethylamino)-5-fluorophenyl)-N-(4-(3-morpholino-1H-1,2,4-triazol-1-yl)phenyl)pyrimidin-2-amine was obtained by following procedure E using 3-(2-chloropyrimidin-4-yl)-5-fluoro-N,N-dimethylaniline and 4-(3-morpholino-1H-1,2,4-triazol-1-yl)aniline. MS (ESI) 461.27 (M+H).

Example 313

1-(1-(4-(4-(3-(dimethylamino)-5-fluorophenyl)pyrimidin-2-ylamino)phenyl)-1H-1,2,4-triazol-3-yl)piperidin-4-ol

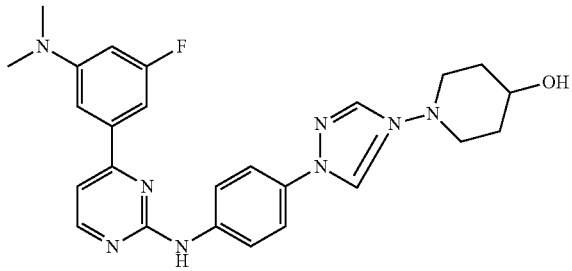

1-(1-(4-(4-(3-(dimethylamino)-5-fluorophenyl)pyrimidin-2-ylamino)phenyl)-1H-1,2,4-triazol-3-yl)piperidin-4-ol was obtained by following procedure E using 3-(2-chloropyrimidin-4-yl)-5-fluoro-N,N-dimethylaniline and 1-(1-(4-aminophenyl)-1H-1,2,4-triazol-3-yl)piperidin-4-ol. MS (ESI) 475.24 (M+H).

Example 314

4-(3-(dimethylamino)-5-fluorophenyl)-N-(4-(3-(4-methoxypiperidin-1-yl)-1H-1,2,4-triazol-1-yl)phenyl)pyrimidin-2-amine

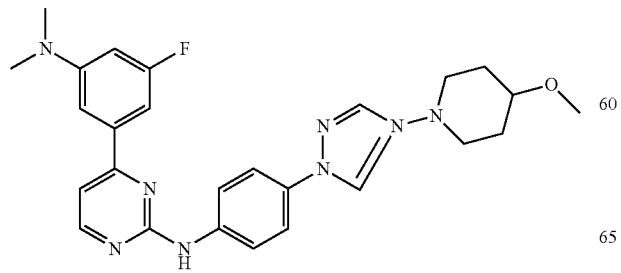

4-(3-(dimethylamino)-5-fluorophenyl)-N-(4-(3-(4-methoxypiperidin-1-yl)-1H-1,2,4-triazol-1-yl)phenyl)pyrimidin-2-amine was obtained by following procedure E using 3-(2-chloropyrimidin-4-yl)-5-fluoro-N,N-dimethylaniline and 4-(3-(4-methoxypiperidin-1-yl)-1H-1,2,4-triazol-1-yl)aniline. MS (ESI) 489.22 (M+H).

Example 315

4-(3-(dimethylamino)-5-fluorophenyl)-N-(4-(3-(6-methylpyridin-3-yl)-1H-1,2,4-triazol-1-yl)phenyl)pyrimidin-2-amine

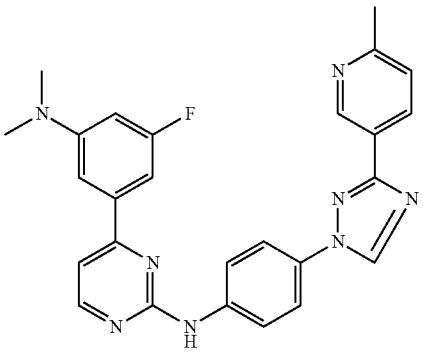 [SMILES: Cc1ccc(-c2ncn(-c3ccc(Nc4nccc(-c5cc(F)cc(N(C)C)c5)n4)cc3)n2)cn1]

4-(3-(dimethylamino)-5-fluorophenyl)-N-(4-(3-(6-methylpyridin-3-yl)-1H-1,2,4-triazol-1-yl)phenyl)pyrimidin-2-amine was obtained by following procedure E using 3-(2-chloropyrimidin-4-yl)-5-fluoro-N,N-dimethylaniline and 4-(3-(6-methylpyridin-3-yl)-1H-1,2,4-triazol-1-yl)aniline. MS (ESI) 467.32 (M+H).

Example 316

4-(3-fluoro-5-morpholinophenyl)-N-(4-(3-(2-methylpyridin-4-yl)-1H-1,2,4-triazol-1-yl)phenyl)pyrimidin-2-amine

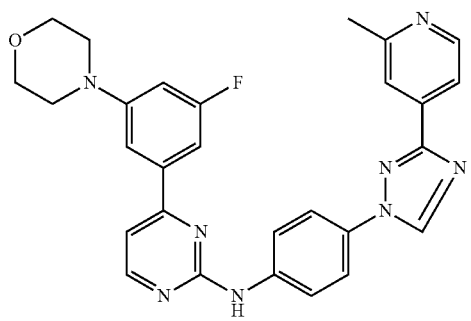 [SMILES: Cc1cc(-c2ncn(-c3ccc(Nc4nccc(-c5cc(F)cc(N6CCOCC6)c5)n4)cc3)n2)ccn1]

4-(3-fluoro-5-morpholinophenyl)-N-(4-(3-(2-methylpyridin-4-yl)-1H-1,2,4-triazol-1-yl)phenyl)pyrimidin-2-amine was obtained by following procedure E using 4-(3-(2-chloropyrimidin-4-yl)-5-fluorophenyl) morpholine and 4-(3-(2-methylpyridin-4-yl)-1H-1,2,4-triazol-1-yl)aniline. MS (ESI) 509.40 (M+H).

Example 317

3-(2-(4-(3-(2-methylpyridin-4-yl)-1H-1,2,4-triazol-1-yl)phenylamino)pyrimidin-4-yl)-5-morpholinobenzonitrile

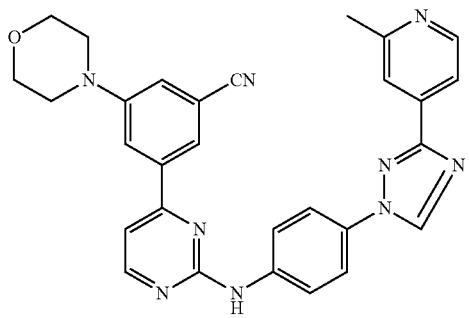 [SMILES: Cc1cc(-c2ncn(-c3ccc(Nc4nccc(-c5cc(C#N)cc(N6CCOCC6)c5)n4)cc3)n2)ccn1]

3-(2-(4-(3-(2-methylpyridin-4-yl)-1H-1,2,4-triazol-1-yl)phenylamino)pyrimidin-4-yl)-5-morpholinobenzonitrile was obtained by following procedure E using 3-(2-chloropyrimidin-4-yl)-5-morpholinobenzonitrile and 4-(3-(2-methylpyridin-4-yl)-1H-1,2,4-triazol-1-yl)aniline. MS (ESI) 516.42 (M+H).

Example 318

4-(3-(dimethylamino)-5-fluorophenyl)-N-(4-(3-(2-methylpyridin-4-yl)-1H-1,2,4-triazol-1-yl)phenyl)pyrimidin-2-amine

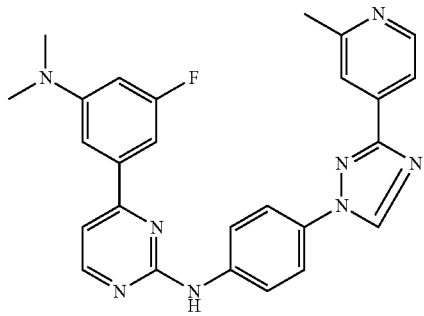 [SMILES: Cc1cc(-c2ncn(-c3ccc(Nc4nccc(-c5cc(F)cc(N(C)C)c5)n4)cc3)n2)ccn1]

4-(3-(dimethylamino)-5-fluorophenyl)-N-(4-(3-(2-methylpyridin-4-yl)-1H-1,2,4-triazol-1-yl)phenyl)pyrimidin-2-amine was obtained by following procedure E using 3-(2-chloropyrimidin-4-yl)-5-fluoro-N,N-dimethylaniline and 4-(3-(2-methylpyridin-4-yl)-1H-1,2,4-triazol-1-yl)aniline. MS (ESI) 467.35 (M+H).

Example 319

3-(3-hydroxypyrrolidin-1-yl)-5-(2-(4-(3-methyl-1H-1,2,4-triazol-1-yl)phenylamino)pyrimidin-4-yl)benzonitrile

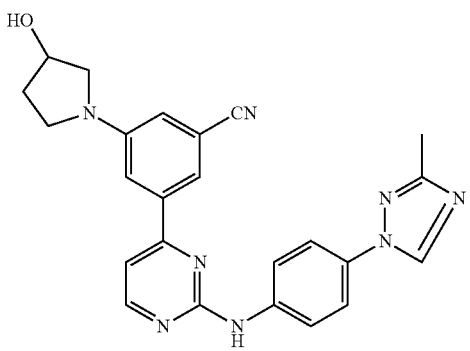 [SMILES: Cc1ncn(-c2ccc(Nc3nccc(-c4cc(C#N)cc(N5CCC(O)C5)c4)n3)cc2)n1]

3-(3-hydroxypyrrolidin-1-yl)-5-(2-(4-(3-methyl-1H-1,2,4-triazol-1-yl)phenylamino)pyrimidin-4-yl)benzonitrile was obtained by following procedure G using 3-(2-chloropyrimidin-4-yl)-5-(3-hydroxypyrrolidin-1-yl)benzonitrile and N-(4-(3-methyl-1H-1,2,4-triazol-1-yl)phenyl)-4-(trimethylstannyl)pyrimidin-2-amine. MS (ESI) 439.29 (M+H).

Example 320

N-(4-(1H-1,2,4-triazol-1-yl)phenyl)-4-(3-fluoro-5-morpholinophenyl)pyrimidin-2-amine

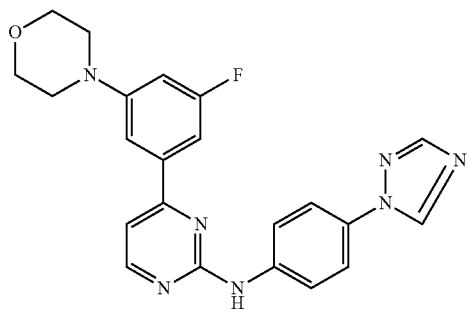

N-(4-(1H-1,2,4-triazol-1-yl)phenyl)-4-(3-fluoro-5-morpholinophenyl)pyrimidin-2-amine was obtained by following procedure E using 4-(3-(2-chloropyrimidin-4-yl)-5-fluorophenyl)morpholine and 4-(1H-1,2,4-triazol-1-yl)aniline. MS (ESI) 418.28 (M+H).

Example 321

4-(3-fluoro-5-morpholinophenyl)-N-(4-(3-(4-methylpyridin-3-yl)-1H-1,2,4-triazol-1-yl)phenyl)pyrimidin-2-amine

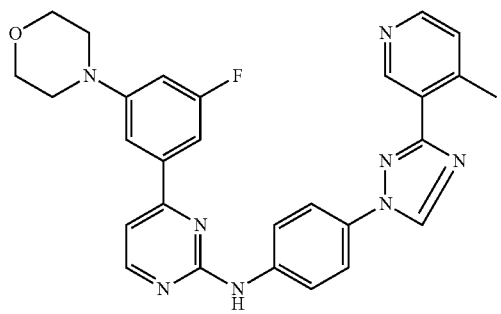 [SMILES: Cc1ccncc1-c1ncn(-c2ccc(Nc3nccc(-c4cc(F)cc(N5CCOCC5)c4)n3)cc2)n1]

4-(3-fluoro-5-morpholinophenyl)-N-(4-(3-(4-methylpyridin-3-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 3-bromo-4-methylpyridine. MS (ESI) 509.39 (M+H).

Example 322

3-(3-hydroxypiperidin-1-yl)-5-(2-(4-(3-(4-methylpiperazin-1-yl)-1H-1,2,4-triazol-1-yl)phenylamino)pyrimidin-4-yl)benzonitrile

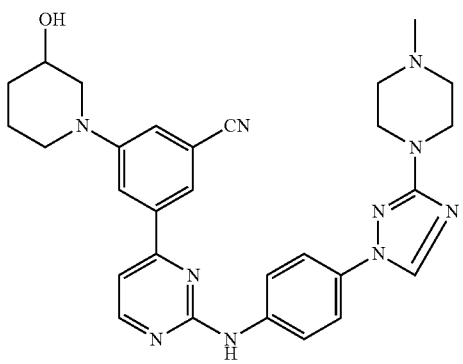 [SMILES: CN1CCN(c2ncn(-c3ccc(Nc4nccc(-c5cc(C#N)cc(N6CCCC(O)C6)c5)n4)cc3)n2)CC1]

3-(3-hydroxypiperidin-1-yl)-5-(2-(4-(3-(4-methylpiperazin-1-yl)-1H-1,2,4-triazol-1-yl)phenylamino)pyrimidin-4-yl)benzonitrile was obtained by following procedure G using 3-(2-chloropyrimidin-4-yl)-5-(3-hydroxypiperidin-1-yl)benzonitrile and 4-(3-(4-methylpiperazin-1-yl)-1H-1,2,4-triazol-1-yl)aniline. MS (ESI) 537.34 (M+H).

Example 323

N-(4-(2-(4-(3-(4-methylpiperazin-1-yl)-1H-1,2,4-triazol-1-yl)phenylamino)pyrimidin-4-yl)phenyl)methanesulfonamide

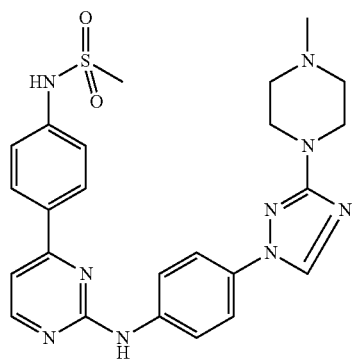 [SMILES: CN1CCN(c2ncn(-c3ccc(Nc4nccc(-c5ccc(NS(C)(=O)=O)cc5)n4)cc3)n2)CC1]

N-(4-(2-(4-(3-(4-methylpiperazin-1-yl)-1H-1,2,4-triazol-1-yl)phenylamino)pyrimidin-4-yl)phenyl)methanesulfonamide was obtained by following procedure G using N-(4-(2-chloropyrimidin-4-yl)phenyl)methanesulfonamide and 4-(3-(4-methylpiperazin-1-yl)-1H-1,2,4-triazol-1-yl)aniline. MS (ESI) 506.21 (M+H).

Example 324

4-(3-fluoro-5-morpholinophenyl)-N-(4-(3-(Pyridin-2-yl)-1H-1,2,4-triazol-1-yl)phenyl)pyrimidin-2-amine

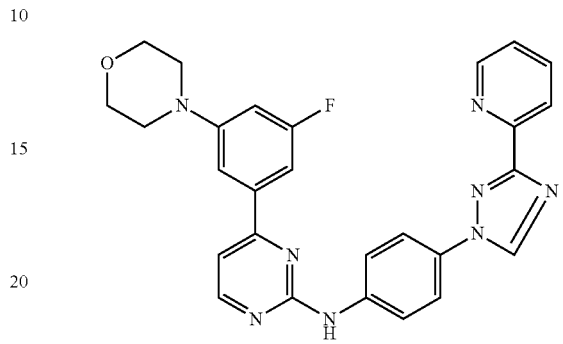

4-(3-fluoro-5-morpholinophenyl)-N-(4-(3-(pyridin-2-yl)-1H-1,2,4-triazol-1-yl)phenyl)pyrimidin-2-amine was obtained by following procedure G using N-(4-(3-bromo-1H-1,2,4-triazol-1-yl)phenyl)-4-(3-fluoro-5-morpholinophenyl)pyrimidin-2-amine and 2-(trimethylstannyl)pyridine with toluene/DMF as the solvent. MS (ESI) 495.34 (M+H).

Example 325

4-(3-fluoro-5-morpholinophenyl)-N-(4-(3-(2-methylpyridin-3-yl)-1H-1,2,4-triazol-1-yl)phenyl)pyrimidin-2-amine

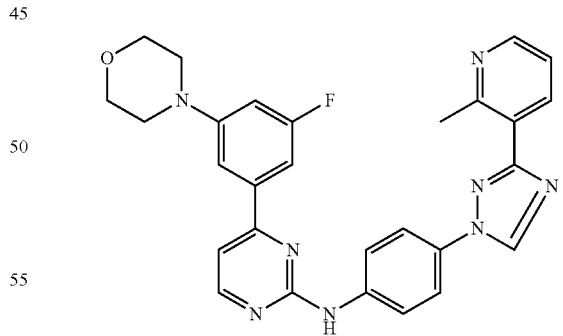

4-(3-fluoro-5-morpholinophenyl)-N-(4-(3-(2-methylpyridin-3-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 3-bromo-2-methylpyridine. MS (ESI) 509.39 (M+H).

Example 326

N-(4-(3-(5-chloropyridin-3-yl)-1H-1,2,4-triazol-1-yl)phenyl)-4-(3-fluoro-5-morpholinophenyl)pyrimidin-2-amine

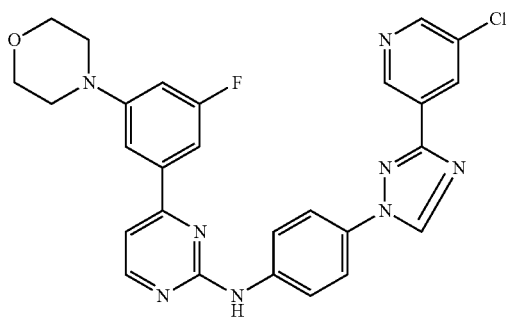 [SMILES: Fc1cc(-c2ccnc(Nc3ccc(-n4cnc(-c5cncc(Cl)c5)n4)cc3)n2)cc(N2CCOCC2)c1]

N-(4-(3-(5-chloropyridin-3-yl)-1H-1,2,4-triazol-1-yl)phenyl)-4-(3-fluoro-5-morpholinophenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 3-bromo-5-chloropyridine. MS (ESI) 529.30/531.28 (M+H) (Cl isotope).

Example 327

4-(3-fluoro-5-morpholinophenyl)-N-(4-(3-(6-(trifluoromethyl)pyridin-3-yl)-1H-1,2,4-triazol-1-yl)phenyl)pyrimidin-2-amine

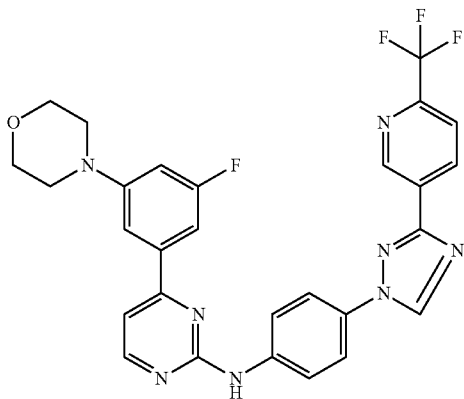

4-(3-fluoro-5-morpholinophenyl)-N-(4-(3-(6-(trifluoromethyl)pyridin-3-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 5-bromo-2-(trifluoromethyl)pyridine. MS (ESI) 563.32 (M+H).

Example 328

4-(3-fluoro-5-morpholinophenyl)-N-(4-(3-(6-methylpyridin-2-yl)-1H-1,2,4-triazol-1-yl)phenyl)pyrimidin-2-amine

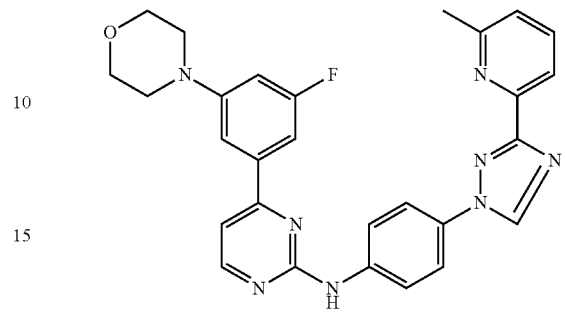

4-(3-fluoro-5-morpholinophenyl)-N-(4-(3-(6-methylpyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-6-methylpyridine. MS (ESI) 509.41 (M+H).

Example 329

N-(4-(3-methyl-1H-1,2,4-triazol-1-yl)phenyl)-4-(3-(methylsulfonyl)phenyl)pyrimidin-2-amine

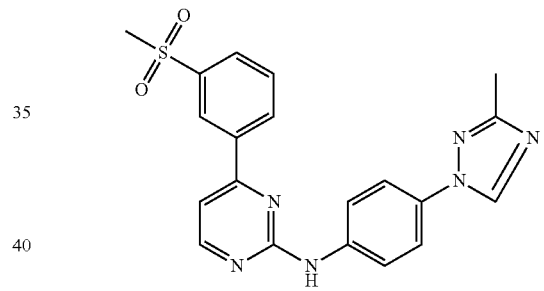

N-(4-(3-methyl-1H-1,2,4-triazol-1-yl)phenyl)-4-(3-(methylsulfonyl)phenyl)pyrimidin-2-amine was obtained by following procedure E using 2-chloro-4-(3-(methylsulfonyl)phenyl)pyrimidine and 4-(3-methyl-1H-1,2,4-triazol-1-yl)aniline. MS (ESI) 407.22 (M+H).

Example 330

4-(3-fluoro-5-morpholinophenyl)-N-(4-(3-(3-methylpyridin-2-yl)-1H-1,2,4-triazol-1-yl)phenyl)pyrimidin-2-amine

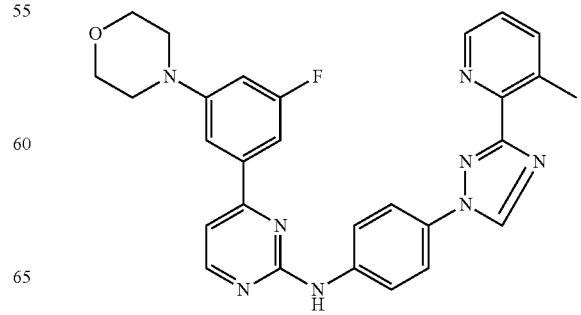

4-(3-fluoro-5-morpholinophenyl)-N-(4-(3-(3-methylpyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-3-methylpyridine. MS (ESI) 509.40 (M+H).

Example 331

4-(3-fluoro-5-morpholinophenyl)-N-(4-(3-(4-methylpyridin-2-yl)-1H-1,2,4-triazol-1-yl)phenyl)pyrimidin-2-amine

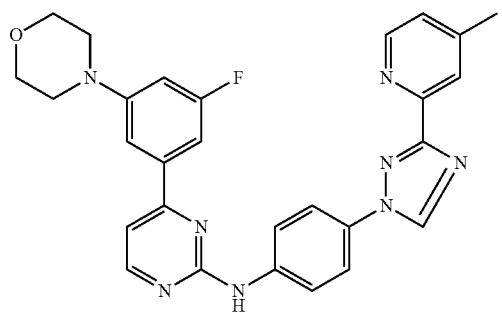 [SMILES: Cc1ccnc(-c2ncn(-c3ccc(Nc4nccc(-c5cc(F)cc(N6CCOCC6)c5)n4)cc3)n2)c1]

4-(3-fluoro-5-morpholinophenyl)-N-(4-(3-(4-methylpyridin-2-yl)-1H-1,2,4-triazol-1-yl)phenyl)pyrimidin-2-amine was obtained by following procedure V using N-(4-(3-bromo-1H-1,2,4-triazol-1-yl)phenyl)-4-(3-fluoro-5-morpholinophenyl)pyrimidin-2-amine and 2-bromo-4-methylpyridine. MS (ESI) 509.40 (M+H).

Example 332

3-morpholino-5-(2-(4-(pyridin-4-yl)phenylamino)pyrimidin-4-yl)benzonitrile

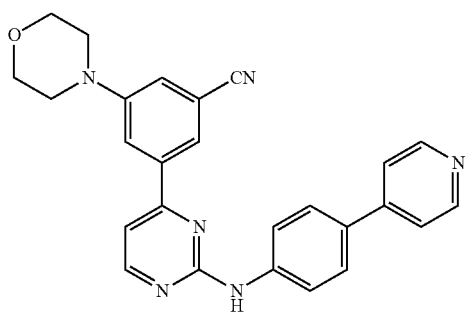 [SMILES: N#Cc1cc(-c2ccnc(Nc3ccc(-c4ccncc4)cc3)n2)cc(N2CCOCC2)c1]

3-morpholino-5-(2-(4 (pyridin-4-yl)phenylamino)pyrimidin-4-yl)benzonitrile was obtained by following procedure K using pyridin-4-ylboronic acid and 3-(2-(4-bromophenylamino)pyrimidin-4-yl-5-morpholinobenzonitrile which was obtained by following procedure E using 3-(2-chloropyrimidin-4-yl)-5-morpholinobenzonitrile and 4-bromoaniline. MS (ESI) 435.67 (M+H).

Example 333

N-(4-(3,5-dimethyl-1H-1,2,4-triazol-1-yl)phenyl)-4-(3-fluoro-5-morpholinophenyl)pyrimidin-2-amine

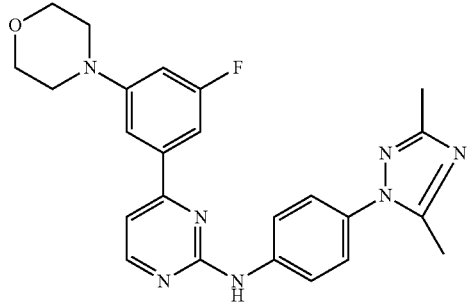 [SMILES: Cc1nc(C)n(-c2ccc(Nc3nccc(-c4cc(F)cc(N5CCOCC5)c4)n3)cc2)n1]

N-(4-(3,5-dimethyl-1H-1,2,4-triazol-1-yl)phenyl)-4-(3-fluoro-5-morpholinophenyl)pyrimidin-2-amine was obtained by following procedure E using 4-(3-(2-chloropyrimidin-4-yl)-5-fluorophenyl)morpholine and 4-(3,5-dimethyl-1H-1,2,4-triazol-1-yl)aniline. MS (ESI) 446.34 (M+H).

Example 334

4-(benzo[d][1,3]-dioxol-5-yl)-N-(4-(3-(4-ethylpiperazin-1-yl)-1H-1,2,4-triazol-1-yl)phenyl)pyrimidin-2-amine

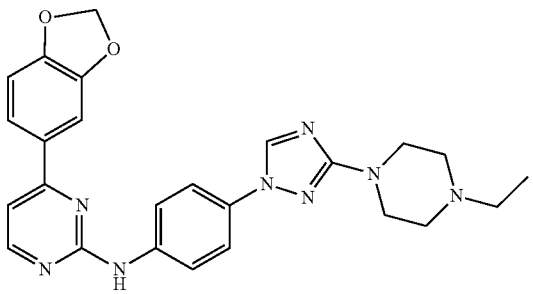 [SMILES: CCN1CCN(c2ncn(-c3ccc(Nc4nccc(-c5ccc6c(c5)OCO6)n4)cc3)n2)CC1]

4-(benzo[d][1,3]dioxol-5-yl)-N-(4-(3-(4-ethylpiperazin-1-yl)-1H-1,2,4-triazol-1-yl)phenyl)pyrimidin-2-amine was obtained by following procedure E using 4-(benzo[d][1,3]dioxol-5-yl)-2-chloropyrimidine and 4-(3-(4-ethylpiperazin-1-yl)-1H-1,2,4-triazol-1-yl)aniline. MS (ESI) 472.28 (M+H).

Example 335

N-(4-(3-(4-ethylpiperazin-1-yl)-1H-1,2,4-triazol-1-yl)phenyl)-4-(3-morpholinophenyl)pyrimidin-2-amine

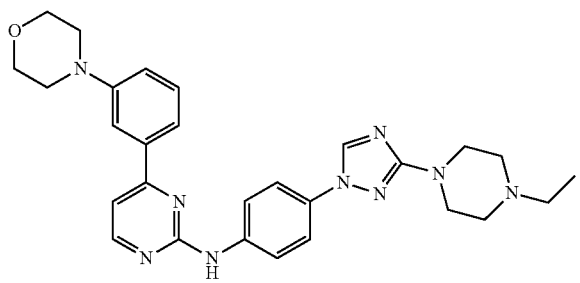 [SMILES: CCN1CCN(c2ncn(-c3ccc(Nc4nccc(-c5cccc(N6CCOCC6)c5)n4)cc3)n2)CC1]

N-(4-(3-(4-ethylpiperazin-1-yl)-1H-1,2,4-triazol-1-yl)phenyl)-4-(3-morpholinophenyl)pyrimidin-2-amine was obtained by following procedure Q using 4-(3-(2-chloropyrimidin-4-yl)phenyl)morpholine and 4-(3-(4-ethylpiperazin-1-yl)-1H-1,2,4-triazol-1-yl)aniline. MS (ESI) 512.33 (M+H).

Example 336

N-(4-(3-(4-ethylpiperazin-1-yl)-1H-1,2,4-triazol-1-yl)phenyl)-4-(3-morpholino-5-(trifluoromethyl)phenyl)pyrimidin-2-amine

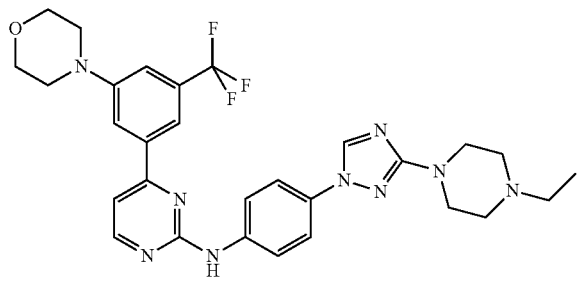 [SMILES: CCN1CCN(c2ncn(-c3ccc(Nc4nccc(-c5cc(N6CCOCC6)cc(C(F)(F)F)c5)n4)cc3)n2)CC1]

N-(4-(3-(4-ethylpiperazin-1-yl)-1H-1,2,4-triazol-1-yl)phenyl)-4-(3 morpholino-5-(trifluoromethyl)phenyl)pyrimidin-2-amine was obtained by following procedure Q using 4-(3-(2-chloropyrimidin-4-yl)-5-(trifluoromethyl)phenyl)morpholine and 4-(3-(4-ethylpiperazin-1-yl)-1H-1,2,4-triazol-1-yl)aniline. MS (ESI) 580.33 (M+H).

Example 337

N-(4-(3-(4-ethylpiperazin-1-yl)-1H-1,2,4-triazol-1-yl)phenyl)-4-(3-fluoro-5-morpholinophenyl)pyrimidin-2-amine

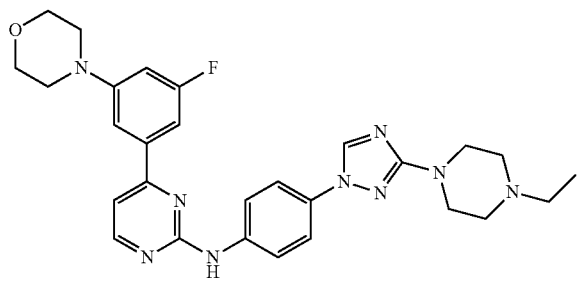 [SMILES: CCN1CCN(c2ncn(-c3ccc(Nc4nccc(-c5cc(F)cc(N6CCOCC6)c5)n4)cc3)n2)CC1]

N-(4-(3-(4-ethylpiperazin-1-yl)-1H-1,2,4-triazol-1-yl)phenyl)-4-(3-fluoro-5-morpholinophenyl)pyrimidin-2-amine was obtained by following procedure Q using 4-(3-(2-chloropyrimidin-4-yl)-5-fluorophenyl)morpholine and 4-(3-(4-ethylpiperazin-1-yl)-1H-1,2,4-triazol-1-yl)aniline. MS (ESI) 530.31 (M+H).

Biology

The compounds of the present invention are expected to be inhibitors of c-Jun N-terminal kinases (e.g., JNK-1, JNK-2, and JNK-3), particularly JNK-1 and JNK-3. c-Jun N-terminal kinase assays are known in the art and can be used to test compounds of the present invention. Examples of such assays are described below.

Expression and Purification of JNK3α1

A truncated JNK3α1 (pDest14_JNK3α1_39-422) plasmid expression construct expressing amino acids 39 to 422 of JNK3α1 was expressed in *E. coli* strain BL21(DE3) (Invitrogen) under the following conditions. 5 ml of a log phase culture grown in Luria Broth (Invitrogen) supplemented with 50 mg/ml ampicillin (Sigma) was transferred to 500 mls of the same medium and grown with shaking at 240 rpm at 30° C. At $A_{600}$=0.8 the culture was induced with 0.8 mM (final concentration) isopropylthio-b-D-galactoside (IPTG) (Invitrogen) and grown with shaking at 240 rpm at 30° C. for a further 2 hr and harvested by centrifugation 3000×g at 4° C. The cell pellet was resuspended in 10 ml of B-per lysis buffer (Pierce) and 1× protease inhibitor cocktail (Roche Biosciences) and lysed on ice for 10 min. The cell lysate was centrifuged at 20000×g for 30 min at 4° C. The lysate was diluted 10 fold with buffer A (20 mM HEPES pH7.0, 10% glycerol, 2 mM DTT) and applied to a 5 ml Fast Flow Sepharose SP column (GE Healthcare). The column was washed with 8 column volumes of buffer A and eluted with a 10 column volume linear gradient of 0-1M NaCl in buffer A. Fractions collected were analyzed by polyacrylamide gel electrophoresis (PAGE) and protein visualized by see blue stain (Invitrogen). Fractions containing JNK3α1 were pooled, diluted 10 fold with buffer A. and loaded on to a 1 ml mono s column (GE Healthcare). The column was washed with 8 column volumes of buffer A and eluted with a 10 column volume linear gradient of 0-1M NaCl in buffer A. Fractions collected were analyzed by PAGE and protein visualized by see blue stain (Invitrogen). Fractions containing JNK3α1 were pooled and concentrated using an Amicon Ultra centrifugation filter device (Milipore). The concentrated sample was loaded onto a gel filtration column and the fractions collected were analyzed by PAGE and see blue stain as before. Fractions containing JNK3α1 were estimated to be greater than 95% pure. These fractions were pooled, concentrated to 10 mg/ml using Amicon Ultra centrifugation filter device (Milipore) and stored at −80° C.

Expression and Purification of Bioease-ATF-2 (1-115)

The expression construct Bioease-ATF-2-Flag (pdest14_Bio_ATF-2_1-115_Flag) together with a construct containing the BirA gene (Avidity) was expressed in *E. coli* strain BL21(DE3) (Invitrogen) under the following conditions. 5 ml of a log phase culture grown in Luria Broth (Invitrogen) supplemented with 50 mg/ml ampicillin and 50 mg/ml chloramphenicol (Sigma) was transferred to 500 mls of the same medium and grown with shaking at 240 rpm and 30 C. At $A_{600}$=0.8 D-Biotin was added to the culture (50 μM final concentration). The culture was then induced with 0.8 mM (final concentration) isopropylthio-b-D-galactoside (IPTG) (invitrogen) and grown with shaking at 240 rpm at 30° C. for a further 2 hr and harvested by centrifugation 3000×g at 4 C. The cell pellet was resuspended in 10 ml of B-per lysis buffer (Pierce) and 1× protease inhibitor cocktail (Roche Biosciences) and lysed on ice for 10 min. Cell lysate was then centrifuged at 20000×g for 30 min at 4° C. The lysate was diluted 10 fold with buffer B (20 mM HEPES pH7.0, 150 mM NaCl) and applied to a 5 ml Flag M2 column (Sigma). The column was washed with 10 column volumes of buffer B and eluted via competition with the Flag peptide (100 ug/ml). Fractions collected were analyzed by polyacrylamide gel electrophoresis (PAGE) and protein visualized by see blue stain (Invitrogen) Fractions containing Bioease ATF-2 Flag were pooled and concentrated using Amicon Ultra centrifugation filter device (Milipore) and stored at −80° C.

Activation of JNK3α1

The JNK3α1 enzyme was activated as described by Lisnock J et al (2000). JNK3α1 (250 nM) enzyme was incubated for 2 hrs at 30° C. with 100 nM GST-MKK4, 50 nM GST-MKK7 (Upstate Biotechnology) and 200 µM ATP in 25 mM HEPES, pH 7.4, containing 0.1 mM $Na_3VO4$, 10 mM $MgCl_2$, 2 mM DTT, 20 mM b-glycerophosphate (SigmaAldrich). The phosphorylated JNK3α1 was diluted to the appropriate concentration and used as active enzyme in the enzyme inhibition studies.

JNK3α1 Inhibition Assay

Compounds were assayed for inhibition of JNK3α1 by a Homogenous Time Resolved Fluorescence (HTRF) assay, similar to Fricker et al (2005) (1). In this assay a fixed concentration of Bioease-ATF2 (400 nM) and ATP (1□M) was incubated with various concentrations of potential inhibitor dissolved in DMSO in a buffer containing 50 mM HEPES pH7.5, 2.5 mM $MgCl_2$, 1 mM DTT, 0.01% Triton X-100 and 01 mg/ml BSA. The assay was initiated by the addition of activated JNK3α1 (0.3 nM) and incubated at room temperature for 30 min. The assay was conducted in a 384 low volume plate in a total volume of 10 µl per well. The enzymatic reaction was stopped by the addition of an equal volume of detection reagents, 200 nM Streptavidin XL665 and 1 nM Europium Cryptate anti-p ATF-2 (ser71) antibody (CisBio) in a buffer containing 50 mM HEPES pH7.5, 14 mM EDTA, 200 mM KF and 0.01% Triton X-100. The assay was incubated for 1 hr at room temperature and the plate inserted into a Perkin Elmer Viewlux spectrophotometer. Following laser excitation at 337 nM, a ratio is calculated from the long lived energy transfer signal from the acceptor engaged in the FRET process with the Europium Cryptate p-ATF-2 antibody (665 nM) and the emission signal of the Cryptate (620 nM). The signal produced is proportional to the amount of JNK3α1 kinase activity present during the reaction phase of the assay. $IC_{50}$ values were determined using a four parameter logistic and a 10 point dilution curve for each of the inhibitors covering four orders of magnitude of inhibitor concentration. A basal activity control in the absence of kinase and a maximal activity control in the absence of any inhibitor were included for statistical analysis.

JNK1α1 Inhibition Assay.

Compounds were assayed for inhibition of JNK1α1 (Upstate Biotechnology) by a Homogenous Time Resolved Fluorescence (HTRF) assay. In this assay a fixed concentration of Bioease-ATF2 (400 nM) and ATP (1 µM) was incubated with various concentrations of potential inhibitor dissolved in DMSO in a buffer containing 50 mM HEPES pH7.5, 2.5 mM $MgCl_2$, 1 mM DTT, 0.01% Triton X-100 and 01 mg/ml BSA. The assay was initiated by the addition of activated JNK1α1 (0.25 nM) and incubated at room temperature for 15 min. The assay was conducted in a 384 low volume plate in a total volume of 10 µl per well. The enzymatic reaction was stopped by the addition of an equal volume of detection buffer, containing 200 nM Streptavidin XL665 and 1 nM Europium Cryptate anti-p ATF-2 (ser71) antibody (CisBio) in a buffer containing 50 mM HEPES pH7.5, 14 mM EDTA, 200 mM KF and 0.01% Triton X-100. The assay was incubated for 1 hr at room temperature and the plate inserted into a Perkin Elmer Viewlux spectrophotometer. After excitation at 337 nM, the long lived energy transfer signal from the acceptor engaged in the FRET process with the Europium Cryptate p-ATF-2 antibody was measured together with the emission signal of the Cryptate. $IC_{50}$ values were determined in a similar manner to the JNK3α1 inhibition assay Cell Based $IC_{50}$ Determination Compounds were assayed for their ability to inhibit phosphorylation of c-jun within the cell by an Enzyme Linked Immunoabsorbent Sandwich Assay (ELISA). In this assay INS-1β pancreatic cells were plated in a 96 well tissue culture plate at $3.5 \times 10^5$ cells/well (Corning) in a media containing DMEM and 10% FBS (Gibco) and incubated overnight at 37° C. in 5% $CO_2$. An assay plate was prepared by coating a 96 half well plate (Costar) with 500 µl/well p-c-jun capture antibody (Cell Signaling). The plate was covered tight and stored at 4° C. for 16 hr. The contents of the assay plate were discarded and the plate was washed with wash buffer C (Phosphate buffered saline pH7.4 0.5% Tween20). 100 µl of blocking buffer (Cell Signaling) was added to each well of the assay plate, covered tight and incubated at room temperature for 2 hr. The contents of the assay plate were discarded and the plate was washed with wash buffer C as before. The cell lysates for the assay were prepared in the following manner. The cells were first incubated with 4 mM Streptozoicin containing various concentrations of potential inhibitor dissolved in DMSO for 3 hr at 37° C. in 5% $CO_2$. A basal activity control in the absence of Streptozoicin and a maximal activity control in the absence of any inhibitor were included for statistical analysis. After treatment the media was removed and the cells were washed in ice cold PBS. The PBS was removed and the cells were lysed in ice cold lysis buffer (100 µl/well. Cell Signaling) containing 1× protease (Roche) and 1× phosphatase inhibitors (Sigma). The lysates were then transferred to the corresponding well of the blocked assay plate, covered tight and incubated 16 hr at 4° C. The assay plate was then washed in buffer C four times. The c-jun detection antibody (50 µl/well Cell Signaling) was added to each well and incubated at room temperature for 1 hr. The assay plate was then washed in buffer C four times. A secondary anti mouse coupled HRP is added (50 µl/well Cell Signaling) and incubated at room temperature for 1 hr. The assay plate was then washed in buffer C four times. 50 µl of TMB substrate (BioFX Laboratories) is added to each well and incubated for 5-10 min at room temperature. 50 µl of stop solution is added to each well and the plate is read immediately on a microplate reader at an absorbance of 450 nm. $IC_{50}$ values were determined using a four parameter logistic and a 10 point dilution curve for each of the inhibitors covering four orders of magnitude of inhibitor concentration. [See Fricker, M., Lograsso, P., Ellis, S., Wilkie, N., Hunt, P., and Pollack, S. J. (2005), *Substituting c-Jun N-terminal kinase-3 (JNK3) ATP-binding site amino acid residues with their p38 counterparts affects binding of JNK-and p38-selective inhibitors*, Arch Biochem Biophys 438, 195-205.

Compounds tested in the assays described herein are considered to be active if they exhibit an $IC_{50}$ of ≤10 µM. Additional examples of activity include $IC_{50}$'s of ≤1 µM, ≤0.1 µM, ≤0.01 µM, and of ≤0.001 µM. Using the methodology described herein, a number of compounds of the present invention were found to exhibit $IC_{50}$'s of ≤10 µM, thereby confirming the utility of the compounds of the present invention as effective JNK inhibitors.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and

211 modifications can be made without departing from the spirit of the invention. It is, therefore, intended that the appended claims cover all such equivalent variations as fall within the true spirit and scope of the invention.

Embodiment 1

A compound or pharmaceutically acceptable salt thereof of formula Ib:

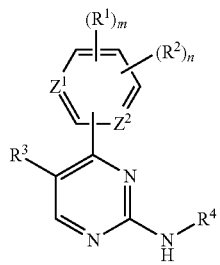

Ib wherein:

$Z^1$ and $Z^2$ are each independently CH or N;

each $R^1$ is independently Cl, F, Br, I, $CF_3$, $OCF_3$, $C_{1-6}$alkyl substituted with 0-2 $R^5$, $C_{2-6}$alkenyl substituted with 0-2 $R^5$, $C_{2-6}$alkynyl substituted with 0-2 $R^5$, $(CH_2)_pNO_2$, $(CH_2)_pCN$, $(CH_2)_pOR$, $(CH_2)_pN(R)_2$, $(CH_2)_pCOR$, $(CH_2)_pOCOR$, $(CH_2)_pCO_2R$, $(CH_2)_pCON(R)_2$, $(CH_2)_pOCON(R)_2$, $(CH_2)_pNRCOR$, $(CH_2)_pNRCO_2R$, $(CH_2)_pNRCON(R)_2$, $(CH_2)_pC(=NH)NH_2$, $(CH_2)_pSOR$, $(CH_2)_pSO_2R$, $(CH_2)_pSO_2N(R)_2$, $(CH_2)_pNRSO_2R$, $(CH_2)_pNRSO_2N(R)_2$, $(CH_2)_p$-(3- to 10-membered carbocyclic ring substituted with 0-2 $R^5$), or $(CH_2)_p$-(4- to 10-membered heterocyclic ring having 1 to 4 heteroatom ring members selected from O, $S(O)_q$, and N), wherein the heterocyclic ring is substituted with 0-2 $R^5$, or two of $R^1$ that are attached to adjacent ring carbon atoms are taken together with the ring atoms through which they are connected to form a 5- to 6-membered heterocycloalkyl having 1 or 2 oxygen ring heteroatoms;

each $R^2$ is independently Cl, F, Br, I, $CF_3$, $OCF_3$, $C_{1-4}$alkyl, $C_{2-4}$alkenyl, $C_{2-4}$alkynyl, $NO_2$, —CN, $OR^a$, $N(R^a)_2$, $COR^a$, $CO_2R^a$, or $CON(R^a)_2$; or $R^1$ and $R^2$ that are attached to adjacent ring carbon atoms are taken together with the ring atoms through which they are connected to form a 5- to 6-membered heterocycloalkyl having 1 or 2 oxygen ring members;

$R^3$ is H, $CH_3$, $CH_2CH_3$, cyano, Cl, F, Br, or I;

$R^4$ is 3- to 10-membered carbocyclic ring substituted with 0-2 $R^{4a}$ or 5- to 10-membered heterocyclic ring having 1 to 4 heteroatom ring members selected from O, $S(O)_q$, and N, wherein the heterocyclic ring is substituted with 0-2 $R^{4a}$;

each $R^{4a}$ is independently =O, Cl, F, Br, I, $CF_3$, $OCF_3$, $C_{1-6}$alkyl substituted with 0-3 $R^5$, $C_{2-6}$alkenyl substituted with 0-3 $R^5$, $C_{2-6}$alkynyl substituted with 0-3 $R^5$, $(CH_2)_pNO_2$, $(CH_2)_pCN$, $(CH_2)_pOR$, $(CH_2)_pN(R)_2$, $(CH_2)_pCOR$, $(CH_2)_pOCOR$, $(CH_2)_pCO_2R$, $(CH_2)_pCON(R)_2$, $(CH_2)_pOCON(R)_2$, $(CH_2)_pNRCOR$, $(CH_2)_pNRCO_2R$, $(CH_2)_pNRCON(R)_2$, $(CH_2)_pC(=NH)NH_2$, $(CH_2)_pSO_2R$, $(CH_2)_pSO_2N(R)_2$, $(CH_2)_pNRSO_2R$, $(CH_2)_pNRSO_2N(R)_2$, $CH(CF_3)NH_2$, or $(CH_2)_p$-(5- to 6-membered heterocyclic ring) having 1 to 4 heteroatom ring members selected from O, $S(O)_q$, and N), wherein the heterocyclic ring is substituted with 0-3 $R^{5a}$;

212 each R is independently H, $C_{1-6}$alkyl substituted with 0-2 $R^5$, $C_{2-6}$alkenyl substituted with 0-2 $R^5$, $C_{2-6}$alkynyl substituted with 0-2 $R^5$, 3- to 10-membered carbocyclic ring substituted with 0-2 $R^5$, or 5- to 10-membered heterocyclic ring having 1 to 4 heteroatom ring members selected from O, $S(O)_q$, and N, wherein the heterocyclic ring is substituted with 0-2 $R^5$; or two R attached to the same N atom are taken together with the nitrogen atom to which they are attached to form a 5- to 8-membered heterocyloalkyl substituted with 0-2 $R^5$ each $R^5$ is independently =O, Cl, F, Br, I, $CF_3$, $OCF_3$, $C_{1-4}$alkyl, $C_{2-4}$alkenyl, $C_{2-4}$alkynyl, $NO_2$, —CN, $OR^a$, $N(R^a)_2$, $COR^a$, $CO_2R^a$, $CON(R^a)_2$, $NR^aCOR^a$, $NR^aCO_2R^a$, $NR^aCON(R^a)_2$, $C(=NH)NH_2$, $SO_2R^a$, $SO_2N(R^a)_2$, $NR^aSO_2R^a$, $NR^aSO_2N(R^a)_2$, $(CH_2)_p$-(3- to 10-membered carbocyclic ring substituted with 0-2 $R^b$), or $(CH_2)_p$-(5- to 10-membered heterocyclic ring having 1 to 4 heteroatom ring members selected from O, $S(O)_q$, and N), wherein the heterocyclic ring is substituted with substituted with 0-2 $R^b$; or two $R^5$ taken together with a carbon atom to which they are both connected form a 1,3-dioxolane ring wherein the two oxygen ring atoms are attached to the connecting carbon atom;

$R^{5a}$ is selected from =O, Cl, F, Br, I, $CF_3$, $OCF_3$, $C_{1-4}$alkyl, $C_{2-4}$alkenyl, $C_{2-4}$alkynyl, $NO_2$, —CN, $(CH_2)_pOR^a$, $N(R^a)_2$, $COR^a$, $CO_2R^a$, $CON(R^a)_2$, $NR^aCOR^a$, $NR^aCO_2R^a$, $NR^aCON(R^a)_2$, $C(=NH)NH_2$, $SO_2R^a$, $SO_2N(R^a)_2$, $NR^aSO_2R^a$, $NR^aSO_2N(R^a)_2$, $(CH_2)_p$-(3- to 10-membered carbocyclic ring substituted with 0-2 $R^b$, or $(CH_2)_p$-(5- to 10-membered heterocyclic ring having 1 to 4 heteroatom ring members selected from O, $S(O)_q$, and N), wherein the heterocyclic ring is substituted with 0-2 $R^b$;

each $R^a$ is independently H, $C_{1-4}$alkyl, $C_{3-6}$ cycloalkyl, $CH_2$—$C_{3-6}$ cycloalkyl, phenyl, or benzyl; or two $R^a$ attached to the same N atom are taken together with the nitrogen atom to which they are attached to form a 5- to 8-membered heterocycloalkyl;

$R^b$ is H, Cl, F, Br, I, $CF_3$, $OCF_3$, $C_{1-4}$alkyl optionally substituted with $OR^a$, $C_{2-4}$alkenyl, $C_{2-4}$alkynyl, $NO_2$, —CN, $OR^a$, $N(R^a)_2$, $COR^a$, $CO_2R^a$, or $CON(R^a)_2$;

p is 0, 1, 2, 3, or 4; and m and n are each independently the integer 0, 1, or 2, provided that the sum of m+n is 0, 1, or 2;

with the provisos that:

(1) when $R^4$ is:

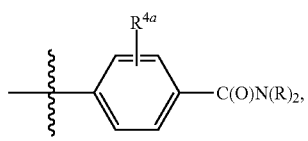

then $R^{4a}$ is other than =O, halo, $C_{1-6}$alkyl, OH, or O—$C_{1-6}$alkyl;

(2) when $R^4$ is:

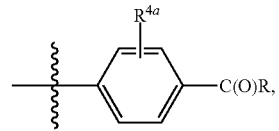

wherein R is a heterocyclic ring attached through a nitrogen ring atom; then $R^{4a}$ is other than halo, alkyl, OH, or O-alkyl.

(3) when $R^4$ is phenyl and at least one of $R^{4a}$ is $(CH_2)_p$-(5- to 6-membered heterocyclic ring wherein p is 0, 1, or 2, then the heterocyclic ring has 3 or 4 heteroatom ring members;

(4) when $R^4$ is phenyl and at least one of $R^{4a}$ is $(CH_2)_p$-(5- to 6-membered heterocyclic ring having one or two heteroatom ring members, then p is 3 or 4, (5) when $R^4$ is phenyl and is substituted with only one $R^{4a}$, then $R^{4a}$ is =O, Br, I, $CF_3$, $OCF_3$, $C_{1-6}$alkyl substituted with 0-3 $R^5$, $C_{2-6}$alkenyl substituted with 0-3 $R^5$, $C_{2-6}$alkynyl substituted with 0-3 $R^5$, $(CH_2)_pNO_2$, $(CH_2)_pOCOR$, $(CH_2)_pO$-$CON(R)_2$, $(CH_2)_pNRCON(R)_2$, $(CH_2)_pC(=NH)NH_2$, $(CH_2)_pNRSO_2N(R)_2$, $CH(CF_3)NH_2$, or $(CH_2)_p$-(5- to 6-membered heterocyclic ring; and (6) the compound of formula I or pharmaceutically acceptable salt thereof is other than:
N-[3-({4-[4-(acetylamino)phenyl]pyrimidin-2-yl}amino)cyclohexyl]-2,6-dichlorobenzamide;
N-[4-(2-{[4-(1,4-dioxa-8-azaspiro[4.5]dec-8-yl)phenyl]amino}pyrimidin-4-yl)phenyl]acetamide;
N-{4-[2-(1H-indazol-6-ylamino)-5-methylpyrimidin-4-yl]phenyl}acetamide;
N-{4-[2-(1H-indol-5-ylamino)-5-methylpyrimidin-4-yl]phenyl}acetamide;
N-{4-[2-(1H-indazol-5-ylamino)-5-methylpyrimidin-4-yl]phenyl}acetamide;
'N-[6-({4-[4-(acetylamino)phenyl]pyrimidin-2-yl}amino)pyridin-2-yl]-2,6-dichlorobenzamide
'N-[6-({4-[4-(acetylamino)phenyl]pyrimidin-2-yl}amino)pyrimidin-4-yl]-2,6-dichlorobenzamide;
N-(4-{2-[(6-aminopyridin-2-yl)amino]pyrimidin-4-yl}phenyl)acetamide;
N-(4-{2-[(6-aminopyrimidin-4-yl)amino]pyrimidin-4-yl}phenyl)acetamide;
(R)—N-(4-(2-(1,2,3,4-tetrahydroquinolin-6-ylamino)pyrimidin-4-yl)phenyl) pyrrolidine-2-carboxamide;
(R)—N-(4-(2-(6-morpholinopyridin-3-ylamino)pyrimidin-4-yl)phenyl)pyrrolidine-2-carboxamide;
N-{4-[2-(1H-benzimidazol-6-ylamino)-5-methylpyrimidin-4-yl]phenyl}acetamide;
ethyl 4-({4-[(acetylamino)phenyl]pyrimidin-2-yl}aminopiperidine-1-carboxylate;
1,1-dimethylethyl 4-({4-[4-(acetylamino)phenyl]pyrimidin-2-yl}amino)piperidine-1-carboxylate;
N-{4-[2-(piperidin-4-ylamino)pyrimidin-4-yl]phenyl}acetamide; or
N-{4-[2-({1-[(2,6-dichlorophenyl)carbonyl]piperidin-4-yl}amino)pyrimidin-4-yl]phenyl}acetamide.

Embodiment 2

A compound or pharmaceutically acceptable salt thereof according to Embodiment 1, wherein $R^4$ is an aromatic carbocyclic ring.

Embodiment 3

A compound or pharmaceutically acceptable salt thereof according to Embodiment 1 or 2, wherein $R^4$ is phenyl substituted with 0-2 $R^{4a}$.

Embodiment 4

A compound or pharmaceutically acceptable salt thereof according to Embodiment 1, 2, or 3, wherein at least one of $R^{4a}$ is —$(CH_2)_p$-(5- to 6-membered heterocyclic ring).

Embodiment 5

A compound or pharmaceutically acceptable salt thereof according to Embodiment 1, 2, 3, or 4, wherein p is 0 or 1.

Embodiment 6

A compound or pharmaceutically acceptable salt thereof according to Embodiment 1, 2, 3, 4, or 5, wherein p is 0.

Embodiment 7

A compound or pharmaceutically acceptable salt thereof according to Embodiment 1, 2, 3, 4, 5, or 6, wherein $R^{4a}$ is -(5- to 6-membered heteroaromatic ring).

Embodiment 8

A compound or pharmaceutically acceptable salt thereof according to Embodiment 1, 2, 3, 4, 5, 6, or 7, wherein $R^{4a}$ is -(5-membered heteroaromatic ring).

Embodiment 9

A compound or pharmaceutically acceptable salt thereof according to Embodiment 1, 2, 3, 4, 5, 6, 7, or 8, wherein the heteroaromatic ring of $R^{4a}$ has 2, 3, or 4 heteroatom ring members are selected from N, O, and S heteroatoms.

Embodiment 10

A compound or pharmaceutically acceptable salt thereof according to Embodiment 1, 2, 3, 4, 5, 6, 7, 8, or 9, wherein the heteroaromatic ring of $R^{4a}$ heteroatom ring members are selected from N and O heteroatoms.

Embodiment 11

A compound or pharmaceutically acceptable salt thereof according to Embodiment 1, 2, 3, 4, 5, 6, 7, 8, 9, or 10, wherein the heteroaromatic ring of $R^{4a}$ has 3 or 4 heteroatom ring members.

Embodiment 12

A compound or pharmaceutically acceptable salt thereof according to Embodiment 1, 2, 3, 4, 5, 6, 7, 8, 9, 10, or 11, wherein the heteroaromatic ring of $R^{4a}$ is substituted with Cl, F, Br, $CF_3$, $C_{1-4}$alkyl, $C_{2-4}$alkenyl, $(CH_2)_pOR^a$, $N(R^a)_2$, $(CH_2)_p$-(3- to 10-membered carbocyclic ring substituted with 0-2 $R^b$, or $(CH_2)_p$-(5- to 10-membered heterocyclic ring having 1 to 4 heteroatom ring members selected from O, $S(O)_q$, and N, wherein the heterocyclic ring is substituted with 0-2 $R^b$.

Embodiment 13

A compound or pharmaceutically acceptable salt thereof according to Embodiment 1, 2, 3, 4, 5, 6, 7, 8, 9, 10, 11, or 12, wherein the heteroaromatic ring of $R^{4a}$ is substituted with phenyl or benzyl.

Embodiment 14

A compound or pharmaceutically acceptable salt thereof according to Embodiment 1, 2, 3, 4, 5, 6, 7, 8, 9, 10, 11, or 12, wherein the heteroaromatic ring of $R^{4a}$ is substituted with CH$_2$)$_p$-(5- to 10-membered heterocyclic ring, and wherein the (CH$_2$)$_p$-(5- to 10-membered heterocyclic ring is optionally substituted with Cl, F, CF$_3$, C$_{1-4}$alkyl optionally substituted with OR$^a$, —CN, or OR$^a$.

Embodiment 15

A compound or pharmaceutically acceptable salt thereof according to Embodiment 1, 2, or 3, wherein when the heteroaromatic ring of R$^{4a}$ is substituted with (CH$_2$)$_p$-(5- to 10-membered heterocyclic ring, wherein the 5- to 10-membered heterocyclic ring is pyridinyl, morpholinyl, piperidinyl, or piperazinyl, each optionally substituted.

Embodiment 16

A compound or pharmaceutically acceptable salt thereof according to Embodiment 1, 3, or 15, wherein R$^4$ is a 5- to 10-membered heterocyclic ring having 1 to 4 heteroatom ring members selected from O, S(O)$_q$, and N, wherein the heterocyclic ring is substituted with 0-2 R$^{4a}$.

Embodiment 17

A compound or pharmaceutically acceptable salt thereof according to Embodiment 1, 3, 15, 16, wherein the heterocyclic ring is indazolyl, pyrazolyl, or piperidinyl, each optionally substituted.

Embodiment 18

A compound or pharmaceutically acceptable salt thereof according to Embodiment 1, 3, 15, 16, or 17, wherein the indazolyl, pyrazolyl, or piperidinyl, is optionally substituted with Cl, F, C$_{1-6}$alkyl substituted with 0-3 R$^5$, (CH$_2$)$_p$OR, (CH$_2$)$_p$CON(R)$_2$, (CH$_2$)$_p$NRCO$_2$R, or CH(CF$_3$)NH$_2$.

Embodiment 19

A compound or pharmaceutically acceptable salt thereof according to Embodiment 1, 2, 3, 4, 5, 6, 7, 8, 9, 10, 11, 12, 13, 14, 15, 16, 17, or 18, wherein at least one of Z$^1$ and Z$^2$ is CH.

Embodiment 20

A compound or pharmaceutically acceptable salt thereof according to Embodiment 1, 2, 3, 4, 5, 6, 7, 8, 9, 10, 11, 12, 13, 14, 15, 16, 17, 18, or 19, wherein Z$^1$ and Z$^2$ are each CH.

Embodiment 21

A compound or pharmaceutically acceptable salt thereof according to Embodiment 1, 2, 3, 4, 5, 6, 7, 8, 9, 10, 11, 12, 13, 14, 15, 16, 17, 18, 19, or 20, wherein R$^3$ is H or F.

Embodiment 22

A compound or pharmaceutically acceptable salt thereof according to Embodiment 1, 2, 3, 4, 5, 6, 7, 8, 9, 10, 11, 12, 13, 14, 15, 16, 17, 18, 19, 20, or 21, wherein R$^3$ is H.

Embodiment 23

A compound or pharmaceutically acceptable salt thereof according to Embodiment 1, 2, 3, 4, 5, 6, 7, 8, 9, 10, 11, 12, 13, 14, 15, 16, 17, 18, 19, 20, 21, or 22, wherein R$^1$ is Cl, F, Br, CF$_3$, (CH$_2$)$_p$CN, (CH$_2$)$_p$OR, (CH$_2$)$_p$N(R)$_2$, (CH$_2$)$_p$COR, (CH$_2$)$_p$OCOR, (CH$_2$)$_p$CO$_2$R, (CH$_2$)$_p$CON(R)$_2$, (CH$_2$)$_p$OCON(R)$_2$, (CH$_2$)$_p$SOR, (CH$_2$)$_p$SO$_2$R, (CH$_2$)$_p$NRSO$_2$R, (CH$_2$)$_p$-(3- to 10-membered carbocyclic ring substituted with 0-2 R$^5$), or (CH$_2$)$_p$-(4- to 10-membered heterocyclic ring having 1 to 4 heteroatom ring members selected from O, S(O)$_q$, and N), wherein the heterocyclic ring is substituted with 0-2 R$^5$, or two of R$^1$ that are attached to adjacent ring carbon atoms are taken together with the ring atoms through which they are connected to form a 5- to 6-membered heterocycloalkyl having 1 or 2 oxygen ring heteroatoms.

Embodiment 24

A compound or pharmaceutically acceptable salt thereof according to Embodiment 1, 2, 3, 4, 5, 6, 7, 8, 9, 10, 11, 12, 13, 14, 15, 16, 17, 18, 19, 20, 21, 22, or 23, wherein R$^2$ is Cl, F, Br, CF$_3$, NO$_2$, —CN, OR$^a$, N(R$^a$)$_2$, or CON(R$^a$)$_2$; or R$^1$ and R$^2$ that are attached to adjacent ring carbon atoms are taken together with the ring atoms through which they are connected to form a 5- to 6-membered heterocycloalkyl having 1 or 2 oxygen ring members.

Embodiment 25

A compound or pharmaceutically acceptable salt thereof according to Embodiment 1, wherein the compound is selected from Examples 1, 4-25, 27-43, 45-47, 49-55, 57, 59, 72-77, 79-85, 89-94, 96, 98-101, 103, 105-119, 121, 122, 125-174, and 176-337.

Embodiment 26

A compound or pharmaceutically acceptable salt thereof selected from the group consisting of Examples 2, 3, 26, 44, 48, 56, 58, 60, 61, 78, 86, 87, 88, 95, 97, 102, 104, 120, 123, 124, and 175.

Embodiment 27

A pharmaceutical composition, comprising:
a pharmaceutically acceptable carrier; and
an effective amount of a compound or a pharmaceutically acceptable salt thereof according to Embodiment 1 or Embodiment 26.

Embodiment 28 method of treating a disease or condition responsive to the inhibition of the JNK pathway, comprising: administering to a patient in need thereof a therapeutically effective amount of a compound or a pharmaceutically acceptable salt thereof of formula Ic:

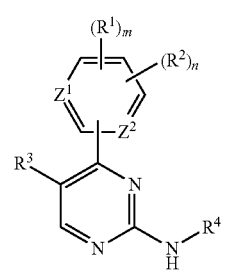

Ic wherein:
Z$^1$ and Z$^2$ are each independently CH or N;
each R$^1$ is independently Cl, F, Br, I, CF$_3$, OCF$_3$, C$_{1-6}$alkyl substituted with 0-2 R$^5$, C$_{2-6}$alkenyl substituted with 0-2 R$^5$, C$_{2-6}$alkynyl substituted with 0-2 R$^5$, (CH$_2$)$_p$NO$_2$, (CH$_2$)$_p$CN, (CH$_2$)$_p$OR, (CH$_2$)$_p$N(R)$_2$, (CH$_2$)$_p$COR, (CH$_2$)$_p$OCOR, (CH$_2$)$_p$CO$_2$R, (CH$_2$)$_p$CON(R)$_2$, (CH$_2$)$_p$OCON(R)$_2$, (CH$_2$)$_p$NRCOR, (CH$_2$)$_p$NRCO$_2$R, (CH$_2$)$_p$ NRCON(R)$_2$, (CH$_2$)$_p$C(=NH)NH$_2$, (CH$_2$)$_p$SOR, (CH$_2$)$_p$SO$_2$R, (CH$_2$)$_p$SO$_2$N(R)$_2$, (CH$_2$)$_5$NRSO$_2$R, (CH$_2$)$_p$NRSO$_2$N(R)$_2$, (CH$_2$)$_p$-(3- to 10-membered carbocyclic ring substituted with 0-2 R$^5$), or (CH$_2$)$_p$-(4- to 10-membered heterocyclic ring having 1 to 4 heteroatom ring members selected from O, S(O)$_q$, and N), wherein the heterocyclic ring is substituted with 0-2 R$^5$, or two of R$^1$ that are attached to adjacent ring carbon atoms are taken together with the ring atoms through which they are connected to form a 5- to 6-membered heterocycloalkyl having 1 or 2 oxygen ring heteroatoms;

each R$^2$ is independently Cl, F, Br, I, CF$_3$, OCF$_3$, C$_{1-4}$alkyl, C$_{2-4}$alkenyl, C$_{2-4}$alkynyl, NO$_2$, —CN, OR$^a$, N(R$^a$)$_2$, COR$^a$, CO$_2$R$^a$, or CON(R$^a$)$_2$; or R$^1$ and R$^2$ that are attached to adjacent ring carbon atoms are taken together with the ring atoms through which they are connected to form a 5- to 6-membered heterocycloalkyl having 1 or 2 oxygen ring members;

R$^3$ is H, CH$_3$, CH$_2$CH$_3$, cyano, Cl, F, Br, or I;

R$^4$ is 3- to 10-membered carbocyclic ring substituted with 0-2 R$^{4a}$ or 5- to 10-membered heterocyclic ring having 1 to 4 heteroatom ring members selected from O, S(O)$_q$, and N, wherein the heterocyclic ring is substituted with 0-2 R$^{4a}$;

each R$^{4a}$ is independently =O, Cl, F, Br, I, CF$_3$, OCF$_3$, C$_{1-6}$alkyl substituted with 0-3 R$^5$, C$_{2-6}$alkenyl substituted with 0-3 R$^5$, C$_{2-6}$alkynyl substituted with 0-3 R$^5$, (CH$_2$)$_p$NO$_2$, (CH$_2$)$_p$CN, (CH$_2$)$_p$OR, (CH$_2$)$_p$N(R)$_2$, (CH$_2$)$_p$COR, (CH$_2$)$_p$OCOR, (CH$_2$)$_p$CO$_2$R, (CH$_2$)$_p$CON(R)$_2$, (CH$_2$)$_p$OCON(R)$_2$, (CH$_2$)$_p$NRCOR, (CH$_2$)$_5$NRCO$_2$R, (CH$_2$)$_p$NRCON(R)$_2$, (CH$_2$)$_p$C(=NH)NH$_2$, (CH$_2$)$_p$SO$_2$R, (CH$_2$)$_p$SO$_2$N(R)$_2$, (CH$_2$)$_p$NRSO$_2$R, (CH$_2$)$_p$NRSO$_2$N(R)$_2$, CH(CF$_3$)NH$_2$, or (CH$_2$)$_p$-(5- to 6-membered heterocyclic ring) having 1 to 4 heteroatom ring members selected from O, S(O)$_q$, and N), wherein the heterocyclic ring is substituted with 0-3 R$^{5a}$;

each R is independently H, C$_{1-6}$alkyl substituted with 0-2 R$^5$, C$_{2-6}$alkenyl substituted with 0-2 R$^5$, C$_{2-6}$alkynyl substituted with 0-2 R$^5$, 3- to 10-membered carbocyclic ring substituted with 0-2 R$^5$, or 5- to 10-membered heterocyclic ring having 1 to 4 heteroatom ring members selected from O, S(O)$_q$, and N, wherein the heterocyclic ring is substituted with 0-2 R$^5$; or two R attached to the same N atom are taken together with the nitrogen atom to which they are attached to form a 5- to 8-membered heterocyloalkyl substituted with 0-2 R$^5$ each R$^5$ is independently =O, Cl, F, Br, I, CF$_3$, OCF$_3$, C$_{1-4}$alkyl, C$_{2-4}$alkenyl, C$_{2-4}$alkynyl, NO$_2$, —CN, OR$^a$, N(R$^a$)$_2$, COR$^a$, CO$_2$R$^a$, CON(R$^a$)$_2$, NR$^a$COR$^a$, NR$^a$CO$_2$R$^a$, NR$^a$CON(R$^a$)$_2$, C(=NH)NH$_2$, SO$_2$R$^a$, SO$_2$N(R$^a$)$_2$, NR$^a$SO$_2$R$^a$, NR$^a$SO$_2$N(R$^a$)$_2$, (CH$_2$)$_p$-(3- to 10-membered carbocyclic ring substituted with 0-2 R$^b$), or (CH$_2$)$_p$-(5- to 10-membered heterocyclic ring having 1 to 4 heteroatom ring members selected from O, S(O)$_q$, and N), wherein the heterocyclic ring is substituted with substituted with 0-2 R$^b$; or two R$^5$ taken together with a carbon atom to which they are both connected form a 1,3-dioxolane ring wherein the two oxygen ring atoms are attached to the connecting carbon atom;

R$^{5a}$ is selected from =O, Cl, F, Br, I, CF$_3$, OCF$_3$, C$_{1-4}$alkyl, C$_{2-4}$alkenyl, C$_{2-4}$alkynyl, NO$_2$, —CN, (CH$_2$)$_p$OR$^a$, N(R$^a$)$_2$, COR$^a$, CO$_2$R$^a$, CON(R$^a$)$_2$, NR$^a$COR$^a$, NR$^a$CO$_2$R$^a$, NR$^a$CON(R$^a$)$_2$, C(=NH)NH$_2$, SO$_2$R$^a$, SO$_2$N(R$^a$)$_2$, NR$^a$SO$_2$R$^a$, NR$^a$SO$_2$N(R$^a$)$_2$, (CH$_2$)$_p$-(3- to 10-membered carbocyclic ring substituted with 0-2 R$^b$, or (CH$_2$)$_p$-(5- to 10-membered heterocyclic ring having 1 to 4 heteroatom ring members selected from O, S(O)$_q$, and N), wherein the heterocyclic ring is substituted with 0-2 R$^b$;

each R$^a$ is independently H, C$_{1-4}$alkyl, C$_{3-6}$ cycloalkyl, CH$_2$—C$_{3-6}$ cycloalkyl, phenyl, or benzyl; or two R$^a$ attached to the same N atom are taken together with the nitrogen atom to which they are attached to form a 5- to 8-membered heterocycloalkyl;

R$^b$ is H, Cl, F, Br, I, CF$_3$, OCF$_3$, C$_{1-4}$alkyl optionally substituted with OR$^a$, C$_{2-4}$alkenyl, C$_{2-4}$alkynyl, NO$_2$, —CN, OR$^a$, N(R$^a$)$_2$, COR$^a$, CO$_2$R$^a$, or CON(R$^a$)$_2$;

p is 0, 1, 2, 3, or 4; and m and n are each independently the integer 0, 1, or 2, provided that the sum of m+n is 0, 1, or 2.

Embodiment 29

A method of treating a disease or condition responsive to the inhibition of the JNK pathway, comprising: administering to a patient in need thereof a therapeutically effective amount of a compound or a pharmaceutically acceptable salt thereof according to Embodiment 1 or 26.

Embodiment 30

A method of Embodiment 28 or Embodiment 29, wherein the disease or condition is selected from an inflammatory disease, an autoimmune disease, a cardiovascular disease, a metabolic disease, an ischemic disease, an infectious disease, and a proliferative disease.

Embodiment 31

A method of Embodiment 30, wherein the disease or condition is selected from Parkinson's disease, stroke, diabetes, cancer, myocardial infarction, multiple sclerosis, pulmonary fibrosis, and Alzheimers and pre-Alzheimers diseases.

What is claimed is:

1. A method of treating a disease or condition responsive to the inhibition of the JNK pathway, wherein the disease or condition is any of Parkinson's disease, stroke, diabetes, cancer, myocardial infarction, multiple sclerosis, pulmonary fibrosis, and Alzheimers and pre-Alzheimers diseases, comprising: administering to a patient in need thereof a therapeutically effective amount of a compound or a pharmaceutically acceptable salt thereof of formula Ic:

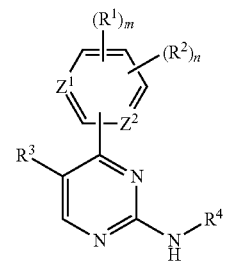

wherein:

Z$^1$ and Z$^2$ are each CH;

R$^1$ is a (4- to 10-membered) heterocyclic ring having 1 to 4 heteroatom ring members selected from O, S(O)$_q$, and N, wherein the heterocyclic ring is substituted with 0-2 R$^5$;

R² is independently Cl, F, Br, I, CF₃, OCF₃, C₁₋₄-alkyl, C₂₋₄alkenyl, C₂₋₄alkynyl, NO₂, —CN, OR$^a$, N(R$^a$)₂, COR$^a$, CO₂R$^a$, or CON(R$^a$)₂;

R³ is H, CH₃, CH₂CH₃, cyano, Cl, F, Br, or I;

R⁴ is a phenyl group substituted with 1-2 R$^{4a}$;

each R$^{4a}$ is independently Cl, F, Br, I, CF₃, OCF₃, C₁₋₆alkyl substituted with 0-3 R⁵, C₂₋₆alkenyl substituted with 0-3 R⁵, C₂₋₆alkynyl substituted with 0-3 R⁵, (CH₂)$_p$NO₂, (CH₂)$_p$CN, (CH₂)$_p$OR, (CH₂)$_p$N(R)₂, (CH₂)$_p$COR, (CH₂)$_p$OCOR, (CH₂)$_p$CO₂R, (CH₂)$_p$CON(R)₂, (CH₂)$_p$OCON(R)₂, (CH₂)$_p$NRCOR, (CH₂)$_p$NRCO₂R, (CH₂)$_p$NRCON(R)₂, (CH₂)$_p$C(=NH)NH₂, (CH₂)$_p$SO₂R, (CH₂)$_p$SO₂N(R)₂, (CH₂)$_p$NRSO₂R, (CH₂)$_p$NRSO₂N(R)₂, CH(CF₃)NH₂, or (CH₂)$_p$-(5- to 6-membered heterocyclic ring) having 1 to 4 heteroatom ring members selected from O, S(O)$_q$, and N), wherein the heterocyclic ring is substituted with 0-3 R$^{5a}$, wherein provided that a first R$^{4a}$ group is a 5- to 6-membered heteroaromatic ring comprising 3 or 4 heteroatom ring members selected from O, S(O)$_q$, and N, and substituted with 0-3 R$^{5a}$;

each R is independently H, C₁₋₆alkyl substituted with 0-2 R⁵, C₂₋₆alkenyl substituted with 0-2 R⁵, C₂₋₆alkynyl substituted with 0-2 R⁵, 3- to 10-membered carbocyclic ring substituted with 0-2 R⁵, or 5- to 10-membered heterocyclic ring having 1 to 4 heteroatom ring members selected from O, S(O)$_q$, and N, wherein the heterocyclic ring is substituted with 0-2 R⁵; or two R attached to the same N atom are taken together with the nitrogen atom to which they are attached to form a 5- to 8-membered heterocyloalkyl substituted with 0-2 R⁵ each R⁵ is independently =O, Cl, F, Br, I, CF₃, OCF₃, C₁₋₄-alkyl, C₂₋₄alkenyl, C₂₋₄alkynyl, NO₂, —CN, OR$^a$, N(R$^a$)₂, COR$^a$, CO₂R$^a$, CON(R$^a$)₂, NR$^a$COR$^a$, NR$^a$CO₂R$^a$, NR$^a$CON(R$^a$)₂, C(=NH)NH₂, SO₂R$^a$, SO₂N(R$^a$)₂, NR$^a$SO₂R$^a$, NR$^a$SO₂N(R$^a$)₂, (CH₂)$_p$-(3- to 10-membered carbocyclic ring substituted with 0-2 R$^b$), or (CH₂)$_p$-(5- to 10-membered) heterocyclic ring having 1 to 4 heteroatom ring members selected from O, S(O)$_q$, and N, wherein the heterocyclic ring is substituted with substituted with 0-2 R$^b$; or two R⁵ taken together with a carbon atom to which they are both connected form a 1,3-dioxolane ring wherein the two oxygen ring atoms are attached to the connecting carbon atom;

R$^{5a}$ is selected from =O, Cl, F, Br, I, CF₃, OCF₃, C₁₋₄-alkyl, C₂₋₄alkenyl, C₂₋₄alkynyl, NO₂, —CN, (CH₂)$_p$OR$^a$, N(R$^a$)₂, COR$^a$, CO₂R$^a$, CON(R$^a$)₂, NR$^a$COR$^a$, NR$^a$CO₂R$^a$, NR$^a$CON(R$^a$)₂, C(=NH)NH₂, SO₂R$^a$, SO₂N(R$^a$)₂, NR$^a$SO₂R$^a$, NR$^a$SO₂N(R$^a$)₂, (CH₂)$_p$-(3- to 10-membered carbocyclic ring substituted with 0-2 R$^b$, or (CH₂)$_p$-(5- to 10-membered heterocyclic ring having 1 to 4 heteroatom ring members selected from O, S(O)$_q$, and N), wherein the heterocyclic ring is substituted with 0-2 R$^b$;

each R$^a$ is independently H, C₁₋₄-alkyl, C₃₋₆ cycloalkyl, CH₂—C₃₋₆ cycloalkyl, phenyl, or benzyl; or two R$^a$ attached to the same N atom are taken together with the nitrogen atom to which they are attached to form a 5- to 8-membered heterocycloalkyl;

R$^b$ is H, Cl, F, Br, I, CF₃, OCF₃, C₁₋₄-alkyl optionally substituted with OR$^a$, C₂₋₄alkenyl, C₂₋₄alkynyl, NO₂, —CN, OR$^a$, N(R$^a$)₂, COR$^a$, CO₂R$^a$, or CON(R$^a$)₂;

p is 0;

q is 0, 1, or 2; and m is 1 and n is 0 or 1.

2. The method of claim 1, wherein the first R$^{4a}$ is (5-membered heteroaromatic ring).

3. The method of claim 1, wherein the heteroaromatic ring of R$^{4a}$ heteroatom ring members are selected from N and O heteroatoms.

4. The method of claim 1, wherein the heteroaromatic ring of the first R$^{4a}$ group is substituted with Cl, F, Br, CF₃, C₁₋₄-alkyl, C₂₋₄alkenyl, (CH₂)$_p$OR$^a$, N(R$^a$)₂, (CH₂)$_p$-(3- to 10-membered carbocyclic ring substituted with 0-2 R$^b$, or (CH₂)$_p$-(5- to 10-membered heterocyclic ring having 1 to 4 heteroatom ring members selected from O, S(O)$_q$, and N, wherein the heterocyclic ring is substituted with 0-2 R$^b$.

5. The method of claim 1, wherein the heteroaromatic ring of the first R$^{4a}$ group is substituted with phenyl or benzyl.

6. The method of claim 1, wherein the heteroaromatic ring of the first R$^{4a}$ group is substituted with (CH₂)$_p$-(5- to 10)-membered heterocyclic ring, and wherein the (CH₂)$_p$-(5- to 10-membered)heterocyclic ring is optionally substituted with Cl, F, CF₃, C₁₋₄-alkyl optionally substituted with OR$^a$, —CN, or OR$^a$.

7. The method of claim 1, wherein the compound of formula (Ic) is selected from the group consisting of

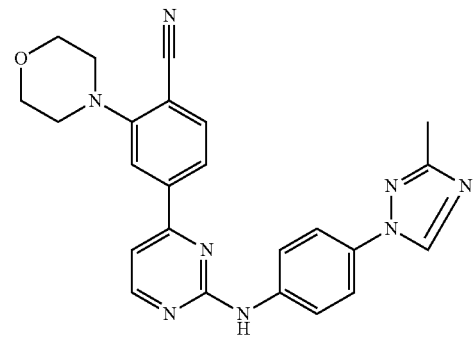

8

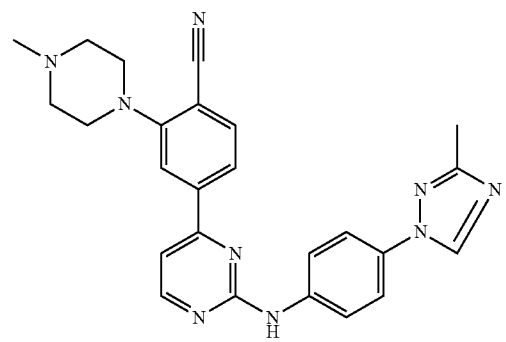

9

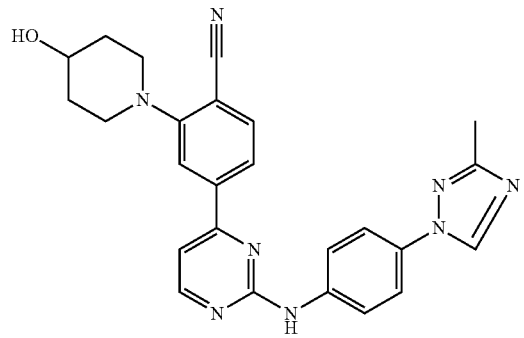

10

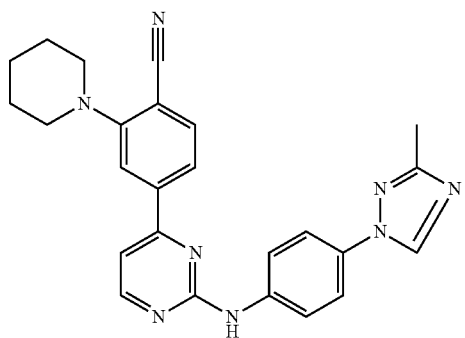 11
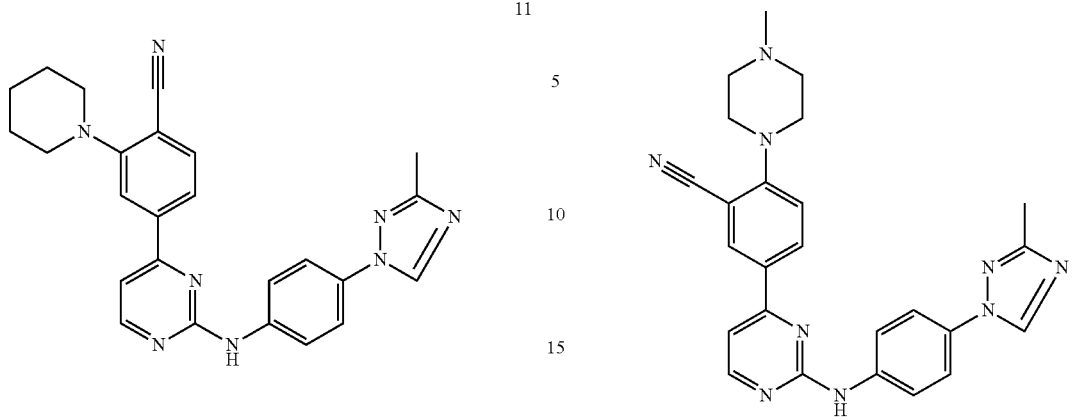 20
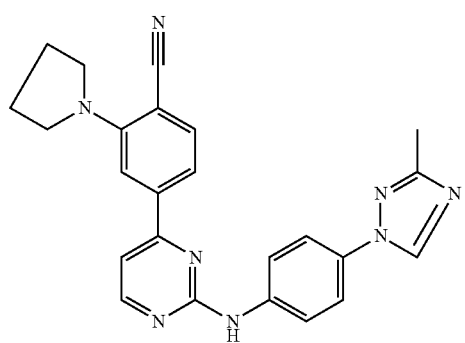 12
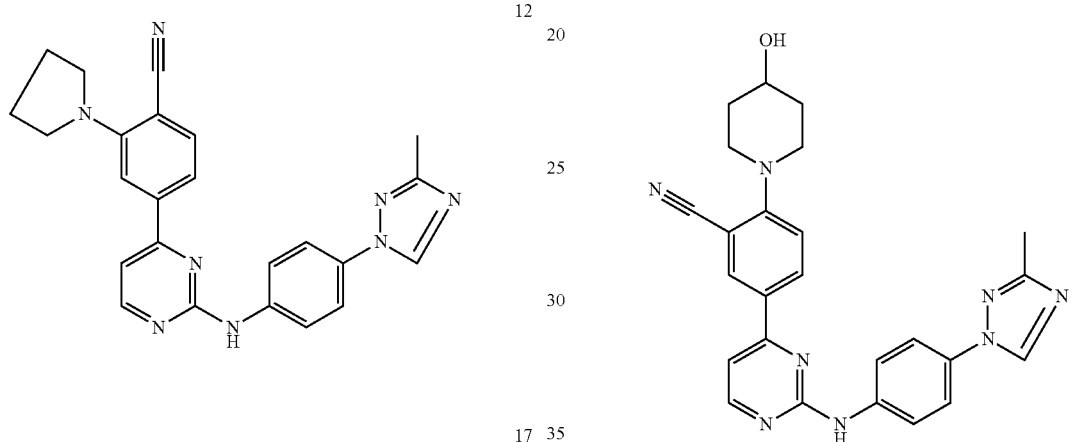 21
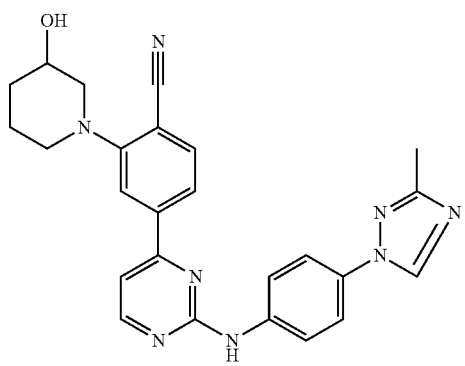 17
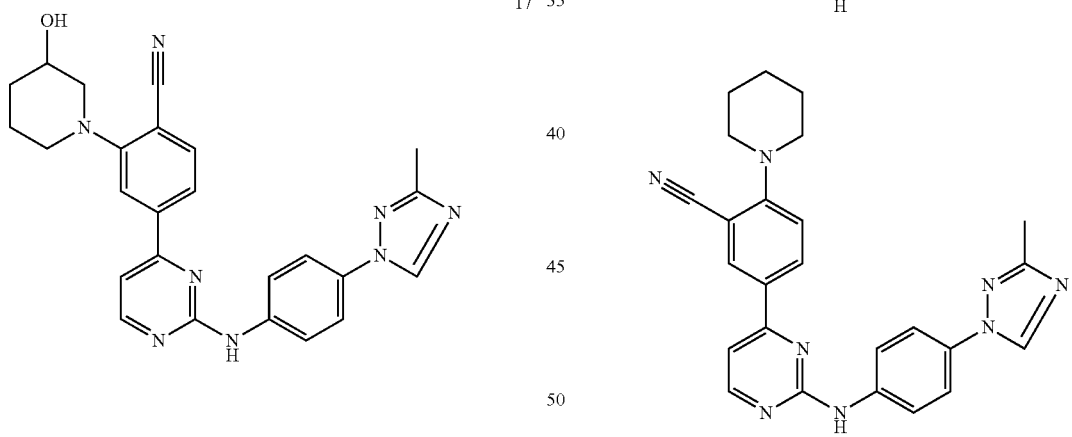 22
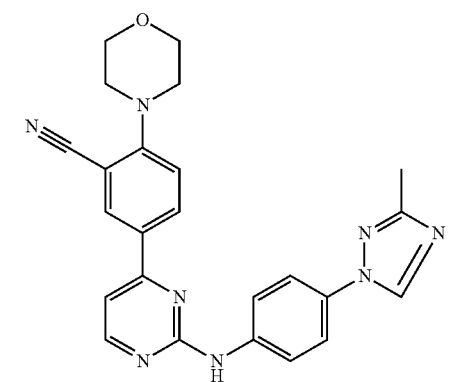 19
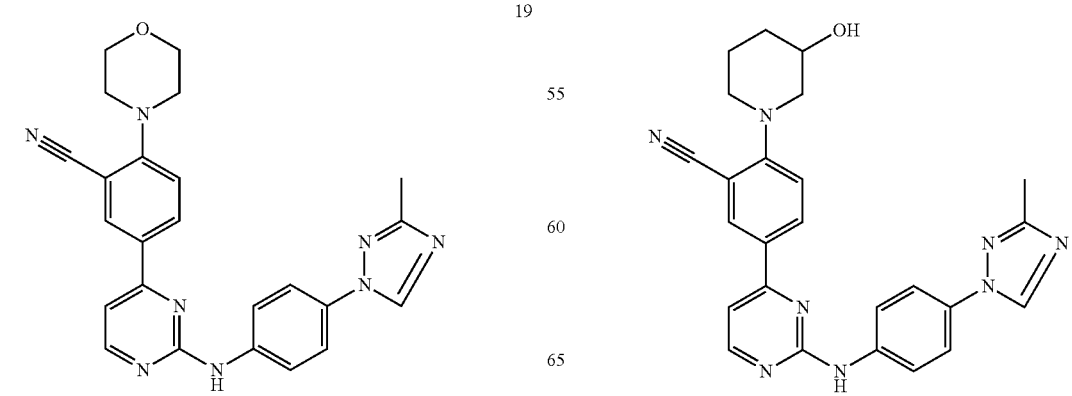 25

26
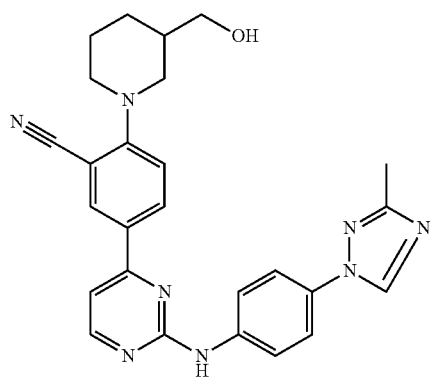
27
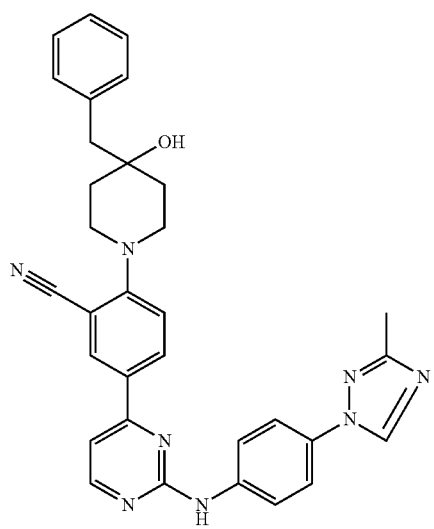
28
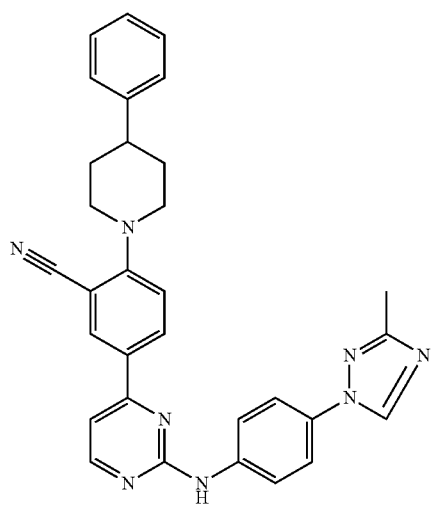
29
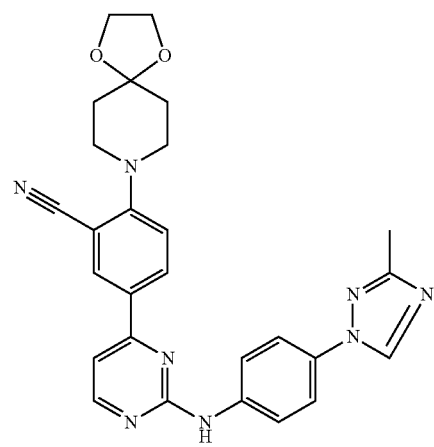
32
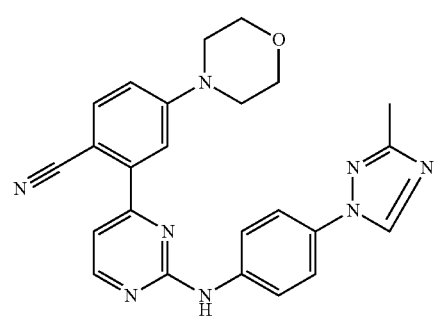
33
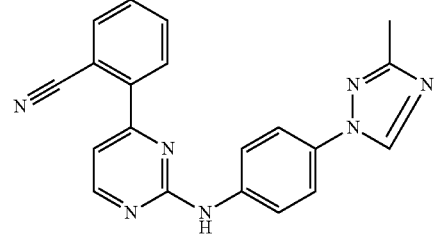
34
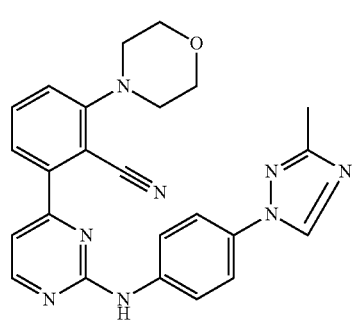

38
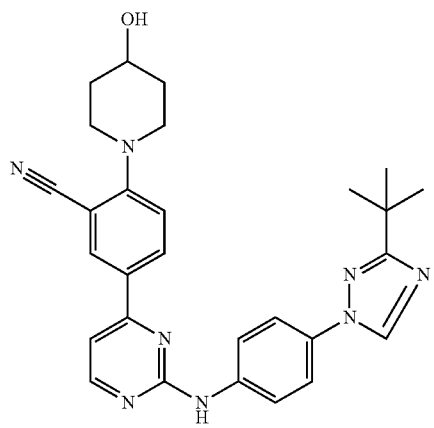
39
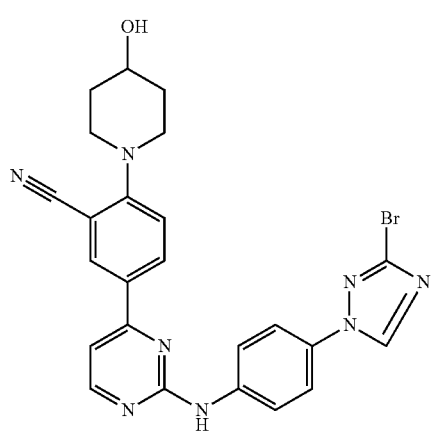
40
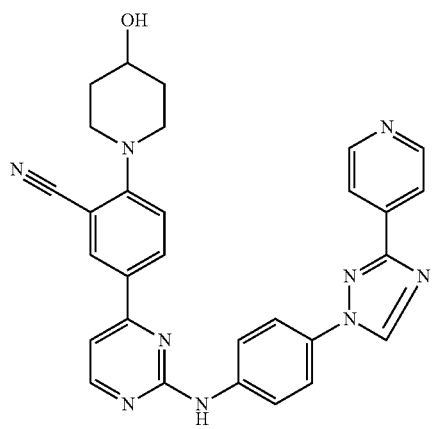
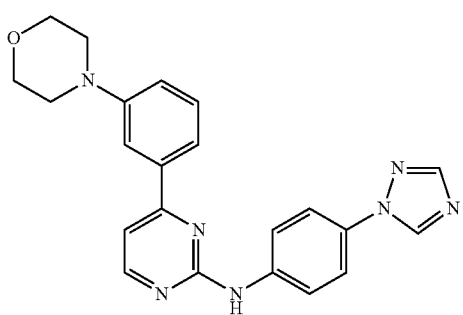
52
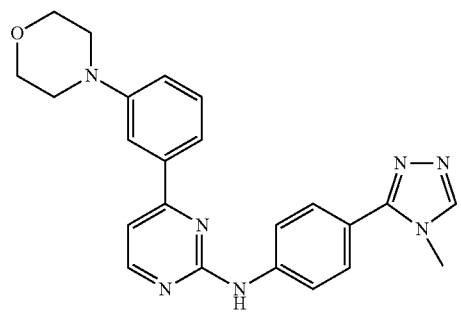
76
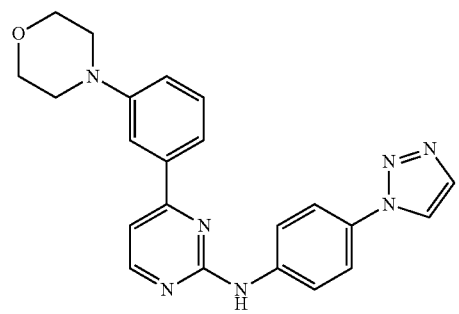
77
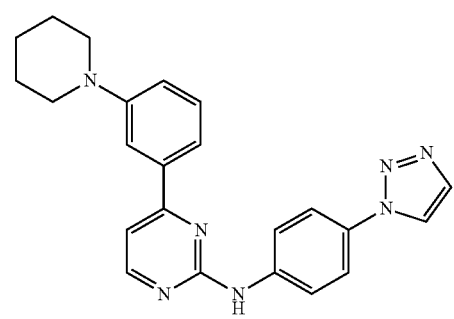
89
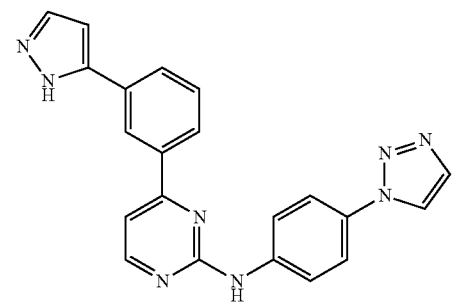
90
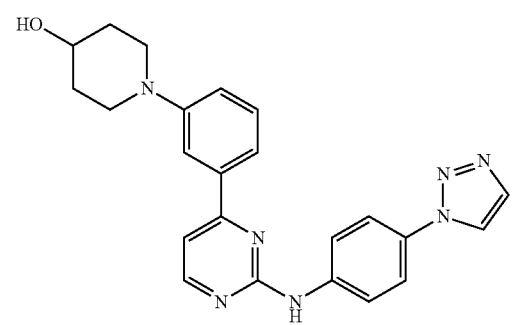

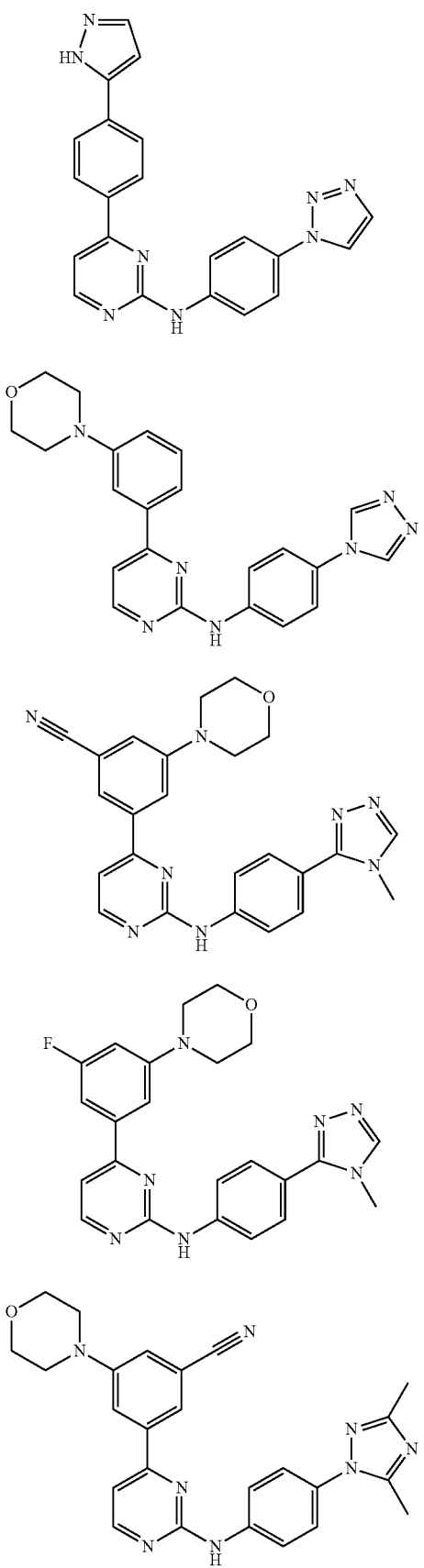
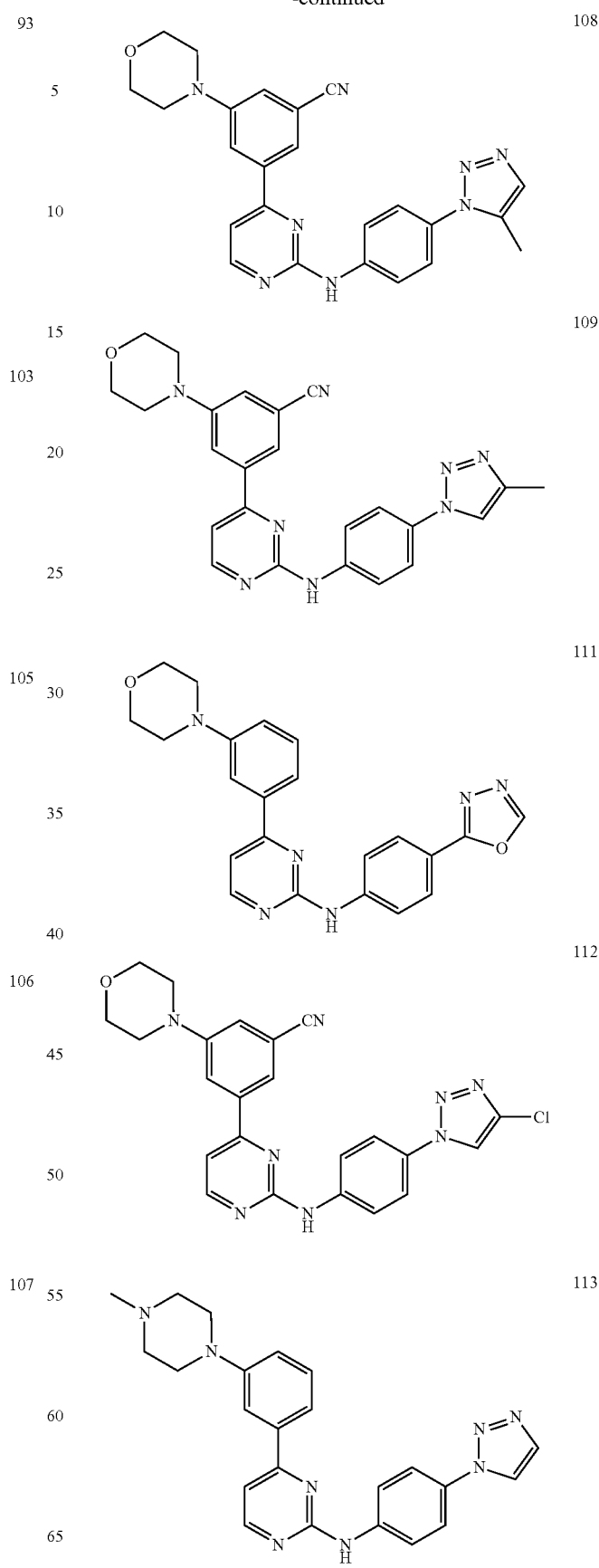

114
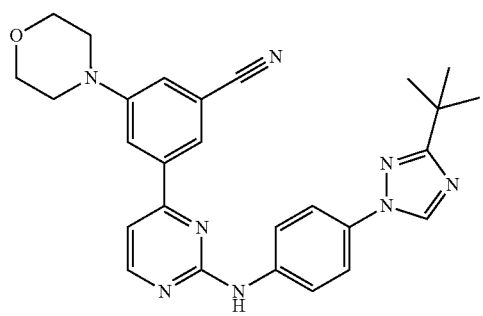
115
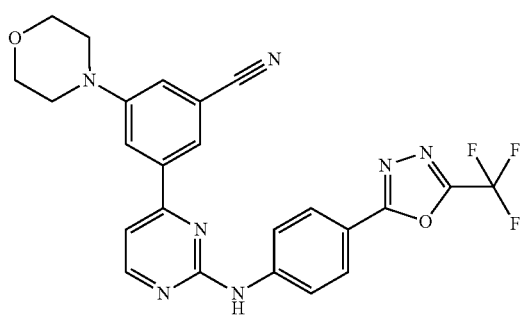
116
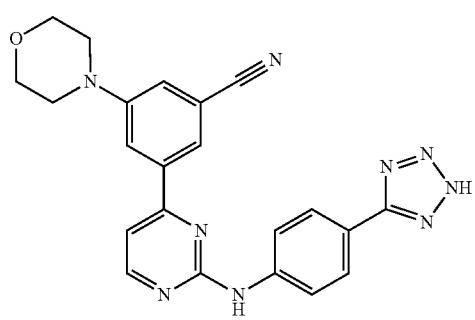
117
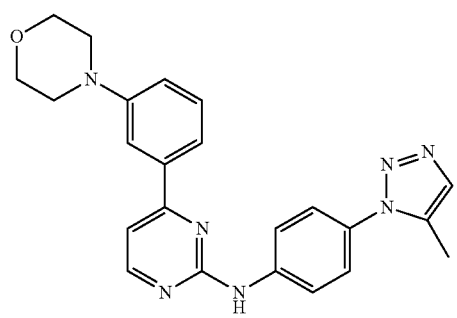
118
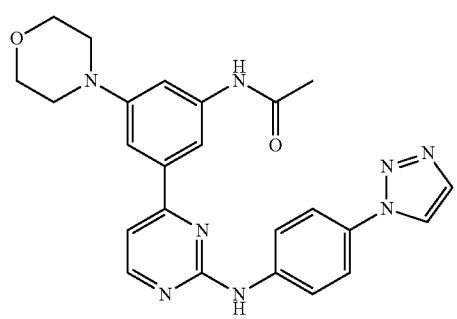
119
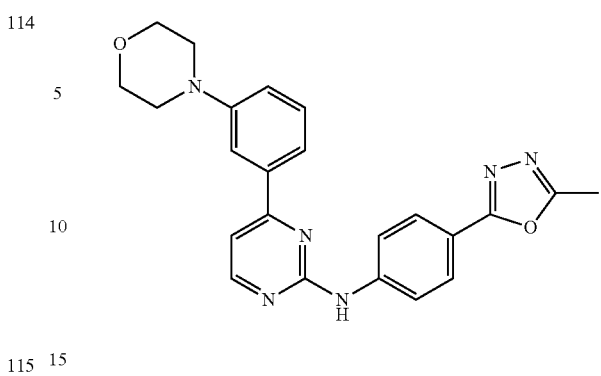
122
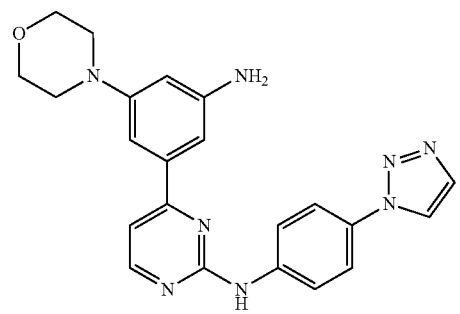
126
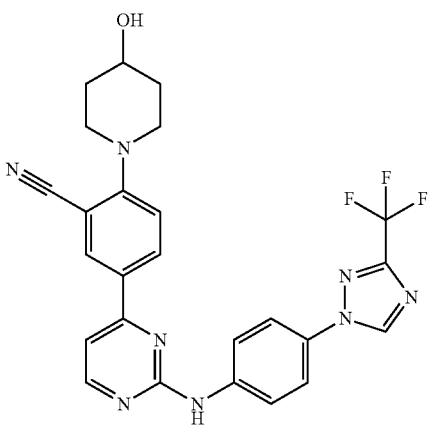
127
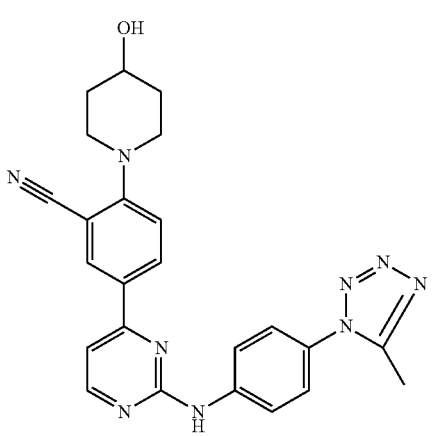

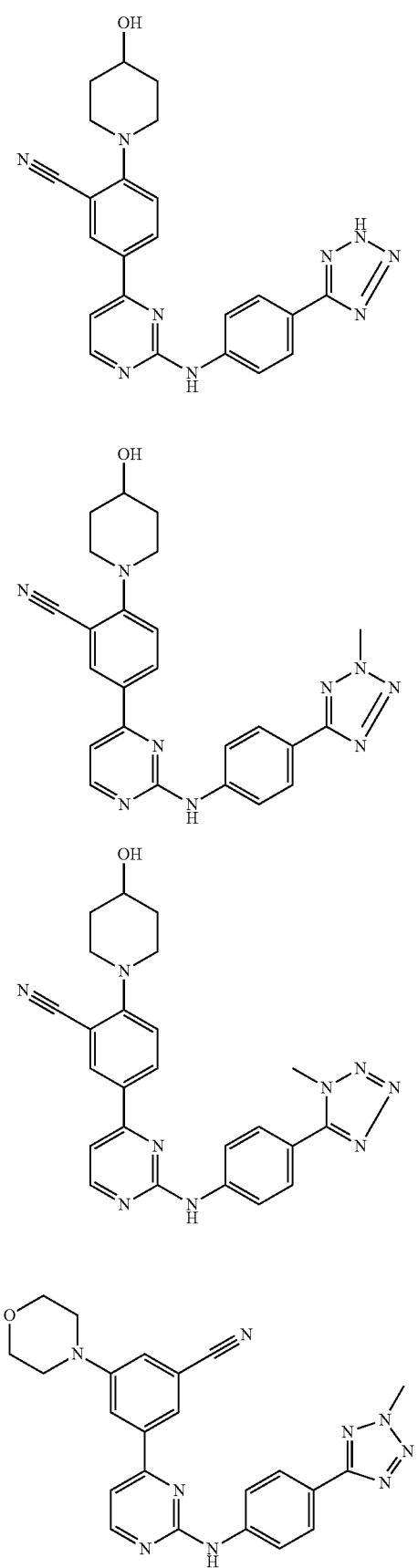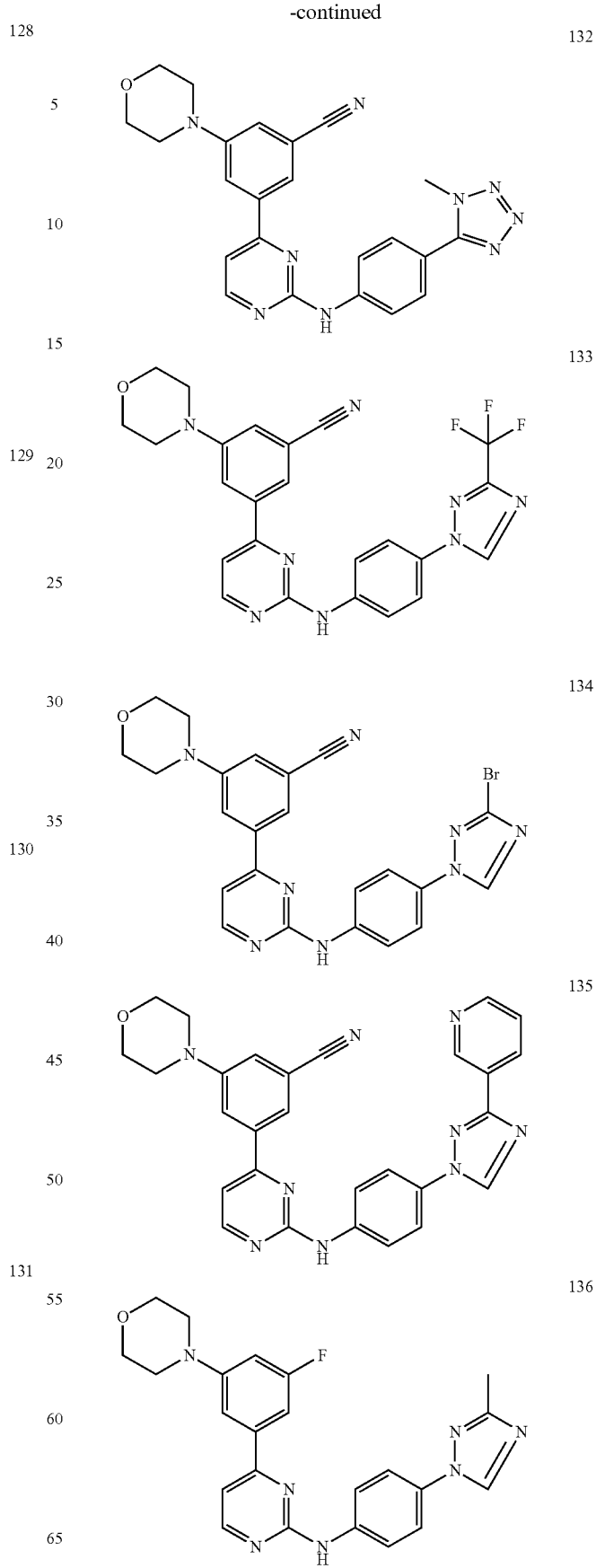

137 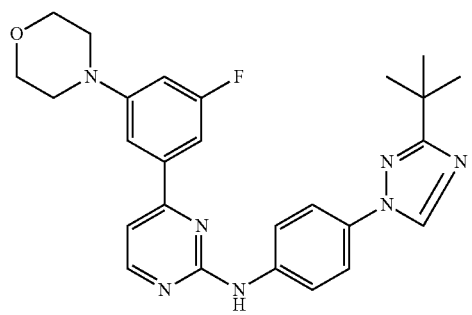
138 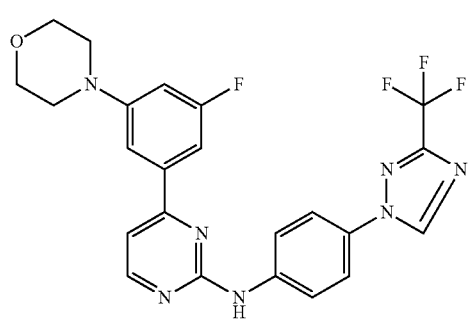
139 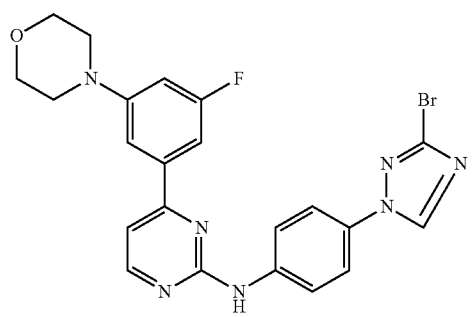
140 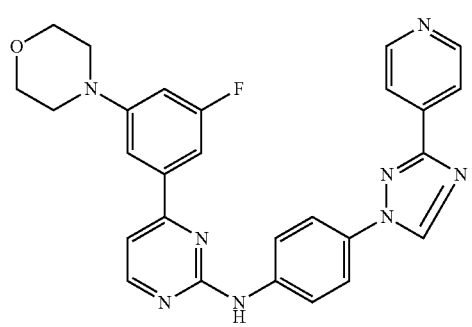
141 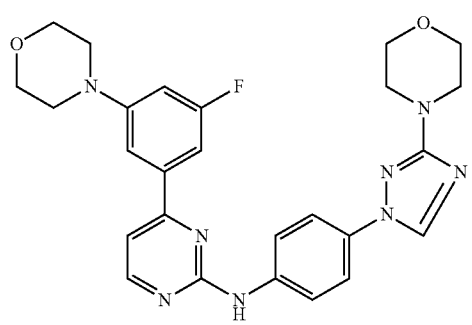
142 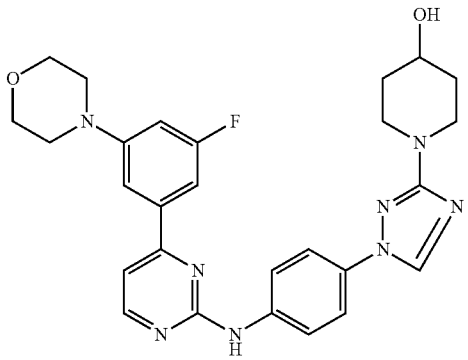
143 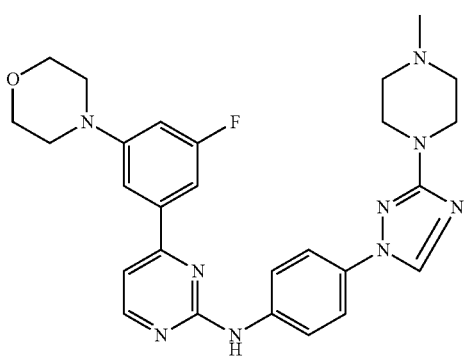
144 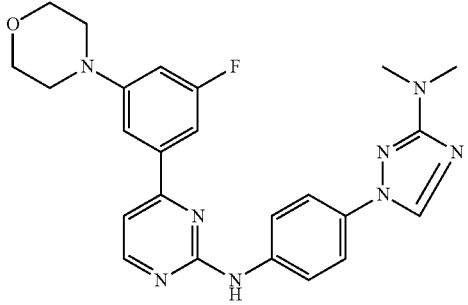
145 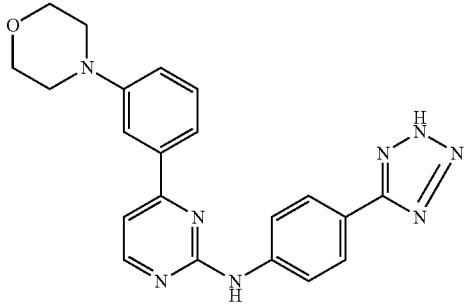

| | |
|---|---|
| 146 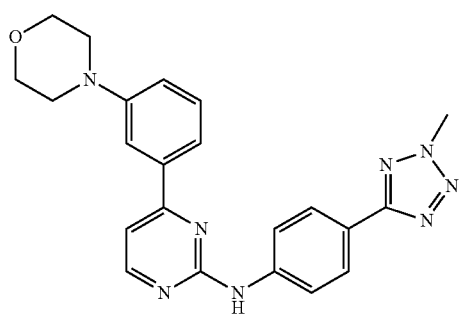 | 151 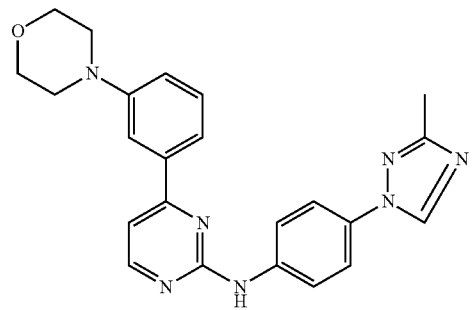 |
| 147 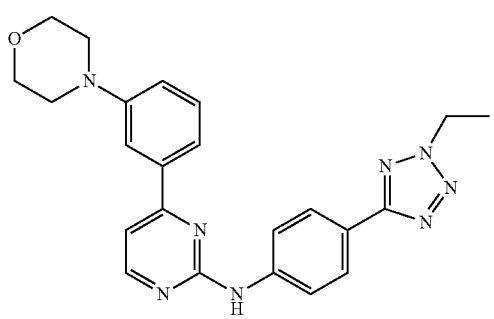 | 152 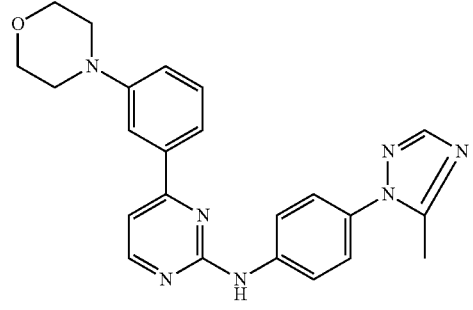 |
| 148 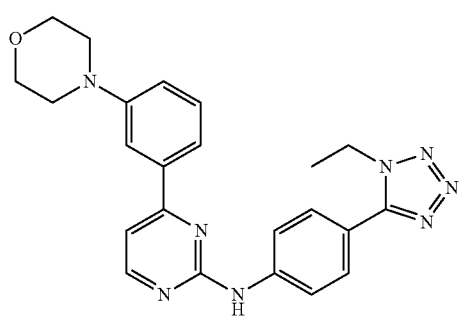 | 153 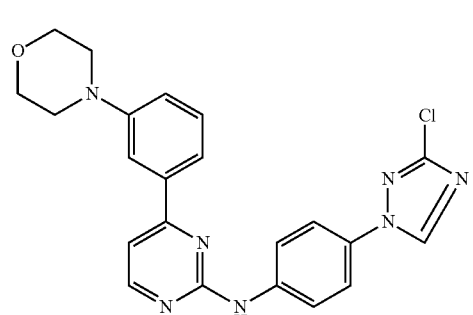 |
| 149 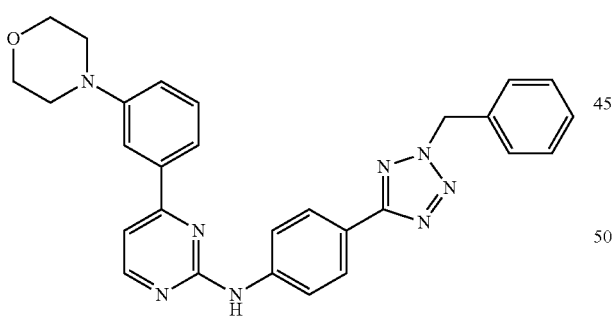 | 154 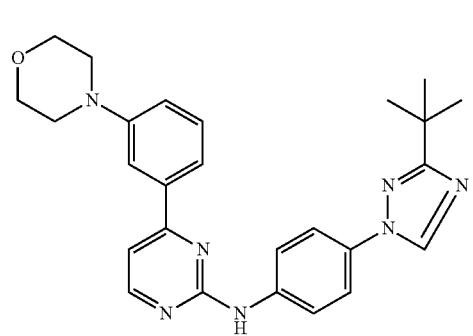 |
| 150 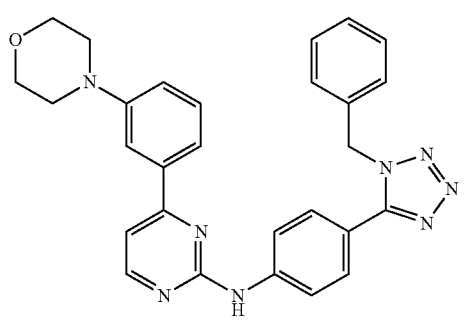 | 155 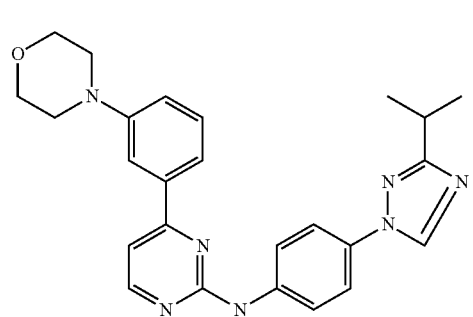 |

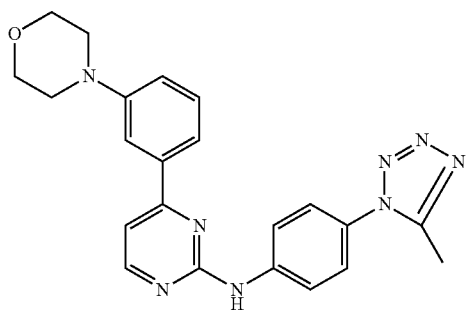
156
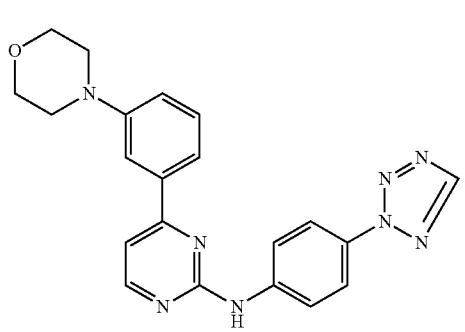
158
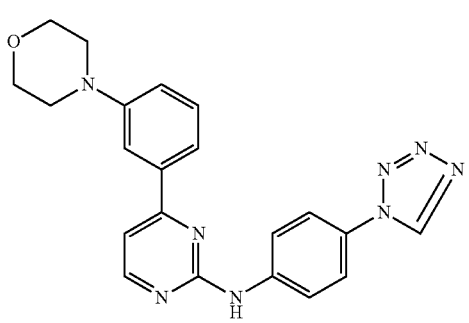
159
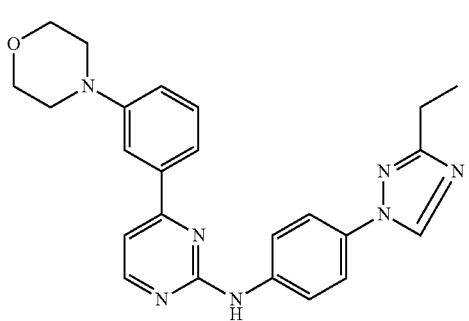
160
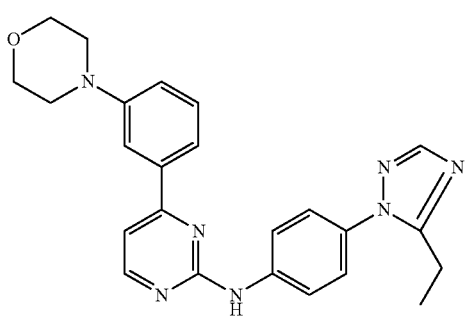
161
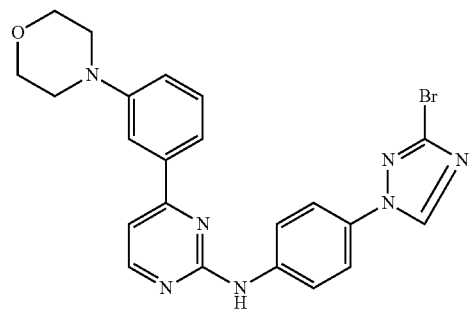
162
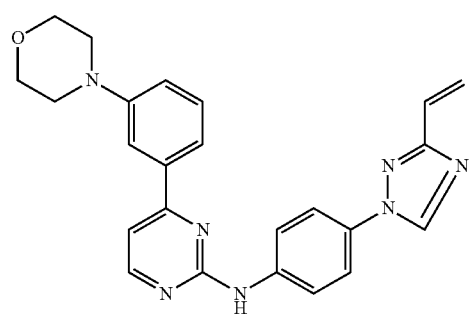
163
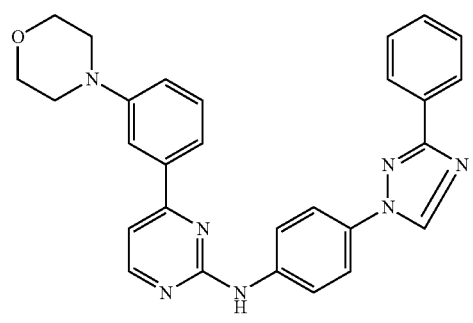
164
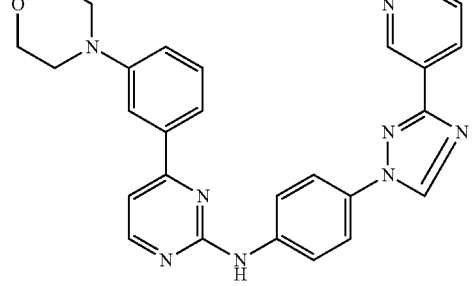
165
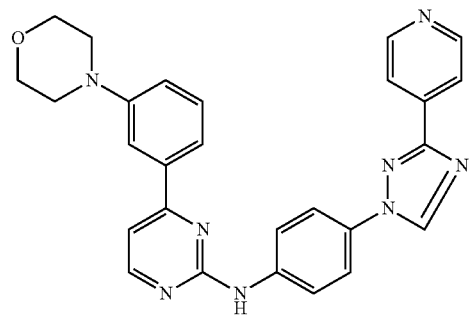
166

167 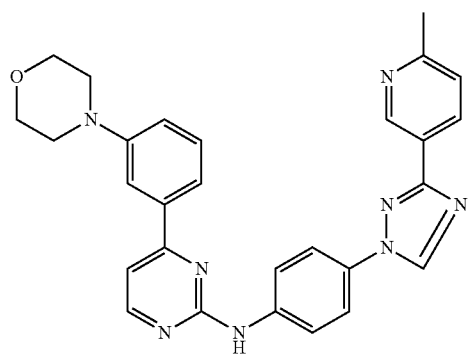
168 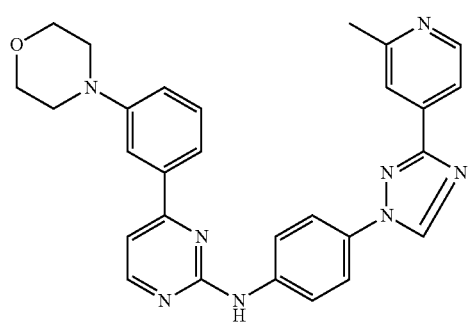
169 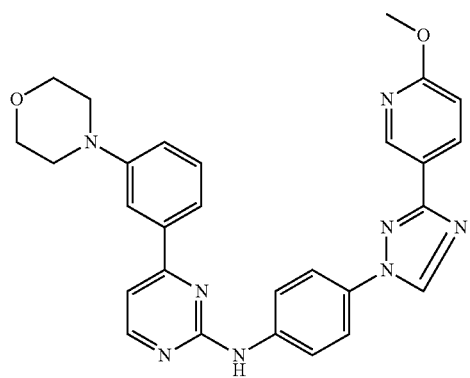
180 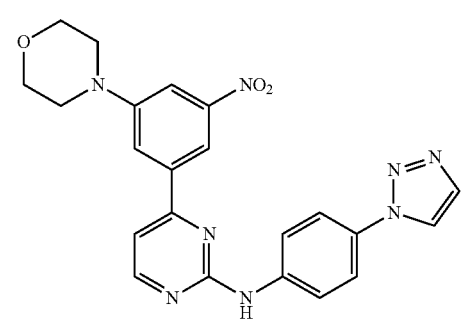
181 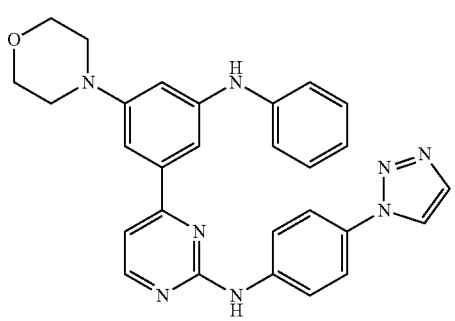
182 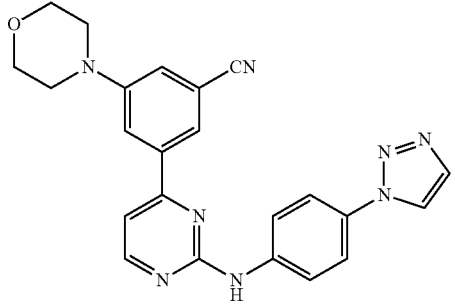
183 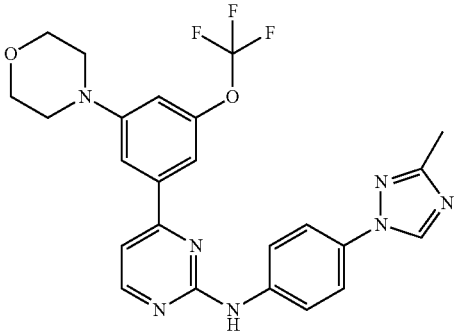
184 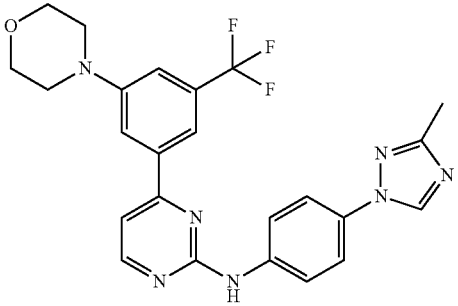
186 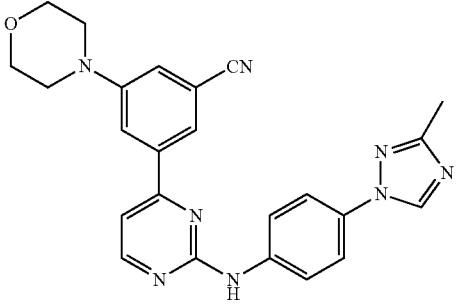

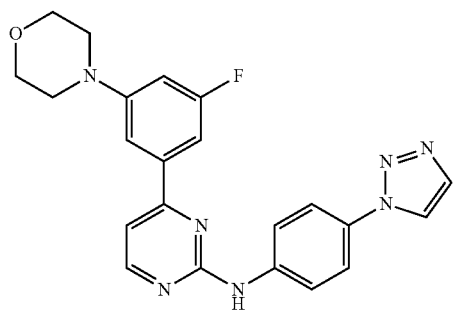
187
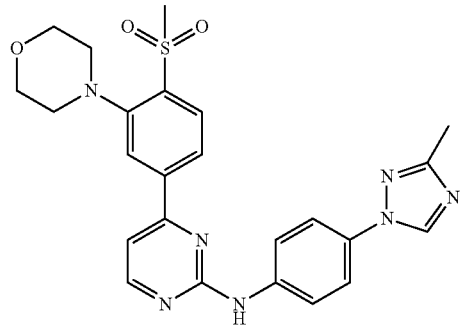
196
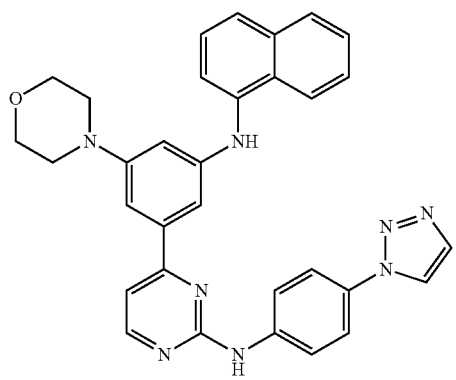
188
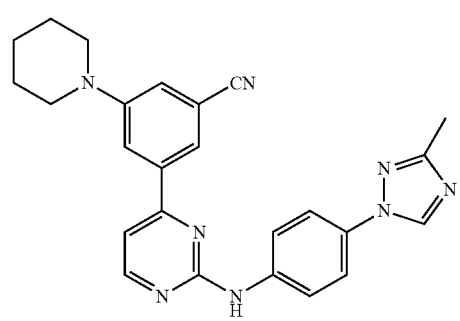
198
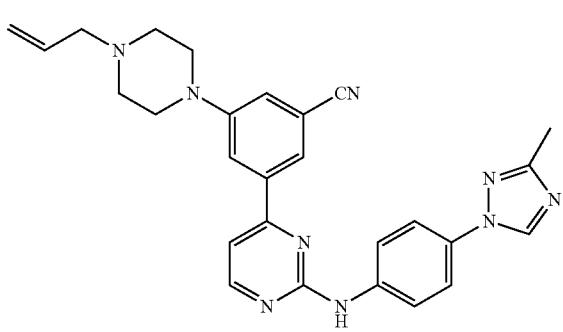
189
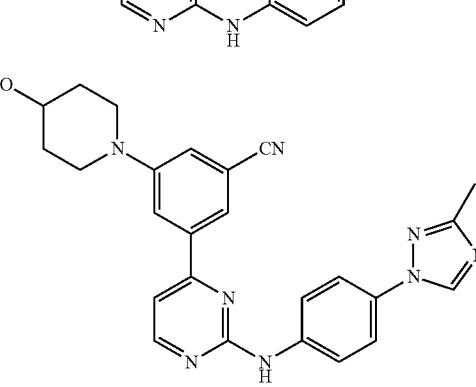
199
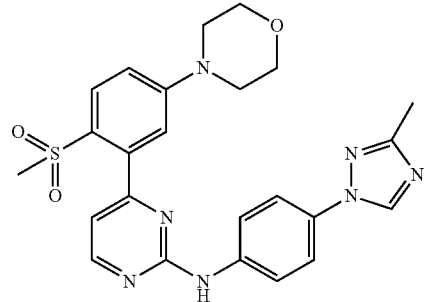
195
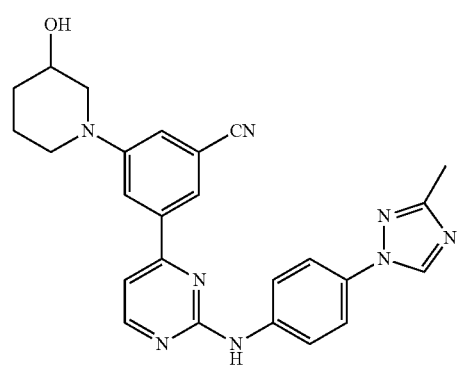
206
207

208
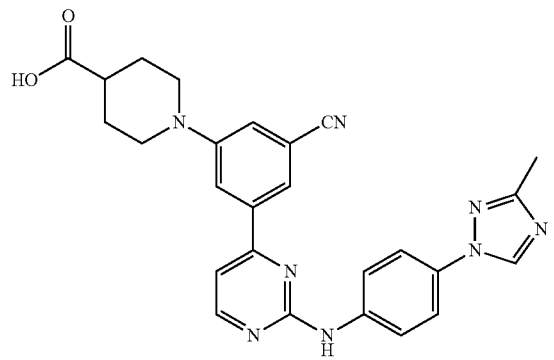
209
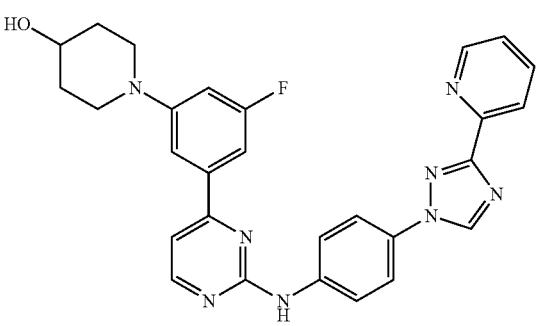
215
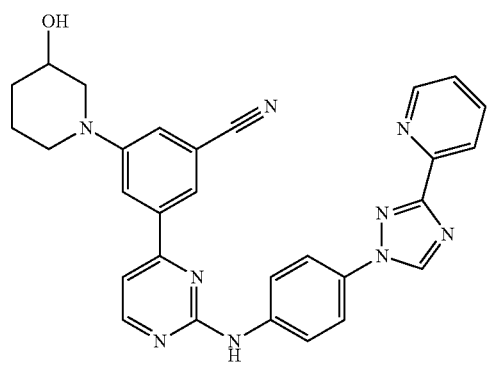
216
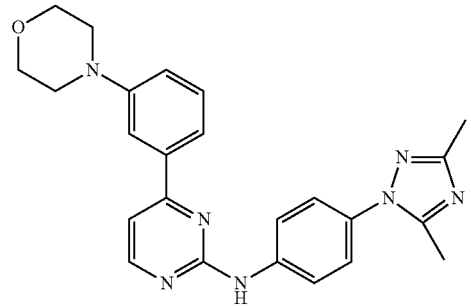
223
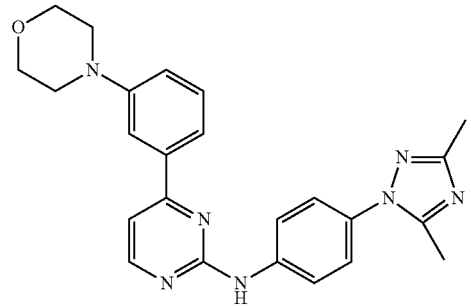
227
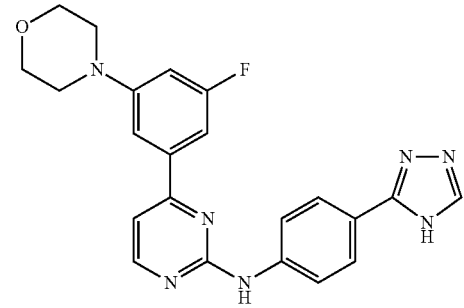
228
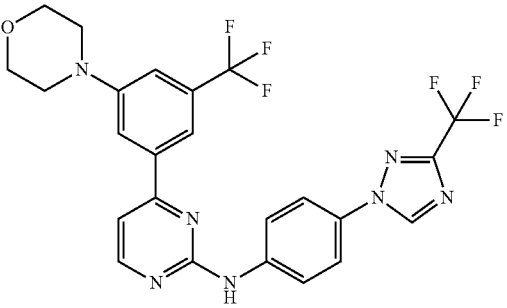
229
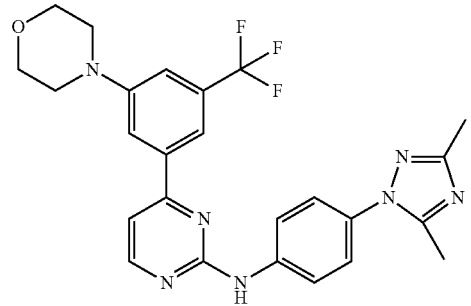
230
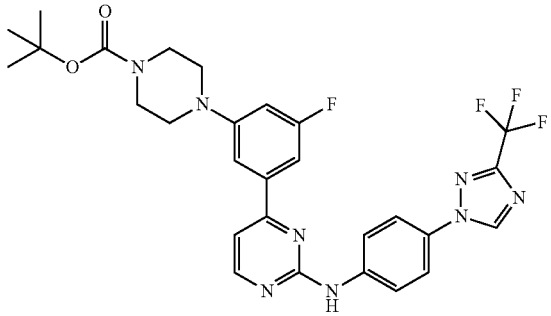

231 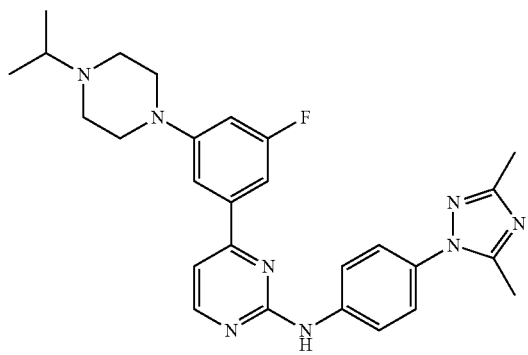
235 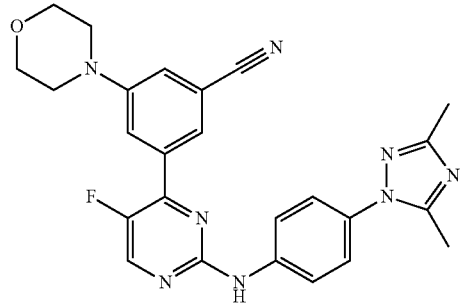
232 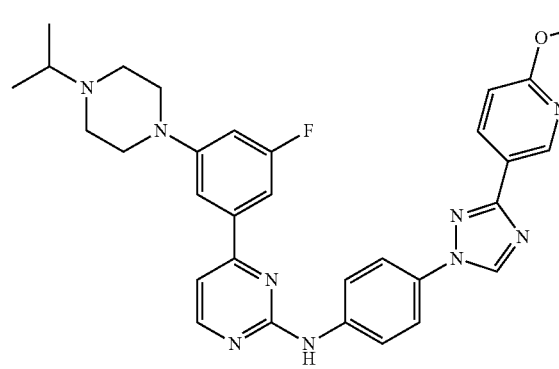
236 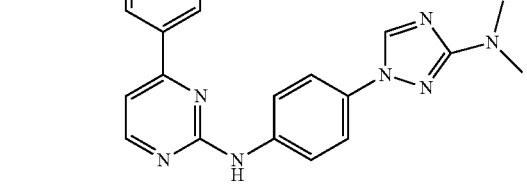
237
233 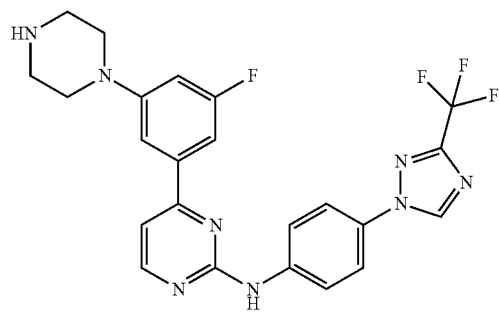
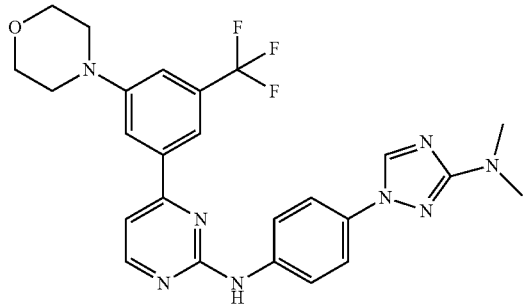
243
234 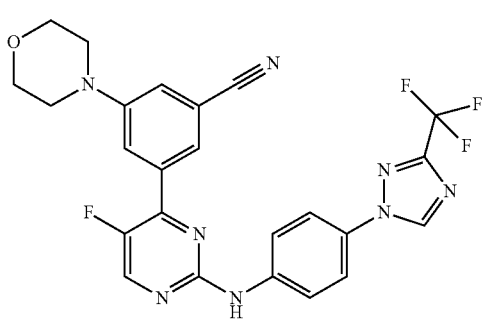
244 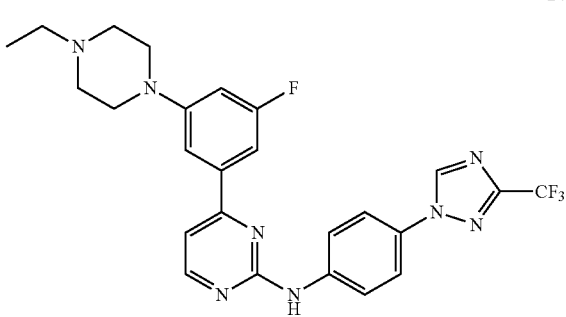

245
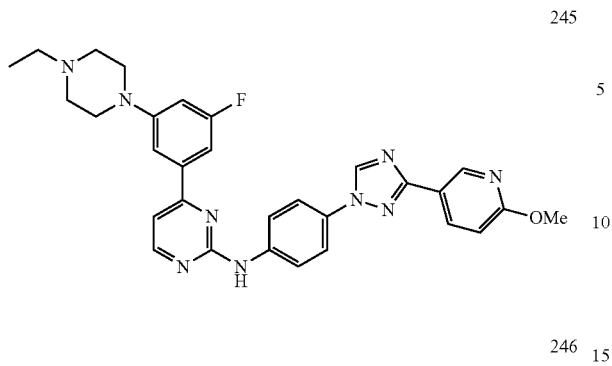
246
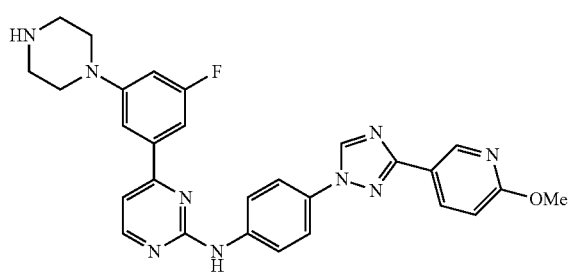
247
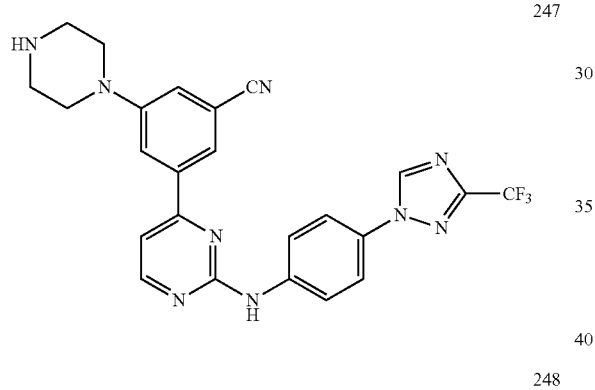
248
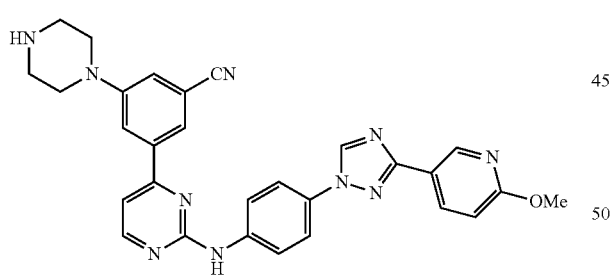
249
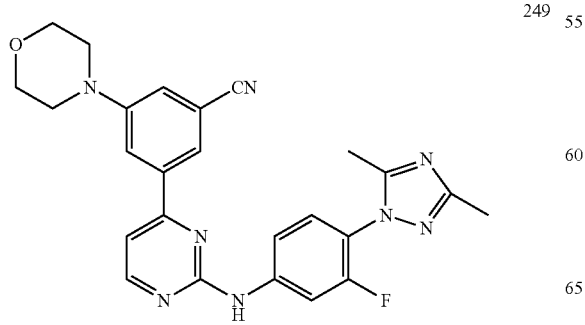
250
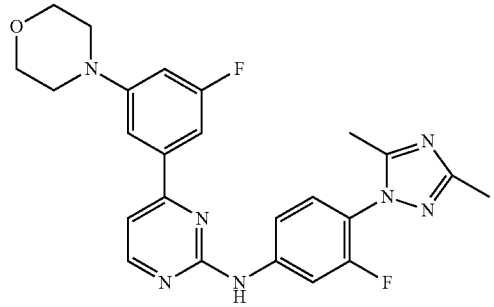
251
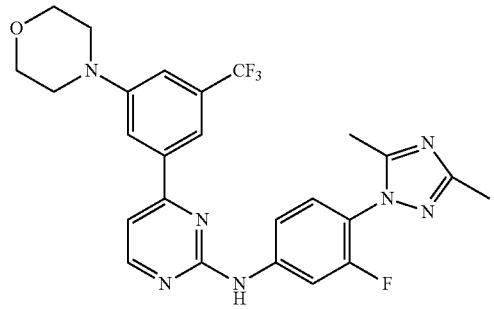
252
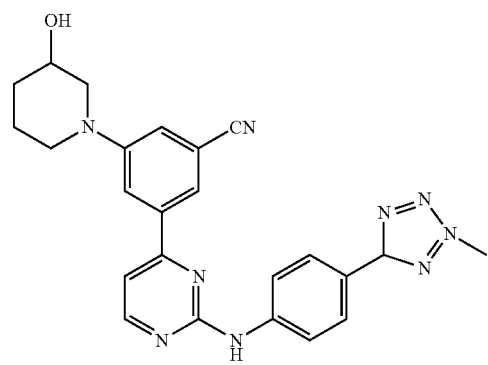
253
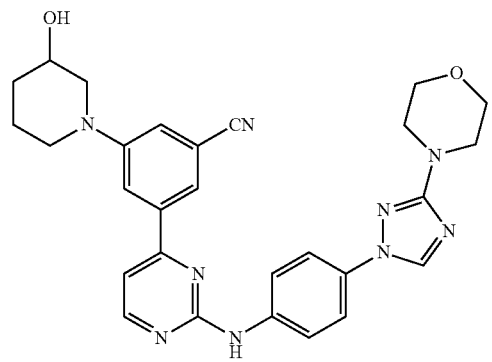

249
-continued
254
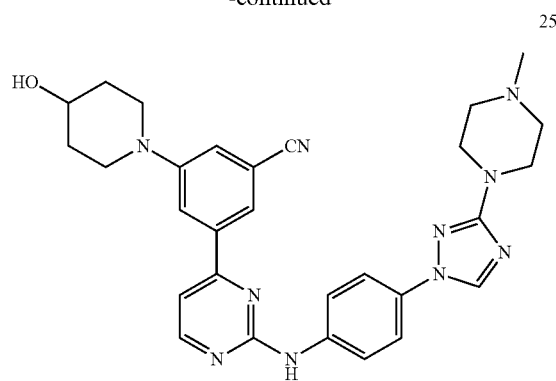
255
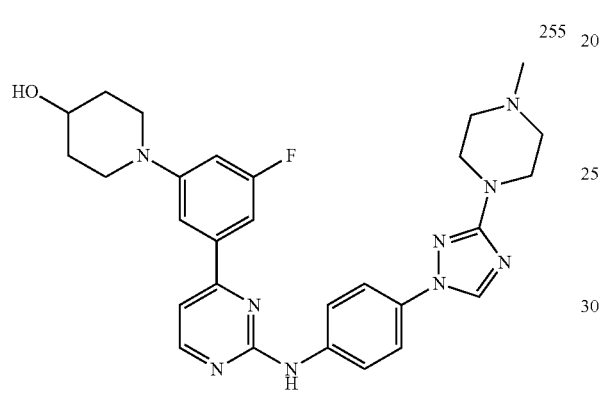
258
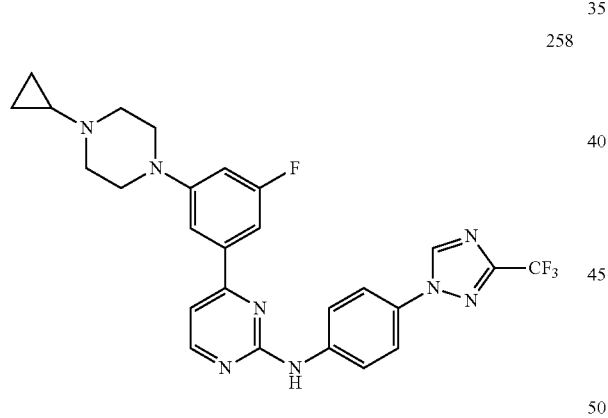
259
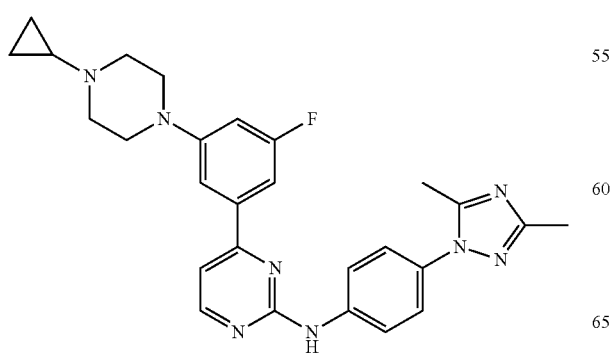
250
-continued
260
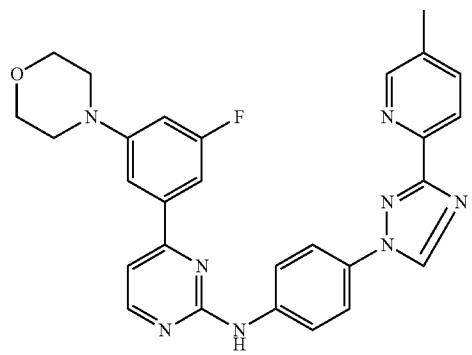
261
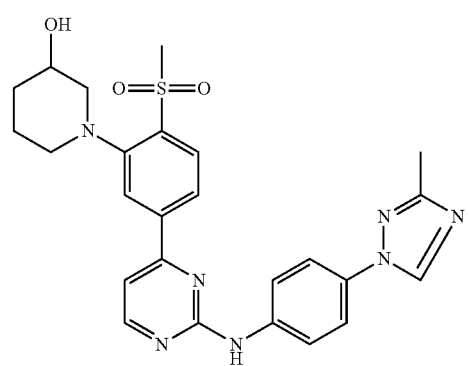
262
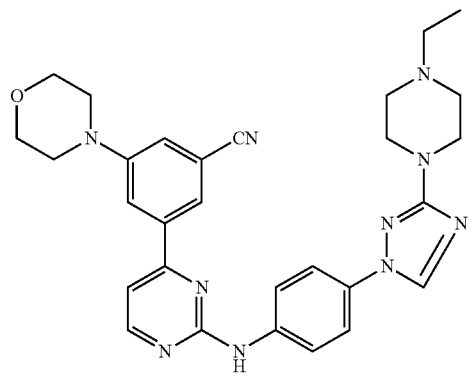
263
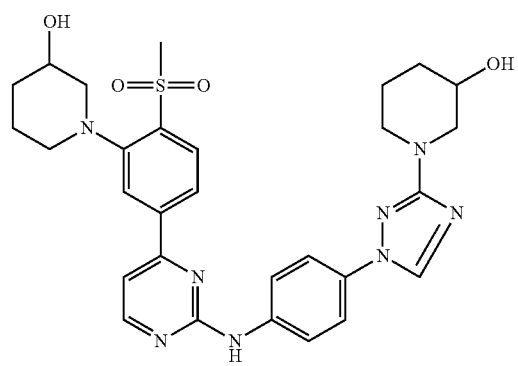

251
-continued
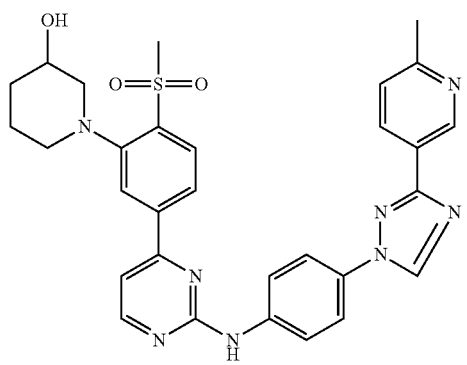
264
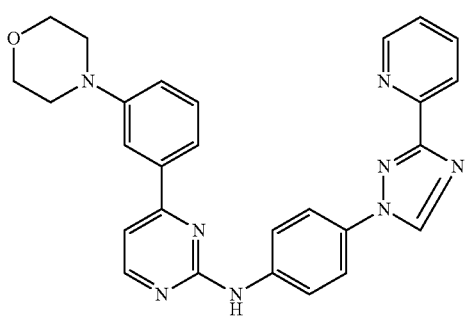
265
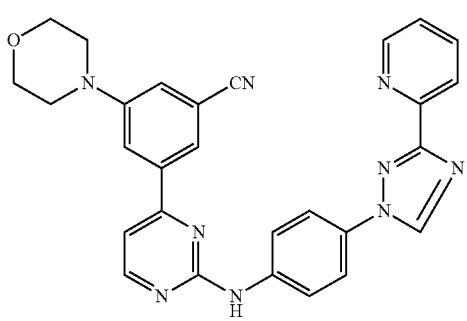
266
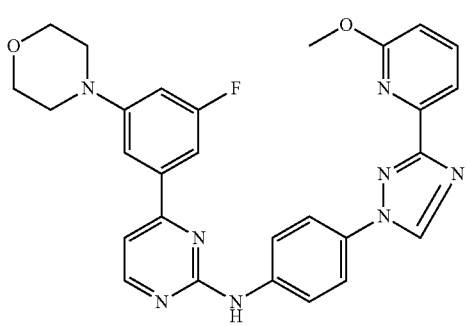
267
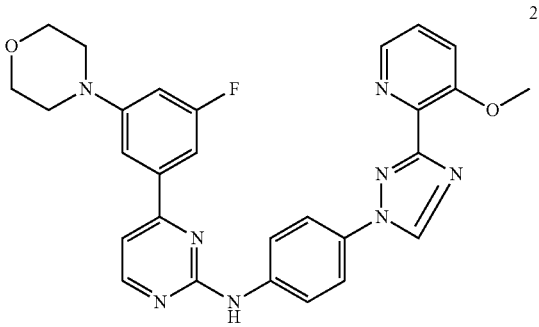
268
252
-continued
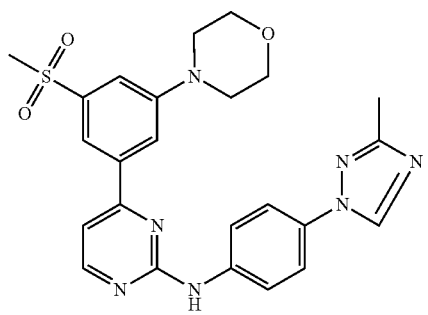
269
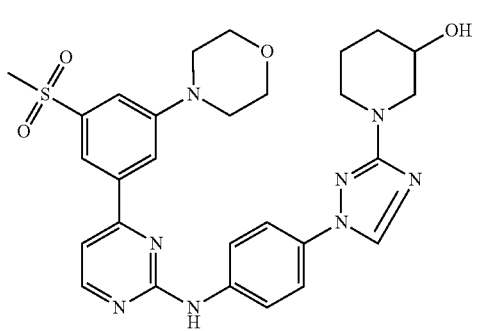
270
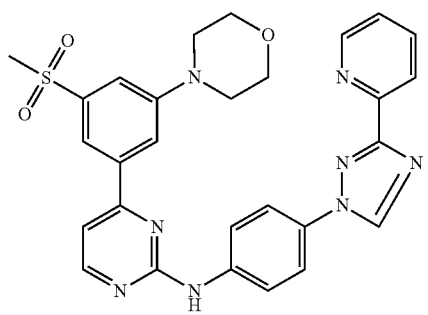
271
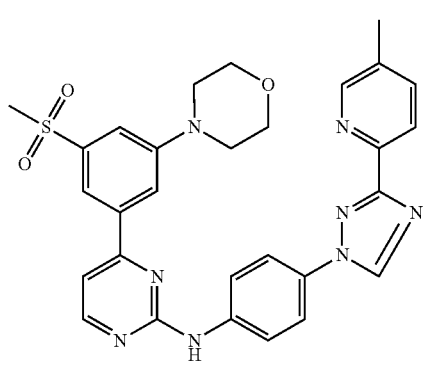
272

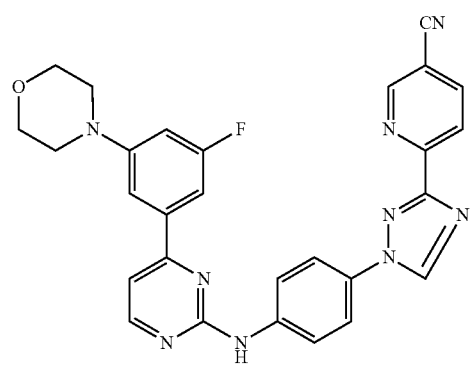
273
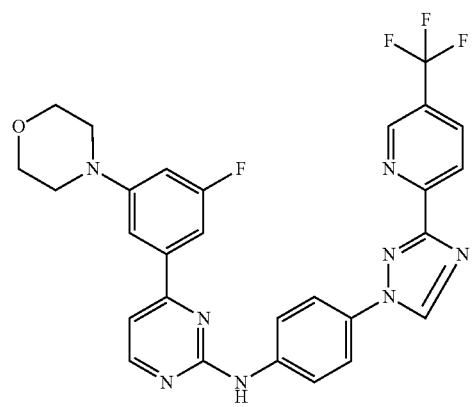
274
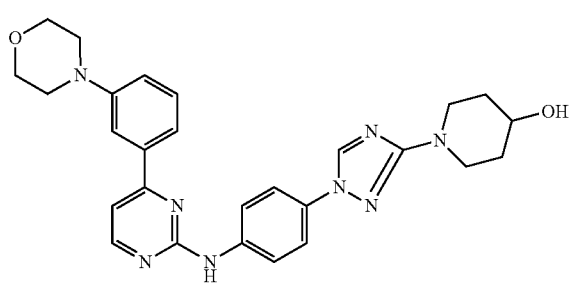
275
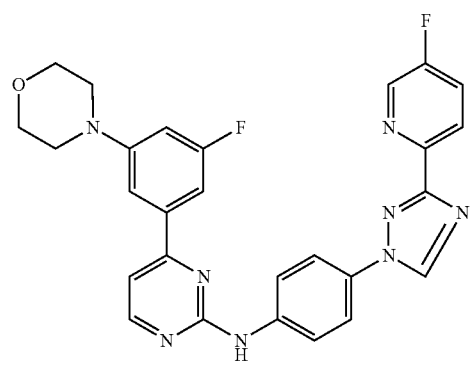
276
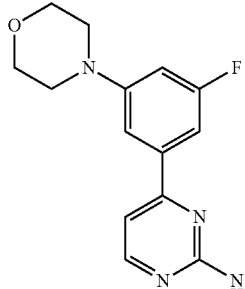
277
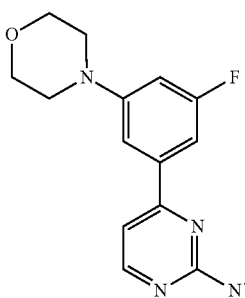
278
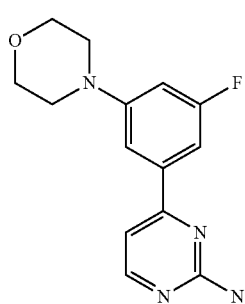
279
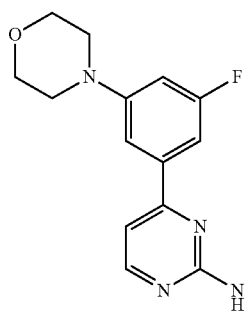
280
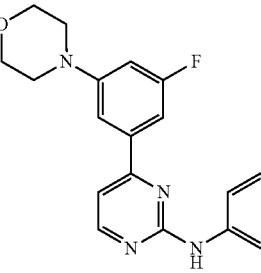
281

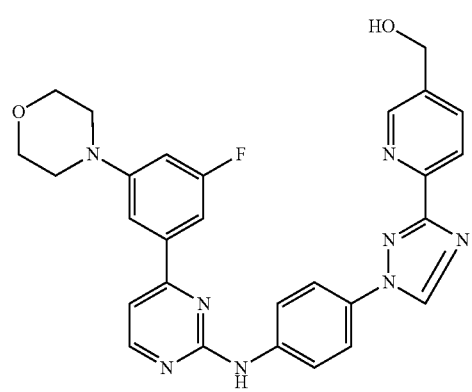
282
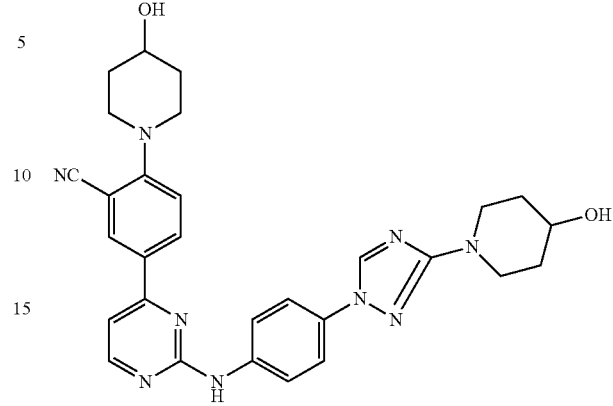
286
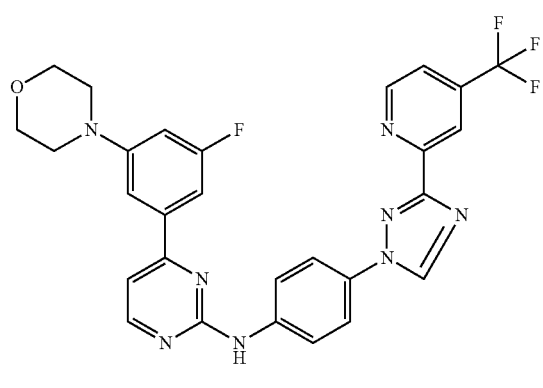
283
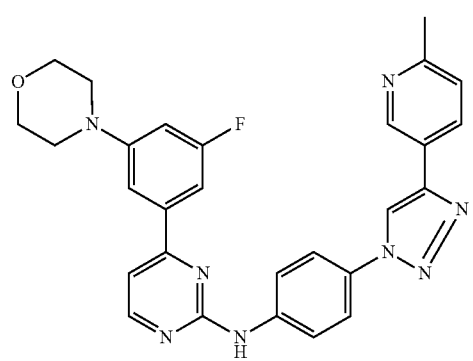
287
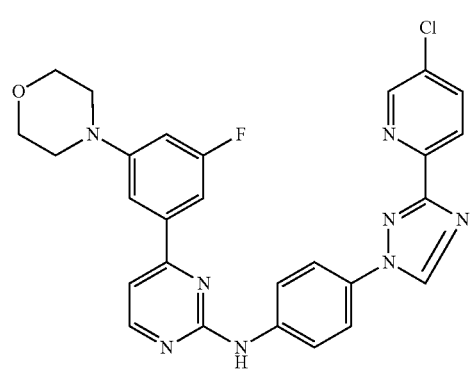
284
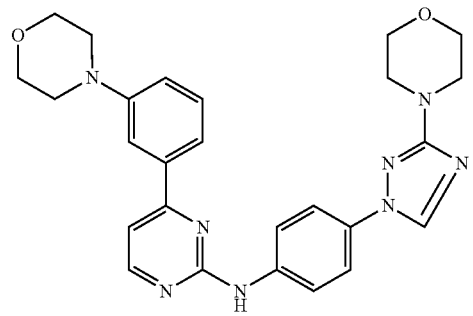
288
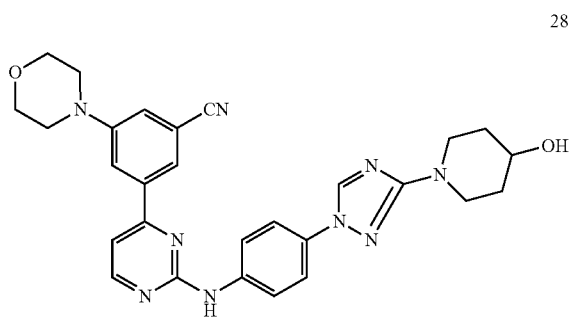
285
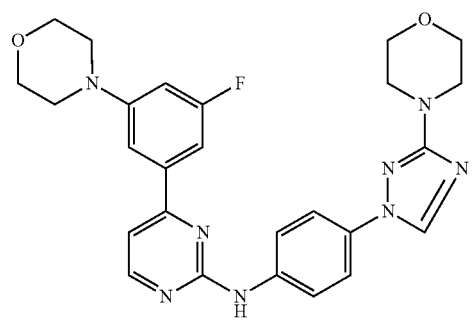
289

290 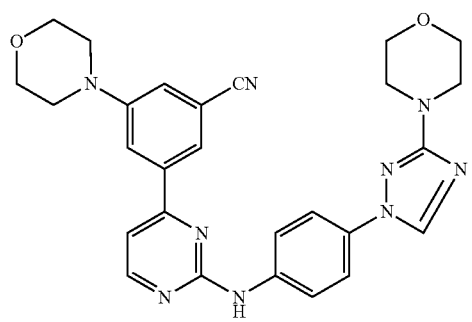
291 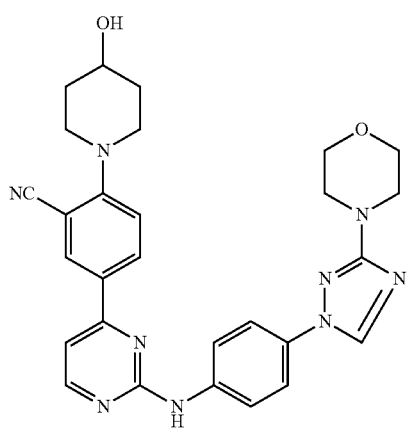
292 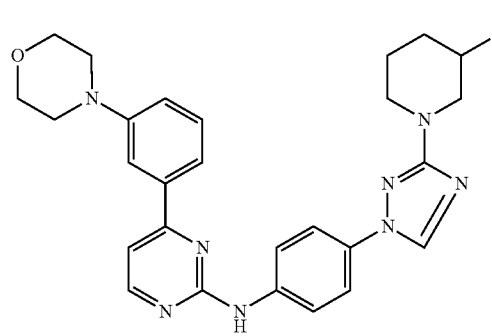
293 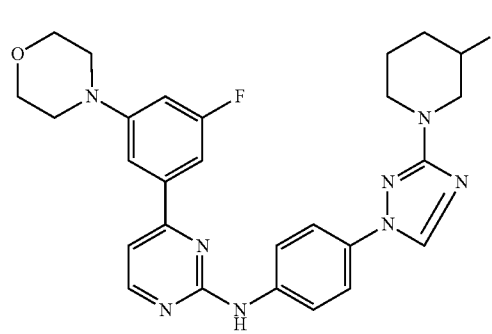
294 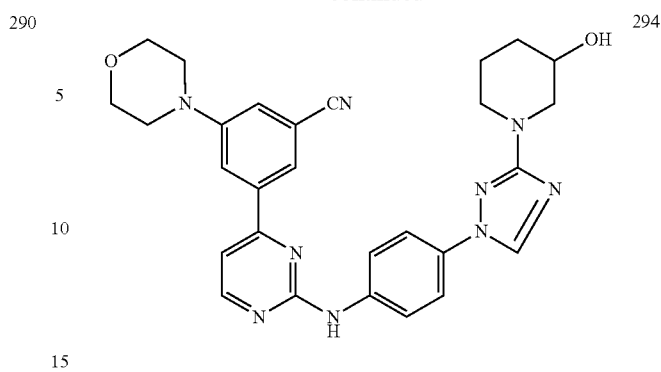
295 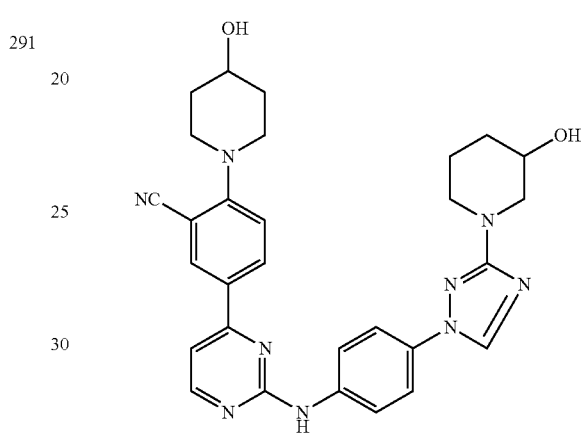
296 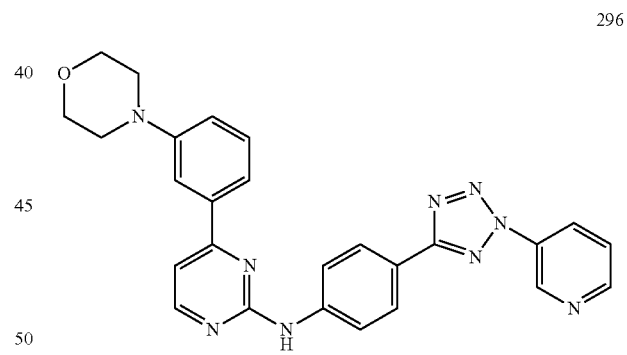
297 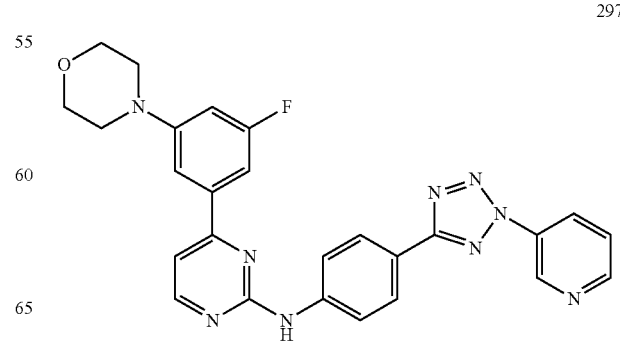

298 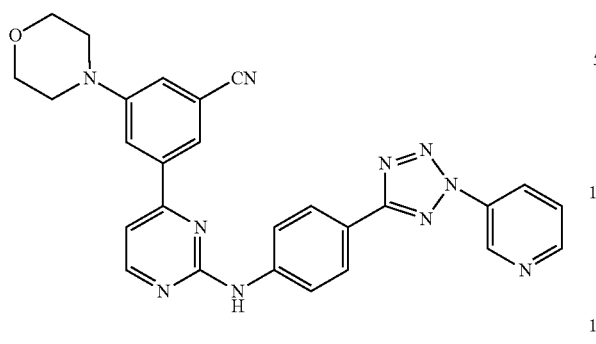
302 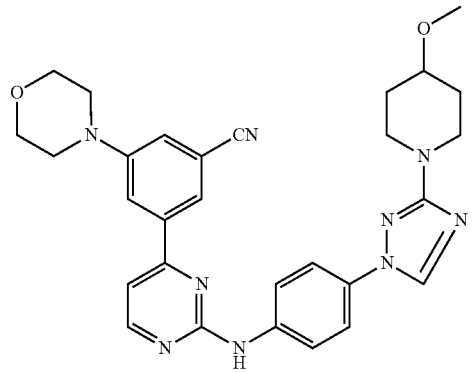
299 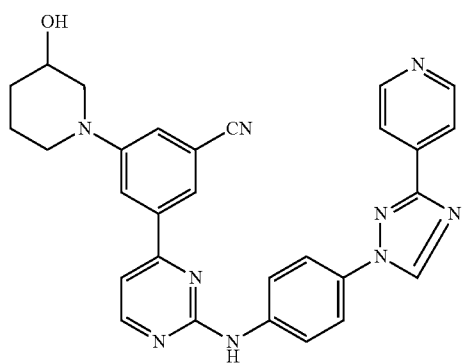
303 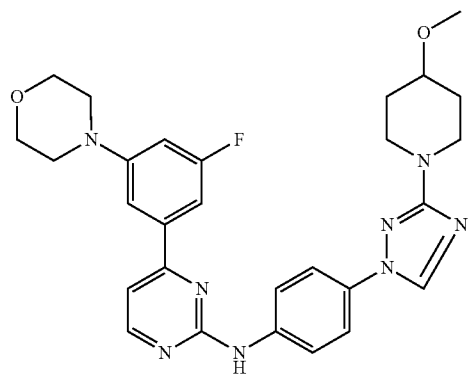
300 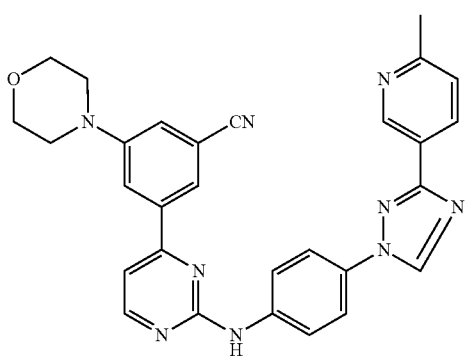
304 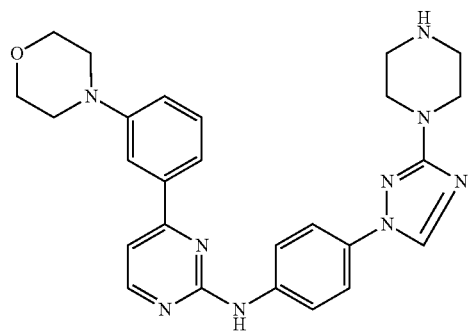
301 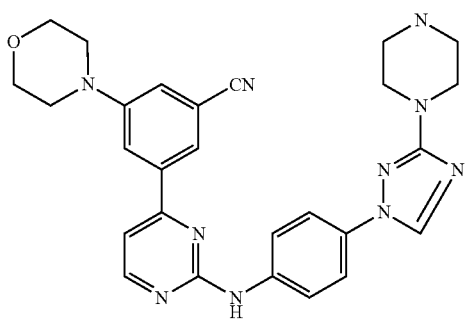
305 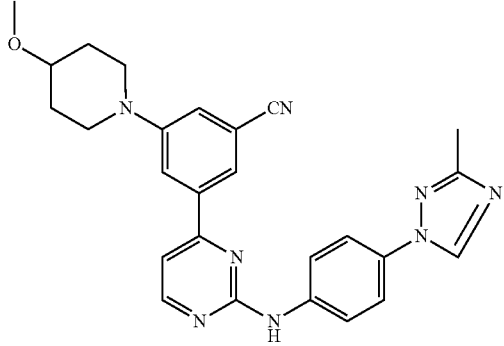

307
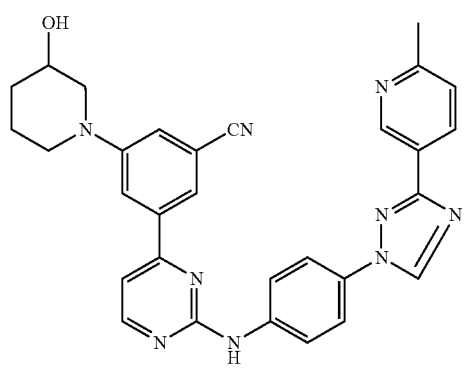
308
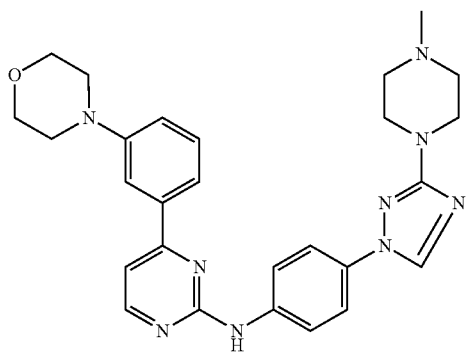
309
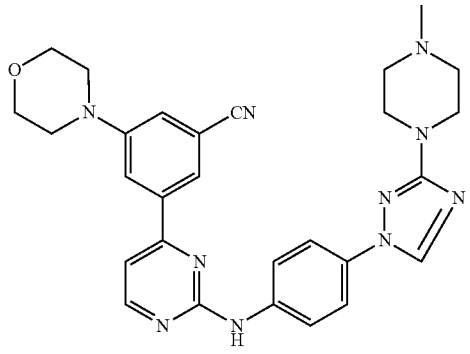
311
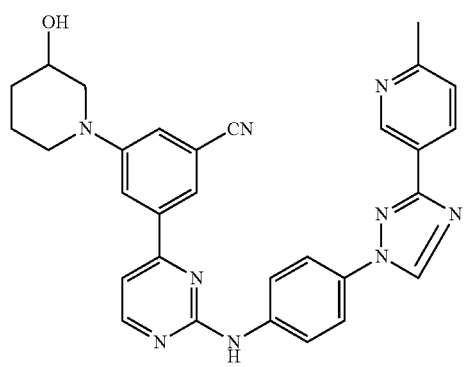
316
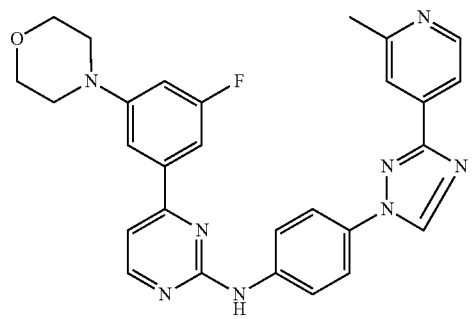
317
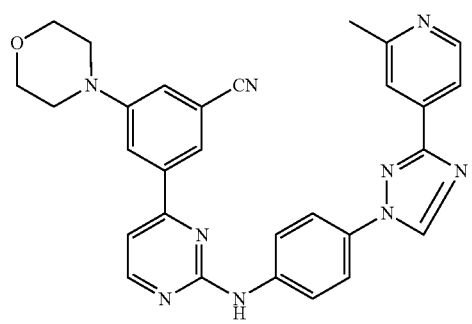
319
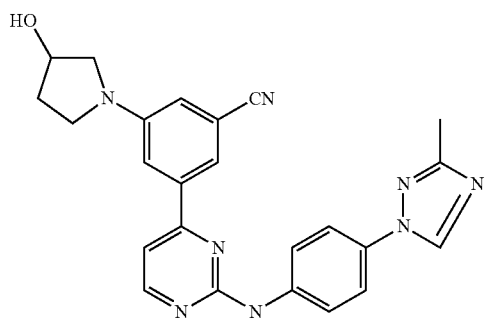
320
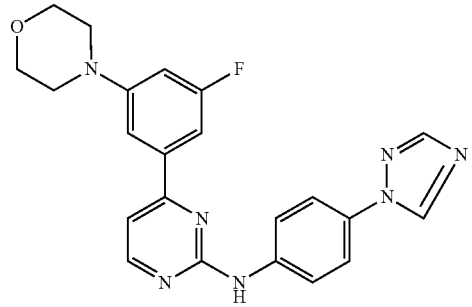
321
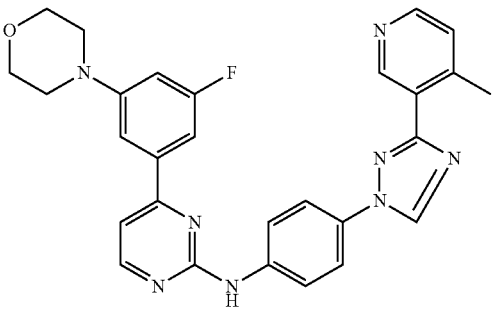

322
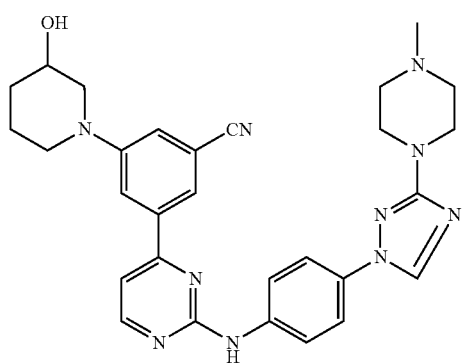
327
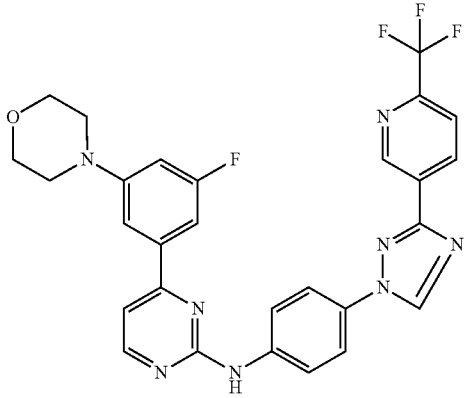
324
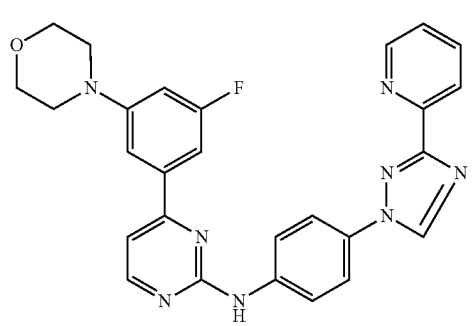
328
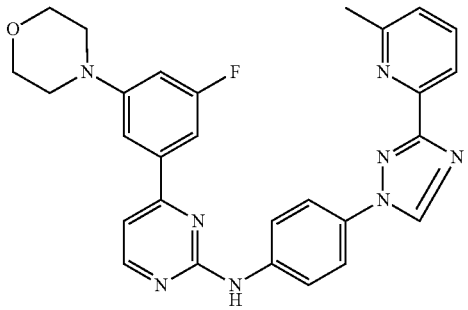
325
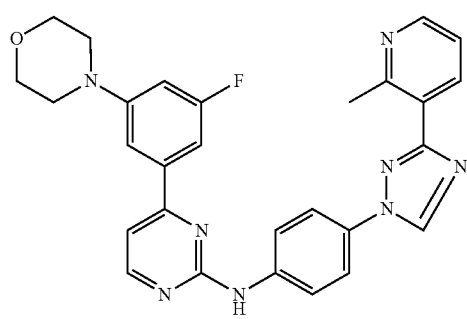
330
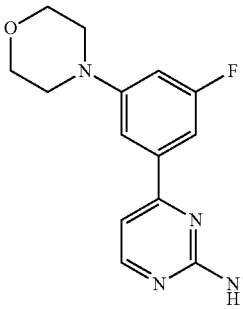
326
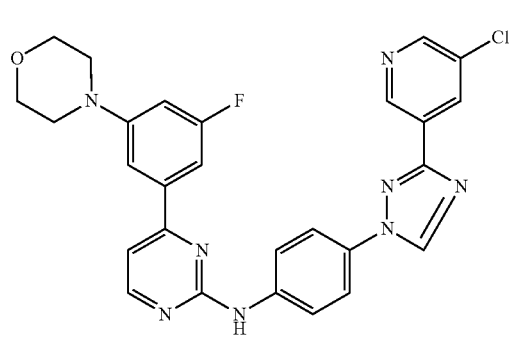
331
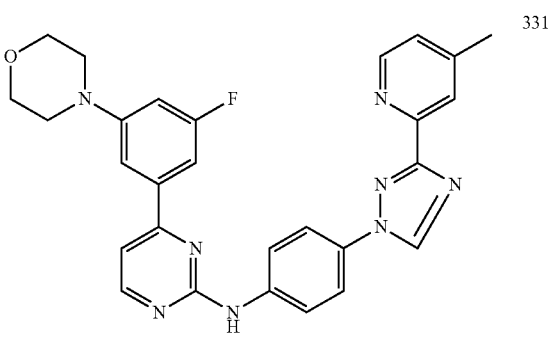

333

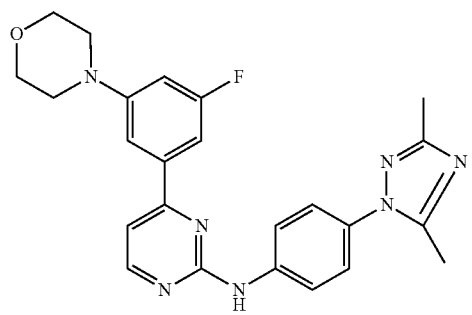

335

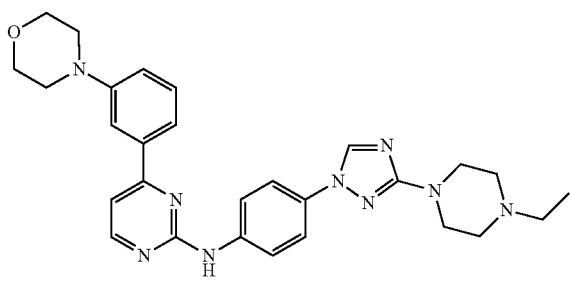

336

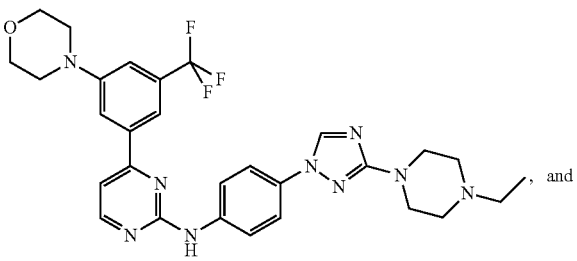

337

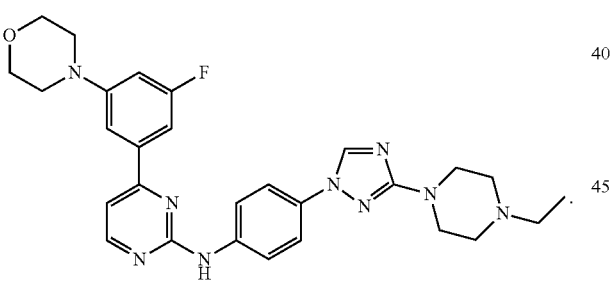

8. The method of claim 1, wherein the compound of formula (Ic) is administered as a pharmaceutical composition, comprising:
a pharmaceutically acceptable carrier.

9. A method of treating a disease or condition responsive to the inhibition of the JNK pathway, wherein the disease or condition is any of Parkinson's disease, stroke, diabetes, cancer, myocardial infarction, multiple sclerosis, pulmonary fibrosis, and Alzheimers and pre-Alzheimers diseases, comprising: administering to a patient in need thereof a therapeutically effective amount of a compound of formula 167

167

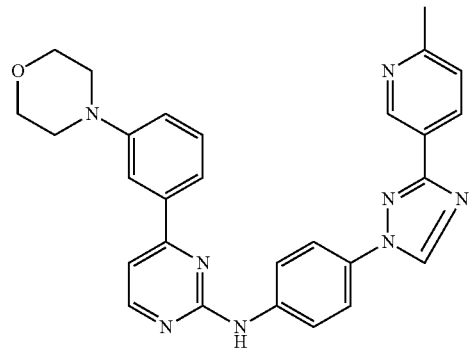

or a pharmaceutically acceptable salt thereof.

10. A method of treating a disease or condition responsive to the inhibition of the JNK pathway, comprising: administering to a patient in need thereof a therapeutically effective amount of a compound of formula 167

167

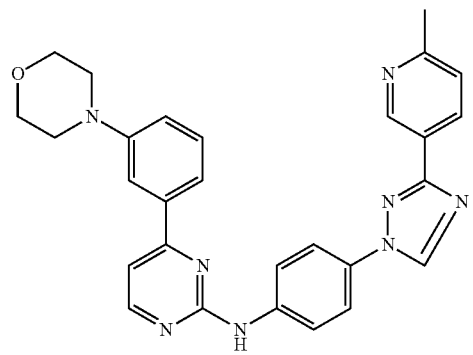

or a pharmaceutically acceptable salt thereof, and a pharmaceutically acceptable excipient.

* * * * *

UNITED STATES PATENT AND TRADEMARK OFFICE
CERTIFICATE OF CORRECTION

PATENT NO. : 9,018,205 B2
APPLICATION NO. : 13/766075
DATED : April 28, 2015
INVENTOR(S) : Kamenecka et al.

It is certified that error appears in the above-identified patent and that said Letters Patent is hereby corrected as shown below:

On the Title page, in item (57), in "Abstract", in column 2, line 3, delete "kinases" and insert --Kinases--, therefor On Title page 2, in item (56), in column 2, under "Other Publications", line 34, after "Mediator", insert --Release--, therefor In the Specification In column 1, line 28, delete "c-jun-N-terminal" and insert --c-Jun-N-terminal--, therefor In column 1, line 37, delete "(Jnk1$^1$, Jnk2$^{2,3}$, and Jnk3$^4$)" and insert --(JNK1$^1$, JNK2$^{2,3}$, and JNK3$^4$)--, therefor In column 2, line 9, delete "45beta" and insert --45 beta--, therefor In column 2, line 20, delete "Jnk3" and insert --JNK3--, therefor In column 2, line 46, delete "c-jun" and insert --c-Jun--, therefor In column 2, line 54, delete "Jnk3" and insert --JNK3--, therefor In column 3, line 13, delete "Thou," and insert --Zhou,--, therefor In column 5, line 53, delete "(CH$_4$NO$_2$," and insert --(CH$_2$)$_p$NO$_2$,--, therefor In column 5, line 57, delete "(CH$_4$SO$_2$NR$_2$," and insert --(CH$_2$)$_p$SO$_2$NR$_2$,--, therefor In column 8, line 50, after "0-2 R$^5$", insert --;--, therefor Signed and Sealed this
Twenty-second Day of December, 2015

Michelle K. Lee
*Director of the United States Patent and Trademark Office*

CERTIFICATE OF CORRECTION (continued)

U.S. Pat. No. 9,018,205 B2

In column 9, line 3, after "10-membered", insert --)--, therefor

In column 10, line 23, after "0-2 $R^5$", insert --;--, therefor

In column 10, line 44, delete "0-2 $R^b$," and insert --0-2 $R^b$),--, therefor

In column 11, line 15, after "6-membered", insert --)--, therefor

In column 11, line 18, after "6-membered", insert --)--, therefor

In column 11, line 27, after "6-membered", insert --)--, therefor

In column 11, line 41-42, after ""N-[6-({4-[4-(acetylamino)phenyl]pyrimidin-2-yl}amino)pyridin-2-yl]-2,6-dichlorobenzamide", insert --;--, therefor In column 11, line 55-56, delete "ethyl 4-({4-[(acetylamino)phenyl]pyrimidin-2-yl}aminopiperidine-1-carboxylate;" and insert --ethyl 4-({4-[(acetylamino)phenyl]pyrimidin-2-yl}amino)piperidine-1-carboxylate;--, therefor In column 13, line 39, delete "ring)." and insert --ring),--, therefor In column 14, line 5, after "10-membered", insert --)--, therefor In column 14, line 50, delete "Jnk3" and insert --JNK3--, therefor In column 14, line 52, delete "Jnk3" and insert --JNK3--, therefor In column 14, line 55, delete "Jnk3" and insert --JNK3--, therefor In column 14, line 56, delete "Jnk1 and Jnk2" and insert --JNK1 and JNK2--, therefor In column 14, line 57, delete "Jnk3" and insert --JNK3--, therefor In column 14, line 58, delete "Jnk3" and insert --JNK3--, therefor In column 14, line 67, delete "Jnk3" and insert --JNK3--, therefor In column 15, line 4, delete "Jnk3" and insert --JNK3--, therefor In column 15, line 4, delete "Jnk2" and insert --JNK2--, therefor In column 15, line 5, delete "Jnk3/Jnk2" and insert --JNK3/JNK2--, therefor In column 15, line 22, delete "Jnk1-/-" and insert --JNK1-/- --, therefor

CERTIFICATE OF CORRECTION (continued)
U.S. Pat. No. 9,018,205 B2

In column 15, line 26, delete "Jnk1-/-" and insert --JNK1-/- --, therefor

In column 18, line 59, delete "Halo"" and insert --"Halo"--, therefor

In column 19, line 18, delete "CO," and insert --$C_6$,--, therefor

In column 26, line 46, delete "70-190° C." and insert --70-190°C.--, therefor

In column 27, line 27, delete "150° C." and insert --150°C.--, therefor

In column 27, Scheme 4, line 42-52, delete " 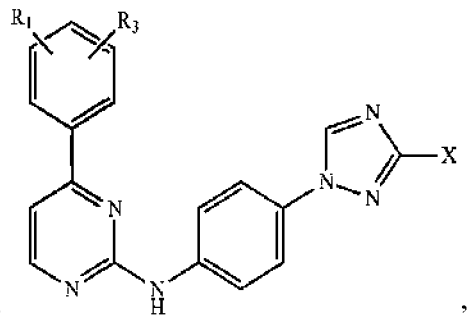 " and insert -- 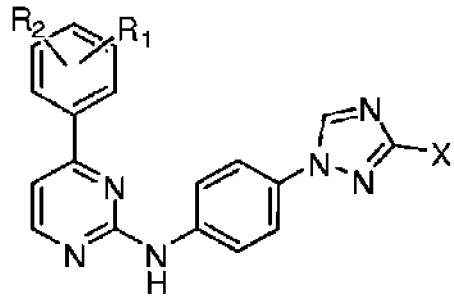 --, therefor In column 27, Scheme 4, line 53-62, delete " 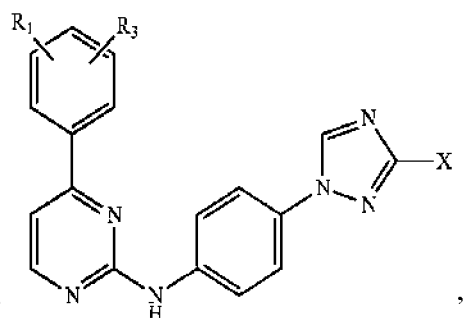 " and insert -- 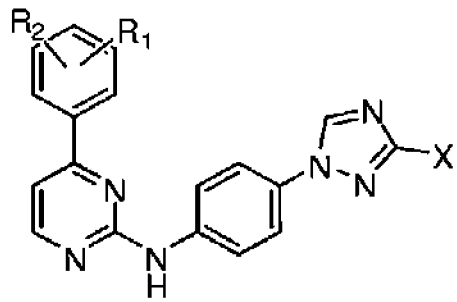 --, therefor In column 28, line 11, delete "50-120° C." and insert --50-120°C.--, therefor In column 28, line 30, delete "100-190° C." and insert --100-190°C.--, therefor In column 28, line 64, delete "18-25° C." and insert --18-25°C.--, therefor In column 28, line 67, delete "60° C." and insert --60°C.--, therefor In column 31, line 28, delete "3-methyl-1-(4 nitrophenyl)-1H-1,2,4-triazole" and insert --3-methyl-1-(4-nitrophenyl)-1H-1,2,4-triazole--, therefor In column 31, Part IV, line 43-50, delete " 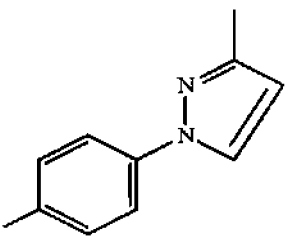 " and insert -- 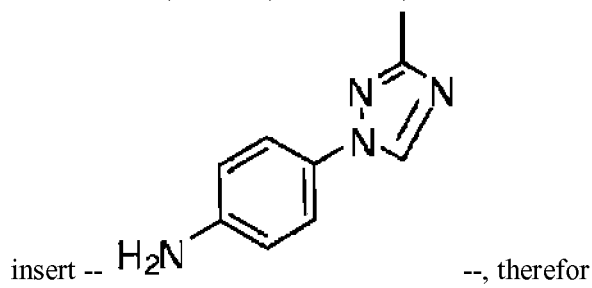 --, therefor In column 40, line 24-25, delete "2,4-dicholorrpyrimidine" and insert --2,4-dichloropyrimidine--, therefor In column 44, line 1, delete "(m 1H)" and insert --(m, 1H)--, therefor In column 44, line 35, delete "(m 1H)" and insert --(m, 1H)--, therefor In column 46, line 50-51, delete "2-Methoxy-5-(2-(4-(3-methyl-1H-1,2,4-triazol-1-yl)phenylamino)pyrimidin-4-ylbenzonitrile" and insert --2-Methoxy-5-(2-(4-(3-methyl-1H-1,2,4-triazol-1-yl)phenylamino)pyrimidin-4-yl)benzonitrile--, therefor In column 55, line 27-28, delete "5-(2-Chloropyrimidin-4-yl)-2-(4 hydroxypiperidin-1-yl)benzonitrile" and insert --5-(2-Chloropyrimidin-4-yl)-2-(4-hydroxypiperidin-1-yl)benzonitrile--, therefor In column 55, line 30, delete "2,4-dicholorrpyrimidine" and insert --2,4-dichloropyrimidine--, therefor

CERTIFICATE OF CORRECTION (continued)
U.S. Pat. No. 9,018,205 B2

In column 55, line 39-40, delete "5-(2-chloropyrimidin-4-yl)-2-(4 hydroxypiperidin-1-yl)benzonitrile" and insert --5-(2-chloropyrimidin-4-yl)-2-(4-hydroxypiperidin-1-yl)benzonitrile--, therefor In column 56, line 53, delete "δ8.28" and insert --δ 8.28--, therefor In column 56, line 60-61, delete "5-(2-chloropyrimidin-4-yl)-2-(4 hydroxypiperidin-1-yl)benzonitrile" and insert --5-(2-chloropyrimidin-4-yl)-2-(4-hydroxypiperidin-1-yl)benzonitrile--, therefor In column 80, line 66, delete "(EST)" and insert --(ESI)--, therefor In column 88, line 63, delete "0° C." and insert --0 °C.--, therefor In column 93, line 32-33, delete "5-(2-(4-(2H-Tetrazol-5-yl)phenylamino)pyrimidin-4-yl)-2-(4 hydroxypiperidin-1-yl)benzonitrile" and insert --5-(2-(4-(2H-Tetrazol-5-yl)phenylamino)pyrimidin-4-yl)-2-(4-hydroxypiperidin-1-yl)benzonitrile--, therefor In column 107, line 66-67, delete "N-(4-(5-Methyl-1H-1,2,4-triazol-1-yl)phenyl)-4-(3 morpholinophenyl)pyrimidin-2-amine" and insert --N-(4-(5-Methyl-1H-1,2,4-triazol-1-yl)phenyl)-4-(3-morpholinophenyl)pyrimidin-2-amine--, therefor In column 110, line 36, delete "3-Isopropyl-1-(4 nitrophenyl)-1H-1,2,4-triazole" and insert --3-Isopropyl-1-(4-nitrophenyl)-1H-1,2,4-triazole--, therefor In column 111, line 62-63, delete "1,1,1,3,3,3-Hexafluoro-2-(4-(4-(3 morpholinophenyl)pyrimidin-2-ylamino)phenyl)propan-2-ol" and insert --1,1,1,3,3,3-Hexafluoro-2-(4-(4-(3-morpholinophenyl)pyrimidin-2-ylamino)phenyl)propan-2-ol--, therefor In column 113, line 41, delete "3-Ethyl-1-(4 nitrophenyl)-1H-1,2,4-triazole" and insert --3-Ethyl-1-(4-nitrophenyl)-1H-1,2,4-triazole--, therefor In column 118, line 65, delete "2,4-dicholorrpyrimidine" and insert --2,4-dichloropyrimidine--, therefor In column 121, line 21-22, delete "Methyl 3-chloro-4-(4 phenylpyrimidin-2-ylamino)benzoate" and insert --Methyl 3-chloro-4-(4-phenylpyrimidin-2-ylamino)benzoate--, therefor In column 121, line 39-40, delete "(3-chloro-4-(4 phenylpyrimidin-2-ylamino)benzamide." and insert --(3-chloro-4-(4-phenylpyrimidin-2-ylamino)benzamide.--, therefor In column 122, line 27, delete "2,4-dicholorpyrimidine" and insert --2,4-dichloropyrimidine--, therefor

CERTIFICATE OF CORRECTION (continued)
U.S. Pat. No. 9,018,205 B2

In column 122, line 63, delete "2,4-dicholorpyrimidine" and insert --2,4-dichloropyrimidine--, therefor In column 124, line 5-6, delete "2,4-dicholorpyrimidine" and insert --2,4-dichloropyrimidine--, therefor In column 127, line 58, delete "2,4-dicholorrpyrimidine" and insert --2,4-dichloropyrimidine--, therefor In column 137, line 64-65, delete "3-bromo-5-(4 hydroxypiperidin-1-yl)benzonitrile" and insert --3-bromo-5-(4-hydroxypiperidin-1-yl)benzonitrile--, therefor In column 138, line 25-26, delete "3-bromo-5-(3 hydroxypiperidin-1-yl)benzonitrile" and insert --3-bromo-5-(3-hydroxypiperidin-1-yl)benzonitrile--, therefor In column 145, line 29-30, delete "N-(4-(3,5-dimethyl-1H-1,2,4-triazol-1-1/1)phenyl)-4-phenylpyrimidin-2-amine" and insert --N-(4-(3,5-dimethyl-1H-1,2,4-triazol-1-yl)phenyl)-4-phenylpyrimidin-2-amine--, therefor In column 150, line 52, delete "stifling" and insert --stirring--, therefor In column 150, line 59, delete "(M+H" and insert --(M+H).--, therefor In column 150, line 62-64, delete "N-(4-(3,5-dimethyl-1H-1,2,4-triazol-1-yl)phenyl)-4-(3-fluoro-5-(4 isopropylpiperazin-1-yl)phenyl)pyrimidin-2-amine" and insert --N-(4-(3,5-dimethyl-1H-1,2,4-triazol-1-yl)phenyl)-4-(3-fluoro-5-(4-isopropylpiperazin-1-yl)phenyl)pyrimidin-2-amine--, therefor In column 152, line 48-60 (Approx.), delete " 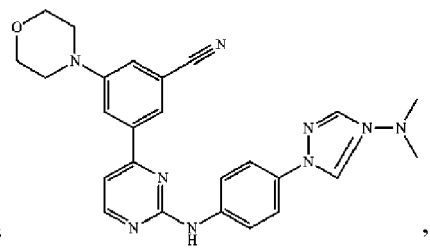 " and insert -- 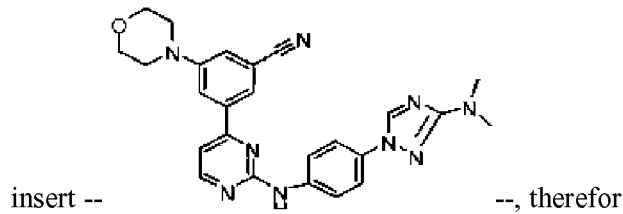 --, therefor In column 153, line 8-19 (Approx.), delete " 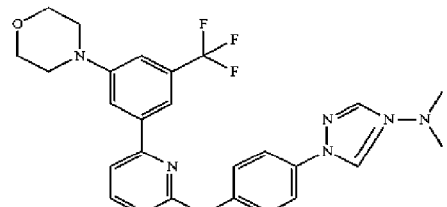 " and insert -- 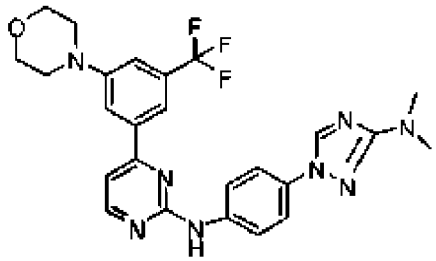 --, therefor
In column 154, line 5-6, delete "34244-bromophenylamino)pyrimidin-4-yl)-5-morpholinobenzonitrile" and insert --3-(2-(4-bromophenylamino)pyrimidin-4-yl)-5-morpholinobenzonitrile--, therefor
In column 155, line 46-58 (Approx.), delete " 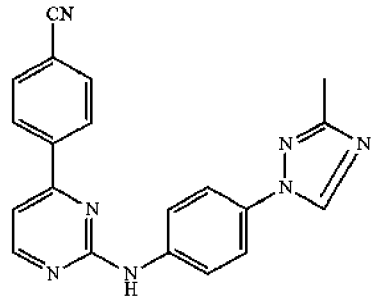 " and insert -- 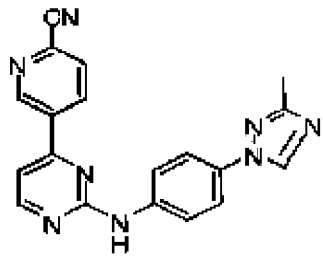 --, therefor
In column 156, line 27-35 (Approx.), delete " 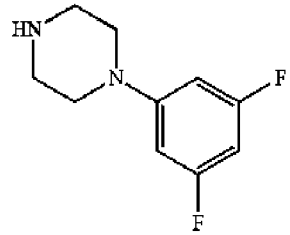 " and insert -- 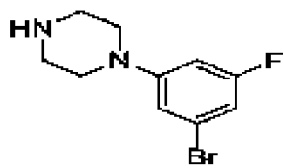 --, therefor In column 156, line 37, delete "(1-(3-Bromo-5-fluorophenyl)" and insert --1-(3-Bromo-5-fluorophenyl)--, therefor In column 156, line 63, delete "(1-(3-Bromo-5-fluorophenyl)" and insert --1-(3-Bromo-5-fluorophenyl)--, therefor In column 156, line 64, delete "0° C." and insert --0 °C.--, therefor In column 158, line 47, delete "2-Cloro-4-(3-fluoro-5-(piperazin-1-yl)phenyl)pyrimidine" and insert --2-Chloro-4-(3-fluoro-5-(piperazin-1-yl)phenyl)pyrimidine--, therefor In column 158, line 60-61, delete "2-chloro-4-(3-(4 ethylpiperazin-1-yl)-5-fluorophenyl)pyrimidine" and insert --2-chloro-4-(3-(4-ethylpiperazin-1-yl)-5-fluorophenyl)pyrimidine--, therefor In column 158, line 62, delete "d9.72" and insert --δ 9.72--, therefor In column 159, line 21-22, delete "2-chloro-4-(3-(4 ethylpiperazin-1-yl-5-fluorophenyl)pyrimidine" and insert --2-chloro-4-(3-(4-ethylpiperazin-1-yl)-5-fluorophenyl)pyrimidine--, therefor In column 159, line 23, delete "δ." and insert --δ--, therefor In column 159, line 31-33, delete "4-(3-(4-Ethylpiperazin-1-yl)-5-fluorophenyl)-N-(4-(3-(6-methoxypyridin-3-1H)-1H-1,2,4-triazol-1-yl)phenyl)pyrimidin-2-amine" and insert --4-(3-(4-Ethylpiperazin-1-yl)-5-fluorophenyl)-N-(4-(3-(6-methoxypyridin-3-yl)-1H-1,2,4-triazol-1-yl)phenyl)pyrimidin-2-amine--, therefor In column 160, line 1-3, delete "4-(3-(4-Ethylpiperazin-1-yl)-5-fluorophenyl)-N-(4-(3-(6-methoxypyridin-3-yl)-1H-1,2,4-triazol-1-yl-phenyl)pyrimidin-2-amine" and insert --4-(3-(4-Ethylpiperazin-1-yl)-5-fluorophenyl)-N-(4-(3-(6-methoxypyridin-3-yl)-1H-1,2,4-triazol-1-yl)phenyl)pyrimidin-2-amine--, therefor In column 164, line 1, delete "δ." and insert --δ--, therefor In column 164, line 59-61, delete "3-(2-(4-(3-(6-methoxypyridin-3-yl)-1H-1,2,4-triazol-1-yl)phenylamino)pyrimidin-4-yl-5-(piperazin-1-yl)benzonitrile." and insert --3-(2-(4-(3-(6-methoxypyridin-3-yl)-1H-1,2,4-triazol-1-yl)phenylamino)pyrimidin-4-yl)-5-(piperazin-1-yl)benzonitrile.--, therefor In column 164, line 62, delete "δ." and insert --δ--, therefor In column 165, line 29, delete "δ." and insert --δ--, therefor In column 165, line 62, delete "δ." and insert --δ--, therefor In column 168, line 23-24, delete "3-(3-Hydroxypiperidin-1-yl)-5-(2-(4-(3 morpholino-1H-1,2,4-triazol-1-yl)phenylamino)pyrimidin-4-yl)benzonitrile" and insert --3-(3-Hydroxypiperidin-1-yl)-5-(2-(4-(3-morpholino-1H-1,2,4-triazol-1-yl)phenylamino)pyrimidin-4-yl)benzonitrile--, therefor In column 169, line 24-25, delete "3-(2-Chloropyrimidin-4-yl)-5-(4-hydroxypiperidin-1-ylbenzonitrile" and insert --3-(2-Chloropyrimidin-4-yl)-5-(4-hydroxypiperidin-1-yl)benzonitrile--, therefor In column 169, line 43-45, delete "3-(4-Hydroxypiperidin-1-yl)-5-(2-(4-(3-(4 methylpiperazin-1-yl)-1H-1,2,4-triazol-1-yl)phenylamino)pyrimidin-4-yl)benzonitrile" and insert --3-(4-Hydroxypiperidin-1-yl)-5-(2-(4-(3-(4-methylpiperazin-1-yl)-1H-1,2,4-triazol-1-yl)phenylamino)pyrimidin-4-yl)benzonitrile--, therefor In column 169, line 46-47, delete "3-(2-chloropyrimidin-4-yl)-5-(4 hydroxypiperidin-1-yl)benzonitrile" and insert --3-(2-chloropyrimidin-4-yl)-5-(4-hydroxypiperidin-1-yl)benzonitrile--, therefor In column 170, line 42-43, delete "3-Bromo-5-(4 hydroxypiperidin-1-yl)benzonitrile" and insert --3-Bromo-5-(4-hydroxypiperidin-1-yl)benzonitrile--, therefor In column 171, line 1-3, delete "1-(3-Fluoro-5-(2-(4-(3-(4 methylpiperazin-1-yl)-1H-1,2,4-triazol-1-yl)phenylamino)pyrimidin-4-yl)phenyl)piperidin-4-ol" and insert --1-(3-Fluoro-5-(2-(4-(3-(4-methylpiperazin-1-yl)-1H-1,2,4-triazol-1-yl)phenylamino)pyrimidin-4-yl)phenyl)piperidin-4-ol--, therefor In column 173, line 6, delete "NMR" and insert --$^1$H NMR--, therefor In column 173, line 6, delete "δ." and insert --δ--, therefor In column 173, line 60, delete "70 C", insert --70°C.--, therefor In column 174, line 62, delete "NMR" and insert --$^1$H NMR--, therefor In column 174, line 63, delete "δ." and insert --δ--, therefor In column 175, line 29, delete "NMR" and insert --$^1$H NMR--, therefor In column 175, line 29, delete "δ." and insert --δ--, therefor

CERTIFICATE OF CORRECTION (continued)

In column 177, line 3-5, delete "1-(5-(2-(4-(3-(3-hydroxypiperidin-1-yl)-1H-1,2,4-triazol-1-yl)phenylamino)pyrimidin-4-yl-2-(methylsulfonyl)phenyl)piperidin-3-ol" and insert --1-(5-(2-(4-(3-(3-hydroxypiperidin-1-yl)-1H-1,2,4-triazol-1-yl)phenylamino)pyrimidin-4-yl)-2-(methylsulfonyl)phenyl)piperidin-3-ol--, therefor In column 178, line 8-9 (Approx.), delete "3-morpholino-5-(2-(4-(3-(pyridin-2-yl)-1H-1,2,4-triazol-1-yl)phenylamino)pyrimidin-4-ylbenzonitrile" and insert --3-morpholino-5-(2-(4-(3-(pyridin-2-yl)-1H-1,2,4-triazol-1-yl)phenylamino)pyrimidin-4-yl)benzonitrile--, therefor In column 178, line 21-22 (Approx.), delete "3-morpholino-5-(2-(4-(3 (pyridin-2-yl)-1H-1,2,4-triazol-1-yl)phenylamino)pyrimidin-4-yl)benzonitrile" and insert --3-morpholino-5-(2-(4-(3-(pyridin-2-yl)-1H-1,2,4-triazol-1-yl)phenylamino)pyrimidin-4-yl)benzonitrile--, therefor In column 192, line 62-63, delete "3-(2-(4-(3-(4-methoxypiperidin-1-yl)-1H-1,2,4-triazol-1-yl)phenylamino)pyrimidin-4-yl-5-morpholinobenzonitrile" and insert --3-(2-(4-(3-(4-methoxypiperidin-1-yl)-1H-1,2,4-triazol-1-yl)phenylamino)pyrimidin-4-yl)-5-morpholinobenzonitrile--, therefor In column 194, line 1-2, delete "3-(4-methoxypiperidin-1-yl)-5-(2-(4-(3 methyl-1H-1,2,4-triazol-1-yl)phenylamino)pyrimidin-4-yl)benzonitrile" and insert --3-(4-methoxypiperidin-1-yl)-5-(2-(4-(3-methyl-1H-1,2,4-triazol-1-yl)phenylamino)pyrimidin-4-yl)benzonitrile--, therefor In column 197, line 7-16 (Approx.), delete " 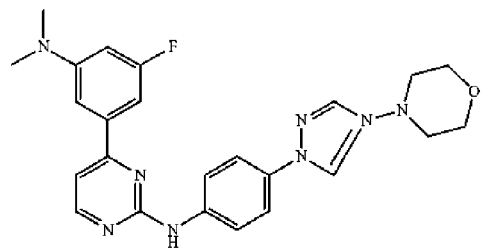 " and insert -- 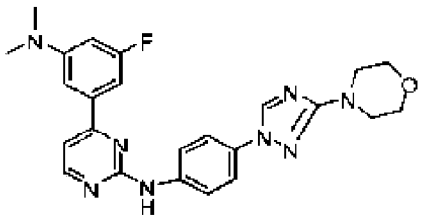 --, therefor In column 197, line 32-41 (Approx.), delete " 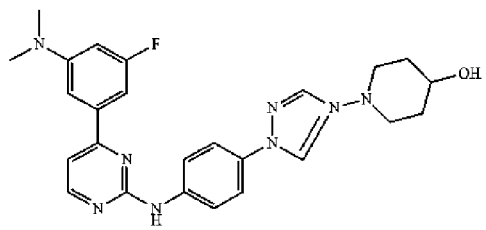 " and insert -- 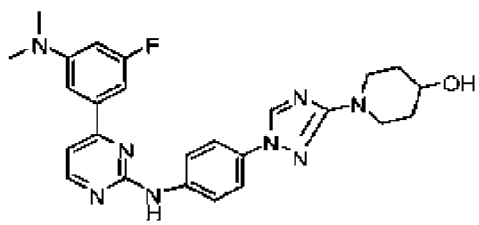 --, therefor In column 197, line 57-66 (Approx.), delete " 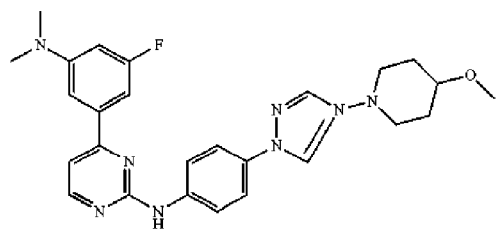 " and insert -- 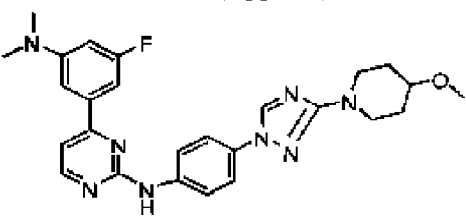 --, therefor In column 205, line 62-63, delete "3-(2-(4-bromophenylamino)pyrimidin-4-yl-5-morpholinobenzonitrile" and insert --3-(2-(4-bromophenylamino)pyrimidin-4-yl)-5-morpholinobenzonitrile--, therefor In column 208, line 12, delete "4° C." and insert --4°C.--, therefor In column 208, line 17, delete "4° C." and insert --4°C.--, therefor In column 208, line 40, delete "-80° C." and insert -- -80°C.--, therefor In column 208, line 50, delete "30 C." and insert --30°C.--, therefor In column 208, line 55, delete "4 C." and insert --4°C.--, therefor In column 208, line 58, delete "4° C." and insert --4°C.--, therefor In column 209, line 6, delete "Na₃VO4," and insert --Na$_3$VO$_4$,--, therefor In column 209, line 16, delete "(1□M)" and insert --1μM--, therefor In column 210, line 3, delete "c-jun" and insert --c-Jun--, therefor In column 210, line 9, delete "500" and insert --50--, therefor In column 210, line 9, delete "c-jun" and insert --c-Jun--, therefor

CERTIFICATE OF CORRECTION (continued)

U.S. Pat. No. 9,018,205 B2

In column 210, line 30, delete "4° C." and insert --4°C.--, therefor

In column 210, line 31, delete "c-jun" and insert --c-Jun--, therefor

In column 212, line 29, delete "0-2 Rb," and insert --0-2 Rb),--, therefor

In column 213, line 2, after "6-membered", insert --)--, therefor

In column 213, line 5, after "6-membered", insert --)--, therefor

In column 213, line 13, after "6-membered", insert --)--, therefor

In column 213, line 27-28, after "'N-[6-({4-[4-(acetylamino)phenyl]pyrimidin-2-yl}amino)pyridin-2-yl]-2,6-dichlorobenzamide", insert --;--, therefor In column 214, line 50, after "10-membered", insert --)--, therefor In column 214, line 51, after "10-membered", insert --)--, therefor In column 215, line 1, delete "$CH_2)_p$-(5-" and insert --$(CH_2)_p$-(5- --, therefor In column 215, line 1, after "10-membered", insert --)--, therefor In column 215, line 2, after "10-membered", insert --)--, therefor In column 215, line 11, after "10-membered", insert --)--, therefor In column 216, line 43, delete "method" and insert --A method--, therefor In the Claims In column 219, line 31, in Claim 1, after "0-2 $R^5$", insert --;--, therefor In column 219, line 50, in Claim 1, after "10-membered", insert --)--, therefor In column 220, line 7, in Claim 4, delete "0-2$R^b$" and insert --0-2$R^b$),--, therefor In column 220, line 8, in Claim 4, after "membered", insert --)--, therefor In column 220, line 14-15, in Claim 6, delete "10)-membered" and insert --10-membered)--, therefor In column 220, line 22, in Claim 7, after "of", insert --:--, therefor

CERTIFICATE OF CORRECTION (continued)
U.S. Pat. No. 9,018,205 B2

In column 240, line 15-26, in Claim 7, delete " 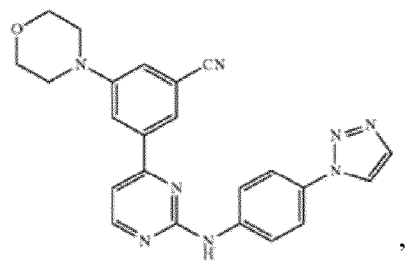 " and insert -- 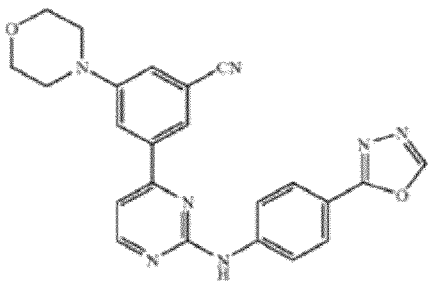 --, therefor